United States Patent
Brown et al.

(10) Patent No.: US 9,708,313 B2
(45) Date of Patent: Jul. 18, 2017

(54) SUBSTITUTED PYRIDO[3,4-B]PYRAZINES AS GPR6 MODULATORS

(71) Applicants: Jason W. Brown, San Diego, CA (US); Stephen Hitchcock, San Diego, CA (US); Maria Hopkins, San Diego, CA (US); Shota Kikuchi, San Diego, CA (US); Holger Monenschein, San Diego, CA (US); Holly Reichard, San Diego, CA (US); Kristin Schleicher, San Diego, CA (US); Huikai Sun, San Diego, CA (US); Todd Macklin, Brooklyn Park, MN (US)

(72) Inventors: Jason W. Brown, San Diego, CA (US); Stephen Hitchcock, San Diego, CA (US); Maria Hopkins, San Diego, CA (US); Shota Kikuchi, San Diego, CA (US); Holger Monenschein, San Diego, CA (US); Holly Reichard, San Diego, CA (US); Kristin Schleicher, San Diego, CA (US); Huikai Sun, San Diego, CA (US); Todd Macklin, Brooklyn Park, MN (US)

(73) Assignee: Takeda Pharmaceutical Company Limited, Osaka (JP)

( * ) Notice: Subject to any disclaimer, the term of this patent is extended or adjusted under 35 U.S.C. 154(b) by 90 days.

(21) Appl. No.: 14/883,174

(22) Filed: Oct. 14, 2015

(65) Prior Publication Data

US 2016/0031881 A1    Feb. 4, 2016

Related U.S. Application Data

(62) Division of application No. 14/577,480, filed on Dec. 19, 2014, now Pat. No. 9,181,249.

(60) Provisional application No. 61/919,661, filed on Dec. 20, 2013.

(51) Int. Cl.
*C07D 241/38* (2006.01)
*C07D 471/04* (2006.01)

(52) U.S. Cl.
CPC ............... *C07D 471/04* (2013.01)

(58) Field of Classification Search
CPC ............... C07D 241/38
USPC ............... 544/350, 362; 546/199
See application file for complete search history.

(56) References Cited

U.S. PATENT DOCUMENTS

| | | |
|---|---|---|
| 2003/0229113 A1 | 12/2003 | Hashimoto et al. |
| 2015/0232469 A1 | 8/2015 | Hitchcock et al. |

FOREIGN PATENT DOCUMENTS

| | | |
|---|---|---|
| WO | 01/62765 A2 | 8/2001 |
| WO | 2004/069162 A2 | 8/2004 |
| WO | 2006/039718 A2 | 4/2006 |
| WO | 2007/122466 A1 | 11/2007 |
| WO | 2007/125405 A2 | 11/2007 |
| WO | 2008/149162 A2 | 12/2008 |
| WO | 2010/143170 A2 | 12/2010 |
| WO | 2013/087808 A1 | 6/2013 |
| WO | 2013/087815 A1 | 6/2013 |
| WO | 2013/169964 A1 | 11/2013 |
| WO | 2014/028479 A1 | 2/2014 |

*Primary Examiner* — Douglas M Willis
(74) *Attorney, Agent, or Firm* — Matthew J. Russo; David M. Stemerick

(57) ABSTRACT

This present invention provides compounds of formula II:

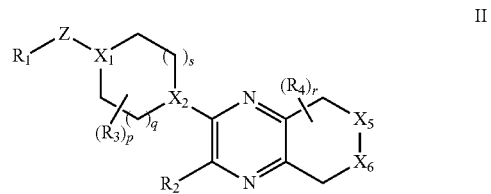

which are useful as modulators of GPR6, pharmaceutical compositions thereof, methods for treatment of conditions associated with GPR6, processes for making the compounds and intermediates thereof.

15 Claims, No Drawings

SUBSTITUTED PYRIDO[3,4-B]PYRAZINES AS GPR6 MODULATORS

CROSS-REFERENCE TO RELATED APPLICATIONS

This application is a divisional of U.S. application Ser. No. 14/577,480, filed Dec. 19, 2014, which claims the benefit of U.S. Provisional Application No. 61/919,661, filed Dec. 20, 2013, which are incorporated herein by reference.

FIELD OF THE INVENTION

The present invention relates to medicinal chemistry, pharmacology, and medicine.

BACKGROUND OF THE INVENTION

The present invention provides compounds that are G-Protein-Coupled Receptor 6 (hereinafter referred to as GPR6) modulators. GPR6 is GPCR that signals via the Gs pathway. GPR6 receptors are highly expression in the central nervous system (CNS), particularly medium spiny neurons (MSNs) of the striatum, with minimal expression in peripheral tissues. The major striatal targets of dopaminergic innervation reside in the medium spiny neurons (MSNs) of the striatopallidal (indirect) and striatonigral (direct) output pathways. The MSNs of the direct output pathway express D1 dopamine receptors whereas those in the indirect pathway express D2 receptors. GPR6 is enriched in D2 receptor expressing MSNs in the striatum where GPR6 activity is functionally opposed to D2 receptor signaling. Antagonism or inverse agonism of Gs coupled GPR6 decreases cAMP in MSNs and provides a functional alternative to dopamine mediated activation of D2 receptors. Therefore, the compounds of the present invention are useful to treat a variety of neurological and psychiatric disorders, including Parkinson's disease.

SUMMARY OF THE INVENTION

The present invention provides a compound of formula I:

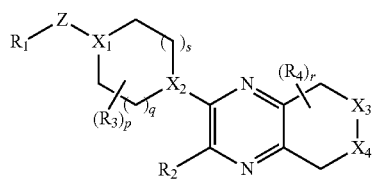

I wherein
$R_1$ is selected from the group consisting of optionally substituted $C_{3-8}$ cycloalkyl, optionally substituted $C_{3-6}$ heterocyclyl, optionally substituted $C_{6-10}$ aryl, and optionally substituted $C_{1-10}$ heteroaryl;
$X_1$ is N and $X_2$ is CH; or
$X_1$ is CH and $X_2$ is N; or
$X_1$ is N and $X_2$ is N;
when $X_1$ is N, Z is selected from the group consisting of $C_{1-6}$ alkylene, $C_{1-6}$ haloalkylene, —C(O)—, and —S(O)$_2$—;
when $X_1$ is CH, Z is selected from the group consisting of $C_{1-6}$ alkylene, $C_{1-6}$ haloalkylene, —O—, —C(O)—, —NH—, —S—, —S(O)—, and —S(O)$_2$—;
q is 0, 1, or 2;
s is 0, 1, or 2;
$R_2$ is —OR$_5$ or —NR$_6$R$_7$;
$R_3$, each time taken, is independently selected from the group consisting of $C_{1-6}$ alkyl, $C_{3-8}$ cycloalkyl, and trifluoromethyl;
p is 0, 1, or 2;
$R_4$, each time taken, is independently selected from the group consisting of $C_{1-6}$ alkyl, hydroxy, and halo;
r is 0 or 1;
$R_5$ is selected from the group consisting of $C_{1-6}$ alkyl and $C_{3-8}$ cycloalkyl;
$R_6$ is selected from the group consisting of hydrogen and $C_{1-6}$ alkyl;
$R_7$ is selected from the group consisting of optionally substituted $C_{1-6}$ alkyl, $C_{3-8}$ cycloalkyl, optionally substituted $C_{6-10}$ aryl, optionally substituted $C_{1-10}$ heteroaryl, and optionally substituted $C_{3-6}$ heterocyclyl;
$X_3$ is selected from the group consisting of CH and CR$_4$ and $X_4$ is NR$_8$; or
$X_3$ is NR$_8$ and $X_4$ is selected from the group consisting of CH and CR$_4$;
$R_8$ is selected from the group consisting of $C_{1-6}$ alkyl, $C_{1-6}$ haloalkyl, $C_{3-8}$ cycloalkyl, —S(O)$_2$—R$_9$, —C(O)—R$_{10}$, —C(O)—N(R$_{11}$)(R$_{12}$), and —C(O)—OR$_{13}$;
$R_9$ is selected from the group consisting of $C_{1-6}$ alkyl, $C_{3-8}$ cycloalkyl, and optionally substituted phenyl;
$R_{10}$ is selected from the group consisting of hydrogen, optionally substituted $C_{1-6}$ alkyl, $C_{3-8}$ cycloalkyl, optionally substituted $C_{6-10}$ aryl, optionally substituted $C_{1-10}$ heteroaryl, and optionally substituted $C_{3-6}$ heterocyclyl;
$R_{11}$ is selected from the group consisting of hydrogen and $C_{1-6}$ alkyl;
$R_{12}$ is selected from the group consisting of hydrogen, $C_{1-6}$ alkyl and $C_{3-8}$ cycloalkyl; or
$R_{11}$ and $R_{12}$ are taken together with the nitrogen to which they are attached form a 4 to 7 membered, saturated, ring optionally having 1 additional ring heteroatom selected from the group N, O, and S and optionally substituted on any of the ring carbon atoms with 1 to 5 substituents independently selected from the group consisting of cyano, halo, hydroxy, amino, optionally substituted $C_{3-6}$ heterocyclyl, $C_{1-9}$ amide, optionally substituted $C_{1-6}$ alkyl, and $C_{1-4}$ alkoxy and substituted on any additional ring nitrogen by a substituent selected from the group consisting of hydrogen, $C_{3-8}$ cycloalkyl, and optionally substituted $C_{1-6}$ alkyl;
$R_{13}$ is selected from the group consisting of $C_{1-6}$ alkyl and $C_{3-8}$ cycloalkyl; or a pharmaceutically acceptable salt thereof.

The present invention also provides pharmaceutical compositions, comprising: a compound of formula I or a pharmaceutically acceptable salt thereof and a pharmaceutically acceptable excipient.

The compounds of the present invention are modulators of GPR6 and are useful to treat a variety of neurological and psychiatric disorders, for example movement disorders including Parkinson's disease, levodopa induced dyskinesias, and Huntington's disease, drug addiction, eating disorders, cognitive disorders, schizophrenia, bipolar disorders, and depression. Thus, the present invention also provides methods of treating the conditions associated with GPR6 described herein comprising, administering to a patient in need thereof an effective amount of the compounds of the invention. The present invention provides for the use of the compounds of the invention as a medicament, including for treatment of the conditions associated with GPR6 described herein, and including for the manufacture of a medicament for treating the conditions associated with GPR6 described herein.

The present invention also provides processes from making GPR6 modulators and intermediates thereof.

DETAILED DESCRIPTION OF THE INVENTION

The term "$C_{1-4}$ alkyl" refers to a straight or branched alkyl chain of one to four carbon atoms.

The term "optionally substituted $C_{1-4}$ alkyl" refers to a $C_{1-4}$ alkyl optionally substituted with 1 to 6 substituents independently selected from the group consisting of optionally substituted $C_{1-4}$ alkoxy, $C_{1-4}$ thioalkoxy, $C_{1-9}$ amide, $C_{1-7}$ amido, amino, $C_{1-8}$ alkylamino, $C_{1-5}$ oxycarbonyl, $C_{1-5}$ carbonyloxy, $C_{1-8}$ sulfonyl, cyano, optionally substituted $C_{3-8}$ cycloalkyl, $C_{3-8}$ cycloalkoxy, halo, hydroxy, nitro, oxo, optionally substituted $C_{3-6}$ heterocyclyl, optionally substituted $C_{1-10}$ heteroaryl, and optionally substituted $C_{6-10}$ aryl.

More particularly "optionally substituted $C_{1-4}$ alkyl" refers to a $C_{1-4}$ alkyl optionally substituted with 1 to 6 substituents independently selected from the group consisting of $C_{1-4}$ alkoxy, $C_{1-9}$ amide, amino, $C_{1-8}$ alkylamino, $C_{1-5}$ oxycarbonyl, cyano, $C_{3-8}$ cycloalkyl, halo, hydroxy, $C_{3-6}$ heterocyclyl optionally substituted on any ring nitrogen by $C_{1-4}$ alkyl, $C_{1-10}$ heteroaryl, and optionally substituted phenyl.

Even more particularly "optionally substituted $C_{1-4}$ alkyl" refers to a $C_{1-4}$ alkyl optionally substituted with 1 to 6 substituents independently selected from the group consisting of $C_{1-4}$ alkoxy, cyano, $C_{3-8}$ cycloalkyl, halo, hydroxy, $C_{3-6}$ heterocyclyl optionally substituted on any ring nitrogen by $C_{1-4}$ alkyl, and optionally substituted phenyl.

The term "$C_{1-6}$ alkyl" refers to a straight or branched alkyl chain of one to six carbon atoms.

The term "optionally substituted $C_{1-6}$ alkyl" refers to a $C_{1-6}$ alkyl optionally substituted with 1 to 7 substituents independently selected from the group consisting of amino, $C_{1-8}$ alkylamino, optionally substituted $C_{1-4}$ alkoxy, $C_{1-4}$ thioalkoxy, $C_{1-9}$ amide, $C_{1-7}$ amido, $C_{1-5}$ oxycarbonyl, $C_{1-5}$ carbonyloxy, $C_{1-8}$ sulfonyl, cyano, optionally substituted $C_{3-8}$ cycloalkyl, halo, hydroxy, oxo, optionally substituted $C_{1-10}$ heteroaryl, optionally substituted $C_{3-6}$ heterocyclyl, and optionally substituted $C_{6-10}$ aryl.

More particularly "optionally substituted $C_{1-6}$ alkyl" refers to a $C_{1-6}$ alkyl optionally substituted with 1 to 7 substituents independently selected from the group consisting of $C_{1-4}$ alkoxy, $C_{1-9}$ amide, amino, $C_{1-8}$ alkylamino, $C_{1-5}$ oxycarbonyl, cyano, $C_{3-8}$ cycloalkyl, halo, hydroxy, $C_{3-6}$ heterocyclyl optionally substituted on any ring nitrogen by $C_{1-4}$ alkyl, $C_{1-10}$ heteroaryl, and optionally substituted phenyl.

Even more particularly "optionally substituted $C_{1-6}$ alkyl" refers to a $C_{1-6}$ alkyl optionally substituted with 1 to 7 substituents independently selected from the group consisting of $C_{1-4}$ alkoxy, cyano, $C_{3-8}$ cycloalkyl, halo, hydroxy, $C_{3-6}$ heterocyclyl optionally substituted on any ring nitrogen by $C_{1-4}$ alkyl, and optionally substituted phenyl.

The term "$C_{1-6}$ haloalkyl" refers to a straight or branched alkyl chain of one to six carbon atoms substituted with 1 to 3 halogen atoms. More particularly, the term "$C_{1-6}$ haloalkyl" refers to fluoromethyl and difluoromethyl.

The term "$C_{1-8}$ sulfonyl" refers to a sulfonyl linked to a $C_{1-6}$ alkyl group, $C_{3-8}$ cycloalkyl, or an optionally substituted phenyl.

The term "$C_{1-6}$ alkylene" refers to a straight or branched, divalent, alkylene chain of one to six carbon atoms.

The term "$C_{1-6}$ haloalkylene" refers to a straight or branched, divalent, alkylene chain of one to six carbon atoms substituted with 1 to 3 halogen atoms. More particularly, the term "$C_{1-6}$ haloalkylene" refers fluoromethylene and difluoromethylene.

The term "$C_{1-4}$ alkoxy" refers to a $C_{1-4}$ alkyl attached through an oxygen atom.

The term "optionally substituted $C_{1-4}$ alkoxy" refers to a $C_{1-4}$ alkoxy optionally substituted with 1 to 6 substituents independently selected from the group consisting of $C_{1-4}$ alkoxy, $C_{1-9}$ amide, $C_{1-5}$ oxycarbonyl, cyano, optionally substituted $C_{3-8}$ cycloalkyl, halo, hydroxy, optionally substituted $C_{1-10}$ heteroaryl, and optionally substituted $C_{6-10}$ aryl. While it is understood that where the optional substituent is $C_{1-4}$ alkoxy or hydroxy then the substituent is generally not alpha to the alkoxy attachment point, the term "optionally substituted $C_{1-4}$ alkoxy" includes stable moieties and specifically includes trifluoromethoxy, difluoromethoxy, and fluoromethoxy.

More particularly "optionally substituted $C_{1-4}$ alkoxy" refers to a $C_{1-4}$ alkoxy optionally substituted with 1 to 6 substituents independently selected from the group consisting of $C_{1-4}$ alkoxy, cyano, $C_{3-8}$ cycloalkyl, halo, hydroxy, and optionally substituted phenyl. Even more particularly "optionally substituted $C_{1-4}$ alkoxy" refers to trifluoromethoxy, difluoromethoxy, and fluoromethoxy.

The term "$C_{1-9}$ amide" refers to a —C(O)NR$_a$R$_b$ group in which R$_a$ is selected from the group consisting of hydrogen and $C_{1-4}$ alkyl, and R$_b$ is selected from the group consisting of hydrogen, $C_{1-3}$ alkyl, and optionally substituted phenyl.

The term "$C_{1-7}$ amido" refers to a —NHC(O)R$_c$ group in which R$_c$ is selected from the group consisting of hydrogen, $C_{1-6}$ alkyl, and optionally substituted phenyl.

The term "$C_{1-5}$ carbamoyl" refers to an O- or N-linked carbamate substituted with a terminal $C_{1-4}$ alkyl.

The term "$C_{1-5}$ ureido" refers to a urea optionally substituted with a $C_{1-4}$ alkyl.

The term "$C_{1-8}$ alkylamino" refers to a —NR$_d$R$_e$ group in which R$_d$ is a $C_{1-4}$ alkyl and R$_e$ is selected from the group consisting of hydrogen and $C_{1-4}$ alkyl.

The term "$C_{6-10}$ aryl" refers to a monocyclic and polycyclic unsaturated, conjugated hydrocarbon having five to ten carbon atoms, and includes phenyl, and naphthyl.

More particularly "$C_{6-10}$ aryl" refers to phenyl.

The term "optionally substituted $C_{6-10}$ aryl" refers to a $C_{6-10}$ aryl optionally substituted with 1 to 5 substituents independently selected from the group consisting of optionally substituted $C_{1-4}$ alkyl, optionally substituted $C_{1-4}$ alkoxy, $C_{1-4}$ thioalkoxy, amino, $C_{1-8}$ alkylamino, $C_{1-9}$ amide, $C_{1-7}$ amido, $C_{1-5}$ oxycarbonyl, $C_{1-5}$ carbonyloxy, $C_{1-8}$ sulfonyl, $C_{1-5}$ carbamoyl, $C_{1-6}$ sulfonylamido, aminosulfonyl, $C_{1-10}$ aminosulfonyl, $C_{1-5}$ ureido, cyano, halo, and hydroxyl.

More particularly "optionally substituted $C_{6-10}$ aryl" refers to a $C_{6-10}$ aryl optionally substituted with 1 to 5 substituents independently selected from the group consisting of $C_{1-4}$ alkyl, $C_{1-4}$ alkoxy, cyano, halo, hydroxy, amino, trifluoromethyl, and trifluoromethoxy.

Even more particularly "optionally substituted $C_{6-10}$ aryl" refers to phenyl optionally substituted with 1 to 5 substituents independently selected from the group consisting of $C_{1-4}$ alkyl, $C_{1-4}$ alkoxy, cyano, halo, trifluoromethyl, and trifluoromethoxy.

The term "$C_{1-5}$ oxycarbonyl" refers to an oxycarbonyl group (—CO$_2$H) and $C_{1-4}$ alkyl ester thereof.

The term "$C_{1-5}$ carbonyloxy" refers to a carbonyloxy group (—$O_2CR_f$), in which $R_f$ is selected from the group consisting of hydrogen and $C_{1-4}$ alkyl, for example, acetoxy.

The term "$C_{3-8}$ cycloalkyl" refers to monocyclic or bicyclic, saturated or partially (but not fully) unsaturated alkyl ring of three to eight carbon atoms, and includes cyclopropyl, cyclobutyl, cyclopentyl, cyclohexyl, and the like. It is understood that the term includes benzofused cyclopentyl and cyclohexyl.

The term "optionally substituted $C_{3-8}$ cycloalkyl" refers to a $C_{3-8}$ cycloalkyl optionally substituted with 1 to 6 substituents independently selected from the group consisting of optionally substituted $C_{1-4}$ alkyl, optionally substituted $C_{1-4}$ alkoxy, $C_{1-6}$ amide, $C_{1-2}$ amido, amino, $C_{1-8}$ alkylamino, $C_{1-5}$ oxycarbonyl, cyano, $C_{3-8}$ cycloalkyl, $C_{3-8}$ cycloalkoxy, halo, hydroxy, nitro, oxo, optionally substituted $C_{1-10}$ heteroaryl, and optionally substituted phenyl.

More particularly "optionally substituted $C_{3-8}$ cycloalkyl" refers to a $C_{3-8}$ cycloalkyl optionally substituted with 1 to 3 substituents independently selected from the group consisting of $C_{1-4}$ alkoxy, halo, hydroxy, and $C_{1-4}$ alkyl optionally substituted with $C_{1-4}$ alkoxy, halo, and hydroxy.

The term "$C_{3-8}$ cycloalkoxy" refers to a $C_{3-8}$ cycloalkyl attached through and oxygen.

The terms "halogen" and "halo" refers to a chloro, fluoro, bromo or iodo atom.

The term "$C_{3-6}$ heterocyclyl" refers to a 4 to 8 membered monocyclic or bicyclic, saturated or partially (but not fully) unsaturated ring having one or two heteroatoms selected from the group consisting of nitrogen, oxygen, and sulfur and the ring optionally includes a carbonyl to form a lactam or lactone. It is understood that where sulfur is included that the sulfur may be either —S—, —SO—, and —$SO_2$—. It is also under that the term includes spirofused bicyclic systems. For example, but not limiting, the term includes azetidinyl, pyrrolidinyl, piperidinyl, piperazinyl, morpholinyl, thiomorpholinyl, oxetanyl, dioxolanyl, tetrahydropyranyl, tetrahydrothiopyranyl, tetrahydrofuryl, hexahydropyrimidinyl, tetrahydropyrimidinyl, dihydroimidazolyl, and the like. It is understood that a $C_{3-6}$ heterocyclyl can be attached as a substituent through a ring carbon or a ring nitrogen atom.

More particularly "$C_{3-6}$ heterocyclyl" is selected from the group consisting of azetidinyl, pyrrolidinyl, piperidinyl, piperazinyl, morpholinyl, oxetanyl, tetrahydropyranyl, tetrahydrothiopyranyl, and tetrahydrofuryl.

The term "optionally substituted $C_{3-6}$ heterocyclyl" refers to a $C_{3-6}$ heterocyclyl optionally substituted on the ring carbons with 1 to 4 substituents independently selected from the group consisting of optionally substituted $C_{1-4}$ alkyl, optionally substituted $C_{1-4}$ alkoxy, $C_{1-9}$ amide, $C_{1-7}$ amido, amino, $C_{1-8}$ alkylamino, $C_{1-5}$ oxycarbonyl, cyano, optionally substituted $C_{3-8}$ cycloalkyl, $C_{3-8}$ cycloalkoxy, halo, hydroxy, nitro, oxo, and optionally substituted phenyl; and optionally substituted on any ring nitrogen with a substituent independently selected from the group consisting of optionally substituted $C_{1-4}$ alkyl, $C_{3-8}$ cycloalkyl, optionally substituted $C_{3-6}$ heterocyclyl, optionally substituted $C_{1-10}$ heteroaryl, and optionally substituted phenyl.

More particularly "optionally substituted $C_{3-6}$ heterocyclyl" refers to a $C_{3-6}$ heterocyclyl optionally substituted on the ring carbons with 1 to 4 substituents independently selected from the group consisting of $C_{1-4}$ alkyl, $C_{1-4}$ alkoxy, halo, and hydroxy and optionally substituted on any ring nitrogen with a $C_{1-4}$ alkyl.

The term "$C_{1-10}$ heteroaryl" refers to a five to thirteen membered, monocyclic or polycyclic fully unsaturated, ring or ring system with one to ten carbon atoms and one or more, typically one to four, heteroatoms selected from the group consisting of nitrogen, oxygen, and sulfur. For example, but not limiting, the term includes furyl, thienyl, pyrrolyl, imidazolyl, isothiazolyl, isoxazolyl, oxadiazolyl, oxazolyl, thiazolyl, thiadiazolyl, triazolyl, tetrazolyl, pyrazinyl, pyrazolyl, pyridazinyl, pyridyl, pyrimidyl, azepinyl, diazepinyl, benzazepinyl, benzodiazepinyl, benzofuryl, benzothienyl, indolyl, isoindolyl, benzimidazolyl, benzisothiazolyl, benzisoxazolyl, benzoxadiazolyl, benzoxazolyl, benzopyrazinyl, benzopyrazolyl, imidazopyridyl, pyrazolopyridyl, pyrrolopyridyl, quinazolyl, thienopyridyl, imidazopyridyl, quinolyl, isoquinolyl benzothiazolyl, and the like. It is understood that a $C_{1-10}$ heteroaryl can be attached as a substituent through a ring carbon or a ring nitrogen atom where such an attachment mode is available, for example for a pyrrolyl, indolyl, imidazolyl, pyrazolyl, azepinyl, triazolyl, pyrazinyl, etc.

More particularly "$C_{1-10}$ heteroaryl" is selected from the group consisting of furyl, thienyl, pyrrolyl, imidazolyl, oxazolyl, thiazolyl, pyrazolyl, triazolyl, pyridyl, and pyrimidyl.

The term "optionally substituted $C_{1-10}$ heteroaryl" refers to a $C_{1-10}$ heteroaryl optionally substituted with 1 to 5 substituents on carbon independently selected from the group consisting of amino, $C_{1-8}$ alkylamino, $C_{1-9}$ amide, $C_{1-7}$ amido, $C_{1-5}$ carbamoyl, $C_{1-6}$ sulfonylamido, aminosulfonyl, $C_{1-10}$ aminosulfonyl, $C_{1-5}$ ureido, optionally substituted $C_{1-4}$ alkyl, optionally substituted $C_{1-4}$ alkoxy, cyano, halo, hydroxyl, oxo, nitro, $C_{1-5}$ carbonyloxy, $C_{1-5}$ oxycarbonyl, and $C_{1-8}$ sulfonyl and optionally substituted with a substituent on each nitrogen independently selected from the group consisting of optionally substituted $C_{1-4}$ alkyl, $C_{1-8}$ sulfonyl, optionally substituted $C_{3-6}$ heterocyclyl, and optionally substituted phenyl.

More particularly "optionally substituted $C_{1-10}$ heteroaryl" refers to a $C_{1-10}$ heteroaryl optionally substituted with 1 to 3 substituents on carbon independently selected from the group consisting of amino, $C_{1-8}$ alkylamino, $C_{1-9}$ amide, $C_{1-4}$ alkyl, $C_{1-4}$ alkoxy, cyano, halo, hydroxyl, oxo, trifluoromethyl, and trifluoromethoxy and optionally substituted on a ring nitrogen with a $C_{1-4}$ alkyl.

Even more particularly "optionally substituted $C_{1-10}$ heteroaryl" refers to a $C_{1-10}$ heteroaryl selected from the group consisting of furyl, thienyl, pyrrolyl, imidazolyl, oxazolyl, thiazolyl, pyrazolyl, diazolyl, pyridyl, pyrimidyl, and triazolyl each optionally substituted with 1 to 3 substituents independently selected from the group consisting of $C_{1-4}$ alkyl, $C_{1-4}$ alkoxy, cyano, halo, trifluoromethyl, and trifluoromethoxy and optionally substituted on a ring nitrogen with a methyl.

The term "oxo" refers to an oxygen atom doubly bonded to the carbon to which it is attached to form the carbonyl of a ketone or aldehyde. For example, a pryidone radical is contemplated as an oxo substituted $C_{1-10}$ heteroaryl.

The term "optionally substituted phenyl" refers to a phenyl group optionally substituted with 1 to 5 substituents independently selected from the group consisting of $C_{1-4}$ alkyl, $C_{1-4}$ alkoxy, $C_{1-9}$ amide, amino, $C_{1-8}$ alkylamino, $C_{1-5}$ oxycarbonyl, cyano, halo, hydroxyl, nitro, $C_{1-8}$ sulfonyl, and trifluoromethyl.

More particularly "optionally substituted phenyl" refers to a phenyl group optionally substituted with 1 to 5 substituents independently selected from the group consisting of $C_{1-4}$ alkyl, $C_{1-4}$ alkoxy, $C_{1-9}$ amino, $C_{1-8}$ alkylamino, $C_{1-5}$ oxycarbonyl, cyano, halo, hydroxyl, nitro, and trifluoromethyl.

The term "$C_{1-6}$ sulfonylamido" refers to a —NHS(O)$_2$—$R_g$ group wherein $R_g$ is selected from the group consisting of $C_{1-6}$ alkyl and optionally substituted phenyl.

The term "aminosulfonyl" refers to a —S(O)$_2$NH$_2$.

The term "$C_{1-10}$ aminosulfonyl" refers to a —S(O)$_2$NR$_h$R$_i$ group wherein $R_h$ is selected from the group consisting of hydrogen and $C_{1-4}$ alkyl and $R_i$ is selected from the group consisting of $C_{1-4}$ alkyl, and optionally substituted phenyl.

The term "$C_{1-4}$ thioalkoxy" refers to a $C_{1-4}$ alkyl attached through a sulfur atom.

The term "pharmaceutically acceptable salt" refers to salts of pharmaceutically acceptable organic acids and bases or inorganic acids and bases. Such salts are well known in the art and include those described in Journal of Pharmaceutical Science, 66, 2-19 (1977). An example is the hydrochloride salt.

The term "substituted," including when used in "optionally substituted" refers to one or more hydrogen radicals of a group are replaced with non-hydrogen radicals (substituent(s)). It is understood that the substituents may be either the same or different at every substituted position. Combinations of groups and substituents envisioned by this invention are those that are stable or chemically feasible.

The term "stable" refers to compounds that are not substantially altered when subjected to conditions to allow for their production. In a non-limiting example, a stable compound or chemically feasible compound is one that is not substantially altered when kept at a temperature of 40° C. or less, in the absence of moisture or other chemically reactive conditions, for about a week.

It is understood that, where the terms defined herein mention a number of carbon atoms, the mentioned number refers to the mentioned group and does not include any carbons that may be present in any optional substituent(s) thereon.

The skilled artisan will appreciate that certain of the compounds of the present invention exist as isomers. All stereoisomers of the compounds of the invention, including geometric isomers, enantiomers, and diastereomers, in any ratio, are contemplated to be within the scope of the present invention.

The skilled artisan will appreciate that certain of the compounds of the present invention exist as tautomers. All tautomeric forms the compounds of the invention are contemplated to be within the scope of the present invention.

Compounds of the invention also include all pharmaceutically acceptable isotopic variations, in which at least one atom is replaced by an atom having the same atomic number, but an atomic mass different from the predominant atomic mass. Isotopes suitable for inclusion in compounds of formula I include radioactive isotopes.

The terms "compounds of the invention" and "a compound of the invention" and "compounds of the present invention, and the like include the embodiment of formula I and the other more particular embodiments encompassed by formula I described herein and exemplified compounds described herein and a pharmaceutically acceptable salt of each of these embodiments.

The present invention provides a compound of formula II:

wherein
$R_1$ is selected from the group consisting of optionally substituted $C_{3-8}$ cycloalkyl, optionally substituted $C_{3-6}$ heterocyclyl, optionally substituted $C_{6-10}$ aryl, and optionally substituted $C_{1-10}$ heteroaryl;
$X_1$ is N and $X_2$ is CH; or
$X_1$ is CH and $X_2$ is N; or
$X_1$ is N and $X_2$ is N;
when $X_1$ is N, Z is selected from the group consisting of $C_{1-6}$ alkylene, $C_{1-6}$ haloalkylene, —C(O)—, and —S(O)$_2$—;
when $X_1$ is CH, Z is selected from the group consisting of $C_{1-6}$ alkylene, $C_{1-6}$ haloalkylene, —O—, —C(O)—, —NH—, —S—, —S(O)—, and —S(O)$_2$—;
q is 0, 1, or 2;
s is 0, 1, or 2;
$R_2$ is —OR$_5$ or —NR$_6$R$_7$;
$R_3$, each time taken, is independently selected from the group consisting of $C_{1-6}$ alkyl, $C_{3-8}$ cycloalkyl, and trifluoromethyl;
p is 0, 1, or 2;
$R_4$, each time taken, is independently selected from the group consisting of $C_{1-6}$ alkyl, hydroxy, and halo;
r is 0 or 1;
$R_5$ is selected from the group consisting of $C_{1-6}$ alkyl and $C_{3-8}$ cycloalkyl;
$R_6$ is selected from the group consisting of hydrogen and $C_{1-6}$ alkyl;
$R_7$ is selected from the group consisting of optionally substituted $C_{1-6}$ alkyl, $C_{3-8}$ cycloalkyl, optionally substituted $C_{6-10}$ aryl, optionally substituted $C_{1-10}$ heteroaryl, and optionally substituted $C_{3-6}$ heterocyclyl;
$X_5$ is selected from the group consisting of CH and CR$_4$ and $X_6$ is selected from the group consisting of NH and N—CH$_2$-(optionally substituted phenyl); or
$X_5$ is selected from the group consisting of NH and N—CH$_2$-(optionally substituted phenyl) and $X_6$ is selected from the group consisting of CH and CR$_4$;
or a pharmaceutically acceptable salt thereof.

(Ia) One embodiment relates to compounds of formula I wherein $X_1$ is CH and $X_2$ is N.

(Ib) One embodiment relates to compounds of formula I wherein $X_1$ is N and $X_2$ is N.

(Ic) One embodiment relates to compounds of formula I and embodiment (Ia) and (Ib) wherein $X_3$ is selected from the group consisting of CH and CR$_4$ and $X_4$ is NR$_8$.

(Id) One embodiment relates to compounds of formula I and embodiment (Ia) and (Ib) wherein $X_3$ is NR$_8$ and $X_4$ is selected from the group consisting of CH and CR$_4$.

(Ie) One embodiment relates to compounds of formula I and embodiments (Ia), (Ib), (Ic), and (Id) wherein $R_1$ is optionally substituted $C_{6-10}$ aryl.

(If) One embodiment relates to compounds of formula I and embodiments (Ia), (Ib), (Ic), and (Id) wherein Z is $C_{1-6}$ alkylene.

(Ig) One embodiment relates to compounds formula I and embodiments (Ia), (Ib), (Ic), and (Id) wherein Z is $C_{1-6}$ haloalkylene.

(Ih) One embodiment relates to compounds formula I and embodiments (Ia), (Ic), and (Id) wherein Z is —O—.

(Ii) One embodiment relates to compounds of formula I and embodiments (Ia), (Ib), (Ic), and (Id) wherein Z is —C(O)—.

(Ij) One embodiment relates to compounds of formula I and embodiments (Ia), (Ib), (Ic), (Id), (Ie), (If), (Ig), (Ih), and (Ii) wherein $R_2$—$NR_6R_7$. In another embodiment within embodiment (Ij), $R_6$ is hydrogen and $R_7$ is $C_{1-6}$ alkyl. In yet another embodiment within embodiment (Ij), $R_6$ is hydrogen and $R_7$ is $C_{3-8}$ cycloalkyl. In yet another embodiment within embodiment (Ij), $R_6$ is hydrogen and $R_7$ is $C_{3-6}$ heterocyclyl.

(Ik) One embodiment relates to compounds of formula I and embodiments (Ia), (Ib), (Ic), (Id), (Ie), (If), (Ig), (Ih), (Ii), and (Ij) wherein s is 1.

(Il) One embodiment relates to compounds of formula I and embodiments (Ia), (Ib), (Ic), (Id), (Ie), (If), (Ig), (Ih), (Ii), (Ij), and (Ik) wherein q is 1.

(Im) One embodiment relates to compounds of formula I and embodiments (Ia), (Ib), (Ic), (Id), (Ie), (If), (Ig), (Ih), (Ii), (Ij), (Ik), and (Il) wherein $R_8$ is selected from the group consisting —C(O)—$R_{10}$, —C(O)—N($R_{11}$)($R_{12}$), and —C(O)—$OR_{13}$.

(In) One embodiment relates to compounds of formula I and embodiments (Ia), (Ib), (Ic), (Id), (Ie), (If), (Ig), (Ih), (Ii), (Ij), (Ik), and (Il) wherein $R_8$ is —(O)—$R_{10}$ and $R_{10}$ is $C_{1-6}$ alkyl.

(IIa) One embodiment relates to compounds of formula II wherein $X_1$ is CH and $X_2$ is N.

(IIb) One embodiment relates to compounds of formula II wherein $X_1$ is N and $X_2$ is N.

(IIc) One embodiment relates to compounds of formula II and embodiment (IIa) and (IIb) wherein $X_3$ is $NR_8$ and $X_4$ is selected from the group consisting of CH and $CR_4$.

(IId) One embodiment relates to compounds of formula II and embodiments (IIa), (IIb), and (IIc) wherein $R_1$ is optionally substituted $C_{6-10}$ aryl.

(IIe) One embodiment relates to compounds of formula II and embodiments (IIa), (IIb), (IIc), and (IId) wherein Z is $C_{1-6}$ alkylene.

(IIf) One embodiment relates to compounds formula II and embodiments (IIa), (IIb), (IIc), and (IId) wherein Z is $C_{1-6}$ haloalkylene.

(IIg) One embodiment relates to compounds formula II and embodiments (IIa), (IIc), and (IId) wherein Z is —O—.

(IIh) One embodiment relates to compounds formula II and embodiments (IIa), (IIb), (IIc), and (IId) wherein Z is —C(O)—.

(IIi) One embodiment relates to compounds of formula II and embodiments (IIa), (IIb), (IIc), (IId), (IIe), (IIf), (IIg), and (IIh) wherein $R_2$—$NR_6R_7$. In another embodiment within embodiment (IIj), $R_6$ is hydrogen and $R_7$ is $C_{1-6}$ alkyl. In yet another embodiment within embodiment (IIj), $R_6$ is hydrogen and $R_7$ is $C_{3-8}$ cycloalkyl. In yet another embodiment within embodiment (IIj), $R_6$ is hydrogen and $R_7$ is $C_{3-6}$ heterocyclyl.

(IIj) One embodiment relates to compounds of formula II and embodiments (IIa), (IIb), (IIc), (IId), (IIe), (IIf), (IIg), (IIh), and (IIi) wherein s is 1.

(IIk) One embodiment relates to compounds of formula II and embodiments (IIa), (IIb), (IIc), (IId), (IIe), (IIf), (IIg), (IIh), (IIi), and (IIj) wherein q is 1.

(III) One embodiment relates to compounds of formula II and embodiments (IIa), (IIb), (IIe), (IIf), (IIg), (IIh), (IIi), (IIj), and (IIk) wherein $X_5$ is selected from the group consisting of CH and $CR_4$ and $X_6$ is NH.

(IIm) One embodiment relates to compounds of formula II and embodiments (IIa), (IIb), (IIe), (IIf), (IIg), (IIh), (IIi), (IIj), and (IIk) wherein $X_5$ is selected from the group consisting of NH $X_6$ is selected from the group consisting of CH and $CR_4$.

(IIn) One embodiment relates to compounds of formula II and embodiments (IIa), (IIb), (IIe), (IIf), (IIg), (IIh), (IIi), (IIj), and (IIk) wherein $X_5$ is selected from the group consisting of CH and $CR_4$ and $X_6$ is N—$CH_2$-(optionally substituted phenyl).

(IIo) One embodiment relates to compounds of formula II and embodiments (IIa), (IIb), (IIe), (IIf), (IIg), (IIh), (IIi), (IIj), (IIk), and (III) wherein $X_5$ is selected from the group consisting of CH and $CR_4$ and $X_6$ is N—$CH_2$-(optionally substituted phenyl).

(ay) Another embodiment relates to a pharmaceutically acceptable salt of each of the above embodiments.

(az) Another embodiment relates to a pharmaceutically acceptable salt of each of the exemplified compounds.

The compounds of the invention can be prepared by a variety of procedures, some of which are described below. All substituents, unless otherwise indicated, are as previously defined. The products of each step can be recovered by conventional methods including extraction, evaporation, precipitation, chromatography, filtration, trituration, crystallization, and the like. The procedures may require protection of certain groups, for example hydroxy, amino, or carboxy groups to minimize unwanted reactions. The selection, use, and removal of protecting groups are well known and appreciated as standard practice, for example T. W. Greene and P. G. M. Wuts in Protective Groups in Organic Chemistry (John Wiley and Sons, 1991). In the schemes below starting materials are either commercially available or can be ready prepared by methods well known in the art.

Scheme A

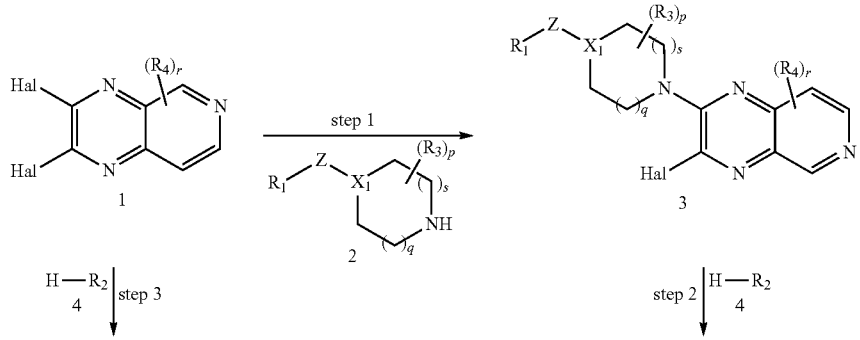

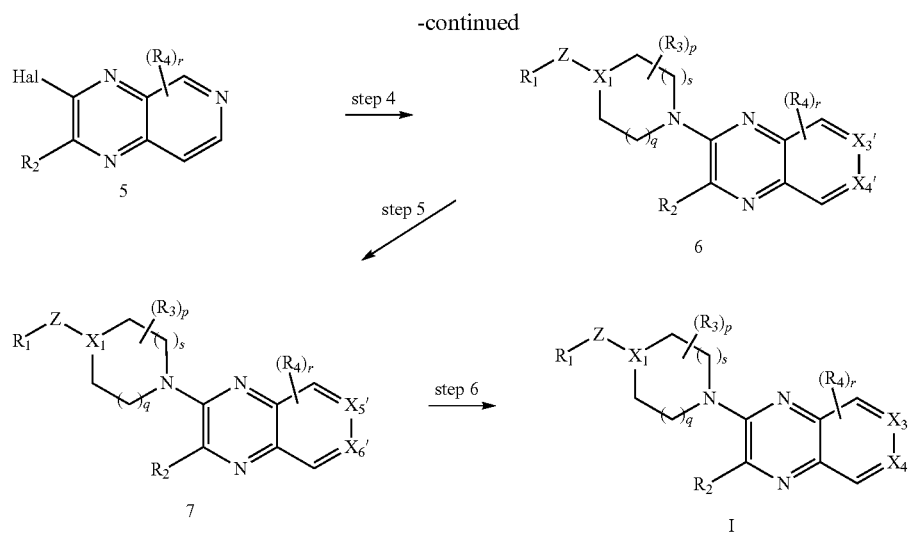

Scheme A depicts the formation of compounds in which $X_2$ is N.

In Scheme A, step 1, an appropriate compound of formula 1 is contacted with an appropriate compound of formula 2 to give a compound of formula 3. An appropriate compound of formula 1 is one in which Hal is a halogen and $R_4$ and r are as desired in the final compound of formula I. An appropriate compound of formula 2 is one in which $R_1$, Z, $R_3$, p, s, and q are as desired in the final compound of formula I or give rise to $R_1$, Z, and $R_3$ as desired in the final compound of formula I. Compounds of formula 2 are either commercially available or they can be readily prepared by methods well known in the art. For example, compounds of formula 2 where Z is oxygen can be prepared by Mitsunobu reaction between a piperidinol and an aryl alcohol.

The reaction is carried out in a suitable organic solvent like dioxane, n-butanol, dimethyl sulfoxide and the like with or without base such as diisopropylethylamine and triethylamine. The reaction is generally carried out at a temperature of from 0 to 80° C.

It is understood that a compound of formula 1 can also be treated with piperazine to give rise to compounds in which $X_1$ is N. The piperazine derivative can be further modified by reductive amination, alkylation, arylation, amidation, sulfonylation and the like to provide a compound of formula 3. Also the piperazine can be protected and elaborated as mentioned above after deprotection in a later step if desired.

In Scheme A, step 2, a compound of formula 3 is contacted with an appropriate compound of formula 4 to give a compound of formula 6 in which $X_{3'}$ and $X_{4'}$ give rise to $X_3$ and $X_4$ as desired in the final product of formula I. An appropriate compound of formula 4 is $HOR_5$ or $HNR_6R_7$ in which $R_5$ or $R_6$ and $R_7$ are as desired in the final compound of formula I.

Where the compound of formula 4 is an amine, $HNR_6R_7$, the reaction is carried out in a suitable organic solvent like dioxane, ethanol, tetrahydrofuran, dimethyl sulfoxide, N,N-dimethylformamide and the like, with or without a base such as sodium hydroxide, diisopropylethylamine or triethylamine. The reaction is generally carried out at temperature between 20 to 150° C.

Where the compound of formula 4 is an alcohol, $HOR_5$, the reaction is carried out in a suitable organic solvent like dioxane, tetrahydrofuran, dimethyl sulfoxide, N,N-dimethylformamide and the like, with a base such as sodium hydride, lithium hydride, potassium t-butoxide, and the like. The reaction is generally carried out at temperature between 0 to 150° C.

Alternatively, as depicted in Scheme A, step 3, using the methodology described above, an appropriate compound of formula 1 can be contacted with an appropriate compound of formula 2 to give a compound of formula 5. As depicted in Scheme A, step 4, a compound of formula 5 can be contacted with a compound of formula 2 to give a compound of formula 6.

In Scheme A, step 5, a compound of formula 6 is partially reduced to a compound of formula 7 in which the variables are defined above and $X_{5'}$ is selected from the group consisting of CH, $CR_4$ and NH and $X_{6'}$ is selected from the group consisting of CH, $CR_4$ and NH provided that one of $X_{5'}$ or $X_{6'}$ is NH and the other is CH or $CR_4$.

Such partial reductions are well known in the art. The reaction is carried out in a suitable organic solvent like dioxane, ethanol, methanol, isopropanol, tetrahydrofuran, and the like. The reaction is generally carried out using hydrogen and a catalyst, such as platinum or palladium catalyst.

In Scheme A, step 6, a compound of formula 7 is alkylated, cycloalkylated, sulfonated, acylated, or converted to a urea or carbamate using appropriate reagents that give $R_8$ being $C_{1-6}$ alkyl, $C_{1-6}$ haloalkyl, $C_{3-8}$ cycloalkyl, —S(O)$_2$—R$_9$, —(O)—R$_{10}$, —C(O)—N(R$_{11}$)(R$_{12}$), or —C(O)—OR$_{13}$ as desired in the final compound of formula I. Such transformation are readily carried out by reductive amination, alkylation, sulfonylation, amide forming reactions, urea forming reactions, and carbamylation conditions that are well known in the art.

It will be recognized by one of ordinary skill in the art that the steps in Scheme A may be varied to provide compounds of formula I. In particular, the order of the steps required to produce the compounds of formula I is dependent upon the particular compound being synthesized, the starting compound, and the relative lability of the substituted moieties. Other variations are possible and are readily understood by the skilled person.

An example of a variation of Scheme A is depicted in Scheme B below.

Scheme B
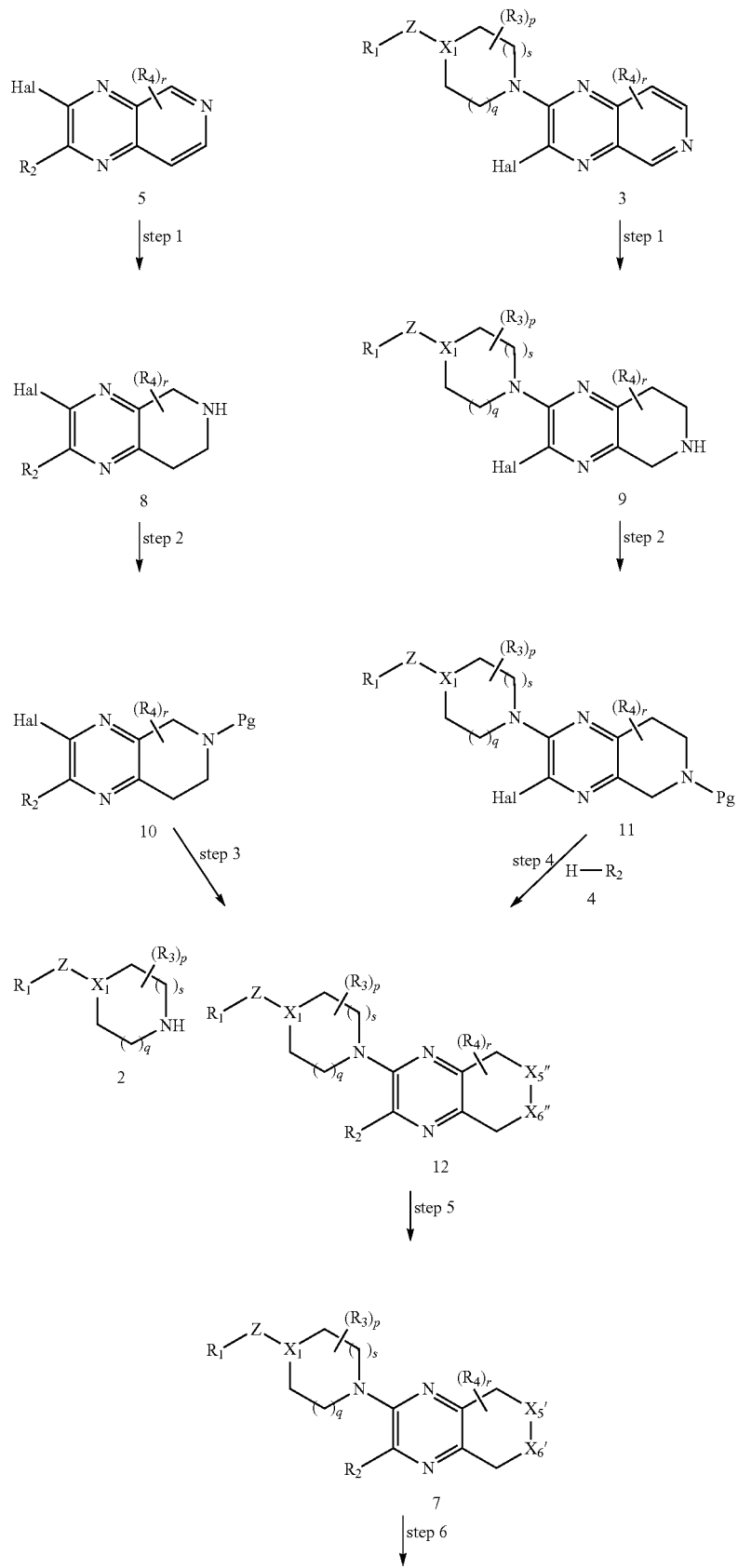

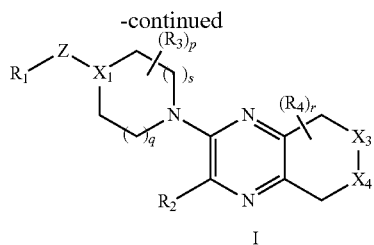

Scheme B depicts the formation of compounds in which X₂ is N.

In Scheme B, step 1, an appropriate compound of formula 5 or 3, as provided above, is partially reduced to a compound of formula 8 or 9, respectively. Such partial reductions are described above in Scheme A, step 5. In one embodiment the present invention provides compounds of formula 8 in which Hal is halogen and $R_2$, $R_4$, and r are as described for formula I. In another embodiment the present invention provides compounds of formula 9 in which Hal is halogen and $R_1$, Z, $R_3$, $R_4$, p, r, q, and s are s described for formula I.

In Scheme B, step 2, an appropriate compound of formula 8 or 9 is protected to give compounds of formulae 10 or 11, respectively, in which Pg is an amine protecting group. The selection, use, and removal of protecting groups are well known and appreciated as standard practice, for example T. W. Greene and P. G. M. Wuts in Protective Groups in Organic Chemistry (John Wiley and Sons, 1991). In one embodiment the present invention provides compounds of formula 10 in which Pg is —CH₂-(optionally substituted phenyl) and $R_2$, $R_4$, and r are as described for formula I. In another embodiment the present invention provides compounds of formula 11 in which Pg is —CH₂-(optionally substituted phenyl) and $R_1$, Z, $R_3$, $R_4$, p, r, q, and s are s described for formula I. In another embodiment of the embodiments of formulae 10 and 11 is one in which Pg is benzyl.

In Scheme B, step 3, a compound of formula 10 is contacted with an appropriate compound of formula 2, as described above, to give a compound of formula 12 in which $X_{5''}$ is a protected amine and $X_{6''}$ is CH or CR₄. The reaction is carried out as described in Scheme A, step 1.

In Scheme B, step 4, a compound of formula 11 is contacted with an appropriate compound of formula 4 to give a compound of formula 12 in which $X_{5''}$ is CH or CR₄ and $X_{6''}$ is a protected amine. An appropriate compound of formula 4 as described above. The reaction is carried out as described in Scheme A, step 2.

In Scheme B, step 5, a compound of formula 12 is deprotected to give a compound of formula 7 as described above.

In Scheme B, step 6, a compound of formula 7 is alkylated, cycloalkylated, sulfonated, acylated, or converted to a urea or carbamate using appropriate reagents that give $R_8$ being $C_{1-6}$ alkyl, $C_{1-6}$ haloalkyl, $C_{3-8}$ cycloalkyl, —S(O)₂—R₉, —(O)—R₁₀, —C(O)—N(R₁₁)(R₁₂), or —C(O)—OR₁₃ as desired in the final compound of formula I as described in Scheme A, step 6, above.

Scheme C

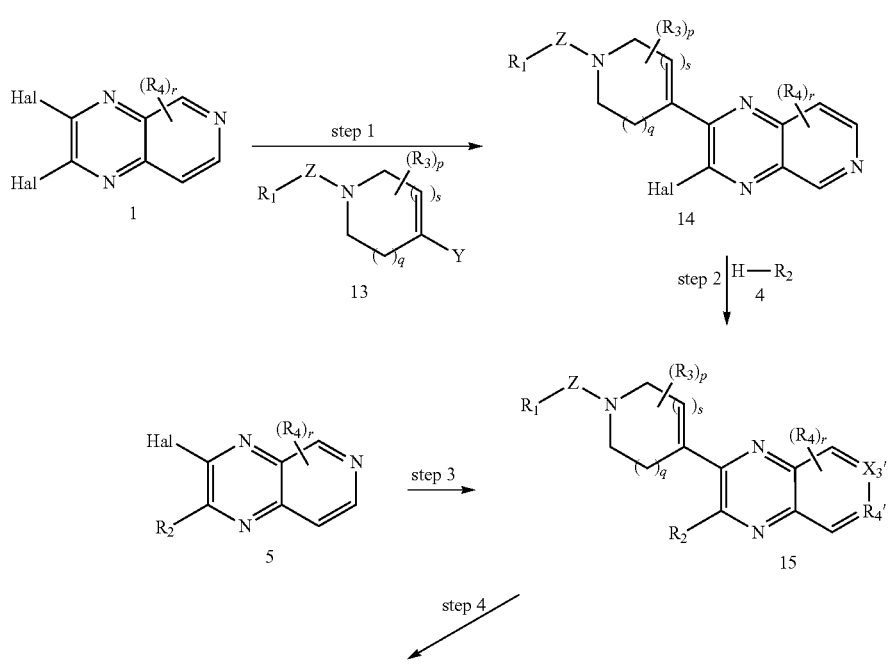

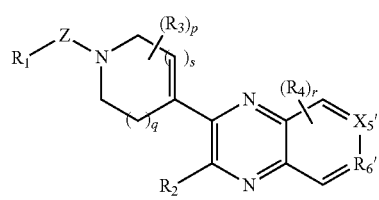
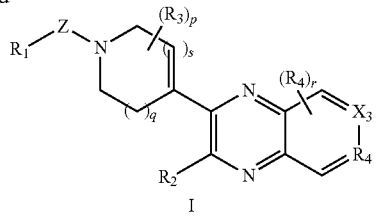

Scheme C depicts the formation of compounds in which $X_2$ is CH.

In Scheme C, step 1, an appropriate compound of formula 1, as described above, is contacted with an appropriate compound of formula 13 to give a compound of formula 9. An appropriate compound of formula 13 is one in which $R_1$, Z, $R_3$, p, s, and q are as desired in the final compound of formula I or give rise to $R_1$, Z, and $R_3$ as desired in the final compound of formula I and Y a boronic acid or boronic ester. It is also understood that the group depicted as $R_1$—Z— can be replaced by an appropriate protecting group, such a methyl, benzyl, t-BOC, or Cbz, subsequent removal of the protecting group and installation of $R_1$—Z— as desired in the final product of formula I.

Such reactions are generally known as a Suzuki reaction and are well known in the art. While a Suzuki reaction is depicted in Scheme C it is understood that other carbon-carbon bond forming coupling reactions can be used with compounds of formula 13 having Y other than boronic acid or esters to produce compounds of formula I.

In Scheme C, step 2, a compound of formula 14 is contacted with an appropriate compound of formula 4 to give a compound of formula 15. An appropriate compound of formula 4 and general reaction conditions are described above in Scheme A, step 2.

Alternately, Scheme C, step 3, depicts Suzuki reaction with an appropriate compound of formula 13 and an appropriate compound of formula 5 as described above to give a compound of formula 15.

In Scheme C, step 4, a compound of formula 15 is reduced to a compound of formula 11 in which the variables are defined above and $X_{5'}$ is selected from the group consisting of CH, $CR_4$ and NH and $X_{6'}$ is selected from the group consisting of CH, $CR_4$ and NH provided that one of $X_{5'}$ or $X_{6'}$ is NH and the other is CH or $CR_4$. The conditions are similar to those described above for Scheme A, step 7.

In Scheme C, step 5, a compound of formula 7 is alkylated, cycloalkylated, sulfonated, acylated, or converted to a urea or carbamate using appropriate reagents that give $R_8$ being $C_{1-6}$ alkyl, $C_{1-6}$ haloalkyl, $C_{3-8}$ cycloalkyl, —S(O)$_2$—R$_9$, —(O)—R$_{10}$, —C(O)—N(R$_{11}$)(R$_{12}$), or —C(O)—OR$_{13}$ as desired in the final compound of formula I. Such transformations are readily carried out by reductive amination, alkylation, sulfonylation, amide forming reactions, amidation, and carbamylation conditions that are well known in the art.

It will be recognized by one of ordinary skill in the art that the steps in Scheme C may be varied to provide compounds of formula I. In particular, the order of the steps required to produce the compounds of formula I is dependent upon the particular compound being synthesized, the starting compound, and the relative lability of the substituted moieties. For example, a compound of formula 9 or 5 can undergo step 4 and the NH of $X_{3'}$ or $X_{4'}$ can be protected, followed being contacted with a compound of formula 13 or 4 to give a compound of formula 11 which as depicted above can be elaborated to a compound of formula I. Alternately, the double bond of the ring bearing $R_1$—Z— may be reduced separately from the partial reduction of the ring ultimately bearing $X_3$ and $X_4$. Other variations are possible and are readily understood by the skilled person.

It is also understood that some compounds of formula I may be elaborated to other compounds of formula I, in an additional steps not shown. Compounds of formula I may be elaborated in a variety of ways. Such reactions include hydrolysis, oxidation, reduction, alkylation, amidations, and the like. Also, in an optional step, not shown in the schemes above, the compounds of formula I can be converted to pharmaceutically acceptable salts by methods well known and appreciated in the art.

The following examples are intended to be illustrative and non-limiting, and represent specific embodiments of the present invention.

Proton nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). Other abbreviations have their usual meaning unless otherwise indicated. The mass spectra, unless otherwise indicated, were recorded using either electrospray ionization (ESI) or atmospheric pressure chemical ionization.

The examples below were carried out in appropriate vessels and were typically stirred. Where indicated, products of certain preparations and examples are purified by HPLC. Where indicated products of the preparations and examples were purified by HPLC.

HPLC Method A: Pump: Shimadzu LC-8A; UV/Vis: SPD-20A; Software: LCSolution. A Phenomenex Gemini® C18, 5 μm, ID 30×100 mm column was used and eluted with gradients of ACN (containing 0.035% TFA) and water (containing 0.005% TFA). A 10% to 100% ACN gradient was used unless otherwise indicated.

HPLC Method B: Pump: Waters 2525 or 2545; MS: ZQ; Software: MassLynx. A Xbridge™ C18, 5 μm, ID 30×75 mm column was used and eluted with gradients of ACN (containing 0.035% TFA) and water (containing 0.005% TFA).

After isolation by chromatography, the solvent is removed and the product is obtained by evaporating product containing fractions (e.g., GeneVac™), rotary evaporator, evacuated flask, lyophilization, etc.

The abbreviations used throughout have their conventional meanings unless indicated otherwise. For example, the following abbreviations are used: ACN (acetonitrile); aq (aqueous); Boc or t-BOC (tert-butoxycarbonyl); Cbz (carbobenzyloxy); DCM (dichloromethane); DMSO (dimethyl sulfoxide); TFA (trifluoroacetic acid); HOAc (acetic acid), MeOH (methanol), PE (petroleum ether), EA or EtOAc (ethyl acetate) and the like.

Preparation 1
(5-chloro-2-fluorophenyl)(piperidin-4-yl)methanone

A solution of 2-bromo-4-chloro-1-fluorobenzene (175 µL, 1.377 mmol) in THF (4.59 mL) at −78° C. was treated with n-BµLi (2.6 M, 741 µL, 1.928 mmol) and the reaction mixture was stirred for 30 min. To this was added tert-butyl 4-(methoxy(methyl)carbamoyl)piperidine-1-carboxylate (250 mg, 0.918 mmol) in one portion. The cooling bath was removed and the resulting reaction mixture was allowed to warm to rt and stirred for 1.5 h. Purification by automated flash silica gel chromatography using 10% EtOAc in hexanes afforded tert-butyl 4-(5-chloro-2-fluorobenzoyl)piperidine-1-carboxylate (287.9 mg, 92%) as a yellow oil. ESI-MS m/z [M+Na]$^+$ 364.20.

A solution of tert-butyl 4-(5-chloro-2-fluorobenzoyl)piperidine-1-carboxylate (287.9 mg, 0.843 mmol) in dioxane (2.41 mL) was treated with HCl (2.11 mL, 8.43 mmol) at rt and the resulting reaction mixture was stirred overnight. The reaction mixture was diluted with hexanes and filtered by suction to afford (5-chloro-2-fluorophenyl)(piperidin-4-yl)methanone as its HCl salt (146 mg, 62.3%) as a yellow solid. ESI-MS m/z [M+H]$^+$ 242.20.

Preparation 2 4-(2,4-difluorophenoxy)piperidine

To a solution of 2,4-difluorophenol (10 g, 77 mmol), PPh$_3$ (30.2 g, 115 mmol) and tert-butyl 4-hydroxypiperidine-1-carboxylate (30.9 g, 154 mmol) in THF (400 mL) was added DEAD (18.3 mL, 115 mmol) at 0° C. dropwise. After the addition was completed, the resulting mixture was allowed to stir at 40° C. for 16 h. The mixture was poured into water and extracted with EtOAc (3×400 mL). The combined organic layers were dried over Na$_2$SO$_4$, filtered and concentrated to give the crude product. Purification by flash silica gel chromatography, eluting with 80:1 PE:EtOAc, gave tert-butyl 4-(2,4-difluorophenoxy)piperidine-1-carboxylate as an oil (20 g, 83%).

A solution of tert-butyl 4-(2,4-difluorophenoxy)piperidine-1-carboxylate (20 g, 63.8 mmol) in 4:1 HCl/EtOAc (250 mL) was stirred at 25° C. for 1 h. The mixture was concentrated to give the title compound, as its HCl salt, as a white solid (15.4 g, 97%). $^1$H NMR (400 MHz, DMSO-d6) δ ppm 1.84 (m, 2H), 2.08 (m, 2H), 3.05 (m, 2H), 3.20 (m, 2H), 4.57 (m, 1H), 7.04 (m, 1H), 7.31 (m, 2H), 8.95 (br d, 2H).

Preparation 3
3-fluoro-4-(piperidin-4-yloxy)benzonitrile

A solution of 3,4-difluorobenzonitrile (28 g, 201 mmol) and tert-butyl 4-hydroxypiperidine-1-carboxylate (40.5 g, 201 mmol) in THF (500 mL) was treated with sodium hydride (4 g, 100 mmoL) and stirred at 25° C. for 16 h. The reaction mixture was washed with water, extracted with EtOAc, and the crude product purified by flash silica gel chromatography gave tert-butyl 4-(4-cyano-2-fluorophenoxy)piperidine-1-carboxylate (25 g, 39%).

A solution of tert-butyl 4-(4-cyano-2-fluorophenoxy)piperidine-1-carboxylate (42 g, 131 mmol) dissolved in 4:1 HCl/EtOAc (100 mL) was stirred for 5 h. The mixture was concentrated to give the title compound as its HCl salt (12 g, 36%). $^1$H NMR (400 MHz, DMSO-d6) δ ppm 1.89 (m, 2H), 2.14 (m, 2H); 3.08 (m, 2H), 3.21 (m, 2H), 4.86 (m, 1H), 7.48 (t, J=8.4 Hz, 1H), 7.70 (d, J=8.4 Hz, 1H), 7.89 (m, 1H); ESI-MS m/z [M+H]+ 220.7.

Preparation 4 6
4-((2,4-difluorophenyl)fluoromethyl)piperidine

To a 0° C. solution of tert-butyl 4-(2,4-difluorobenzoyl)piperidine-1-carboxylate (1.28 g, 3.93 mmol) in MeOH (15.7 mL) was added NaBH$_4$ (0.372 g, 9.84 mmol). The ice bath was removed and the reaction mixture stirred for 2 h at room temperature then was quenched with saturated aqueous NH$_4$Cl. The organic layer was extracted with EtOAc, washed with H$_2$O and dried over MgSO$_4$. The solvent was removed under reduced pressure gave tert-butyl 4-((2,4-difluorophenyl)(hydroxy)methyl)piperidine-1-carboxylate as a white hygroscopic solid.

To a −78° C. solution of tert-butyl 4-((2,4-difluorophenyl) (hydroxy)methyl)piperidine-1-carboxylate (200 mg, 0.611 mmol) in DCM (3.055 mL) was added DAST (242 µL, 1.833 mmol). The mixture was stirred at −78° C. for 30 min, then quenched with MeOH. Flash silica gel chromatography using a gradient of 0% to 100% EtOAc in hexanes gave tert-butyl 4-((2,4-difluorophenyl)fluoromethyl)piperidine-1-carboxylate as a colorless oil.

To a solution of racemic tert-butyl 4-((2,4-difluorophenyl) fluoromethyl)piperidine-1-carboxylate (148 mg, 0.449 mmol) in dioxane (1.50 mL) was added HCl (4 M in dioxane, 337 µL, 1.348 mmol). The mixture was heated at 45° C. for 16 h then concentrated in vacuo to give the title compound as its HCl salt (109 mg, 91%) as a white solid.

Preparation 5 (R)-4-((2,4-difluorophenyl)fluoromethyl)piperidine tert-Butyl 4-((2,4-difluorophenyl) fluoromethyl)piperidine-1-carboxylate as a Colorless Oil tert-Butyl 4-((2,4-difluorophenyl)fluoromethyl)piperidine-1-carboxylate was subjected to chiral SFC separation to give (R)-tert-butyl 4-((2,4-difluorophenyl)fluoromethyl)piperidine-1-carboxylate.

(R)-tert-butyl 4-((2,4-difluorophenyl)fluoromethyl)piperidine-1-carboxylate (2.8 g, 8.50 mmol) was dissolved in EtOAc (20 mL) and HCl (4 M in EtOAc, 21 mL) was added. The reaction mixture was stirred at 23° C. for 2 h. Evaporation of the solvent gave the title compound as its HCl salt (2.1 g, 93%). ESI-MS m/z [M+H]$^+$ 229.9.

Preparation 6
(S)-4-((2,4-difluorophenyl)fluoromethyl)piperidine tert-Butyl 4-((2,4-difluorophenyl)fluoromethyl)piperidine-1-carboxylate as was subjected to chiral SFC separation to give (R)-tert-butyl 4-((2,4-difluorophenyl)fluoromethyl)piperidine-1-carboxylate.

The HCl salt of the title compound was prepared in similar fashion to Preparation 5a, using (S)-tert-butyl 4-((2, 4-difluorophenyl)fluoromethyl)piperidine-1-carboxylate. ESI-MS m/z [M+H]$^+$ 229.9.

Preparation 7 4-((2-fluorophenyl)sulfonyl)piperidine

A mixture of 2-fluorobenzenethiol (0.764 mL, 7.15 mmol), tert-butyl 4-((methylsulfonyl)oxy)piperidine-1-carboxylate (1.816 g, 6.5 mmol), and K$_2$CO$_3$ (1.348 g, 9.75 mmol) in ACN (16.25 mL) was heated at 80° C. overnight.

The reaction mixture was poured into water and extracted twice with EtOAc. The combined organics were dried over Na$_2$SO$_4$, filtered, and concentrated under reduced pressure gave tert-butyl 4-((2-fluorophenyl)thio)piperidine-1-carboxylate as a yellow oil (1.98 g, 98%), which was carried forward without purification.

A solution of tert-butyl 4-((2-fluorophenyl)thio)piperidine-1-carboxylate (1.98 g, 6.36 mmol) in THF (54.5 mL) and MeOH (18.2 mL) at 0° C. was treated with a cold solution of Oxone® (9.77 g, 15.9 mmol) in water (54.5 mL). The reaction mixture was stirred for 5 h, gradually warming to room temperature. The reaction mixture was poured into water and extracted twice with EtOAc. The combined organics were washed with water and then saturated aqueous NaCl, dried over Na$_2$SO$_4$, filtered, and concentrated under reduced pressure. The residue was purified by flash silica gel chromatography using a gradient of 10% to 50% EtOAc with 0.1% triethylamine in heptanes gave tert-butyl 4-((2-fluorophenyl)sulfonyl)piperidine-1-carboxylate as a pale yellow oil (1.31 g, 60%).

A solution of tert-butyl 4-((2-fluorophenyl)sulfonyl)piperidine-1-carboxylate (1.31 g, 3.82 mmol) in dioxane (12.7 mL) at room temperature was treated with 4M HCl in dioxane (9.55 ml, 38.2 mmol). The reaction mixture was allowed to stir at room temperature overnight. The reaction mixture was concentrated under reduced pressure. The resulting white solid was triturated with hexanes, filtered, collected, and lyophilized overnight to give the title compound, as its HCl salt, as a white solid (815.1 mg, 76%). ESI-MS m/z [M+H]$^+$ 243.95.

Preparation 8
4-((2-fluoro-4-methoxyphenyl)sulfonyl)piperidine

A mixture of 2,4-difluorobenzenethiol (0.810 mL, 7.15 mmol), tert-butyl 4-((methylsulfonyl)oxy)piperidine-1-carboxylate (1.816 g, 6.5 mmol), and K$_2$CO$_3$ (1.348 g, 9.75 mmol) in ACN (16.25 mL) was heated at 80° C. overnight. The reaction mixture was poured into water and extracted twice with EtOAc. The organic layer was dried over Na$_2$SO$_4$, filtered, and concentrated under reduced pressure to afford tert-butyl 4-((2,4-difluorophenyl)thio)piperidine-1-carboxylate (2.141 g) as a yellow oil, which was carried forward without purification.

A solution of tert-butyl 4-((2,4-difluorophenyl)thio)piperidine-1-carboxylate (2.141 g, 6.50 mmol) in THF/MeOH (3:1, 74 mL) at 0° C. was treated with a cold solution of Oxone® (9.99 g, 16.25 mmol) in water (56 mL). The reaction mixture was allowed to stir overnight, gradually warming to room temperature. The reaction mixture was poured into water and extracted twice with EtOAc. The combined organics were washed with water and then saturated aqueous NaCl, dried over Na$_2$SO$_4$, filtered, and concentrated under reduced pressure. The residue was purified by flash silica gel chromatography using a gradient of 10% to 40% EtOAc with 0.1% triethylamine in heptanes gave tert-butyl 4-((2,4-difluorophenyl)sulfonyl)piperidine-1-carboxylate (1.32 g, 56%) as a white solid. ESI-MS m/z [M+Na]$^+$ 383.80.

To a suspension of tert-butyl 4-((2,4-difluorophenyl)sulfonyl)piperidine-1-carboxylate (50 mg, 0.138 mmol) in MeOH (461 µL) was added sodium methoxide (25.6 µL, 0.138 mmol, 5.4 M in MeOH) dropwise. The reaction mixture was allowed to stir at 45° C. for 20 min then concentrated in vacuo. Boc deprotection was carried out by addition of HCl (138 µL, 0.553 mmol, 4 M in dioxane) to the crude reaction mixture in 300 µL dioxane. Stirring at 50° C. for 24 h followed by concentration in vacuo yielded the title compound as its HCl salt (57 mg) as a white solid (10:1 regioisomeric mixture). ESI-MS m/z [M+H]$^+$ 274.00.

Preparation 9 4-((3-fluorophenyl)sulfonyl)piperidine

A mixture of tert-butyl 4-((methylsulfonyl)oxy)piperidine-1-carboxylate (1.0 g, 3.58 mmol), K$_2$CO$_3$ (0.742 g, 5.37 mmol), and 3-fluorobenzenethiol (0.363 mL, 4.30 mmol) in ACN (7.5 mL) was stirred at 23° C. for 5 min. The reaction mixture was stirred at 80° C. for 17 h, cooled to 23° C. and partitioned between EtOAc and water. The layers were separated, the organic phase was washed with brine, dried over Na$_2$SO$_4$, filtered, rinsed with EtOAc, and dried in vacuo gave tert-butyl 4-((3-fluorophenyl)thio)piperidine-1-carboxylate (1.115 g, 100%) as a yellow oil. ESI-MS m/z [M+H]$^+$ 255.9.

A mixture of basic alumina (3.0 g, 29.4 mmol) in water (0.6 mL) was stirred at 23° C. for 5 min. Next, ACN (12 mL) was added followed by a solution of tert-butyl 4-((3-fluorophenyl)thio)piperidine-1-carboxylate (1.115 g, 3.58 mmol) in CHCl$_3$ (8 mL). Next, Oxone® (6.60 g, 10.74 mmol) was added and the reaction mixture was stirred at 60° C. for 19 h. The reaction mixture was cooled to 23° C., filtered, rinsed with CHCl$_3$, and the filtrate was washed with water (10 mL). The organic layer was dried over Na$_2$SO$_4$, filtered, rinsed with CHCl$_3$, and dried in vacuo. The crude residue was dissolved in toluene (5 mL) and purified via medium pressure chromatography using a gradient of 10% to 100% EtOAc with 0.1% triethylamine in heptane on a 80 g silica gel column (Single Step™) gave tert-butyl 4-((3-fluorophenyl)sulfonyl)piperidine-1-carboxylate (0.769 g, 62.5%) as a white solid. ESI-MS m/z [M+Na]$^+$ 365.9.

To a solution of tert-butyl 4-((3-fluorophenyl)sulfonyl)piperidine-1-carboxylate (756 mg, 2.201 mmol) in dioxane (5.0 mL) was added HCl (4 M in dioxane, 5.50 mL, 22.01 mmol) at 23° C. The reaction was stirred at 23° C. for 21 h to furnish a white suspension. The resulting solid was filtered, rinsed with dioxane and dried in vacuo to give the title compound as its HCl salt (582.6 mg, 95%) as a white solid. ESI-MS m/z [M+H]$^+$ 243.9.

Preparation 10
4-((3-methoxyphenyl)sulfonyl)piperidine

The title compound as its HCl salt was prepared in a similar manner to Preparation 11, with the exception that additional chloroform was used in place of ACN in the second step. ESI-MS m/z [M+H]$^+$ 255.9.

Preparation 12
4-((4-fluorophenyl)sulfonyl)piperidine

A mixture of tert-butyl 4-((methylsulfonyl)oxy)piperidine-1-carboxylate (1.42 g, 5.08 mmol), 4-fluorobenzenethiol (0.663 ml, 6.10 mmol) and K$_2$CO$_3$ (1.054 g, 7.62 mmol) in ACN (12.71 mL) was stirred at 85° C. overnight. The reaction mixture was filtered by suction and the solvent removed gave tert-butyl 4-((4-fluorophenyl)thio)piperidine-1-carboxylate (1.5 g, 95%) as a white solid.

A solution of tert-butyl 4-((4-fluorophenyl)thio)piperidine-1-carboxylate (1.5 g) in water (16.06 mL) and MeOH (16.06 mL) was treated with Oxone® (5.92 g, 9.63 mmol) at room temperature and the resulting reaction mixture was stirred for 6 h. The solution was filtered by suction and the solvent removed gave tert-butyl 4-((4-fluorophenyl)sulfonyl)piperidine-1-carboxylate (1.6 g, 4.66 mmol, 97% yield) as a white solid.

A solution of tert-butyl 4-((4-fluorophenyl)sulfonyl)piperidine-1-carboxylate (32.7 mg, 0.095 mmol) in dioxane (238 µL) at room temperature was treated with HCl (4 M in dioxane, 190 µL, 0.762 mmol) and the resulting reaction mixture was stirred for 4 h. The solvent was removed to give the title compound as its HCl salt (25 mg, 94%) as a white solid. ESI-MS m/z [M+H]$^+$ 243.95.

Preparation 13 1-(2,4-difluorobenzyl)piperazine

A mixture of piperazine (26.5 g, 308 mmol) in THF (350 mL) was heated to 70° C. and 1-(chloromethyl)-2,4-difluorobenzene (5 g, 30.8 mmol) was added. The suspension was heated at 70° C. overnight. The solid (piperazine) was filtered off, and the solvent was removed under reduced pressure. The residue was partitioned between EtOAc and water. The organic layer was dried and concentrated to give the title compound (6 g, 92%). ESI-MS m/z [M+H]$^+$ 213.04.

Preparation 14
4-(2-fluoro-4-methoxyphenoxy)piperidine

A solution of tert-butyl 4-hydroxypiperidine-1-carboxylate (2.496 g, 12.03 mmol) in THF (33.4 mL) at room temperature was treated with 2-fluoro-4-methoxyphenol (1.181 mL, 10.03 mmol) and triphenylphosphine (3.16 g, 12.03 mmol). The reaction mixture was cooled to 0° C. and DEAD (40 wt % in toluene, 5.95 mL, 15.04 mmol) was added dropwise via syringe. The resulting reaction mixture was stirred at 65° C. for 5 h, then at room temperature overnight. Flash silica gel chromatography using a gradient of 10% to 100% EtOAc in hexanes gave tert-butyl 4-(2-fluoro-4-methoxyphenoxy)piperidine-1-carboxylate (2.78 g, 85%) as a light yellow oil. ESI-MS m/z [M+Na]$^+$ 348.2.

A solution of tert-butyl 4-(2-fluoro-4-methoxyphenoxy)piperidine-1-carboxylate (2.78 g, 8.54 mmol) in dioxane (21.36 mL) was treated with HCl (4 M in dioxane, 21.36 mL, 85 mmol) at room temperature and the resulting reaction mixture stirred overnight. Flash silica gel chromatography using a gradient of 5% to 30% MeOH in DCM gave the title compound as its HCl salt (1.7 g, 76%) as a white solid. ESI-MS m/z [M+H]$^+$ 226.20.

Preparation 15 3-chloro-2-(4-(2,4-difluorophenoxy)piperidin-1-yl)pyrido[3,4-b]pyrazine A solution of 2,3-dichloropyrido[3,4-b]pyrazine (492 mg, 2.460 mmol) in DCM (5 mL) at 0° C. was treated with 4-(2,4-difluorophenoxy)piperidine hydrochloride (676 mg, 2.71 mmol) and DIPEA (1.29 mL, 7.38 mmol). The reaction mixture was allowed to stir overnight, gradually warming to room temperature. The reaction mixture was quenched with the addition of saturated aqueous NH$_4$Cl and was extracted with DCM. The organic layer was dried over Na$_2$SO$_4$, filtered, and concentrated under reduced pressure. The residue was purified by flash silica gel chromatography using a gradient of 20% to 60% EtOAc in heptanes to give the title compound as a pale yellow solid (736.2 mg, 79%). ESI-MS m/z [M+H]$^+$ 377.4.

Preparation 16 4-((1-(3-chloropyrido[3,4-b]pyrazin-2-yl)piperidin-4-yl)oxy)-3-fluorobenzonitrile To a solution of 2,3-dichloropyrido[3,4-b]pyrazine (1.00 g, 5.00 mmol) in DCM (10.0 mL) at 0° C. was added DIPEA (2.62 mL, 15.00 mmol) and 3-fluoro-4-(piperidin-4-yloxy)benzonitrile hydrochloride (1.283 g, 5.00 mmol). The reaction mixture was stirred for 30 min, warming gradually to room temperature. The reaction mixture was treated with saturated aqueous NH$_4$Cl. The organic layer containing yellow solid was collected and concentrated under reduced pressure. The solid was filtered, washing with water, and was lyophilized overnight to give the title compound as a yellow solid (1.325 g, 69%). ESI-MS m/z [M+H]$^+$ 384.3.

Preparation 17 (R)-3-chloro-2-(4-((2,4-difluorophenyl)fluoromethyl)piperidin-1-yl)pyrido[3,4-b]pyrazine The title compound was prepared in a manner similar to Preparation 18 using (R)-4-((2,4-difluorophenyl)fluoromethyl)piperidine hydrochloride in place of 4-(2,4-difluorophenoxy)piperidine hydrochloride. ESI-MS m/z [M+H]$^+$ 393.4.

Preparation 19 (S)-3-chloro-2-(4-((2,4-difluorophenyl)fluoromethyl)piperidin-1-yl)pyrido[3,4-b]pyrazine The title compound was prepared in a manner similar to Preparation 20 using (S)-4-((2,4-difluorophenyl)fluoromethyl)piperidine hydrochloride in place of 4-(2,4-difluorophenoxy)piperidine hydrochloride. ESI-MS m/z [M+H]$^+$ 393.4.

Preparation 21 3-chloro-2-(4-(2,4-difluorobenzyl)piperazin-1-yl)pyrido[3,4-b]pyrazine To a mixture of 2,3-dichloropyrido[3,4-b]pyrazine (8 g, 40.0 mmol) and 1-(2,4-difluorobenzyl)piperazine (8.49 g, 40.0 mmol) in DCM (100 mL) was added triethylamine (16.72 mL, 120 mmol) at room temperature. Then the mixture was stirred at room temperature for 0.5 h. The reaction mixture was diluted with 30 mL of DCM, washed with brine twice, dried over anhydrous Na$_2$SO$_4$ and concentrated. The residue was purified by silica gel chromatography, eluting with a gradient of 50:1 to 5:1 PE:EtOAc to give the title compound (12 g, 80%). ESI-MS m/z [M+H]$^+$ 376.0.

Preparation 22 3-chloro-2-(4-(2-fluoro-4-methoxyphenoxy)piperidin-1-yl)pyrido[3,4-b]pyrazine A mixture of 4-(2-fluoro-4-methoxyphenoxy)piperidine hydrochloride (144 mg, 0.550 mmol), 2,3-dichloropyrido[3,4-b]pyrazine (100 mg, 0.500 mmol) and DIPEA (260 µL, 1.500 mmol) in DCM (1.0 mL) was stirred at room temperature for 30 min. The mixture was then partitioned between EtOAc and saturated aqueous NH$_4$Cl. The organic layer was washed with brine, dried over Na$_2$SO$_4$, filtered and evaporated. The residue was dissolved in EtOAc and filtered through a silica pad. The filtrate was concentrated to afford the crude title compound (200.7 mg, 100%) as a yellow oil, which was used without further purification. ESI-MS m/z [M+H]$^+$ 389.2.

Preparation 23 tert-butyl 4-(3-chloropyrido[3,4-b]pyrazin-2-yl)piperazine-1-carboxylate Combine 2,3-dichloropyrido[3,4-b]pyrazine (2.0 g, 10.00 mmol), tert-butyl piperazine-1-carboxylate (1.955 g, 10.50 mmol) and DCM (25 mL) to furnish a yellow-orange suspension. Next, DIPEA (5.22 mL, 30.0 mmol) was added to the flask over 1 min at 0° C. The mixture was stirred at 0° C. for 2 h under nitrogen, warmed slowly to 23° C., and stirred for 17 h. The reaction mixture was partitioned between saturated aqueous NH$_4$Cl (20 mL) and EtOAc (80 mL) to furnish two layers. The layers were separated, and the aqueous phase was washed with EtOAc (80 mL). The organic extracts were combined, washed with brine (10 mL), dried over Na$_2$SO$_4$, filtered, rinsed with EtOAc, and dried in vacuo to give the title compound (3.35 g, 96%) as an orange semisolid. $^1$H NMR (500 MHz, DMSO-d$_6$) δ ppm 1.44 (s, 9H), 3.51-3.58 (m, 4H), 3.62-3.68 (m, 4H), 7.67 (d, J=1.0 Hz, 1H), 8.66 (d, J=5.9 Hz, 1H), 9.15 (d, J=1.0 Hz, 1H); ESI-MS m/z [M+H]$^+$ 350.5.

Preparation 24 tert-butyl 4-(3-(isopropylamino) pyrido[3,4-b]pyrazin-2-yl)piperazine-1-carboxylate To a flask charged with tert-butyl 4-(3-chloropyrido[3,4-b]pyrazin-2-yl)piperazine-1-carboxylate (3.35 g, 9.58 mmol) and potassium fluoride (0.723 g, 12.45 mmol) in DMSO (25 mL) was added DIPEA (3.34 mL, 19.15 mmol) and propan-2-amine (2.468 mL, 28.7 mmol) at 23° C. The reaction was stirred at 23° C. for 22 hr and diluted with water (100 mL) to furnish an orange, oily sludge. The mixture was cooled to 0° C. to furnish a yellow-orange suspension. The resulting solid was filtered, rinsed with water, and dried in vacuo. The crude material was dissolved in EtOAc, adsorbed on NH silica gel (11 g), and purified via medium pressure chromatography using a gradient of 10% to 100% EtOAc in heptane on an NH 60 μM size 400 column (Shoko Scientific Purif-Pack™) to give the title compound (2.105 g, 59.0%) as a light yellow solid. $^1$H NMR (500 MHz, DMSO-d$_6$) δ ppm 1.26 (d, J=6.8 Hz, 6H), 1.43 (s, 9H), 3.30-3.33 (m, 4H), 3.52-3.60 (m, 4H), 4.32-4.42 (m, 1H), 6.54 (d, J=7.8 Hz, 1H), 7.43-7.46 (m, 1H), 8.29 (d, J=5.4 Hz, 1H), 8.78 (s, 1H); ESI-MS m/z [M+H]$^+$ 373.0.

Preparation 25 (1s,3s)-3-((2-(4-(2,4-difluorobenzyl) piperazin-1-yl)pyrido[3,4-b]pyrazin-3-yl)amino) cyclobutan-1-ol Combined 3-chloro-2-(4-(2,4-difluorobenzyl)piperazin-1-yl)pyrido[3,4-b]pyrazine (0.75 g, 1.996 mmol), (1s,3s)-3-aminocyclobutanol hydrochloride (0.740 g, 5.99 mmol), and potassium fluoride (0.151 g, 2.59 mmol) in DMSO (7.5 mL) and added DIPEA (1.738 mL, 9.98 mmol) at 23° C. The reaction mixture was stirred at 23° C. for 5 days and diluted with water (30 mL) to furnish a yellow-orange suspension. The resulting solid was filtered, rinsed with water, and dried in vacuo to give the title compound (690 mg, 81%) as a yellow solid. $^1$H NMR (500 MHz, DMSO-d$_6$) δ ppm 1.92-2.02 (m, 2H), 2.61-2.70 (m, 6H), 3.38 (br s, 4H), 3.60 (s, 2H), 3.90-3.98 (m, 1H), 3.99-4.07 (m, 1H), 5.08 (d, J=5.9 Hz, 1H), 6.93-6.98 (m, 1H), 7.09 (td, J=8.4, 2.7 Hz, 1H), 7.20-7.25 (m, 1H), 7.41-7.45 (m, 1H), 7.47-7.53 (m, 1H), 8.28 (d, J=5.9 Hz, 1H), 8.75 (s, 1H); ESI-MS m/z [M+H]$^+$ 427.0.

Preparation 26 (1s,3s)-3-((2-(4-(2,4-difluorophenoxy)piperidin-1-yl)pyrido[3,4-b]pyrazin-3-yl) amino)cyclobutan-1-ol Combined 3-chloro-2-(4-(2,4-difluorophenoxy)piperidin-1-yl)pyrido[3,4-b]pyrazine (0.75 g, 1.991 mmol), (1s,3s)-3-aminocyclobutanol hydrochloride (0.738 g, 5.97 mmol), and potassium fluoride (0.150 g, 2.59 mmol) in DMSO (7.5 mL) and added DIPEA (1.734 mL, 9.95 mmol) at 23° C. The reaction mixture was stirred at 23° C. for 5 days and diluted with water (30 mL) to furnish a yellow-orange suspension. The resulting solid was filtered, rinsed with water, and dried in vacuo to give the title compound (784 mg, 92%) as a yellow-orange solid. $^1$H NMR (500 MHz, DMSO-d$_6$) δ ppm 1.87-2.03 (m, 4H), 2.07-2.18 (m, 2H), 2.61-2.73 (m, 2H), 3.19-3.29 (m, 2H), 3.63-3.73 (m, 2H), 3.89-3.99 (m, 1H), 3.99-4.10 (m, 1H), 4.62 (tt, J=7.9, 3.8 Hz, 1H), 5.08 (d, J=5.9 Hz, 1H), 6.99-7.10 (m, 2H), 7.26-7.38 (m, 2H), 7.44 (d, J=5.4 Hz, 1H), 8.28 (d, J=5.4 Hz, 1H), 8.76 (s, 1H); ESI-MS m/z [M+H]$^+$ 427.9.

Preparation 27 (1r,3r)-3-((2-(4-(2,4-difluorophenoxy)piperidin-1-yl)pyrido[3,4-b]pyrazin-3-yl) amino)cyclobutan-1-ol Combined 3-chloro-2-(4-(2,4-difluorophenoxy)piperidin-1-yl)pyrido[3,4-b]pyrazine (0.75 g, 1.991 mmol), (1r,3r)-3-aminocyclobutanol hydrochloride (0.738 g, 5.97 mmol), and potassium fluoride (0.150 g, 2.59 mmol) in DMSO (7.5 mL) and added DIPEA (1.734 mL, 9.95 mmol) at 23° C. The reaction was stirred at 23° C. for 5 days and diluted with water (30 mL) to furnish a gummy, brown suspension. The suspension was cooled on ice, stirred for 30 min at 0° C., filtered, rinsed with water, and the resulting solid was dried in vacuo to give the title compound (802 mg, 94%) as a light brown solid. $^1$H NMR (500 MHz, DMSO-d$_6$) δ ppm 1.86-1.96 (m, 2H), 2.07-2.15 (m, 2H), 2.23 (ddd, J=12.6, 7.9, 4.4 Hz, 2H), 2.33-2.40 (m, 2H), 3.23-3.30 (m, 2H), 3.67-3.74 (m, 2H), 4.30-4.37 (m, 1H), 4.56-4.65 (m, 2H), 5.03 (d, J=4.9 Hz, 1H), 7.00-7.07 (m, 2H), 7.29-7.37 (m, 2H), 7.44 (d, J=4.9 Hz, 1H), 8.28 (d, J=5.4 Hz, 1H), 8.77 (s, 1H); ESI-MS m/z [M+H]$^+$ 427.9.

Preparation 28 N-cyclobutyl-2-(4-(2,4-difluorophenoxy)piperidin-1-yl)pyrido[3,4-b]pyrazin-3-amine To a solution of 3-chloro-2-(4-(2,4-difluorophenoxy)piperidin-1-yl)pyrido[3,4-b]pyrazine (10 g, 26.5 mmol) in DMF (150 mL) was added cyclobutanamine (15.10 g, 212 mmol) at rt. Then the mixture was stirred at 70° C. for 15 h. After the reaction was done, the reaction mixture was poured into water/ACN (200 mL, 7:3). The suspension was filtered and rinsed with ACN to give the title compound (8.5 g, 78%). ESI-MS m/z [M+H]$^+$ 412.1.

Preparation 28 N-(3,3-difluorocyclobutyl)-2-(4-(2,4-difluorophenoxy)piperidin-1-yl)pyrido[3,4-b] pyrazin-3-amine Combined 3-chloro-2-(4-(2,4-difluorophenoxy)piperidin-1-yl)pyrido[3,4-b]pyrazine (0.46 g, 1.221 mmol), 3,3-difluorocyclobutanamine hydrochloride (0.526 g, 3.66 mmol), and potassium fluoride (0.092 g, 1.587 mmol) in DMSO (5 mL) and added DIPEA (1.063 mL, 6.10 mmol) at 23° C. The reaction was stirred at 23° C. for 5 days and diluted with water (20 mL) to furnish a yellow-orange suspension. The resulting solid was filtered, rinsed with water, and dried in vacuo to give the title compound (516.4 mg, 95%) as a yellow-orange solid. $^1$H NMR (500 MHz, DMSO-d$_6$) δ ppm 1.87-1.98 (m, 2H), 2.07-2.18 (m, 2H), 2.77-2.91 (m, 2H), 2.96-3.07 (m, 2H), 3.23-3.32 (m, 2H), 3.69-3.78 (m, 2H), 4.35-4.45 (m, 1H), 4.63 (tt, J=7.9, 3.8 Hz, 1H), 7.00-7.07 (m, 1H), 7.24-7.40 (m, 3H), 7.48 (d, J=5.4 Hz, 1H), 8.33 (d, J=5.4 Hz, 1H), 8.82 (s, 1H); ESI-MS m/z [M+H]$^+$ 447.9.

Preparation 30 2-(4-(2,4-difluorophenoxy)piperidin-1-yl)-N-isopropylpyrido[3,4-b]pyrazin-3-amine A solution of 3-chloro-2-(4-(2,4-difluorophenoxy)piperidin-1-yl)pyrido[3,4-b]pyrazine (2 g, 5.31 mmol), propan-2-amine (1.36 mL, 15.92 mmol) and DIPEA (1.85 mL, 10.62 mmol) in dioxane (10.62 mL) was heated at 95° C. overnight. After concentration, the residue was purified with silica gel column chromatography using a gradient of 0% to 100% EtOAc in heptanes to give the title compound (1.5 g, 71%) as an off-white solid. ESI-MS m/z [M+H]+ 400.00.

Preparation 31 9 (S)-2-(4-(2,4-difluorophenoxy)piperidin-1-yl)-N-(tetrahydrofuran-3-yl)pyrido[3,4-b]pyrazin-3-amine To a mixture of 3-chloro-2-(4-(2,4-difluorophenoxy)piperidin-1-yl)pyrido[3,4-b]pyrazine (2.5 g, 6.64 mmol) in DMF (30 mL) was added (S)-tetrahydrofuran-3-amine hydrochloride (4.10 g, 33.2 mmol) and Et$_3$N (9.25 mL, 66.4 mmol) at room temperature. The reaction mixture was stirred at 70° C. for 14 h then cooled to room temperature and diluted with EtOAc (80 mL), washed with water (30 mL) and brine (2×30 mL). The organic layer was dried over Na$_2$SO$_4$ and concentrated in vacuo, then the residue was purified by column chromatography (petroleum ether:EtOAc from 10:1 to 1:1) on silica gel to give the title compound as a yellow solid (2.0 g). ESI-MS m/z [M+H]+ 428.1.

Preparation 32 (R)-2-(4-(2,4-difluorobenzyl)piperazin-1-yl)-N-(tetrahydrofuran-3-yl)pyrido[3,4-b]pyrazin-3-amine To a mixture of 3-chloro-2-(4-(2,4-difluorobenzyl)piperazin-1-yl)pyrido[3,4-b]pyrazine (5.06 g, 13.46 mmol) in DMSO (40 mL) was added (R)-tetrahydrofuran-3-amine hydrochloride (4.16 g, 33.7 mmol) and Et$_3$N (24.40 mL, 175 mmol) at room temperature. The reaction mixture was stirred at 50° C. for 14 h then cooled to room temperature and diluted with EtOAc (80 mL), washed with water (30 mL) and brine (2×30 mL). The organic layer was dried over Na$_2$SO$_4$ and concentrated in vacuo, then the residue was purified by column chromatography (petroleum ether:EtOAc from 10:1 to 1:1) on silica gel to give the title compound as a yellow solid (5.0 g). ESI-MS m/z [M+H]+ 427.1.

Preparation 33 (S)-2-(4-(2,4-difluorobenzyl)piperazin-1-yl)-N-(tetrahydrofuran-3-yl)pyrido[3,4-b]pyrazin-3-amine To a solution of 3-chloro-2-(4-(2,4-difluorobenzyl)piperazin-1-yl)pyrido[3,4-b]pyrazine (3.0 g, 7.98 mmol) and Et$_3$N (10 mL, 71.7 mmol) in DMF (30 mL) was added (S)-tetrahydrofuran-3-amine hydrochloride (2.96 g, 23.95 mmol) at room temperature. The mixture was stirred at 60° C. for 16 h then separated between water and EtOAc. The organic layer was washed with brine and water, then dried and concentrated to yield the crude residue, which was purified by column to give the title compound (800 mg) as a yellow oil. ESI-MS m/z [M+H]+ 427.1.

Preparation 34 2-(4-(2,4-difluorobenzyl)piperazin-1-yl)-N-isopropylpyrido[3,4-b]pyrazin-3-amine To a flask charged with 3-chloro-2-(4-(2,4-difluorobenzyl)piperazin-1-yl)pyrido[3,4-b]pyrazine (2.34 g, 6.23 mmol) and potassium fluoride (0.470 g, 8.09 mmol) in DMSO (12 mL) was added DIPEA (2.169 mL, 12.45 mmol) and propan-2-amine (1.605 mL, 18.68 mmol) at 23° C. The reaction was stirred at 23° C. for 22 hr and diluted with water (48 mL) to furnish an orange, oily sludge. The crude product was extracted with EtOAc (25 mL) to furnish a suspension. The resulting solid was filtered, rinsed with EtOAc, and the filtrate was allowed to separate into two layers. The organic phase was washed with brine, dried over Na$_2$SO$_4$, filtered, rinsed with EtOAc, and dried in vacuo. The crude material was dissolved in toluene (5 mL) and purified via medium pressure chromatography using a 20% to 100% gradient eluant of EtOAc in heptane on an NH 60 μM, size 400 column (Shoko Scientific Purif-Pack™) to give the title compound (1.489 g, 60.0%) as a yellow solid. $^1$H NMR (500 MHz, DMSO-d$_6$) δ ppm 1.24 (d, J=6.4 Hz, 6H), 2.62 (t, J=4.9 Hz, 4H), 3.34-3.41 (m, 4H), 3.59 (s, 2H), 4.22-4.42 (m, 1H), 6.46 (d, J=7.8 Hz, 1H), 7.04-7.17 (m, 1H), 7.22 (td, J=10.0, 2.4 Hz, 1H), 7.40-7.44 (m, 1H), 7.49 (td, J=8.5, 6.8 Hz, 1H), 8.27 (d, J=5.9 Hz, 1H), 8.76 (s, 1H); ESI-MS m/z [M+H]+ 399.0.

Preparation 35 N-cyclobutyl-2-(4-(2,4-difluorobenzyl)piperazin-1-yl)pyrido[3,4-b]pyrazin-3-amine Combined 3-chloro-2-(4-(2,4-difluorobenzyl)piperazin-1-yl)pyrido[3,4-b]pyrazine (0.7226 g, 1.923 mmol), cyclobutanamine (0.493 mL, 5.77 mmol), and potassium fluoride (0.145 g, 2.500 mmol) in DMSO (7.2 mL) and DIPEA (0.670 mL, 3.85 mmol) at 23° C. The reaction was stirred at 23° C. for 16 hr and diluted with water (30 mL) to furnish a yellow-orange suspension. The resulting solid was filtered, rinsed with water, and dried in vacuo to give the title compound (0.62 g, 79%) as a yellow solid. $^1$H NMR (500 MHz, DMSO-d$_6$) δ ppm 1.68-1.77 (m, 2H), 2.12 (quind, J=9.3, 2.7 Hz, 2H), 2.27-2.35 (m, 2H), 2.56-2.68 (m, 4H), 3.35-3.42 (m, 4H), 3.60 (s, 2H), 4.57 (sextet, J=8.0 Hz, 1H), 6.98 (d, J=7.3 Hz, 1H), 7.06-7.12 (m, 1H), 7.22 (td, J=9.9, 2.7 Hz, 1H), 7.43 (d, J=5.4 Hz, 1H), 7.46-7.53 (m, 1H), 8.27 (d, J=5.4 Hz, 1H), 8.76 (s, 1H); ESI-MS m/z [M+H]+ 411.0.

Preparation 36 6-benzyl-3-chloro-2-(4-(2-fluoro-4-methoxyphenoxy)piperidin-1-yl)-5,6,7,8-tetrahydropyrido[3,4-b]pyrazine A mixture of 3-chloro-2-(4-(2-fluoro-4-methoxyphenoxy)piperidin-1-yl)pyrido[3,4-b]pyrazine (93 mg, 0.239 mmol) and (bromomethyl)benzene (29 μL, 0.239 mmol) in ACN (1.2 mL) was heated at 80° C. for 14 h. After the mixture was cooled to room temperature, sodium triacetoxyborohydride (152 mg, 0.718 mmol) was added to the mixture at rt. After 1 h, brine (1 mL) was added to the mixture. After bubbling ceased, the mixture was then purified directly by HPLC Method A to give the title compound as a TFA salt (71.2 mg, 49.9%) as a yellow oil. ESI-MS m/z [M+H]+ 483.3.

Preparation 37 3-chloro-2-(4-(2-fluoro-4-methoxyphenoxy)piperidin-1-yl)-6-methyl-5,6,7,8-tetrahydropyrido[3,4-b]pyrazine The title compound as a TFA salt (30.9 mg, 24.8%) was prepared in a manner similar to Preparation 38 using iodomethane. ESI-MS m/z [M+H]+ 407.3.

Preparation 39 6-benzyl-3-chloro-2-(4-((2,4-difluorophenyl)fluoromethyl)piperidin-1-yl)-5,6,7,8-tetrahydropyrido[3,4-b]pyrazine A mixture of 4-((2,4-difluorophenyl)fluoromethyl)piperidine hydrochloride (247 mg, 0.929 mmol), 2,3-dichloropyrido[3,4-b]pyrazine (169 mg, 0.845 mmol) and DIPEA (441 µL, 2.53 mmol) in DCM (1.69 mL) was stirred at 0° C. for 5 min then at rt for 30 min. The mixture was then partitioned between EtOAc and saturated aqueous $NH_4Cl$. The organic layer was washed with brine, dried over $Na_2SO_4$, filtrered, and evaporated. The residue was dissolved in EtOAc and filtered through a pad of silica. The filtrate was concentrated to afford 3-chloro-2-(4-((2,4-difluorophenyl)fluoromethyl)piperidin-1-yl)pyrido[3,4-b]pyrazine (338.4 mg) as a yellow foam. ESI-MS m/z [M+H]+ 393.2.

A mixture of 3-chloro-2-(4-((2,4-difluorophenyl)fluoromethyl)piperidin-1-yl)pyrido[3,4-b]pyrazine (338.4 mg, 0.861 mmol) benzyl bromide (103 µL, 0.861 mmol) in ACN (4.31 mL) was heated at 80° C. for 14 h. After the mixture was cooled to rt, sodium triacetoxyborohydride (548 mg, 2.58 mmol) was added. After 1 h, brine (1 mL) was added to the mixture. After bubbling ceased, the mixture was then purified directly by HPLC Method A to afford the title compound as its TFA salt (141.7 mg, 27.4%) as an orange oil. ESI-MS m/z [M+H]+ 487.3.

Preparation 40 6-benzyl-3-chloro-2-(4-(2,4-difluorophenoxy)piperidin-1-yl)-5-methyl-5,6,7,8-tetrahydropyrido[3,4-b]pyrazine Combined 2,3-dichloro-5-methylpyrido[3,4-b]pyrazine (1 g, 4.67 mmol), DIPEA (2.04 mL, 11.68 mmol), and 4-(2,4-difluorophenoxy)piperidine hydrochloride (1.225 g, 4.91 mmol) in DCM (9.34 mL) were combined in an ice bath then warmed to room temperature overnight. The reaction mixture was poured into 1 M NaOH, extracted with EtOAc (2×), filtered through $MgSO_4$, concentrated in vacuo, and purified by HPLC Method A to give 3-chloro-2-(4-(2,4-difluorophenoxy)piperidin-1-yl)-5-methylpyrido[3,4-b]pyrazine as a TFA salt (1.6 g).

Combined 3-chloro-2-(4-(2,4-difluorophenoxy)piperidin-1-yl)-5-methylpyrido[3,4-b]pyrazine (400 mg, 1.024 mmol) and benzyl bromide (122 µL, 1.024 mmol) in ACN (5.12 mL) was heated at 90° C. overnight. The reaction mixture was cooled to RT, sodium triacetoxyborohydride was added (651 mg, 3.07 mmol), and the reaction mixture was stirred overnight. The crude reaction was poured into 1 M NaOH, extracted with EtOAc (2×), filtered through $MgSO_4$, concentrated in vacuo, and purified by HPLC Method A to yield the title compound as a TFA salt (150 mg).

Preparation 41 6-benzyl-3-chloro-2-(4-(2,4-difluorophenoxy)piperidin-1-yl)-5,6,7,8-tetrahydropyrido[3,4-b]pyrazine Benzyl bromide was purified by passage through a plug of basic alumina prior to use. A solution of 3-chloro-2-(4-(2,4-difluorophenoxy)piperidin-1-yl)pyrido[3,4-b]pyrazine (736.2 mg, 1.954 mmol) in ACN (9.77 mL) was divided into two equal portions. Each solution was treated with a half portion of benzyl bromide (232 µL, 1.954 mmol) and stirred at 80° C. for 3 h. The reaction mixtures were allowed to cool to room temperature, and Each solution was treated with a half portion of sodium triacetoxyborohydride (1.242 g, 5.86 mmol). The reaction mixtures were stirred at room temperature for 1 h, then were quenched with saturated aqueous NaCl. The reaction mixtures were combined and partitioned between EtOAc with $Et_2O$ added to assist in phase separation and saturated aqueous NaCl. The organic layer was dried over $Na_2SO_4$, filtered, and concentrated under reduced pressure. The residue was purified by flash silica gel chromatography using a 20% to 60% gradient of EtOAc in heptanes gave the title compound (522.2 mg, 56.8%). ESI-MS m/z [M+H]+ 471.4.

Preparation 42 4-((1-(6-benzyl-3-chloro-5,6,7,8-tetrahydropyrido[3,4-b]pyrazin-2-yl)piperidin-4-yl)oxy)-3-fluorobenzonitrile Benzyl bromide was purified by filtration through a plug of basic alumina prior to use. A solution of 4-((1-(3-chloropyrido[3,4-b]pyrazin-2-yl)piperidin-4-yl)oxy)-3-fluorobenzonitrile (200 mg, 0.521 mmol) and benzyl bromide (0.062 mL, 0.521 mmol) in ACN (2.60 mL) was heated at 80° C. for 3 h. The reaction mixture was allowed to cool to room temperature and sodium triacetoxyborohydride (331 mg, 1.563 mmol) was added. After stirring for 1 h at room temperature, the reaction mixture was quenched with saturated aqueous NaCl (1 mL). After bubbling ceased, the reaction mixture was purified by HPLC Method B, with the exception that a Waters SunFire™ C18, 5 µm, ID 30×75 mm column was used, using a 35% to 70% ACN gradient to give the title compound, as a TFA salt, as a yellow oil (117.9 mg, 38.2%). ESI-MS m/z [M+H]+ 478.5.

Preparation 43 (R)-6-benzyl-3-chloro-2-(4-((2,4-difluorophenyl)fluoromethyl)piperidin-1-yl)-5,6,7,8-tetrahydropyrido[3,4-b]pyrazine The title compound was prepared in a manner similar to Preparation 44 using (R)-3-chloro-2-(4-((2,4-difluorophenyl)fluoromethyl)piperidin-1-yl)pyrido[3,4-b]pyrazine. The product was purified twice by flash silica gel chromatography using a 10% to 60% gradient of EtOAc in heptanes. ESI-MS m/z [M+H]+ 487.4.

Preparation 45 (S)-6-benzyl-3-chloro-2-(4-((2,4-difluorophenyl)fluoromethyl)piperidin-1-yl)-5,6,7,8-tetrahydropyrido[3,4-b]pyrazine The title compound was prepared in a manner similar to Preparation 46 using (S)-3-chloro-2-(4-((2,4-difluorophenyl)fluoromethyl)piperidin-1-yl)pyrido[3,4-b]pyrazine. The product was purified twice by flash silica gel chromatography using a 10% to 50% gradient of EtOAc in heptanes. ESI-MS m/z [M+H]+ 487.3.

Preparation 47 6-benzyl-N-(2,2-difluoroethyl)-2-(4-(2,4-difluorophenoxy)piperidin-1-yl)-5,6,7,8-tetrahydropyrido[3,4-b]pyrazin-3-amine A solution of 6-benzyl-3-chloro-2-(4-(2,4-difluorophenoxy)piperidin-1-yl)-5,6,7,8-tetrahydropyrido[3,4-b]pyrazine (261.1 mg, 0.554 mmol) and 2,2-difluoroethanamine (156 µL, 2.22 mmol) in toluene (1.85 mL) was treated with sodium tert-butoxide (107 mg, 1.11 mmol), BINAP (69.0 mg, 0.111 mmol), and $Pd_2(dba)_3$ (50.8 mg, 0.055 mmol). Nitrogen gas (balloon) was bubbled through the reaction mixture for 5 min. The reaction mixture was sealed and stirred at 90° C. overnight. The reaction mixture was allowed to cool to room temperature and was opened to air, and the solution was concentrated under reduced pressure. The residue was taken up in MeOH, filtered, and purified by HPLC Method B using a 35% to 60% ACN gradient to give the title compound, as a TFA salt, as a yellow oil (181.2 mg, 51.9%). ESI-MS m/z [M+H]+ 516.4.

Preparation 48 6-benzyl-2-(4-(2,4-difluorophenoxy) piperidin-1-yl)-N-isopropyl-5,6,7,8-tetrahydropyrido [3,4-b]pyrazin-3-amine To a yellow-orange suspension of 2-(4-(2,4-difluorophenoxy)piperidin-1-yl)-N-isopropylpyrido[3,4-b]pyrazin-3-amine (5.1 g, 12.77 mmol) in ACN (63.8 mL) was added benzyl bromide (2.184 g, 12.77 mmol) over 1 minute at 23° C. The mixture was stirred at 80° C. for 4 h to furnish a red-brown solution, cooled to 23° C., and then concentrated via rotary evaporation to give 6-benzyl-2-(4-(2,4-difluorophenoxy)piperidin-1-yl)-3-(isopropylamino)pyrido[3,4-b] pyrazin-6-ium bromide (7.30 g) as a red-brown solid, which was used directly in the next step without further purification.

To a solution of 6-benzyl-2-(4-(2,4-difluorophenoxy)piperidin-1-yl)-3-(isopropylamino)pyrido[3,4-b]pyrazin-6-ium bromide (7.2 g, 12.62 mmol) in DCM (126 ml) was added NaBH(OAc)$_3$ (16.05 g, 76 mmol). The resulting solution was stirred at room temperature for 3 days. After DCM was removed under vacuum, EtOAc (200 mL) was added to re-dissolve the residue. Then saturated NaHCO$_3$ (150 mL) was added and the mixture was vigorously stirred for 30 min. The organic layer was washed with water (50 mL) and brine (50 mL), and dried with anhydrous Na$_2$SO$_4$ overnight. Removal of the solvent gave the title compound (6.43 g) as a yellow solid, which was used without further purification. ESI-MS m/z [M+H]$^+$ 494.10.

Preparation 50 6-benzyl-N-cyclobutyl-2-(4-(2,4-difluorophenoxy)piperidin-1-yl)-5,6,7,8-tetrahydropyrido[3,4-b]pyrazin-3-amine The title compound as a TFA salt was prepared in a manner similar to Preparation 51 using cyclobutanamine in place of 2,2-difluoroethanamine and HPLC Method A. ESI-MS m/z [M+H]$^+$ 506.00.

Preparation 52 (S)-6-benzyl-2-(4-(2,4-difluorophenoxy)piperidin-1-yl)-N-(1-methoxypropan-2-yl)-5,6,7,8-tetrahydropyrido[3,4-b]pyrazin-3-amine The title compound as a TFA salt was prepared in a manner similar to Preparation 53 using (S)-1-methoxypropan-2-amine in place of 2,2-difluoroethanamine and HPLC Method A. ESI-MS m/z [M+H]$^+$ 524.00.

Preparation 54 (R)-6-benzyl-2-(4-(2,4-difluorophenoxy)piperidin-1-yl)-N-(1-methoxypropan-2-yl)-5,6,7,8-tetrahydropyrido[3,4-b]pyrazin-3-amine The title compound as a TFA salt was prepared in a manner similar to Preparation 55 using (R)-1-methoxypropan-2-amine hydrochloride in place of 2,2-difluoroethanamine and HPLC Method A. ESI-MS m/z [M+H]$^+$ 524.00.

Preparation 56 (S)-6-benzyl-N-(sec-butyl)-2-(4-(2,4-difluorophenoxy)piperidin-1-yl)-5,6,7,8-tetrahydropyrido[3,4-b]pyrazin-3-amine The title compound as a TFA salt was prepared in a manner similar to Preparation 57 using (S)-butan-2-amine in place of 2,2-difluoroethanamine and HPLC Method A. ESI-MS m/z [M+H]$^+$ 508.00.

Preparation 58 (R)-6-benzyl-N-(sec-butyl)-2-(4-(2,4-difluorophenoxy)piperidin-1-yl)-5,6,7,8-tetrahydropyrido[3,4-b]pyrazin-3-amine The title compound as a TFA salt was prepared in a manner similar to Preparation 59 using (R)-butan-2-amine in place of 2,2-difluoroethanamine and HPLC Method A. ESI-MS m/z [M+H]$^+$ 508.00.

Preparation 60 4-((1-(6-benzyl-3-(isopropylamino)-5,6,7,8-tetrahydropyrido[3,4-b]pyrazin-2-yl)piperidin-4-yl)oxy)-3-fluorobenzonitrile A solution of 4-((1-(6-benzyl-3-chloro-5,6,7,8-tetrahydropyrido[3,4-b]pyrazin-2-yl)piperidin-4-yl)oxy)-3-fluorobenzonitrile TFA salt (213.9 mg, 0.361 mmol) in toluene (1.44 mL) was treated with propan-2-amine (0.118 mL, 1.445 mmol), sodium tert-butoxide (69.4 mg, 0.723 mmol), BINAP (22.5 mg, 0.036 mmol), and Pd$_2$(dba)$_3$ (16.5 mg, 0.018 mmol). Nitrogen gas was bubbled through the solution for 5 min. The reaction mixture was then sealed and the reaction mixture was heated to 90° C. overnight. The reaction mixture was allowed to cool to room temperature. Solvent was removed under reduced pressure and the residue was purified by HPLC Method B, with the exception that a Waters SunFire™ C18, 5 µm, ID 30×75 mm column was used, using a 40% to 70% ACN gradient to give the title compound, as a TFA salt, as a yellow oil (105 mg, 47.3%). ESI-MS m/z [M+H]$^+$ 501.5.

Preparation 61 (R)-6-benzyl-2-(4-((2,4-difluorophenyl)fluoromethyl)piperidin-1-yl)-N-isopropyl-5,6,7,8-tetrahydropyrido[3,4-b]pyrazin-3-amine A solution of (R)-6-benzyl-3-chloro-2-(4-((2,4-difluorophenyl)fluoromethyl)piperidin-1-yl)-5,6,7,8-tetrahydropyrido[3,4-b]pyrazine (293 mg, 0.602 mmol) and propan-2-amine (197 µL, 2.407 mmol) in toluene (2.01 mL) was treated with sodium tert-butoxide (116 mg, 1.203 mmol), BINAP (74.9 mg, 0.120 mmol), and Pd$_2$(dba)$_3$ (55.1 mg, 0.060 mmol). Nitrogen gas (balloon) was bubbled through the reaction mixture for 5 min. The reaction mixture was sealed and the reaction mixture was stirred at 90° C. overnight. The reaction was opened and the mixture was concentrated under reduced pressure. The residue was taken up in MeOH, filtered, and purified by HPLC Method B using a 40% to 65% ACN gradient to give the title compound as a TFA salt (183.1 mg, 48.8%) as a yellow oil. ESI-MS m/z [M+H]$^+$ 510.4.

Preparation 62 (S)-6-benzyl-2-(4-((2,4-difluorophenyl)fluoromethyl)piperidin-1-yl)-N-isopropyl-5,6,7,8-tetrahydropyrido[3,4-b]pyrazin-3-amine A solution of (S)-6-benzyl-3-chloro-2-(4-((2,4-difluorophenyl)fluoromethyl)piperidin-1-yl)-5,6,7,8-tetrahydropyrido[3,4-b]pyrazine (500 mg, 1.027 mmol) and propan-2-amine (350 µL, 4.11 mmol) in toluene (3.42 mL) was treated with sodium tert-butoxide (197 mg, 2.054 mmol), BINAP (102 mg, 0.164 mmol), and Pd$_2$(dba)$_3$ (75 mg, 0.082 mmol). Nitrogen gas (balloon) was bubbled through the reaction mixture for 5 min. The reaction mixture was then sealed and heated at 90° C. for 16 h. The reaction mixture was allowed to cool to room temperature and was opened to air. The reaction mixture was concentrated under reduced pressure and was taken up in MeOH, filtered, and purified by HPLC Method A to give the title compound as a TFA salt (266 mg) as an orange oil. ESI-MS m/z [M+H]$^+$ 510.4.

Preparation 63 3-fluoro-4-((1-(3-(isopropylamino)-5,6,7,8-tetrahydropyrido[3,4-b]pyrazin-2-yl)piperidin-4-yl)oxy)benzonitrile To a solution of 4-((1-(6-benzyl-3-(isopropylamino)-5,6,7,8-tetrahydropyrido[3,4-b]pyrazin-2-yl)piperidin-4-yl)oxy)-3-fluorobenzonitrile TFA salt (98.8 mg, 0.161 mmol) in THF (1.61 mL) was added Pd(OH)$_2$ (20 wt %, 33.9 mg, 0.048 mmol). Hydrogen gas (balloon) was bubbled through the reaction mixture for 5 min. The reaction mixture was allowed to stir under hydrogen atmosphere for 6 h. The reaction mixture was filtered through a plug of Celite™, eluting with MeOH. The filtrate was collected and concentrated under reduced pressure. The residue was purified by HPLC Method B, with the exception that a Waters SunFire™ C18, 5 μm, ID 30×75 mm column was used, using a 25% to 60% ACN gradient to give the title compound, as a TFA salt, as a yellow oil (12.8 mg), which was carried forward without additional purification. ESI-MS m/z [M+H]$^+$ 411.5.

Preparation 64 N-(2,2-difluoroethyl)-2-(4-(2,4-difluorophenoxy)piperidin-1-yl)-5,6,7,8-tetrahydropyrido[3,4-b]pyrazin-3-amine A solution of 6-benzyl-N-(2,2-difluoroethyl)-2-(4-(2,4-difluorophenoxy)piperidin-1-yl)-5,6,7,8-tetrahydropyrido[3,4-b]pyrazin-3-amine TFA salt (132.5 mg, 0.210 mmol) in THF (2.1 mL) was treated with Pd(OH)$_2$ (20 wt %, 29.6 mg, 0.042 mmol). Hydrogen gas (balloon) was bubbled through the reaction mixture for 5 min. The vent needle was removed and the reaction was stirred under hydrogen atmosphere for 1 h. The reaction mixture was opened to air and was filtered through a pad of Celite™, eluting with EtOAc and MeOH. The filtrate was concentrated under reduced pressure to give the title compound as a TFA salt (114 mg), which was used without further purification. ESI-MS m/z [M+H]$^+$ 426.5.

Preparation 65 N-cyclobutyl-2-(4-(2,4-difluorophenoxy)piperidin-1-yl)-5,6,7,8-tetrahydropyrido[3,4-b]pyrazin-3-amine The title compound as a TFA salt was prepared in a manner similar to Preparation 66, except that the reaction was stirred under hydrogen atmosphere for 2 h. ESI-MS m/z [M+H]$^+$ 416.5.

Preparation 67 (R)-2-(4-((2,4-difluorophenyl)fluoromethyl)piperidin-1-yl)-N-isopropyl-5,6,7,8-tetrahydropyrido[3,4-b]pyrazin-3-amine The title compound as a TFA salt was prepared in a manner similar to Preparation 68, except that the reaction was stirred under hydrogen atmosphere for 2 h. The TFA salt was dissolved in DCM and washed with saturated aqueous K$_2$CO$_3$. The organics were dried over Na$_2$SO$_4$, filtered, and concentrated under reduced pressure to obtain the title compound as the free base. ESI-MS m/z [M+H]$^+$ 420.5.

Preparation 69 (S)-2-(4-((2,4-difluorophenyl)fluoromethyl)piperidin-1-yl)-N-isopropyl-5,6,7,8-tetrahydropyrido[3,4-b]pyrazin-3-amine The title compound as a TFA salt was prepared in a manner similar to Preparation 70. The TFA salt was dissolved in DCM and washed with saturated aqueous K$_2$CO$_3$. The organics were dried over Na$_2$SO$_4$, filtered, and concentrated under reduced pressure to obtain the title compound as the free base. ESI-MS m/z [M+H]$^+$ 420.5.

Preparation 71 N-cyclobutyl-2-(4-(2-fluoro-4-methoxyphenoxy)piperidin-1-yl)-5,6,7,8-tetrahydropyrido[3,4-b]pyrazin-3-amine A mixture of cyclobutanamine (49.9 μL, 0.584 mmol), 6-benzyl-3-chloro-2-(4-(2-fluoro-4-methoxyphenoxy)piperidin-1-yl)-5,6,7,8-tetrahydropyrido[3,4-b]pyrazine TFA salt (116.2 mg, 0.195 mmol), sodium tert-butoxide (56.1 mg, 0.584 mmol), BINAP (18.2 mg, 0.029 mmol) and Pd$_2$(dba)$_3$ (26.7 mg, 0.029 mmol) in toluene (649 μL) was heated at 90° C. in a sealed tube for 16 h. The mixture was directly purified by HPLC Method A to afford 6-benzyl-N-cyclobutyl-2-(4-(2-fluoro-4-methoxyphenoxy)piperidin-1-yl)-5,6,7,8-tetrahydropyrido[3,4-b]pyrazin-3-amine as its TFA salt (103.4 mg, 84%) as a yellow foam. ESI-MS m/z [M+H]$^+$ 518.4

A mixture of 6-benzyl-N-cyclobutyl-2-(4-(2-fluoro-4-methoxyphenoxy)piperidin-1-yl)-5,6,7,8-tetrahydropyrido[3,4-b]pyrazin-3-amine TFA salt (103.4 mg, 0.164 mmol) and Pd(OH)$_2$ on carbon (10 mg, 0.014 mmol) in THF (818 μL) was stirred at rt under an atmosphere of hydrogen gas (balloon) for 4 h. The mixture was filtered through a pad of Celite™, washing with MeOH, and concentrated to afford the title compound as its TFA salt (89 mg, 100%) as a yellow solid. ESI-MS m/z [M+H]$^+$ 428.4.

Preparation 72 1-(3-(isopropylamino)-2-(piperazin-1-yl)-7,8-dihydropyrido[3,4-b]pyrazin-6(5H)-yl)ethan-1-one To a flask charged with tert-butyl 4-(6-acetyl-3-(isopropylamino)-5,6,7,8-tetrahydropyrido[3,4-b]pyrazin-2-yl)piperazine-1-carboxylate (1.015 g, 2.425 mmol) was added HCl (4 M in dioxane, 4.85 mL, 19.40 mmol) at 23° C. The reaction mixture was stirred at 23° C. for 1 h, diluted with dioxane (20 mL), filtered, rinsed with dioxane, and dried in vacuo to provide the HCl salt of the title compound (0.861 g, 100%) as a yellow solid. ESI-MS m/z [M+H]$^+$ 319.5.

Preparation 73 2-(4-(2,4-difluorophenoxy)piperidin-1-yl)-N-isopropyl-5-methyl-5,6,7,8-tetrahydropyrido[3,4-b]pyrazin-3-amine Combined 6-benzyl-3-chloro-2-(4-(2,4-difluorophenoxy)piperidin-1-yl)-5-methyl-5,6,7,8-tetrahydropyrido[3,4-b]pyrazine TFA salt (280 mg, 0.467 mmol), isopropylamine (200 μL, 2.337 mmol), Pd$_2$(dba)$_3$ (42.8 mg, 0.047 mmol), BINAP (58.2 mg, 0.093 mmol), and sodium tert-butoxide (112 mg, 1.169 mmol) in toluene (2.34 mL) and heated at 100° C. for 30 min under microwave conditions. The reaction mixture was cooled, concentrated in vacuo, and purified by HPLC Method A to give 6-benzyl-2-(4-(2,4-difluorophenoxy)piperidin-1-yl)-N-isopropyl-5-methyl-5,6,7,8-tetrahydropyrido[3,4-b]pyrazin-3-amine as a TFA salt (175 mg) as a brown oil.

A 50 mL round-bottomed flask containing 6-benzyl-2-(4-(2,4-difluorophenoxy)piperidin-1-yl)-N-isopropyl-5-methyl-5,6,7,8-tetrahydropyrido[3,4-b]pyrazin-3-amine TFA salt (175 mg, 0.282 mmol) and Pd(OH)$_2$ (20 wt %, 39.5 mg, 0.056 mmol) in THF (2.82 mL) was purged and placed under hydrogen (balloon) for 3 h. Filtration through Celite™

(washed with EtOAc) and concentration in vacuo gave the title compound as a TFA salt (150 mg) as a brown oil.

Preparation 74 N-(2,2-difluoroethyl)-2-(4-(2,4-difluorophenoxy)piperidin-1-yl)-5-methyl-5,6,7,8-tetrahydropyrido[3,4-b]pyrazin-3-amine The title compound (98 mg) was prepared in a manner similar to Preparation 75 using 2,2-difluoroethan-1-amine.

Preparation 76 (5-chloro-2-fluorophenyl)(1-(3-(isopropylamino)-5,6,7,8-tetrahydropyrido[3,4-b]pyrazin-2-yl)piperidin-4-yl)methanone A mixture of (5-chloro-2-fluorophenyl)(piperidin-4-yl)methanone hydrochloride (153 mg, 0.550 mmol), 2,3-dichloropyrido[3,4-b]pyrazine (100 mg, 0.500 mmol) and DIPEA (261 µL, 1.500 mmol) in DCM (1.67 mL) was stirred at rt for 30 min. The mixture was partitioned between aqueous NH$_4$Cl and EtOAc. The organic layer was filtered through a pad of silica, washing with EtOAc, and the filtrate was concentrated under reduced pressure to give (5-chloro-2-fluorophenyl)(1-(3-chloropyrido[3,4-b]pyrazin-2-yl)piperidin-4-yl)methanone (205.5 mg) as an orange solid. ESI-MS m/z [M+H]$^+$ 405.2.

A mixture of (5-chloro-2-fluorophenyl)(1-(3-chloropyrido[3,4-b]pyrazin-2-yl)piperidin-4-yl)methanone (205.5 mg, 0.507 mmol) and benzyl bromide (63.7 µL, 0.532 mmol) in ACN (1.69 mL) was heated at 80° C. for 4 h. After the mixture was cooled to rt, sodium triacetoxyborohydride (537 mg, 2.54 mmol) was added in one portion. After 1 h, the mixture was quenched with brine, extracted with EtOAc, concentrated and purified by HPLC Method A to afford (1-(6-benzyl-3-chloro-5,6,7,8-tetrahydropyrido[3,4-b]pyrazin-2-yl)piperidin-4-yl)(5-chloro-2-fluorophenyl)methanone as its TFA salt (112.4 mg, 36.1%) as a yellow oil. ESI-MS m/z [M+H]$^+$ 499.2.

A mixture of propan-2-amine (31.5 µL, 0.366 mmol), (1-(6-benzyl-3-chloro-5,6,7,8-tetrahydropyrido[3,4-b]pyrazin-2-yl)piperidin-4-yl)(5-chloro-2-fluorophenyl)methanone TFA salt (112.4 mg, 0.183 mmol), sodium tert-butoxide (35.2 mg, 0.366 mmol), BINAP (17.1 mg, 0.027 mmol) and Pd$_2$(dba)$_3$ (8.4 mg, 9.16 µmol) in toluene (611 µL) was heated at 100° C. for 16 h. The mixture was purified by HPLC Method A to afford (1-(6-benzyl-3-(isopropylamino)-5,6,7,8-tetrahydropyrido[3,4-b]pyrazin-2-yl)piperidin-4-yl)(5-chloro-2-fluorophenyl)methanone as its TFA salt (41.7 mg, 35.8%) as a yellow film. ESI-MS m/z [M+H]$^+$ 522.4.

A mixture of (1-(6-benzyl-3-(isopropylamino)-5,6,7,8-tetrahydropyrido[3,4-b]pyrazin-2-yl)piperidin-4-yl)(5-chloro-2-fluorophenyl)methanone TFA salt (41.7 mg, 0.066 mmol) and Pd(OH)$_2$ on carbon (20 wt %, 5 mg, 0.036 mmol) in THF (328 µL) was stirred at rt under an atmosphere of hydrogen gas (balloon). After 3 h, the mixture was diluted with MeOH, filtered through a pad of Celite™, washing with MeOH, and concentrated to afford the title compound as its TFA salt (36 mg, 100%) as a yellow film, which was used without further purification. ESI-MS m/z [M+H]$^+$ 432.3.

Preparation 77
3-chloro-N-isopropylpyrido[3,4-b]pyrazin-2-amine

To a solution of 2,3-dichloropyrido[3,4-b]pyrazine (2.5 g, 12.50 mmol) and DIPEA (6.53 mL, 37.5 mmol) in DCM (25 mL) was added propan-2-amine (1.065 mL, 12.50 mmol) at 0° C. The mixture was stirred at 0° C. for 30 min, warmed slowly to 23° C., and stirred for 12 h. The crude mixture was partitioned between EtOAc (100 mL) and saturated aqueous NH$_4$Cl (100 mL). The layers were separated and the aqueous phase was washed with EtOAc (4×100 mL). The organic extracts were combined, washed with brine (50 mL), dried over Na$_2$SO$_4$, filtered, rinsed with EtOAc, and dried in vacuo. The crude material was dissolved in toluene (5 mL) and purified via medium pressure chromatography using a gradient eluant of 50% to 75% EtOAc in heptane on a 80 g silica gel column (Single Step™) to give the title compound (1.828 g, 65.7%) as a yellow-orange solid. $^1$H NMR (400 MHz, DMSO-d$_6$) δ ppm 1.28 (d, J=6.6 Hz, 6H), 4.39-4.49 (m, 1H), 7.49 (dd, J=5.8, 0.8 Hz, 1H), 7.73 (d, J=7.8 Hz, 1H), 8.52 (d, J=5.6 Hz, 1H), 8.95 (d, J=0.8 Hz, 1H); ESI-MS m/z [M+H]$^+$ 223.1.

Preparation 78
3-chloro-N-cyclopropylpyrido[3,4-b]pyrazin-2-amine

A solution of 2,3-dichloropyrido[3,4-b]pyrazine (3.55 g, 17.75 mmol) in dioxane (71.0 mL) at room temperature was treated with cyclopropanamine (1.63 mL, 23.07 mmol), followed by dropwise addition of DIPEA (6.51 mL, 37.3 mmol). The resulting reaction mixture was stirred at room temperature for 12 h. Purification by flash silica gel chromatography using a gradient of 25% to 100% EtOAc in hexanes gave the title compound (3.15 g, 80%) as an orange solid. ESI-MS m/z [M+H]$^+$ 221.1.

Preparation 79 3-chloro-N-(2,2-difluoroethyl)pyrido[3,4-b]pyrazin-2-amine

A solution of 2,3-dichloropyrido[3,4-b]pyrazine (50 mg, 0.250 mmol) in dioxane (250 µL) was treated with 2,2-difluoroethanamine (21.0 µL, 0.275 mmol) and DIPEA (131 µL, 0.750 mmol). The resulting reaction mixture was stirred at 70° C. for 1 h then purified by flash silica gel chromatography using a gradient of 0% to 60% EtOAc in hexanes to give the title compound (52 mg, 85%) as a light yellow solid.

Preparation 80 6-benzyl-3-chloro-N-cyclopropyl-5,6,7,8-tetrahydropyrido[3,4-b]pyrazin-2-amine A mixture of 3-chloro-N-cyclopropylpyrido[3,4-b]pyrazin-2-amine (301.8 mg, 1.368 mmol) and (bromomethyl)benzene (170 µL, 1.436 mmol) in ACN (4.5 mL) was heated at 80° C. for 3 h. Sodium triacetoxyborohydride (1449 mg, 6.8 mmol) was added to the mixture at rt. After 30 min, brine was added to the mixture. After stirring for 1 h, the layers were separated and the organic layer was purified by HPLC Method A to give the title compound as a TFA salt (290.6 mg, 49.5%) as a yellow solid. ESI-MS m/z [M+H]$^+$ 315.2.

Preparation 81 3-chloro-N-cyclopropyl-6-methyl-5,6,7,8-tetrahydropyrido[3,4-b]pyrazin-2-amine The title compound as a TFA salt (22 mg, 17.2%) was prepared in a manner similar to Preparation 82 using iodomethane. ESI-MS m/z [M+H]$^+$ 239.2.

Preparation 83 6-benzyl-3-chloro-N-isopropyl-5,6,7,8-tetrahydropyrido[3,4-b]pyrazin-2-amine The title compound as a TFA salt (240 mg, 41.3%) was prepared in a manner similar to Preparation 84 using 3-chloro-N-isopropylpyrido[3,4-b]pyrazin-2-amine. ESI-MS m/z [M+H]$^+$ 317.3.

Preparation 85 6-benzyl-3-chloro-N-(2,2-difluoroethyl)-5,6,7,8-tetrahydropyrido[3,4-b]pyrazin-2-amine A solution of 3-chloro-N-(2,2-difluoroethyl)pyrido[3,4-b]pyrazin-2-amine (200 mg, 0.818 mmol) and benzyl bromide (99 µL, 0.818 mmol) in ACN (4.09 mL) was stirred at 80° C. for 3 h, then the reaction mixture was cooled to room temperature and treated with sodium triacetoxyhydroborate (520 mg, 2.453 mmol). After 1 h the solution was poured into 0.5 M NaOH and extracted twice with EtOAc. The extracts were combined, concentrated, diluted in DMF, filtered through a hydrophilic PTFE 0.45 µm filter (Millipore® Millex-LCR), and purified by HPLC Method A to give the title compound as a TFA salt (150 mg, 40.5%).

Preparation 86 6-benzyl-N-(tert-butyl)-3-chloro-5,6,7,8-tetrahydropyrido[3,4-b]pyrazin-2-amine N-(tert-butyl)-3-chloropyrido[3,4-b]pyrazin-2-amine Combined 2,3-dichloropyrido[3,4-b]pyrazine (1 g, 5.00 mmol) and DIPEA (1.75 mL, 10.00 mmol) in DCM (10.00 mL) and cooled to 0° C. and added tert-butylamine (1.590 mL, 15.00 mmol) and stirred for 48 h. The reaction mixture was poured into saturated aqueous $NH_4Cl$ and extracted twice with EtOAc. The organic extracts were combined, filtered through $MgSO_4$, and concentrated in vacuo. The residue was redissolved in EtOAc, filtered through a one inch plug of silica, washing with EtOAc, and concentrated gave N-(tert-butyl)-3-chloropyrido[3,4-b]pyrazin-2-amine (1.04 g, 88%).

A solution of N-(tert-butyl)-3-chloropyrido[3,4-b]pyrazin-2-amine (200 mg, 0.845 mmol) and benzyl bromide (145 mg, 0.845 mmol) in ACN (4.22 mL) was heated to 80° C. for 3 h. The reaction was cooled and sodium triacetoxyborohydride (537 mg, 2.53 mmol) was added. After 1 h, the reaction was poured into 0.5 M NaOH and extracted twice with EtOAc. The extracts were combined, concentrated, and purified by HPLC Method A to give the title compound as a TFA salt (125 mg, 33.3%).

Preparation 87 6-benzyl-3-(4-((2-fluorophenyl)sulfonyl)piperidin-1-yl)-N-isopropyl-5,6,7,8-tetrahydropyrido[3,4-b]pyrazin-2-amine A suspension of 6-benzyl-3-chloro-N-isopropyl-5,6,7,8-tetrahydropyrido[3,4-b]pyrazin-2-amine (117.2 mg, 0.370 mmol) and 4-((2-fluorophenyl)sulfonyl)piperidine hydrochloride (124 mg, 0.444 mmol) in toluene (1.85 mL) was treated with sodium tert-butoxide (107 mg, 1.110 mmol), BINAP (34.6 mg, 0.055 mmol), and $Pd_2(dba)_3$ (16.9 mg, 0.018 mmol). Nitrogen gas (balloon) was bubbled through the reaction mixture for 5 min. The reaction mixture was then sealed and heated at 90° C. for 18 h. The reaction mixture was opened to air and concentrated under reduced pressure. The residue was taken up in DMF/MeOH, filtered through a 0.45 µm syringe filter, and purified by HPLC Method A to give the title compound (99.7 mg, 42.3%). ESI-MS m/z $[M+H]^+$ 523.90.

Preparation 88 6-benzyl-N-cyclopropyl-3-(4-(2-fluoro-4-methoxyphenoxy)piperidin-1-yl)-5,6,7,8-tetrahydropyrido[3,4-b]pyrazin-2-amine A mixture of 4-(2-fluoro-4-methoxyphenoxy)piperidine hydrochloride (73.2 mg, 0.280 mmol), 6-benzyl-3-chloro-N-cyclopropyl-5,6,7,8-tetrahydropyrido[3,4-b]pyrazin-2-amine TFA salt (100 mg, 0.233 mmol), sodium tert-butoxide (67.2 mg, 0.700 mmol), BINAP (21.8 mg, 0.035 mmol) and $Pd_2(dba)_3$ (10.7 mg, 0.012 mmol) in toluene (1.2 mL) was heated at 90° C. for 14 h. The mixture was directly purified by HPLC Method A to give the title compound as a TFA salt (114.2 mg, 97%) as a yellow foam. $^1$H NMR (400 MHz, methanol-$d_4$) δ ppm 0.53-0.60 (m, 2H), 0.78-0.85 (m, 2H), 1.84-1.95 (m, 2H), 1.99-2.09 (m, 2H), 2.65-2.73 (m, 1H), 2.90-2.98 (m, 1H), 3.08-3.23 (m, 3H), 3.33-3.42 (m, 2H), 3.55-3.68 (m, 2H), 3.75 (s, 3H), 4.16-4.24 (m, 1H), 4.28-4.40 (m, 2H), 4.50-4.59 (m, 2H), 6.67 (s, 1H), 6.73 (dd, J=12.9, 3.0 Hz, 1H), 7.01-7.09 (m, 1H), 7.52-7.61 (m, 5H); ESI-MS m/z $[M+H]^+$ 504.4.

Preparation 88 6-benzyl-N-cyclopropyl-2-(4-(2-fluoro-4-methoxyphenoxy)piperidin-1-yl)-5,6,7,8-tetrahydropyrido[3,4-b]pyrazin-3-amine A mixture of cyclopropanamine (27.2 mg, 0.477 mmol), 6-benzyl-3-chloro-2-(4-(2-fluoro-4-methoxyphenoxy)piperidin-1-yl)-5,6,7,8-tetrahydropyrido[3,4-b]pyrazine TFA salt (71.2 mg, 0.119 mmol), sodium tert-butoxide (22.9 mg, 0.239 mmol), BINAP (11.1 mg, 0.018 mmol) and $Pd_2(dba)_3$ (5.5 mg, 5.96 µmol) in toluene (400 µL) was heated at 90° C. for 14 h. The mixture was directly purified by HPLC Method A to give the title compound as a TFA salt (49.2 mg, 66.8%) as a yellow solid. $^1$H NMR (400 MHz, methanol-$d_4$) δ ppm 0.50-0.55 (m, 2H), 0.76 (dd, J=7.0, 1.9 Hz, 2H), 1.86-1.96 (m, 2H), 2.01-2.10 (m, 2H), 2.63 (tt, J=7.0, 3.6 Hz, 1H), 2.93-3.01 (m, 2H), 3.07 (br s, 2H), 3.34-3.41 (m, 2H), 3.56 (br s, 2H), 3.75 (s, 3H), 4.23 (br s, 2H), 4.30-4.37 (m, 1H), 4.53 (br s, 2H,) 6.63-6.68 (m, 1H), 6.73 (dd, J=12.8, 2.9 Hz, 1H), 7.05 (t, J=9.2 Hz, 1H), 7.52-7.61 (m, 5H); ESI-MS m/z $[M+H]^+$ 504.4.

Preparation 90 N-cyclopropyl-3-(4-(2-fluoro-4-methoxyphenoxy)piperidin-1-yl)-5,6,7,8-tetrahydropyrido[3,4-b]pyrazin-2-amine A mixture of 6-benzyl-N-cyclopropyl-3-(4-(2-fluoro-4-methoxyphenoxy)piperidin-1-yl)-5,6,7,8-tetrahydropyrido[3,4-b]pyrazin-2-amine TFA salt (5 mg, 8.10 µmol) and $Pd(OH)_2$ on carbon, (20 wt %, 1 mg, 7.12 µmol) in THF (80 µL) was stirred under atmosphere of hydrogen gas (balloon) at rt. After 1 h, the mixture was purified by HPLC Method A to give the title compound as a TFA salt (4.6 mg, 100%) as a yellow film; ESI-MS m/z $[M+H]^+$ 414.4.

Preparation 91 N-cyclopropyl-2-(4-(2-fluoro-4-methoxyphenoxy)piperidin-1-yl)-5,6,7,8-tetrahydropyrido[3,4-b]pyrazin-3-amine A mixture of 6-benzyl-N-cyclopropyl-2-(4-(2-fluoro-4-methoxyphenoxy)piperidin-1-yl)-5,6,7,8-tetrahydropyrido[3,4-b]pyrazin-3-amine TFA salt (46.8 mg, 0.076 mmol) and $Pd(OH)_2$ on carbon (20 wt %, 5 mg, 0.036 mmol) in THF (760 µL) was stirred under an atmosphere of hydrogen gas (balloon) at rt. After 2 h, the mixture was purified by HPLC Method A to give the title compound as a TFA salt (39.6 mg, 99%) as a yellow oil. $^1$H NMR (400 MHz, methanol-$d_4$) δ ppm 0.52-0.59 (m, 2H), 0.75-0.83 (m, 2H), 1.84-1.97 (m, 2H), 2.02-2.12 (m, 2H), 2.64-2.71 (m, 1H), 2.93-3.16 (m, 4H), 3.35 (s, 2H), 3.52-3.63 (m, 2H), 3.75 (s, 3H), 4.20-4.31 (m, 2H), 4.32-4.40 (m, 1H), 6.63-6.69 (m, 1H), 6.73 (dd, J=12.9, 3.0 Hz, 1H), 7.03-7.10 (m, 1H); ESI-MS m/z $[M+H]^+$ 414.3.

Preparation 92 6-benzyl-N-cyclopropyl-3-(4-((2,4-difluorophenyl)fluoromethyl)piperidin-1-yl)-5,6,7,8-tetrahydropyrido[3,4-b]pyrazin-2-amine A mixture of 4-((2,4-difluorophenyl)fluoromethyl)piperidine hydrochloride (101 mg, 0.381 mmol), 6-benzyl-3-chloro-N-cyclopropyl-5,6,7,8-tetrahydropyrido[3,4-b]pyrazin-2-amine (100 mg, 0.318 mmol), sodium tert-butoxide (92 mg, 0.953 mmol), BINAP (29.7 mg, 0.048 mmol) and Pd$_2$(dba)$_3$ (14.5 mg, 0.016 mmol) in toluene (1.6 mL) was heated at 90° C. for 14 h. The mixture was purified by HPLC Method A to give the title compound as a TFA salt (135.9 mg, 68.8%) as a yellow oil. $^1$H NMR (400 MHz, methanol-d$_4$) δ ppm 0.55 (dt, J=3.5, 1.4 Hz, 2H), 0.77-0.84 (m, 2H), 1.35-1.43 (m, 1H), 1.50-1.71 (m, 2H), 1.91-2.11 (m, 2H), 2.56-2.72 (m, 3H), 3.06-3.15 (m, 2H), 3.36-3.51 (m, 3H), 3.52-3.76 (m, 1H), 4.17 (br s, 2H), 4.52 (s, 2H), 5.50 (dd, J=46.2, 7.6 Hz, 1H) 6.96-7.07 (m, 2H), 7.44-7.60 (m, 6H); ESI-MS m/z [M+H]$^+$ 508.4.

Preparation 93 91 6-benzyl-N-cyclopropyl-2-(4-((2,4-difluorophenyl)fluoromethyl)piperidin-1-yl)-5,6,7,8-tetrahydropyrido[3,4-b]pyrazin-3-amine A mixture of cyclopropanamine (65 μL, 0.943 mmol), 6-benzyl-3-chloro-2-(4-((2,4-difluorophenyl)fluoromethyl)piperidin-1-yl)-5,6,7,8-tetrahydropyrido[3,4-b]pyrazine TFA salt (141.7 mg, 0.236 mmol), sodium tert-butoxide (45.3 mg, 0.472 mmol), BINAP (22.0 mg, 0.035 mmol), and Pd$_2$(dba)$_3$ (10.8 mg, 0.012 mmol) in toluene (800 μL) was heated at 90° C. for 14 h. The mixture was directly purified by HPLC Method A to give the title compound as a TFA salt (98.1 mg, 66.9%) as yellow oil. $^1$H NMR (400 MHz, methanol-d$_4$) δ ppm 0.48-0.54 (m, 2H), 0.71-0.78 (m, 2H), 1.36-1.45 (m, 1H), 1.50-1.72 (m, 2H), 1.92-2.12 (m, 2H), 2.57-2.71 (m, 3H), 2.97-3.10 (m, 2H), 3.39-3.55 (m, 3H), 3.75-3.89 (m, 1H), 4.22 (br s, 2H), 4.53 (br s, 2H), 5.50 (dd, J=46.5, 7.6 Hz, 1H), 6.96-7.07 (m, 2H), 7.45-7.61 (m, 6H); ESI-MS m/z [M+H]$^+$ 508.4.

Preparation 94 N-cyclopropyl-3-(4-((2,4-difluorophenyl)fluoromethyl)piperidin-1-yl)-5,6,7,8-tetrahydropyrido[3,4-b]pyrazin-2-amine A mixture of 6-benzyl-N-cyclopropyl-3-(4-((2,4-difluorophenyl)fluoromethyl)piperidin-1-yl)-5,6,7,8-tetrahydropyrido[3,4-b]pyrazin-2-amine TFA salt (132.1 mg, 0.213 mmol) and Pd(OH)$_2$ (20 wt %, 15 mg, 0.021 mmol) in THF (1.0 mL) was stirred at room temperature under atmosphere of hydrogen gas (balloon). After 2 h, the mixture was directly purified by HPLC Method A to give the title compound as a TFA salt (91.1 mg, 81%) as a yellow oil. $^1$H NMR (400 MHz, methanol-d$_4$) δ ppm 0.55-0.61 (m, 2H), 0.80-0.86 (m, 2H), 1.41 (br d, J=12.4 Hz, 1H), 1.52-1.73 (m, 2H), 1.93-2.13 (m, 2H), 2.60-2.73 (m, 3H), 3.05 (t, J=6.3 Hz, 2H), 3.39-3.52 (m, 2H), 3.55 (t, J=6.3 Hz, 2H), 3.98 (s, 1H), 4.17 (s, 2H), 5.51 (dd, J=46.7, 7.6 Hz, 1H), 6.97-7.08 (m, 2H), 7.45-7.54 (m, 1H); ESI-MS m/z [M+H]$^+$ 418.3.

Preparation 95 N-cyclopropyl-2-(4-((2,4-difluorophenyl)fluoromethyl)piperidin-1-yl)-5,6,7,8-tetrahydropyrido[3,4-b]pyrazin-3-amine A mixture of 6-benzyl-N-cyclopropyl-2-(4-((2,4-difluorophenyl)fluoromethyl)piperidin-1-yl)-5,6,7,8-tetrahydropyrido[3,4-b]pyrazin-3-amine TFA salt (93.5 mg, 0.150 mmol) and Pd(OH)$_2$ (20 wt %, 10 mg, 0.014 mmol) in THF (750 μL) was stirred at room temperature under an atmosphere of hydrogen gas (balloon). After 2 h, the mixture was directly purified by HPLC Method A to give the title compound as a TFA salt (67.7 mg, 85%) as a yellow oil. $^1$H NMR (400 MHz, methanol-d$_4$) δ ppm 0.51-0.57 (m, 2H), 0.75-0.81 (m, 2H), 1.43 (br d, J=13.1 Hz, 1H), 1.52-1.72 (m, 2H), 1.94-2.13 (m, 2H), 2.59-2.72 (m, 3H), 2.97 (t, J=6.3 Hz, 2H), 3.40-3.50 (m, 2H), 3.51-3.56 (m, 2H), 3.98 (s, 1H), 4.22 (s, 2H), 5.51 (dd, J=46.2, 7.3 Hz, 1H), 6.96-7.08 (m, 2H), 7.46-7.54 (m, 1H); ESI-MS m/z [M+H]$^+$ 418.3.

Preparation 96 6-benzyl-3-(4-(2-fluoro-4-methoxyphenoxy)piperidin-1-yl)-N-isopropyl-5,6,7,8-tetrahydropyrido[3,4-b]pyrazin-2-amine A mixture of 4-(2-fluoro-4-methoxyphenoxy)piperidine hydrochloride (72.9 mg, 0.279 mmol), 6-benzyl-3-chloro-N-isopropyl-5,6,7,8-tetrahydropyrido[3,4-b]pyrazin-2-amine TFA salt (100 mg, 0.232 mmol), sodium tert-butoxide (66.9 mg, 0.696 mmol), BINAP (21.7 mg, 0.035 mmol), and Pd$_2$(dba)$_3$ (10.6 mg, 0.012 mmol) in toluene (1.16 mL) was heated at 100° C. in a sealed tube for 14 h. The mixture was purified by HPLC Method A to give the title compound as a TFA salt (122.1 mg, 85%) as a yellow solid. $^1$H NMR (400 MHz, methanol-d$_4$) δ ppm 1.24 (d, J=6.6 Hz, 6H), 1.86-1.97 (m, 2H), 2.03-2.12 (m, 2H), 2.95 (br s, 2H), 3.01-3.12 (m, 2H), 3.33-3.38 (m, 2H), 3.53 (br s, 2H), 3.75 (s, 3H), 4.13-4.24 (m, 3H), 4.31-4.38 (m, 1H), 4.52 (s, 2H), 6.63-6.69 (m, 1H), 6.73 (dd, J=12.8, 2.9 Hz, 1H), 7.06 (t, J=9.2 Hz, 1H), 7.51-7.60 (m, 5H); ESI-MS m/z [M+H]$^+$ 506.4.

Preparation 97 6-benzyl-3-(4-((2,4-difluorophenyl)fluoromethyl)piperidin-1-yl)-N-isopropyl-5,6,7,8-tetrahydropyrido[3,4-b]pyrazin-2-amine A mixture of 4-((2,4-difluorophenyl)fluoromethyl)piperidine hydrochloride (74.0 mg, 0.279 mmol), 6-benzyl-3-chloro-N-isopropyl-5,6,7,8-tetrahydropyrido[3,4-b]pyrazin-2-amine TFA salt (100 mg, 0.232 mmol), sodium tert-butoxide (66.9 mg, 0.696 mmol), BINAP (21.7 mg, 0.035 mmol) and Pd$_2$(dba)$_3$ (10.6 mg, 0.012 mmol) in toluene (1.2 mL) was heated at 100° C. in a sealed tube for 14 h. The mixture was purified by HPLC Method A to give the title compound as a TFA salt (108.3 mg, 74.8%) as a yellow solid. $^1$H NMR (400 MHz, methanol-d$_4$) δ ppm 1.23 (dd, J=6.4, 2.4 Hz, 6H), 1.39-1.47 (m, 1H), 1.51-1.72 (m, 2H), 1.95-2.12 (m, 2H), 2.58-2.70 (m, 2H), 3.04 (br s, 2H), 3.36-3.83 (m, 4H), 4.09-4.21 (m, 3H), 4.51 (br s, 2H), 5.52 (dd, J=46.2, 7.3 Hz, 1H), 6.97-7.07 (m, 2H), 7.45-7.59 (m, 6H); ESI-MS m/z [M+H]$^+$ 510.4.

Preparation 98 3-(4-(2-fluoro-4-methoxyphenoxy)piperidin-1-yl)-N-isopropyl-5,6,7,8-tetrahydropyrido[3,4-b]pyrazin-2-amine A mixture of 6-benzyl-3-(4-(2-fluoro-4-methoxyphenoxy)piperidin-1-yl)-N-isopropyl-5,6,7,8-tetrahydropyrido[3,4-b]pyrazin-2-amine TFA salt (122 mg, 0.197 mmol) and Pd(OH)$_2$ on carbon (20 wt %, 12 mg, 0.017 mmol) in THF (2.0 mL) was stirred under an atmosphere of hydrogen gas (balloon) at rt. After 2 h, the mixture was purified by HPLC Method A to give the title compound as a TFA salt (83.2 mg, 80%) as a yellow oil. $^1$H NMR (400 MHz, methanol-d$_4$) δ ppm 1.25 (d, J=6.6 Hz, 6H), 1.88-1.98 (m, 2H), 2.04-2.13 (m, 2H), 2.93-3.03 (m, 4H), 3.35-3.41 (m, 3H), 3.54 (t, J=6.3 Hz, 2H), 3.76 (s, 3H), 4.14-4.18 (m, 2H), 4.18-4.23 (m, 1H), 4.32-4.40 (m, 1H), 6.67 (ddd, J=9.0, 3.0, 1.4 Hz, 1H), 6.74 (dd, J=12.9, 3.0 Hz, 1H), 7.07 (t, J=9.2 Hz, 1H); ESI-MS m/z [M+H]$^+$ 416.3.

Preparation 99 3-(4-((2,4-difluorophenyl)fluoromethyl)piperidin-1-yl)-N-isopropyl-5,6,7,8-tetrahydropyrido[3,4-b]pyrazin-2-amine A mixture of 6-benzyl-3-(4-((2,4-difluorophenyl)fluoromethyl)piperidin-1-yl)-N-isopropyl-5,6,7,8-tetrahydropyrido[3,4-b]pyrazin-2-amine TFA salt (108.3 mg, 0.174 mmol) and Pd(OH)$_2$ on carbon, (20 wt %, 11 mg, 0.016 mmol) in THF (1.7 mL) was stirred under an atmosphere of hydrogen gas (balloon) at rt. After 2 h, the mixture was purified by HPLC Method A to give the title compound as a TFA salt (67.5 mg, 72.9%) as a yellow film. $^1$H NMR (400 MHz, methanol-d$_4$) δ ppm 1.24 (dd, J=6.6, 2.3 Hz, 6H), 1.41-1.48 (br m, 1H), 1.52-1.74 (m, 2H), 1.97-2.14 (m, 2H), 2.61-2.73 (m, 2H), 2.99 (t, J=6.3 Hz, 2H), 3.38-3.49 (m, 2H), 3.50-3.55 (m, 2H), 4.14 (s, 2H), 4.14-4.21 (m, 1H), 5.53 (dd, J=46.5, 7.3 Hz, 1H), 6.95-7.10 (m, 2H), 7.46-7.55 (m, 1H); ESI-MS m/z [M+H]$^+$ 420.3.

Preparation 100 6-benzyl-2-(4-(2-fluoro-4-methoxyphenoxy)piperidin-1-yl)-N-isopropyl-5,6,7,8-tetrahydropyrido[3,4-b]pyrazin-3-amine A mixture of propan-2-amine (71 µL, 0.827 mmol), 6-benzyl-3-chloro-2-(4-(2-fluoro-4-methoxyphenoxy)piperidin-1-yl)-5,6,7,8-tetrahydropyrido[3,4-b]pyrazine TFA salt (123.4 mg, 0.207 mmol), sodium tert-butoxide (39.7 mg, 0.413 mmol), BINAP (19.3 mg, 0.031 mmol) and Pd$_2$(dba)$_3$ (9.5 mg, 10.33 µmol) in toluene (690 µL) was heated at 100° C. for 16 h. The mixture was then purified by HPLC Method A to give the title compound as a TFA salt (54.7 mg, 42.7%) as a yellow film. $^1$H NMR (400 MHz, methanol-d$_4$) δ ppm 1.22 (d, J=6.6 Hz, 6H), 1.87-2.13 (m, 4H), 2.94-3.10 (m, 4H), 3.35-3.53 (m, 3H), 3.75 (s, 3H), 3.79-3.88 (m, 1H), 4.07-4.27 (m, 3H), 4.31-4.39 (m, 1H), 4.52 (br s, 2H), 6.66 (ddd, J=8.9, 3.0, 1.5 Hz, 1H), 6.73 (dd, J=12.9, 3.0 Hz, 1H), 7.03-7.10 (m, 1H), 7.51-7.60 (m, 5H); ESI-MS m/z [M+H]$^+$ 506.4.

Preparation 101 6-benzyl-2-(4-((2,4-difluorophenyl)fluoromethyl)piperidin-1-yl)-N-isopropyl-5,6,7,8-tetrahydropyrido[3,4-b]pyrazin-3-amine A mixture of propan-2-amine (82 µL, 0.954 mmol), 6-benzyl-3-chloro-2-(4-((2,4-difluorophenyl)fluoromethyl) piperidin-1-yl)-5,6,7,8-tetrahydropyrido[3,4-b]pyrazine TFA (143.3 mg, 0.238 mmol), sodium tert-butoxide (45.8 mg, 0.477 mmol), BINAP (22.3 mg, 0.036 mmol) and Pd$_2$(dba)$_3$ (10.9 mg, 0.012 mmol) in toluene (800 µL) at 100° C. for 16 h. The mixture was then purified by HPLC Method A to give the title compound as a TFA salt (63.8 mg, 42.9%) as a yellow film. $^1$H NMR (400 MHz, methanol-d$_4$) δ ppm 1.21 (dd, J=6.4, 2.4 Hz, 6H), 1.40-1.48 (m, 1H), 1.51-1.74 (m, 2H), 1.95-2.16 (m, 2H), 2.61-2.73 (m, 2H), 3.00 (br s, 2H), 3.40-3.57 (m, 3H), 4.06-4.13 (m, 2H), 4.15-4.20 (br m, 1H), 4.51 (br s, 2H), 5.52 (dd, J=46.0, 7.3 Hz, 1H), 6.97-7.08 (m, 2H), 7.46-7.62 (m, 6H); ESI-MS m/z [M+H]$^+$ 510.4.

Preparation 102 2-(4-(2-fluoro-4-methoxyphenoxy) piperidin-1-yl)-N-isopropyl-5,6,7,8-tetrahydropyrido [3,4-b]pyrazin-3-amine A mixture of 6-benzyl-2-(4-(2-fluoro-4-methoxyphenoxy)piperidin-1-yl)-N-isopropyl-5,6,7,8-tetrahydropyrido [3,4-b]pyrazin-3-amine TFA salt (51 mg, 0.082 mmol) and Pd(OH)$_2$ on carbon (20 wt %, 5 mg, 7.12 µmol) in THF (820 µL) was stirred under an atmosphere of hydrogen gas (balloon) at rt. After 2 h, the mixture was purified by HPLC Method A to give the title compound as a TFA salt (41.2 mg, 95%) as a yellow foam. $^1$H NMR (400 MHz, methanol-d$_4$) δ ppm 1.24 (d, J=6.6 Hz, 6H), 1.88-1.98 (m, 2H), 2.05-2.14 (m, 2H), 2.94-3.03 (m, 4H), 3.35-3.43 (m, 2H), 3.54 (t, J=6.3 Hz, 2H), 3.76 (s, 3H), 4.10-4.21 (m, 3H), 4.32-4.39 (m, 1H), 6.67 (ddd, J=8.9, 3.0, 1.5 Hz, 1H), 6.74 (dd, J=12.8, 2.9 Hz, 1H), 7.07 (t, J=9.2 Hz, 1H); ESI-MS m/z [M+H]$^+$ 416.3.

Preparation 103 2-(4-((2,4-difluorophenyl)fluoromethyl)piperidin-1-yl)-N-isopropyl-5,6,7,8-tetrahydropyrido[3,4-b]pyrazin-3-amine A mixture of 6-benzyl-2-(4-((2,4-difluorophenyl)fluoromethyl)piperidin-1-yl)-N-isopropyl-5,6,7,8-tetrahydropyrido[3,4-b]pyrazin-3-amine TFA salt (60 mg, 0.096 mmol) and Pd(OH)$_2$ on carbon, (20 wt %, 6 mg, 8.54 µmol) in THF (960 µL) was stirred under an atmosphere of hydrogen gas (balloon) at rt. After 2 h, the mixture was purified by HPLC Method A to give the title compound as a TFA salt (47.6 mg, 93%) as a yellow foam. $^1$H NMR (400 MHz, methanol-d$_4$) δ ppm 1.23 (dd, J=6.4, 2.4 Hz, 6H), 1.41-1.49 (m, 1H), 1.52-1.74 (m, 2H), 1.98-2.14 (m, 2H), 2.68 (qd, J=12.6, 2.5 Hz, 2H), 2.96 (t, J=6.3 Hz, 2H), 3.40-3.51 (m, 2H), 3.52 (t, J=6.3 Hz, 2H), 4.10-4.16 (m, 1H), 4.16 (s, 2H), 5.53 (dd, J=46.5, 7.6 Hz, 1H), 6.97-7.08 (m, 2H), 7.47-7.55 (m, 1H); ESI-MS m/z [M+H]$^+$ 420.3.

Preparation 104 2-(4-(2,4-difluorophenoxy)piperidin-1-yl)-N-isopropyl-5,6,7,8-tetrahydropyrido[3,4-b]pyrazin-3-amine A mixture of 6-benzyl-2-(4-(2,4-difluorophenoxy)piperidin-1-yl)-N-isopropyl-5,6,7,8-tetrahydropyrido[3,4-b] pyrazin-3-amine (6.43 g, 13.03 mmol) and 10% Pd/C (640 mg) in MeOH (86 mL) under H$_2$ in a balloon was stirred at room temperature overnight. Removal of the solvent gave the title compound (4.4 g, 84%) as a yellow oil. $^1$H NMR (400 MHz, methanol-d$_4$) δ ppm 1.24 (d, J=6.4 Hz, 6H), 1.89-1.99 (m, 2H), 2.09-2.17 (m, 2H), 2.74 (t, J=5.9 Hz, 2H), 2.95 (ddd, J=12.3, 8.7, 3.4 Hz, 2H), 3.11 (t, J=6.1 Hz, 2H), 3.82 (s, 2H), 4.14 (septet, J=6.4 Hz, 1H), 4.46 (tt, J=7.7, 3.5 Hz, 1H), 6.85-6.92 (m, 1H), 6.99 (ddd, J=11.4, 8.4, 3.2 Hz, 1H), 7.18 (td, J=9.3, 5.4 Hz, 1H); ESI-MS m/z [M+H]$^+$ 404.0.

Preparation 105 2-(4-(2,4-difluorobenzyl)piperazin-1-yl)-N-isopropyl-5,6,7,8-tetrahydropyrido[3,4-b] pyrazin-3-amine To a solution of 1-(2-(4-(2,4-difluorobenzyl)piperazin-1-yl)-3-(isopropylamino)-7,8-dihydropyrido[3,4-b]pyrazin-6 (5H)-yl)ethanone (0.367 g, 0.826 mmol) in MeOH (4 mL) was added NaOH, 15% solution (2.201 g, 8.26 mmol) at 23° C. The reaction mixture was stirred at 65° C. for 16 hr, cooled to 23° C., and neutralized with 1N HCl (9.5 mL) to furnish a suspension. The crude mixture was concentrated via rotary evaporation, cooled to 23° C., and stirred overnight. The resulting solid was filtered, rinsed with water, and dried in vacuo to give the title compound (253 mg, 76%) as a yellow foam. $^1$H NMR (500 MHz, DMSO-d$_6$) δ ppm 1.15 (d, J=6.8 Hz, 6H), 2.42 (br s, 1H), 2.51-2.61 (m, 6H), 2.89-3.00 (m, 6H), 3.58 (s, 2H), 3.63 (s, 2H), 4.00-4.10 (m, 1H), 5.15 (d, J=8.3 Hz, 1H), 7.04-7.11 (m, 1H), 7.21 (td, J=10.0, 2.4 Hz, 1H), 7.44-7.52 (m, 1H); ESI-MS m/z [M+H]$^+$ 403.0.

Preparation 106 4-((1-(6-benzyl-2-(isopropylamino)-5,6,7,8-tetrahydropyrido[3,4-b]pyrazin-3-yl)piperidin-4-yl)oxy)-3-fluorobenzonitrile A mixture of 6-benzyl-3-chloro-N-isopropyl-5,6,7,8-tetrahydropyrido[3,4-b]pyrazin-2-amine acetate (2.765 g, 2.93 mmol), 3-fluoro-4-(piperidin-4-yloxy)benzonitrile hydrochloride (0.904 g, 3.52 mmol), sodium tert-butoxide (1.128 g, 11.74 mmol), BINAP (0.274 g, 0.440 mmol), and Pd$_2$(dba)$_3$ (0.134 g, 0.147 mmol) in toluene (25 mL) was stirred at 100° C. for 22 h. Additional portions of BINAP (0.219 g, 0.352 mmol) and Pd$_2$(dba)$_3$ (0.107 g, 0.117 mmol) were added to the flask and the reaction mixture was stirred for an additional 2 days at 100° C. The mixture was cooled to 23° C., filtered through Celite™ rinsed with toluene, and the filtrate was concentrated via rotary evaporation. The crude material was dissolved in DMSO (10 mL), filtered, rinsed with DMSO, and purified by HPLC Method B, with the exception that a Waters XSelect® CSH C18, 5 µm, ID 4.6×50 mm was used, using an ACN gradient of 30% to 70% to give the title compound as a TFA salt (581 mg, 32.2% yield) as a yellow oil. $^1$H NMR (400 MHz, DMSO-d$_6$) δ ppm 1.05-1.33 (m, 6H), 1.81-1.96 (m, 2H), 2.08-2.18 (m, 2H), 2.84-3.00 (m, 3H), 3.01-3.17 (m, 1H), 3.18-3.32 (m, 2H), 3.33-3.46 (m, 1H), 3.65-3.77 (m, 1H), 3.95-4.06 (m, 1H), 4.08-4.30 (m, 2H), 4.43-4.57 (m, 2H), 4.80-4.87 (m, 1H), 5.91 (d, J=8.1 Hz, 1H), 7.44-7.60 (m, 6H), 7.66-7.70 (m, 1H), 7.84-7.90 (m, 1H), 10.13 (br s, 1H); ESI-MS m/z [M+H]$^+$ 501.5.

Preparation 107 3-fluoro-4-((1-(2-(isopropylamino)-5,6,7,8-tetrahydropyrido[3,4-b]pyrazin-3-yl)piperidin-4-yl)oxy)benzonitrile A mixture of 4-((1-(6-benzyl-2-(isopropylamino)-5,6,7,8-tetrahydropyrido[3,4-b]pyrazin-3-yl)piperidin-4-yl)oxy)-3-fluorobenzonitrile 2,2,2-trifluoroacetate (579 mg, 0.942 mmol) and Pd(OH)$_2$ (20 wt % Pd (dry basis) on carbon, wet, Degussa Type E101 NE/W, 198 mg, 0.283 mmol) in THF (10 mL) was stirred under H$_2$ (1.899 mg, 0.942 mmol) at 23° C. for 4 h. The mixture was filtered, rinsed with THF, concentrated via rotary evaporation, and dried in vacuo to give the title compound as a TFA salt (494 mg, 100%) as a brown oil. ESI-MS m/z [M+H]$^+$ 411.4.

Preparation 108 (5-chloro-2-fluorophenyl)(1-(2-(isopropylamino)-5,6,7,8-tetrahydropyrido[3,4-b]pyrazin-3-yl)piperidin-4-yl)methanone A mixture of (5-chloro-2-fluorophenyl)(piperidin-4-yl)methanone hydrochloride (69.7 mg, 0.251 mmol), 6-benzyl-3-chloro-N-isopropyl-5,6,7,8-tetrahydropyrido[3,4-b]pyrazin-2-amine TFA salt (90 mg, 0.209 mmol), sodium tert-butoxide (60.2 mg, 0.627 mmol), BINAP (19.5 mg, 0.031 mmol) and Pd$_2$(dba)$_3$ (9.6 mg, 10.4 µmol) in toluene (1.04 mL) was heated at 100° C. for 16 h. The mixture was purified by HPLC Method A to afford (1-(6-benzyl-2-(isopropylamino)-5,6,7,8-tetrahydropyrido[3,4-b]pyrazin-3-yl)piperidin-4-yl)(5-chloro-2-fluorophenyl)methanone as its TFA salt (48.9 mg, 36.8%) as a yellow oil. ESI-MS m/z [M+H]$^+$ 523.4.

A mixture of (1-(6-benzyl-2-(isopropylamino)-5,6,7,8-tetrahydropyrido[3,4-b]pyrazin-3-yl)piperidin-4-yl)(5-chloro-2-fluorophenyl)methanone TFA salt (48.9 mg, 0.077 mmol) and Pd(OH)$_2$ on carbon (20 wt %, 5 mg, 0.036 mmol) in THF (384 µL) was stirred at rt under an atmosphere of hydrogen gas (balloon). After 3 h, the mixture was diluted with MeOH, filtered through a pad of Celite™, washing with MeOH, and concentrated to afford the title compound as its TFA salt (37.1 mg, 88%) as a yellow film, which was used without further purification. ESI-MS m/z [M+H]$^+$ 432.3.

Preparation 109 3-(4-(2,4-difluorophenoxy)piperidin-1-yl)-N-isopropyl-5,6,7,8-tetrahydropyrido[3,4-b]pyrazin-2-amine A mixture of 4-(2,4-difluorophenoxy)piperidine hydrochloride (62.6 mg, 0.251 mmol), 6-benzyl-3-chloro-N-isopropyl-5,6,7,8-tetrahydropyrido[3,4-b]pyrazin-2-amine TFA salt (90 mg, 0.209 mmol), sodium tert-butoxide (60.2 mg, 0.627 mmol), BINAP (19.5 mg, 0.031 mmol) and Pd$_2$(dba)$_3$ (9.6 mg, 10.4 µmol) in toluene (1.04 mL) was heated at 100° C. for 16 h. The mixture was purified by HPLC Method A to afford 6-benzyl-3-(4-(2,4-difluorophenoxy)piperidin-1-yl)-N-isopropyl-5,6,7,8-tetrahydropyrido[3,4-b]pyrazin-2-amine as its TFA salt (73.0 mg, 57.5%) as a yellow oil. ESI-MS m/z [M+H]$^+$ 494.4.

A mixture of 6-benzyl-3-(4-(2,4-difluorophenoxy)piperidin-1-yl)-N-isopropyl-5,6,7,8-tetrahydropyrido[3,4-b]pyrazin-2-amine TFA salt (73.0 mg, 0.120 mmol) and Pd(OH)$_2$ on carbon (20 wt %, 7 mg, 9.97 µmol) in THF (601 µL) was stirred at rt under an atmosphere of hydrogen (balloon). After 3 h, the mixture was diluted with MeOH, filtered through a pad of Celite™, washing with MeOH, and concentrated to afford the title compound as its TFA salt (62.3 mg, 100%) as a yellow oil, which was used without further purification. ESI-MS m/z [M+H]$^+$ 404.3.

Preparation 110 N-(2,2-difluoroethyl)-3-(4-(2,4-difluorophenoxy)piperidin-1-yl)-5,6,7,8-tetrahydropyrido[3,4-b]pyrazin-2-amine A solution of 6-benzyl-3-chloro-N-(2,2-difluoroethyl)-5,6,7,8-tetrahydropyrido[3,4-b]pyrazin-2-amine TFA salt (150 mg, 0.331 mmol), 4-(2,4-difluorophenoxy)piperidine hydrochloride (99 mg, 0.398 mmol), Pd$_2$(dba)$_3$ (15.2 mg, 0.017 mmol), BINAP (20.63 mg, 0.033 mmol), and sodium tert-butoxide (96 mg, 0.994 mmol), in toluene (1104 µL) was stirred at 90° C. overnight. The solvent was removed and the crude product diluted in DMF, filtered through a hydrophilic PTFE 0.45 µm filter (Millipore® Millex-LCR), and purified via HPLC Method A to give 6-benzyl-N-(2,2-difluoroethyl)-3-(4-(2,4-difluorophenoxy)piperidin-1-yl)-5,6,7,8-tetrahydropyrido[3,4-b]pyrazin-2-amine as a TFA salt (152 mg).

A solution of 6-benzyl-N-(2,2-difluoroethyl)-3-(4-(2,4-difluorophenoxy)piperidin-1-yl)-5,6,7,8-tetrahydropyrido[3,4-b]pyrazin-2-amine TFA salt (152 mg, 0.241 mmol) and Pd(OH)$_2$ on carbon (33.9 mg, 0.048 mmol) in THF (2.41 mL) was purged with and placed under hydrogen (balloon) atmosphere at room temperature for 2 h. The mixture was then filtered through Celite™ and concentrated to give the title compound as a TFA salt (115 mg, 0.213 mmol).

Preparation 111 N-(tert-butyl)-3-(4-(2,4-difluorophenoxy)piperidin-1-yl)-5,6,7,8-tetrahydropyrido[3,4-b]pyrazin-2-amine A solution of sodium tert-butoxide (81 mg, 0.843 mmol), 6-benzyl-N-(tert-butyl)-3-chloro-5,6,7,8-tetrahydropyrido[3,4-b]pyrazin-2-amine TFA salt (125 mg, 0.281 mmol), Pd$_2$(dba)$_3$ (12.86 mg, 0.014 mmol), 4-(2,4-difluorophenoxy)piperidine hydrochloride (84 mg, 0.337 mmol), and BINAP (17.50 mg, 0.028 mmol) in toluene (937 µL) was stirred at 90° C. overnight. The crude reaction mixture was diluted in DMF, filtered through a hydrophilic PTFE 0.45 µm filter (Millipore® Millex-LCR), and purified via HPLC Method A to give 6-benzyl-N-(tert-butyl)-3-(4-(2,4-difluorophenoxy)piperidin-1-yl)-5,6,7,8-tetrahydropyrido[3,4-b]pyrazin-2-amine as a TFA salt (155 mg).

A solution of 6-benzyl-N-(tert-butyl)-3-(4-(2,4-difluorophenoxy)piperidin-1-yl)-5,6,7,8-tetrahydropyrido[3,4-b]pyrazin-2-amine TFA salt (155 mg, 0.249 mmol) and Pd(OH)$_2$ on carbon (35.0 mg, 0.050 mmol) in THF (2.49 mL) was purged and placed under hydrogen (balloon) atmosphere for 2 h. Filtration through Celite™ and concentration gave the title compound as a TFA salt (125 mg).

Preparation 112 N-cyclobutyl-3-(4-(2-fluoro-4-methoxyphenoxy)piperidin-1-yl)-5,6,7,8-tetrahydropyrido[3,4-b]pyrazin-2-amine A mixture of 2,3-dichloropyrido[3,4-b]pyrazine (100 mg, 0.500 mmol), cyclobutanamine (47.0 µL, 0.550 mmol) and DIPEA (260 µL, 1.500 mmol) was stirred at 0° C. for 15 min then at rt for 30 min. Saturated aqueous NH$_4$Cl was added to the mixture and the product was extracted with EtOAc. The combined organic layers were filtered through a pad of silica (EtOAc wash) and the filtrate was concentrated to afford 3-chloro-N-cyclobutylpyrido[3,4-b]pyrazin-2-amine (116.1 mg, 99%) as a yellow solid, which was used without further purification. ESI-MS m/z [M+H]$^+$ 235.2.

A mixture of 3-chloro-N-cyclobutylpyrido[3,4-b]pyrazin-2-amine (116 mg, 0.494 mmol) and benzyl bromide (59.1 µL, 0.494 mmol) in ACN (2.47 mL) was heated at 80° C. for 3 h. After cooling to rt, the mixture was treated with sodium triacetoxyborohydride (314 mg, 1.483 mmol) at rt. The mixture was purified by HPLC Method A to afford 6-benzyl-3-chloro-N-cyclobutyl-5,6,7,8-tetrahydropyrido[3,4-b]pyrazin-2-amine as its TFA salt (135.3 mg, 61.8%) as a yellow solid. ESI-MS m/z [M+H]$^+$ 329.3.

A mixture of 4-(2-fluoro-4-methoxyphenoxy)piperidine hydrochloride (56.7 mg, 0.217 mmol), 6-benzyl-3-chloro-N-cyclobutyl-5,6,7,8-tetrahydropyrido[3,4-b]pyrazin-2-amine TFA salt (80 mg, 0.181 mmol), sodium tert-butoxide (52.1 mg, 0.542 mmol), BINAP (16.9 mg, 0.027 mmol) and Pd$_2$(dba)$_3$ (24.8 mg, 0.027 mmol) in toluene (602 µL) was heated at 90° C. in a sealed tube for 16 h. The mixture was purified by HPLC Method A to afford 6-benzyl-N-cyclobutyl-3-(4-(2-fluoro-4-methoxyphenoxy)piperidin-1-yl)-5,6,7,8-tetrahydropyrido[3,4-b]pyrazin-2-amine as its TFA salt (85.2 mg, 74.7%) as a yellow foam. ESI-MS m/z [M+H]$^+$ 518.4.

A mixture of 6-benzyl-N-cyclobutyl-3-(4-(2-fluoro-4-methoxyphenoxy)piperidin-1-yl)-5,6,7,8-tetrahydropyrido[3,4-b]pyrazin-2-amine TFA salt (85.2 mg, 0.135 mmol) and Pd(OH)$_2$ on carbon (10 mg, 0.071 mmol) in THF (674 µL) was stirred at rt under an atmosphere of hydrogen gas (balloon). After 4 h, the mixture was filtered, washing with MeOH, and concentrated to afford the title compound as its TFA salt (73 mg, 100%) as a yellow solid, which was used without further purification. ESI-MS m/z [M+H]$^+$ 428.4.

Preparation 113 N-cyclopropyl-3-(4-(2,4-difluorophenoxy)piperidin-1-yl)-5-methyl-5,6,7,8-tetrahydropyrido[3,4-b]pyrazin-2-amine 2,3-Dichloro-5-methylpyrido[3,4-b]pyrazine (1.700 g, 7.94 mmol) was added to dioxane (15.88 mL), then cyclopropanamine (0.864 mL, 12.71 mmol) and DIPEA (2.24 mL, 13.50 mmol) were added sequentially. The mixture was stirred for 12 h at room temperature then concentrated under reduced pressure. Column chromatography using a gradient of 10% to 75% EtOAc in hexanes provided 3-chloro-N-cyclopropyl-5-methylpyrido[3,4-b]pyrazin-2-amine (1.3 g) as a brown solid.

Combined 3-chloro-N-cyclopropyl-5-methylpyrido[3,4-b]pyrazin-2-amine (350 mg, 1.491 mmol) and benzyl bromide (177 µL, 1.491 mmol) in ACN (5.97 mL) was heated at 80° C. overnight, then cooled to room temperature and sodium triacetoxyborohydride (948 mg, 4.47 mmol) was added. After stirring for 1 h, the reaction mixture was poured into 1 M NaOH, extracted with ethyl acetate (2×), concentrated in vacuo, and purified by HPLC Method A gave 6-benzyl-3-chloro-N-cyclopropyl-5-methyl-5,6,7,8-tetrahydropyrido[3,4-b]pyrazin-2-amine as a TFA salt (424 mg).

Combined 6-benzyl-3-chloro-N-cyclopropyl-5-methyl-5,6,7,8-tetrahydropyrido[3,4-b]pyrazin-2-amine TFA salt (106 mg, 0.239 mmol), 4-(2,4-difluorophenoxy)piperidine hydrochloride (65.7 mg, 0.263 mmol), Pd$_2$(dba)$_3$ (21.9 mg, 0.024 mmol), sodium tert-butoxide (57.5 mg, 0.598 mmol), and BINAP (29.8 mg, 0.048 mmol) in toluene (798 µL) was heated at 90° C. overnight. Purification by HPLC Method A gave 6-benzyl-N-cyclopropyl-3-(4-(2,4-difluorophenoxy)piperidin-1-yl)-5-methyl-5,6,7,8-tetrahydropyrido[3,4-b]pyrazin-2-amine as a TFA salt (110 mg).

Combined 6-benzyl-N-cyclopropyl-3-(4-(2,4-difluorophenoxy)piperidin-1-yl)-5-methyl-5,6,7,8-tetrahydropyrido[3,4-b]pyrazin-2-amine TFA salt (110 mg, 0.178 mmol) and Pd(OH)$_2$ (20 wt %, 12.5 mg, 0.018 mmol) in THF (888 µL) was purged with hydrogen and allowed to stir under hydrogen (balloon) overnight. The reaction mixture was filtered through Celite™, washed with EtOAc, and concentrated under reduced pressure to give the title compound as a TFA salt (78 mg).

Preparation 114 3-(4-(2,4-difluorophenoxy)piperidin-1-yl)-N-isopropyl-5-methyl-5,6,7,8-tetrahydropyrido[3,4-b]pyrazin-2-amine A solution of 6-benzyl-3-(4-(2,4-difluorophenoxy)piperidin-1-yl)-N-isopropyl-5-methyl-5,6,7,8-tetrahydropyrido[3,4-b]pyrazin-2-amine TFA salt (150 mg, 0.241 mmol) and Pd(OH)$_2$ on carbon (16.9 mg, 0.024 mmol) in THF (1.21 mL) was purged and placed under hydrogen atmosphere (balloon) overnight. The mixture was then filtered through Celite™ and concentrated to give the title compound as its TFA salt (132 mg).

Preparation 115 N-(2,2-difluoroethyl)-3-(4-(2,4-difluorophenoxy)piperidin-1-yl)-5-methyl-5,6,7,8-tetrahydropyrido[3,4-b]pyrazin-2-amine A solution of 6-benzyl-N-(2,2-difluoroethyl)-3-(4-(2,4-difluorophenoxy)piperidin-1-yl)-5-methyl-5,6,7,8-tetrahydropyrido[3,4-b]pyrazin-2-amine TFA salt (160 mg, 0.249 mmol) and Pd(OH)$_2$ on carbon (17.5 mg, 0.025 mmol) in THF (1.24 mL) was purged and placed under hydrogen atmosphere (balloon) overnight. The mixture was filtered through Celite™ and concentrated to give title compound as its TFA salt (136 mg).

Preparation 116 N-(2,2-difluoroethyl)-3-(4-(2,4-difluorophenoxy)piperidin-1-yl)-7-methyl-5,6,7,8-tetrahydropyrido[3,4-b]pyrazin-2-amine A solution of 2,3-dichloro-7-methylpyrido[3,4-b]pyrazine (125 mg, 0.584 mmol), 2,2-difluoroethanamine (53.6 µL, 0.701 mmol), and DIPEA (306 µL, 1.752 mmol) in DCM (1.17 mL) was stirred at room temperature for 48 h, then poured into a saturated aqueous solution of NH₄Cl and extracted twice with EtOAc. The extracts were combined, filtered through MgSO₄, and concentrated to give 3-chloro-N-(2,2-difluoroethyl)-7-methylpyrido[3,4-b]pyrazin-2-amine (143 mg, 95%).

A solution of 3-chloro-N-(2,2-difluoroethyl)-7-methyl-pyrido[3,4-b]pyrazin-2-amine (143 mg, 0.553 mmol) and benzyl bromide (65.8 µL, 0.553 mmol) in ACN (2.76 mL) was stirred at 100° C. overnight, cooled to room temperature, then treated with sodium triacetoxyhydroborate (352 mg, 1.659 mmol) and stirred for 3 h. The mixture was poured into 1 M NaOH, extracted twice with EtOAc, and the EtOAc extracts were combined and concentrated. The crude material was diluted in DMF, filtered through a hydrophilic PTFE 0.45 µm filter (Millipore® Millex-LCR), and purified via HPLC Method A to give 6-benzyl-N-(2,2-difluoroethyl)-3-(4-(2,4-difluorophenoxy)piperidin-1-yl)-7-methyl-5,6,7,8-tetrahydropyrido[3,4-b]pyrazin-2-amine as a TFA salt (120 mg, 46.5%).

A solution of 6-benzyl-3-chloro-N-(2,2-difluoroethyl)-7-methyl-5,6,7,8-tetrahydropyrido[3,4-b]pyrazin-2-amine TFA salt (120 mg, 0.257 mmol), 4-(2,4-difluorophenoxy) piperidine hydrochloride (77 mg, 0.308 mmol), Pd₂(dba)₃ (23.5 mg, 0.026 mmol), BINAP (32.0 mg, 0.051 mmol), and sodium tert-butoxide (74.1 mg, 0.771 mmol), in toluene (1.28 mL) was stirred at 100° C. overnight. The crude reaction mixture was diluted in DMF, filtered through a hydrophilic PTFE 0.45 µm filter (Millipore® Millex-LCR), and purified via HPLC Method A to give 6-benzyl-N-(2,2-difluoroethyl)-3-(4-(2,4-difluorophenoxy)piperidin-1-yl)-7-methyl-5,6,7,8-tetrahydropyrido[3,4-b]pyrazin-2-amine as a TFA salt (135 mg, 82%).

A solution of 6-benzyl-N-(2,2-difluoroethyl)-3-(4-(2,4-difluorophenoxy)piperidin-1-yl)-7-methyl-5,6,7,8-tetrahydropyrido[3,4-b]pyrazin-2-amine TFA salt (135 mg, 0.210 mmol) and Pd(OH)₂ on carbon (14.7 mg, 0.021 mmol) in THF (1.05 mL) was purged and stirred under hydrogen atmosphere for 3 h. The reaction mixture was filtered through Celite™ and the solvent was removed to give the title compound as a TFA salt (107 mg, 92%).

Example 1 cyclopropyl(2-(4-(2,4-difluorophenoxy) piperidin-1-yl)-3-(isopropylamino)-7,8-dihydro-pyrido[3,4-b]pyrazin-6(5H)-yl)methanone

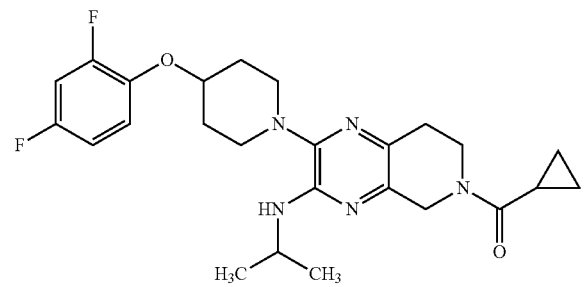 [SMILES: CC(C)Nc1nc2c(nc1N1CCC(Oc3ccc(F)cc3F)CC1)CCN(C(=O)C1CC1)C2]

To a solution of 2-(4-(2,4-difluorophenoxy)piperidin-1-yl)-N-isopropyl-5,6,7,8-tetrahydropyrido[3,4-b]pyrazin-3-amine TFA salt (18.0 mg, 0.035 mmol) in DCM (348 µL) at room temperature was added triethylamine (14.5 µL, 0.104 mmol) and cyclopropanecarbonyl chloride (6.4 µL, 0.070 mmol). The reaction was stirred for 10 min at room temperature. The reaction mixture was concentrated under reduced pressure and was purified by HPLC Method B, with the exception that a Waters SunFire™ C18, 5 µm, ID 30×75 mm column was used, using a 50% to 90% ACN gradient to give the title compound, as a TFA salt, as a yellow film (3.3 mg, 16%). ¹H NMR (400 MHz, methanol-d4, mixture of rotamers) δ ppm 0.81-0.96 (m, 4H), 1.29 (m, 7H), 1.90-2.18 (m, 4H), 2.73 (m, 0.7H), 2.87 (m, 1.3H), 3.07 (m, 2H), 3.42 (m, 2H), 3.88 (m, 0.7H), 4.06 (t, J=5.7 Hz, 1.3H), 4.14 (m, 1H), 4.49 (m, 1H), 4.62 (s, 1.3H), 4.80 (s, 0.7H), 6.88 (m, 1H), 6.99 (ddd, J=11.2, 8.5, 3.0 Hz, 1H), 7.18 ppm (td, J=9.2, 5.6 Hz, 1H); ESI-MS m/z [M+H]⁺ 472.5.

Example 2 1-(2-(4-(2,4-difluorophenoxy)piperidin-1-yl)-3-(isopropylamino)-7,8-dihydropyrido[3,4-b] pyrazin-6(5H)-yl)-2-methoxyethan-1-one

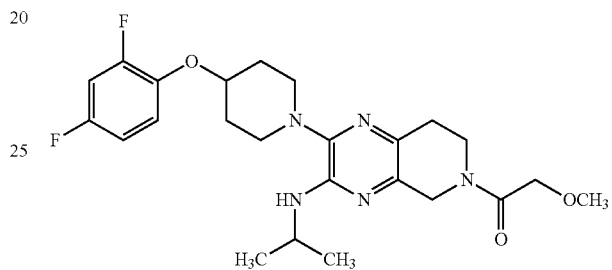

To a solution of 2-(4-(2,4-difluorophenoxy)piperidin-1-yl)-N-isopropyl-5,6,7,8-tetrahydropyrido[3,4-b]pyrazin-3-amine TFA salt (39.0 mg, 0.075 mmol) in DCM (754 µL) at 0° C. was added triethylamine (31.5 µL, 0.226 mmol) and 2-methoxyacetyl chloride (13.8 µL, 0.151 mmol). The reaction was stirred at 0° C. for 30 min. The reaction mixture was concentrated under reduced pressure and was purified by HPLC Method B, with the exception that a Waters Sun-Fire™ C18, 5 µm, ID 30×75 mm column was used, using a 55% to 80% ACN gradient to give the title compound, as a TFA salt, as a yellow oil (14.0 mg, 31.5%). ¹H NMR (400 MHz, methanol-d4, mixture of rotamers) δ ppm 1.30 (m, 6H), 1.96 (m, 2H), 2.13 (m, 2H), 2.75 (t, J=5.7 Hz, 0.7H), 2.83 (t, J=5.7 Hz, 1.3H), 3.08 (m, 2H), 3.44 (m, 5H), 3.77 (t, J=5.8 Hz, 1.3H), 3.88 (t, J=5.9 Hz, 0.7H), 4.14 (m, 1H), 4.24 (s, 0.7H), 4.28 (s, 1.3H), 4.49 (td, J=7.1, 3.5 Hz, 1H), 4.56 (s, 0.7H), 4.63 (s, 1.3H), 6.88 (m, 1H), 6.99 (ddd, J=11.2, 8.5, 3.0 Hz, 1H), 7.18 (td, J=9.2, 5.6 Hz, 1H); ESI-MS m/z [M+H]⁺ 476.5.

Example 3 2-(4-(2,4-difluorophenoxy)piperidin-1-yl)-N-isopropyl-6-(methylsulfonyl)-5,6,7,8-tetrahy-dropyrido[3,4-b]pyrazin-3-amine

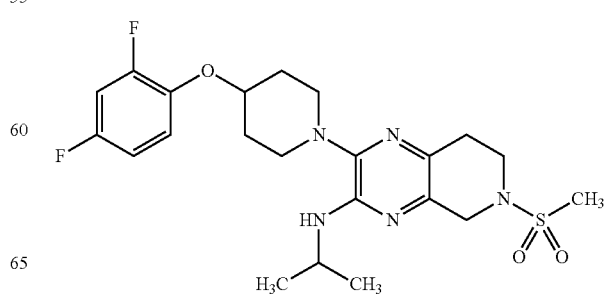

A solution of 2-(4-(2,4-difluorophenoxy)piperidin-1-yl)-N-isopropyl-5,6,7,8-tetrahydropyrido[3,4-b]pyrazin-3-amine TFA salt (735.3 mg, 1.421 mmol) in DCM (14.2 mL) at 0° C. was treated with triethylamine (0.594 mL, 4.26 mmol), followed by methanesulfonyl chloride (0.221 mL, 2.84 mmol). The reaction mixture was stirred at 0° C. for 1 h. The reaction mixture was concentrated under reduced pressure. The residue was taken up in MeOH, filtered through a Millipore® 0.45 μm syringe filter, and purified by HPLC Method A. The corresponding fractions were collected and concentrated under reduced pressure. The resulting residue was taken up in DCM and washed with saturated aqueous $K_2CO_3$ to generate the free base. The organic layer was separated, dried over $Na_2SO_4$, and filtered. Evaporation of the filtrate and lyophilization gave the title compound as an off-white solid (229.6 mg, 33.6%). $^1$H NMR (500 MHz, DMSO-d6) 1.18 (d, J=6.3 Hz, 6H), 1.88 (m, 2H), 2.07 (m, 2H), 2.75 (t, J=5.9 Hz, 2H), 2.89 (m, 2H), 2.97 (s, 3H), 3.29 (m, 2H), 3.45 (t, J=5.9 Hz, 2H), 4.09 (m, 1H), 4.16 (s, 2H), 4.52 (tt, J=8.1, 3.9 Hz, 1H), 5.57 (d, J=8.3 Hz, 1H), 7.01 (m, 1H), 7.30 (m, 2H); ESI-MS m/z [M+H]$^+$ 481.90.

Example 4 2-(4-(2,4-difluorophenoxy)piperidin-1-yl)-3-(isopropylamino)-N-(2-methoxyethyl)-7,8-dihydropyrido[3,4-b]pyrazine-6(5H)-carboxamide

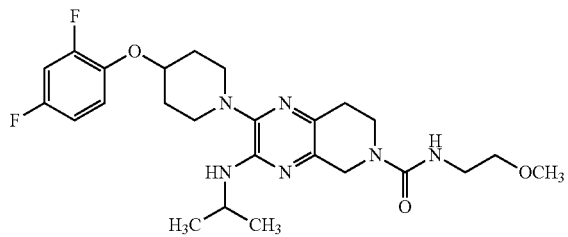 [SMILES: COCCNC(=O)N1CCc2nc(N3CCC(Oc4ccc(F)cc4F)CC3)c(NC(C)C)nc2C1]

To a solution of 2-(4-(2,4-difluorophenoxy)piperidin-1-yl)-N-isopropyl-5,6,7,8-tetrahydropyrido[3,4-b]pyrazin-3-amine TFA salt (39.0 mg, 0.075 mmol) in DCM (754 μL) at 0° C. was added triethylamine (31.5 μL, 0.226 mmol) and 1-isocyanato-2-methoxyethane (11.8 μL, 0.113 mmol). The reaction mixture was stirred for 1 h at 0° C. The reaction mixture was concentrated under reduced pressure and purified by HPLC Method B, with the exception that a Waters SunFire™ C18, 5 μm, ID 30×75 mm column was used, using a 45% to 70% ACN gradient to give the title compound, as a TFA salt, as a yellow oil (24.5 mg, 52.6%). $^1$H NMR (400 MHz, methanol-d4) δ ppm 1.32 (d, J=6.6 Hz, 6H), 1.97 (m, 2H), 2.14 (m, 2H), 2.77 (t, J=5.8 Hz, 2H), 3.12 (m, 2H), 3.37 (m, 5H), 3.46 (m, 4H), 3.71 (t, J=5.8 Hz, 2H), 4.13 (m, 1H), 4.50 (m, 3H), 6.88 (m, 1H), 6.98 (ddd, J=11.2, 8.5, 3.0 Hz, 1H), 7.17 (td, J=9.2, 5.6 Hz, 1H); ESI-MS m/z [M+H]$^+$ 505.6.

Example 5 (2-(4-(2,4-difluorophenoxy)piperidin-1-yl)-3-(isopropylamino)-7,8-dihydropyrido[3,4-b]pyrazin-6(5H)-yl)(tetrahydrofuran-2-yl)methanone

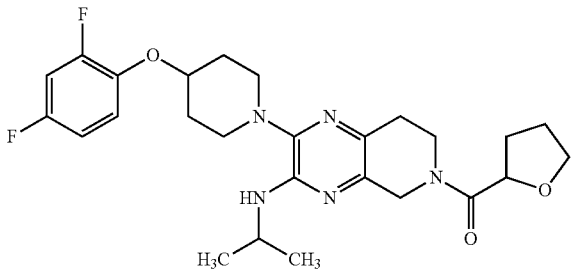 [SMILES: CC(C)Nc1nc2c(nc1N1CCC(Oc3ccc(F)cc3F)CC1)CCN(C(=O)C1CCCO1)C2]

To a solution of tetrahydrofuran-2-carboxylic acid (10.9 μL, 0.113 mmol) in DMA (0.35 mL) at room temperature was added DIPEA (39.5 μL, 0.226 mmol), followed by HATU (43.0 mg, 0.113 mmol). After stirring for 5 min, the reaction mixture was treated with a solution of 2-(4-(2,4-difluorophenoxy)piperidin-1-yl)-N-isopropyl-5,6,7,8-tetrahydropyrido[3,4-b]pyrazin-3-amine TFA salt (39.0 mg, 0.075 mmol) in DMA (0.4 mL). The reaction mixture was stirred at 60° C. for 30 min. The reaction mixture was allowed to cool to room temperature and was purified directly by HPLC Method B, with the exception that a Waters SunFire™ C18, 5 μm, ID 30×75 mm column was used, using a 55% to 80% ACN gradient to give the title compound, as a TFA salt, as a yellow oil (16.0 mg, 34.5%). $^1$H NMR (400 MHz, methanol-d4) δ ppm 1.31 (m, 6H), 1.97 (m, 4H), 2.16 (m, 4H) 2.82 (m, 2H), 3.10 (m, 2H), 3.45 (m, 2H), 3.89 (m, 4H), 4.14 (m, 1H), 4.44-4.87 (m, 4H), 6.88 (m, 1H), 6.99 (ddd, J=11.2, 8.5, 3.0 Hz, 1H), 7.18 (td, J=9.2, 5.3 Hz, 1H); ESI-MS m/z [M+H]$^+$ 502.6.

Example 6 3-(2-(4-(2,4-difluorophenoxy)piperidin-1-yl)-3-(isopropylamino)-7,8-dihydropyrido[3,4-b]pyrazin-6(5H)-yl)-3-oxopropanenitrile

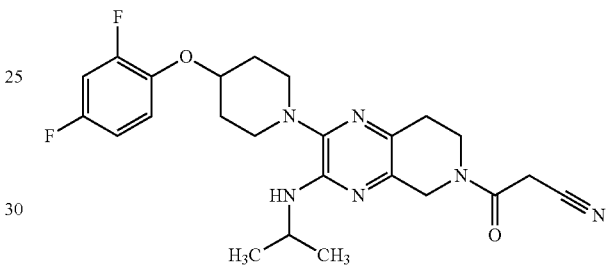

To a solution of 2-cyanoacetic acid (8.3 mg, 0.097 mmol) in DMA (0.3 mL) at room temperature was added DIPEA (33.9 μL, 0.194 mmol), followed by HATU (36.9 mg, 0.097 mmol). This mixture was stirred for 5 min, then was treated with a solution of 2-(4-(2,4-difluorophenoxy)piperidin-1-yl)-N-isopropyl-5,6,7,8-tetrahydropyrido[3,4-b]pyrazin-3-amine TFA salt (33.5 mg, 0.065 mmol) in DMA (0.35 mL). The reaction mixture was heated at 60° C. for 30 min. The reaction mixture was purified directly by HPLC Method B, with the exception that a Waters SunFire™ C18, 5 μm, ID 30×75 mm column was used, using a 55% to 80% ACN gradient to give the title compound, as a TFA salt, as a yellow oil (5.5 mg, 14%). $^1$H NMR (400 MHz, methanol-d4, mixture of rotamers) δ ppm 1.27 (m, 6H), 1.96 (m, 2H), 2.12 (m, 2H), 2.75 (t, J=5.9 Hz, 0.8H), 2.85 (m, 1.2H), 3.01 (m, 2H), 3.39 (m, 2H), 3.75 (t, J=5.8 Hz, 1.2H), 3.89 (t, J=5.9 Hz, 0.8H), 4.00 (m, 2H); 4.14 (m, 1H), 4.48 (m, 1H), 4.50 (s, 0.8H), 4.60 (s, 1.2H), 6.88 (m, 1H), 6.98 (ddd, J=11.4, 8.6, 3.0 Hz, 1H), 7.17 (td, J=9.2, 5.6 Hz, 1H); ESI-MS m/z [M+H]$^+$ 471.5.

Example 7 4-((1-(6-acetyl-3-(isopropylamino)-5,6,7,8-tetrahydropyrido[3,4-b]pyrazin-2-yl)piperidin-4-yl)oxy)-3-fluorobenzonitrile

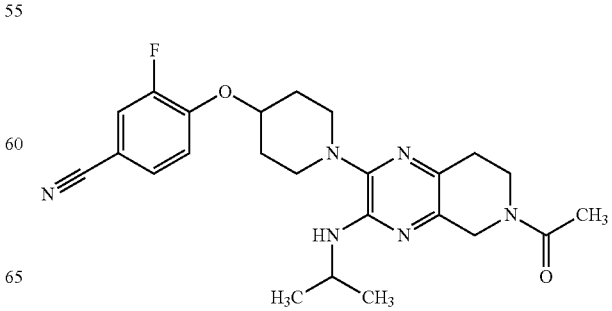

To a solution of 3-fluoro-4-((1-(3-(isopropylamino)-5,6,7,8-tetrahydropyrido[3,4-b]pyrazin-2-yl)piperidin-4-yl)oxy)benzonitrile TFA salt (33.5 mg, 0.064 mmol) in DCM (639 μL) at 0° C. was added pyridine (15.5 μL, 0.192 mmol), followed by acetic anhydride (12.0 μL, 0.128 mmol). The reaction was allowed to stir for 45 min, gradually warming to room temperature. The reaction was concentrated under reduced pressure and purified directly by HPLC Method B, with the exception that a Waters SunFire™ C18, 5 μm, ID 30×75 mm column was used, using a 40% to 70% ACN gradient to give the title compound, as a TFA salt, as a yellow solid (7.1 mg, 20%). $^1$H NMR (400 MHz, methanol-d4, mixture of rotamers) δ ppm 1.31 (m, 6H), 2.02 (m, 2H), 2.20 (m, 5H), 2.74 (t, J=5.9 Hz, 0.7H), 2.85 (m, 1.3H), 3.14 (m, 2H), 3.43 (m, 2H), 3.83 (t, J=5.9 Hz, 1.3H), 3.87 (t, J=5.9 Hz, 0.7H), 4.14 (m, 1H), 4.60 (s, 0.7H), 4.64 (s, 1.3H), 4.80 (m, 1H), 7.34 (m, 1H), 7.54 (m, 2H); ESI-MS m/z [M+H]$^+$ 453.5.

Example 8 1-(2-(4-(2,4-difluorophenoxy)piperidin-1-yl)-3-(isopropylamino)-7,8-dihydropyrido[3,4-b]pyrazin-6(5H)-yl)-2-methoxypropan-1-one

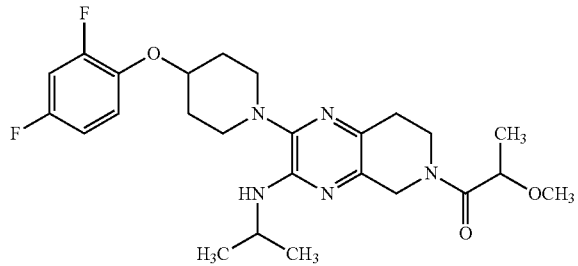 [SMILES: COC(C)C(=O)N1CCc2nc(N3CCC(Oc4ccc(F)cc4F)CC3)c(NC(C)C)nc2C1]

To a solution of 2-methoxypropanoic acid (10.8 μL, 0.113 mmol) in DMA (0.4 mL) at room temperature was added DIPEA (45.5 μL, 0.261 mmol) and HATU (42.9 mg, 0.113 mmol). To this was added a solution of 2-(4-(2,4-difluorophenoxy)piperidin-1-yl)-N-isopropyl-5,6,7,8-tetrahydropyrido[3,4-b]pyrazin-3-amine TFA salt (45.0 mg, 0.087 mmol) in DMA (0.47 mL). The resulting reaction mixture was stirred at 60° C. for 45 min. The reaction mixture was allowed to cool to room temperature and was purified directly by HPLC Method B, with the exception that a Waters SunFire™ C18, 5 μm, ID 30×75 mm column was used, using a 50% to 80% ACN gradient to give the title compound, as a TFA salt, as a pale yellow solid (11.2 mg, 21.4%). $^1$H NMR (400 MHz, methanol-d4) δ ppm 1.36 (m, 9H), 1.98 (m, 2H), 2.14 (m, 2H), 2.83 (m, 2H), 3.16 (m, 2H), 3.35 (s, 3H), 3.49 (m, 2H), 3.90 (m, 1H), 3.93 (t, J=5.8 Hz, 1H), 4.12 (m, 1H), 4.35 (m, 1H), 4.52 (m, 1H), 4.59-4.79 (m, 2H), 6.88 (m, 1H), 6.99 (ddd, J=11.4, 8.6, 3.0 Hz, 1H), 7.18 (td, J=9.2, 5.6 Hz, 1H); ESI-MS m/z [M+H]$^+$ 490.5.

Example 9 Cyclopropyl(3-(4-(2,4-difluorophenoxy)piperidin-1-yl)-2-(isopropylamino)-7,8-dihydropyrido[3,4-b]pyrazin-6(5H)-yl)methanone

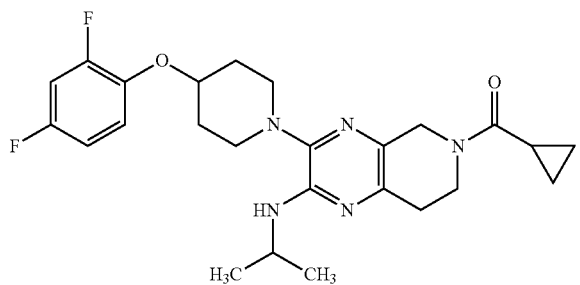 [SMILES: CC(C)Nc1nc2c(nc1N1CCC(Oc3ccc(F)cc3F)CC1)CN(C(=O)C1CC1)CC2]

To a solution of 3-(4-(2,4-difluorophenoxy)piperidin-1-yl)-N-isopropyl-5,6,7,8-tetrahydropyrido[3,4-b]pyrazin-2-amine 2TFA salt (34.2 mg, 0.059 mmol) and triethylamine (0.025 mL, 0.178 mmol) in DCM (0.5 mL) was added cyclopropanecarboxylic acid chloride (10.8 μL, 0.119 mmol) at 0° C. The reaction mixture was stirred at 0° C. for 30 min and then concentrated via rotary evaporation. The crude material was diluted with DMSO, filtered, rinsed with DMSO, and purified by HPLC Method B, with the exception that a Waters XSelect® CSH C18, 5 μm, ID 4.6×50 mm was used, using an ACN gradient of 30% to 70% to give the title compound as a TFA salt (17.7 mg, 51.0%) as a yellow oil. $^1$H NMR (400 MHz, DMSO-d$_6$, mixture of rotamers) δ ppm 0.67-0.81 (m, 4H), 1.19 (d, J=6.3 Hz, 6H), 1.80-1.95 (m, 2H), 2.01-2.07 (m, 2H), 2.51-2.56 (m, 1H), 2.57-2.66 (m, 0.9H), 2.72-2.79 (m, 1.1H), 2.84-2.94 (m, 2H), 3.23-3.33 (m, 2H), 3.70-3.79 (m, 0.9H), 3.92-3.98 (m, 1.1H), 4.08-4.18 (m, 1H), 4.42 (br s, 1.1H), 4.48-4.56 (m, 1H), 4.67 (br s, 0.9H), 5.71 (br s, 1H), 6.99-7.05 (m, 1H), 7.26-7.34 (m, 2H); ESI-MS m/z [M+H]$^+$ 472.5.

Example 10 1-(3-(4-(2,4-difluorophenoxy)piperidin-1-yl)-2-(isopropylamino)-7,8-dihydropyrido[3,4-b]pyrazin-6(5H)-yl)-2-methoxyethan-1-one

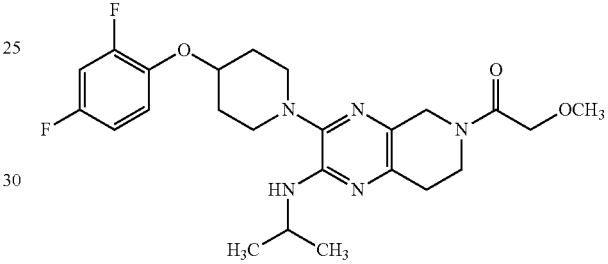

To a solution of 3-(4-(2,4-difluorophenoxy)piperidin-1-yl)-N-isopropyl-5,6,7,8-tetrahydropyrido[3,4-b]pyrazin-2-amine TFA salt (34.2 mg, 0.059 mmol) and triethylamine (0.025 mL, 0.178 mmol) in DCM (0.5 mL) was added methoxyacetyl chloride (10.8 μL, 0.119 mmol) at 0° C. The reaction mixture was stirred at 0° C. for 30 min and then concentrated via rotary evaporation. The crude material was diluted with DMSO, rinsed with DMSO, and purified by HPLC Method B, with the exception that a Waters XSelect® CSH C18, 5 μm, ID 4.6×50 mm was used, using an ACN gradient of 30% to 70% to give the title compound as a TFA salt (19.0 mg, 54.4%) as a yellow oil. $^1$H NMR (400 MHz, DMSO-d$_6$, mixture of rotamers) δ ppm 1.18 (d, J=6.6 Hz, 6H), 1.83-1.93 (m, 2H), 2.03-2.11 (m, 2H), 2.63 (t, J=5.8 Hz, 0.9H), 2.72 (t, J=5.3 Hz, 1.1H), 2.84-2.93 (m, 2H), 3.22-3.36 (m, 5H), 3.66 (t, J=5.8 Hz, 1.1H), 3.74 (t, J=6.1 Hz, 0.9H), 4.10-4.16 (m, 1H), 4.17 (br s, 0.9H), 4.19 (s, 1.1H), 4.49-4.56 (m, 1H), 5.65-5.72 (m, 1H), 6.99-7.05 (m, 1H), 7.26-7.35 (m, 2H); ESI-MS m/z [M+H]$^+$ 476.5.

Example 11 3-(4-(2,4-difluorophenoxy)piperidin-1-yl)-N-isopropyl-6-(methylsulfonyl)-5,6,7,8-tetrahydropyrido[3,4-b]pyrazin-2-amine

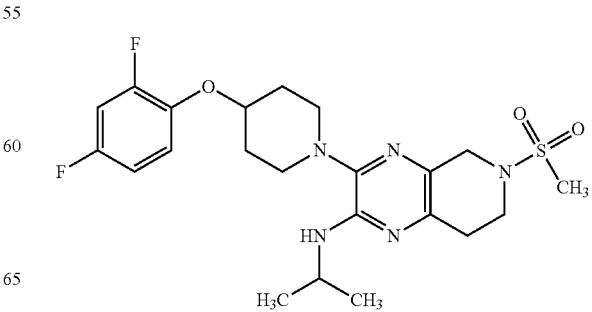

To a solution of 3-(4-(2,4-difluorophenoxy)piperidin-1-yl)-N-isopropyl-5,6,7,8-tetrahydropyrido[3,4-b]pyrazin-2-amine TFA salt (34.2 mg, 0.059 mmol) and triethylamine (0.025 mL, 0.178 mmol) in DCM (0.5 mL) was added methanesulfonyl chloride (6.9 µL, 0.089 mmol) at 0° C. The reaction mixture was stirred at 0° C. for 30 min and then concentrated via rotary evaporation. The crude material was diluted with DMSO, filtered, rinsed with DMSO, and purified by HPLC Method B, with the exception that a Waters XSelect® CSH C18, 5 µm, ID 4.6×50 mm was used, using an ACN gradient of 30% to 70% to give the title compound as a TFA salt (14.7 mg, 41.6%) as a yellow oil. $^1$H NMR (400 MHz, DMSO-$d_6$) δ ppm 1.19 (d, J=6.6 Hz, 6H), 1.82-1.93 (m, 2H), 2.02-2.08 (m, 2H), 2.77 (t, J=5.7 Hz, 2H), 2.84-2.93 (m, 2H), 2.98 (s, 3H), 3.24-3.32 (m, 2H), 3.45 (t, J=5.9 Hz, 2H), 4.10-4.18 (m, 3H), 4.50-4.55 (m, 1H), 5.67 (br s, 1H), 6.99-7.04 (m, 1H), 7.26-7.35 (m, 2H); ESI-MS m/z [M+H]$^+$ 482.4.

Example 12 2-(4-(4-cyano-2-fluorophenoxy)piperidin-1-yl)-3-(isopropylamino)-N,N-dimethyl-7,8-dihydropyrido[3,4-b]pyrazine-6(5H)-carboxamide

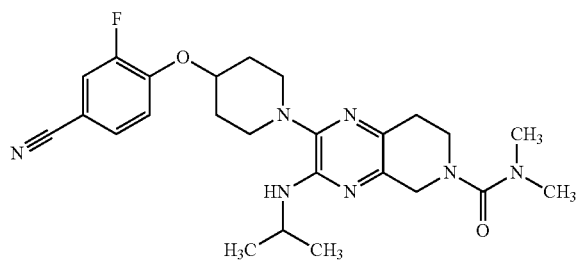 [SMILES: CC(C)Nc1nc2c(nc1N1CCC(Oc3ccc(C#N)cc3F)CC1)CCN(C(=O)N(C)C)C2]

A solution of 3-fluoro-4-((1-(3-(isopropylamino)-5,6,7,8-tetrahydropyrido[3,4-b]pyrazin-2-yl)piperidin-4-yl)oxy)benzonitrile TFA salt (32.5 mg, 0.062 mmol) in DCM (620 µL) at 0° C. was treated with triethylamine (25.9 µL, 0.186 mmol) and dimethylcarbamic chloride (11.4 µL, 0.124 mmol). The reaction mixture was allowed to gradually warm to room temperature and stir for 1 h. The reaction mixture was concentrated under reduced pressure and purified directly by HPLC Method B, with the exception that a Waters SunFire™ C18, 5 µm, ID 30×75 mm column was used, using a 40% to 70% ACN gradient to give the title compound in (about 90% purity), as a TFA salt, as a yellow solid (6.8 mg, 18%). $^1$H NMR (400 MHz, methanol-d4) δ ppm 1.29 (m, 6H), 2.02 (m, 2H), 2.19 (m, 2H), 2.81 (t, J=5.3 Hz, 2H), 2.91 (s, 5H), 3.17 (m, 3H), 3.43 (m, 2H), 3.56 (t, J=5.6 Hz, 2H), 4.13 (m, 1H), 4.32 (s, 2H), 4.80 (m, 1H), 7.34 (m, 1H), 7.54 (t, J=10.9 Hz, 2H); ESI-MS m/z [M+H]$^+$ 482.5.

Example 13 3-fluoro-4-((1-(3-(isopropylamino)-6-methyl-5,6,7,8-tetrahydropyrido[3,4-b]pyrazin-2-yl)piperidin-4-yl)oxy)benzonitrile

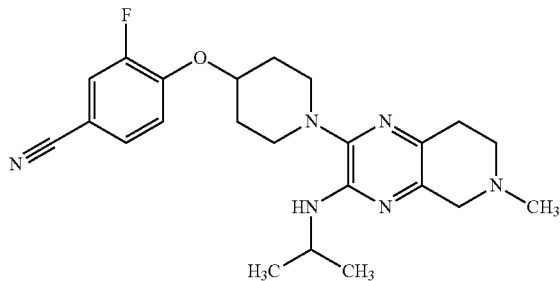 [SMILES: CC(C)Nc1nc2c(nc1N1CCC(Oc3ccc(C#N)cc3F)CC1)CCN(C)C2]

A solution of 3-fluoro-4-((1-(3-(isopropylamino)-5,6,7,8-tetrahydropyrido[3,4-b]pyrazin-2-yl)piperidin-4-yl)oxy)benzonitrile TFA salt (12.8 mg, 0.024 mmol) and formaldehyde (2.2 mg, 0.027 mmol) in MeOH (244 µL) at room temperature was treated with DIPEA (8.5 µL, 0.049 mmol) and sodium triacetoxyhydroborate (10.3 mg, 0.049 mmol). The reaction mixture was stirred for 45 min at room temperature. The crude reaction mixture was purified directly by HPLC Method B, with the exception that a Waters SunFire™ C18, 5 µm, ID 30×75 mm column was used, using a 30% to 55% ACN gradient to give the title compound (about 90% purity), as a TFA salt, as a pale yellow solid. (6.0 mg, 46%). $^1$H NMR (400 MHz, methanol-d4) δ ppm 1.24 (d, J=6.6 Hz, 6H), 1.98 (m, 2H), 2.19 (m, 2H), 3.08 (m, 7H), 3.38 (m, 3H), 3.76 (br s, 1H), 4.16 (m, 1H), 4.29 (m, 2H), 4.79 (m, 1H), 7.34 (m, 1H), 7.53 (m, 2H); ESI-MS m/z [M+H]$^+$ 425.5.

Example 14 (2-(4-(2,4-difluorophenoxy)piperidin-1-yl)-3-(isopropylamino)-7,8-dihydropyrido[3,4-b]pyrazin-6(5H)-yl)(morpholino)methanone

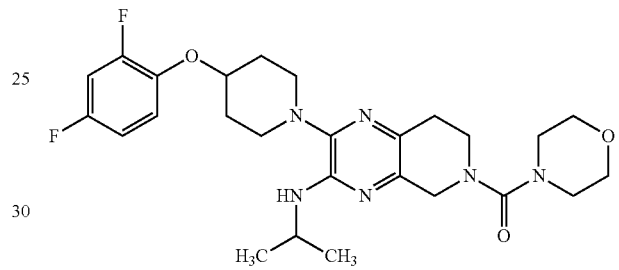

To a solution of 2-(4-(2,4-difluorophenoxy)piperidin-1-yl)-N-isopropyl-5,6,7,8-tetrahydropyrido[3,4-b]pyrazin-3-amine TFA salt (38.1 mg, 0.074 mmol) in DCM (736 µL) at 0° C. was added triethylamine (30.8 µL, 0.221 mmol), followed by morpholine-4-carbonyl chloride (17.2 µL, 0.147 mmol). The reaction mixture was allowed to warm to room temperature and was stirred for 30 min. The reaction mixture was concentrated under reduced pressure and purified directly by HPLC Method B, with the exception that a Phenomenex Gemini® C18, 5 µm, ID 30×75 mm column was used, using a 50% to 75% ACN gradient to give the title compound, as a TFA salt, as a yellow solid (11.9 mg, 25.6%). $^1$H NMR (400 MHz, methanol-d4) δ ppm 1.31 (d, J=6.6 Hz, 6H), 1.96 (m, 2H), 2.13 (m, 2H), 2.81 (t, J=5.8 Hz, 2H), 3.10 (m, 2H), 3.33 (m, 4H), 3.45 (m, 2H), 3.59 (t, J=5.9 Hz, 2H), 3.70 (m, 4H), 4.13 (m, 1H), 4.37 (s, 2H), 4.50 (tt, J=7.2, 3.5 Hz, 1H), 6.88 (m, 1H), 6.99 (ddd, J=11.2, 8.5, 3.0 Hz, 1H), 7.17 (td, J=9.2, 5.6 Hz, 1H); ESI-MS m/z [M+H]$^+$ 517.5.

Example 15 3-(4-(2,4-difluorophenoxy)piperidin-1-yl)-2-(isopropylamino)-N-(2-methoxyethyl)-7,8-dihydropyrido[3,4-b]pyrazine-6(5H)-carboxamide

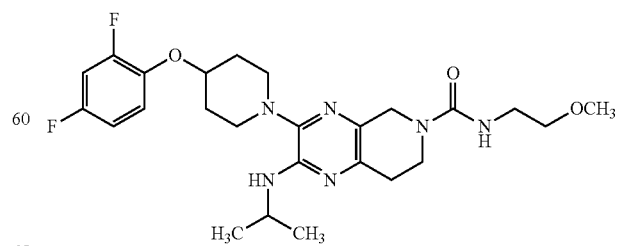

To a solution of 3-(4-(2,4-difluorophenoxy)piperidin-1-yl)-N-isopropyl-5,6,7,8-tetrahydropyrido[3,4-b]pyrazin-2- amine TFA salt (42.8 mg, 0.070 mmol) and triethylamine (0.029 mL, 0.211 mmol) in DCM (0.75 mL) was added 1-isocyanato-2-methoxyethane (11.0 µL, 0.105 mmol) at 0° C. The reaction mixture was stirred at 0° C. for 30 min and then concentrated via rotary evaporation. The crude material was diluted with DMSO, filtered, rinsed with DMSO, and purified by HPLC Method B, with the exception that a Waters XSelect® CSH C18, 5 µm, ID 4.6×50 mm was used, using an ACN gradient of 30% to 70% to give the title compound as a TFA salt (26.3 mg, 60.5%) as a hygroscopic, yellow solid. $^1$H NMR (400 MHz, DMSO-$d_6$) δ ppm 1.18 (d, J=6.3 Hz, 6H), 1.83-1.93 (m, 2H), 2.02-2.11 (m, 2H), 2.61 (t, J=5.6 Hz, 2H), 2.82-2.93 (m, 2H), 3.14-3.21 (m, 2H), 3.23 (s, 3H), 3.24-3.31 (m, 2H), 3.31-3.37 (m, 2H), 3.60 (t, J=5.8 Hz, 2H), 4.08-4.17 (m, 1H), 4.29 (s, 2H), 4.49-4.56 (m, 1H), 5.61-5.70 (m, 1H), 6.66-6.73 (m, 1H), 6.99-7.05 (m, 1H), 7.26-7.34 (m, 2H); ESI-MS m/z [M+H]$^+$ 505.0.

Example 16 (3-(4-(2,4-difluorophenoxy)piperidin-1-yl)-2-(isopropylamino)-7,8-dihydropyrido[3,4-b]pyrazin-6(5H)-yl)(tetrahydrofuran-2-yl)methanone

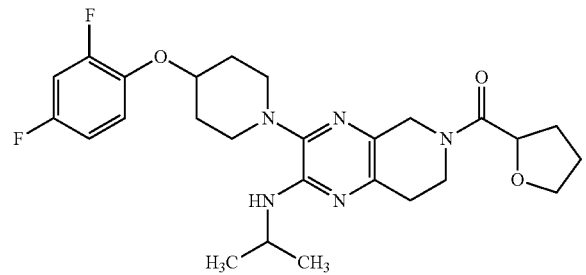 [SMILES: CC(C)Nc1nc2c(nc1N1CCC(Oc3ccc(F)cc3F)CC1)CN(C(=O)C1CCCO1)CC2]

To a suspension of 3-(4-(2,4-difluorophenoxy)piperidin-1-yl)-N-isopropyl-5,6,7,8-tetrahydropyrido[3,4-b]pyrazin-2-amine TFA salt (42.8 mg, 0.070 mmol), 2-tetrahydrofuroic acid (10.1 µL, 0.105 mmol), HATU (40.0 mg, 0.105 mmol) in DMA (0.75 mL) was added DIPEA (0.037 mL, 0.211 mmol) at 23° C. The mixture was stirred at 60° C. for 30 min, cooled to 23° C., filtered, rinsed with DMSO, and purified by HPLC Method B, with the exception that a Waters XSelect® CSH C18, 5 µm, ID 4.6×50 mm was used, using an ACN gradient of 30% to 70% to give the title compound as a TFA salt (20.8 mg, 48.1%) as a hygroscopic, yellow solid. $^1$H NMR (400 MHz, DMSO-$d_6$, mixture of rotamers) δ ppm 1.19 (d, J=6.3 Hz, 6H), 1.78-1.94 (m, 4H), 1.97-2.13 (m, 4H), 2.63 (t, J=5.7 Hz, 0.9H), 2.71-2.77 (m, 1.1H), 2.85-2.95 (m, 2H), 3.24-3.33 (m, 2H), 3.69-3.85 (m, 4H), 4.11 (dt, J=12.9, 6.4 Hz, 1H), 4.38-4.57 (m, 3H), 4.75 (ddd, J=14.0, 7.8, 5.7 Hz, 1H), 5.81 (br s, 1H), 6.99-7.05 (m, 1H), 7.25-7.34 (m, 2H); ESI-MS m/z [M+H]$^+$ 502.5.

Example 17 3-(3-(4-(2,4-difluorophenoxy)piperidin-1-yl)-2-(isopropylamino)-7,8-dihydropyrido[3,4-b]pyrazin-6(5H)-yl)-3-oxopropanenitrile

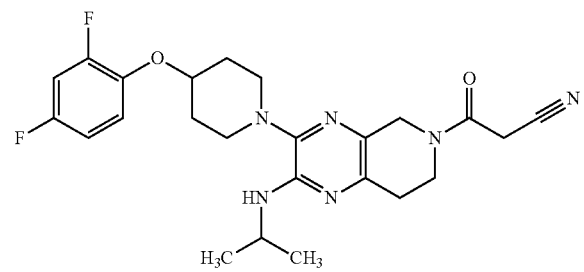 [SMILES: CC(C)Nc1nc2c(nc1N1CCC(Oc3ccc(F)cc3F)CC1)CN(C(=O)CC#N)CC2]

To a suspension of 3-(4-(2,4-difluorophenoxy)piperidin-1-yl)-N-isopropyl-5,6,7,8-tetrahydropyrido[3,4-b]pyrazin-2-amine TFA salt (42.8 mg, 0.070 mmol), cyanoacetic acid (9.0 mg, 0.105 mmol), HATU (40.0 mg, 0.105 mmol) in DMA was added DIPEA (36.7 µL, 0.211 mmol) at 23° C. The mixture was stirred at 60° C. for 30 min, cooled to 23° C., filtered, rinsed with DMSO, and purified by HPLC Method B, with the exception that a Waters XSelect® CSH C18, 5 µm, ID 4.6×50 mm was used, using an ACN gradient of 30% to 70% to give the title compound as a TFA salt (21.0 mg, 51.2%) as a yellow solid. $^1$H NMR (400 MHz, DMSO-$d_6$, mixture of rotamers) δ ppm 1.19 (d, J=6.6 Hz, 6H), 1.80-1.96 (m, 2H), 2.00-2.17 (m, 2H), 2.64 (t, J=5.6 Hz, 0.9H), 2.76 (t, J=5.7 Hz, 1.1H), 2.84-2.97 (m, 2H), 3.22-3.34 (m, 2H), 3.64 (t, J=5.8 Hz, 1.1H), 3.75 (t, J=5.9 Hz, 0.9H), 4.08-4.14 (m, 1H), 4.16 (s, 0.9H), 4.17 (s, 1.1H), 4.37 (s, 0.9H), 4.43 (s, 1.1H), 4.48-4.57 (m, 1H), 5.76 (br s, 1H), 6.98-7.06 (m, 1H), 7.24-7.36 (m, 2H); ESI-MS m/z [M+H]$^+$ 471.5.

Example 18 (2-(4-(2,4-difluorophenoxy)piperidin-1-yl)-3-(isopropylamino)-7,8-dihydropyrido[3,4-b]pyrazin-6(5H)-yl)(isoxazol-5-yl)methanone

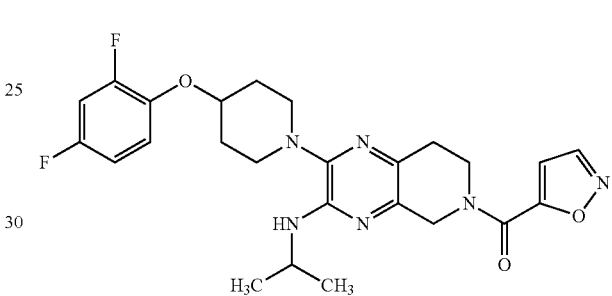

A solution of 2-(4-(2,4-difluorophenoxy)piperidin-1-yl)-N-isopropyl-5,6,7,8-tetrahydropyrido[3,4-b]pyrazin-3-amine TFA salt (38.1 mg, 0.074 mmol) in DCM (736 µL) at 0° C. was treated with triethylamine (30.8 µL, 0.221 mmol), followed by isoxazole-5-carbonyl chloride (14.2 µL, 0.147 mmol). The reaction mixture was allowed to warm to room temperature and stir for 45 min. The reaction mixture was concentrated under reduced pressure and purified directly by HPLC Method B, with the exception that a Phenomenex Gemini® C18, 5 µm, ID 30×75 mm column was used, using a 55% to 90% ACN gradient to give the title compound, as a TFA salt, as a tan oil (18.6 mg, 41.2%). $^1$H NMR (400 MHz, methanol-d4) δ ppm 1.30 (m, 6H), 1.96 (m, 2H), 2.13 (m, 2H), 2.89 (m, 2H), 3.11 (m, 2H), 3.46 (m, 2H), 3.91-4.21 (m, 3H), 4.49 (m, 1H), 4.78 (br s, 2H), 6.87 (m, 1H), 6.92 (s, 1H), 6.98 (ddd, J=11.2, 8.5, 3.0 Hz, 1H), 7.17 (td, J=9.2, 5.6 Hz, 1H), 8.55 (s, 1H); ESI-MS m/z [M+H]$^+$ 499.5.

Example 19 4-((1-(6-acetyl-2-(isopropylamino)-5,6,7,8-tetrahydropyrido[3,4-b]pyrazin-3-yl)piperidin-4-yl)oxy)-3-fluorobenzonitrile

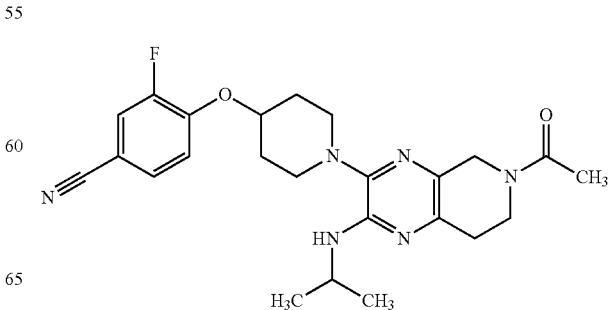

To a solution of 3-fluoro-4-((1-(2-(isopropylamino)-5,6,7,8-tetrahydropyrido[3,4-b]pyrazin-3-yl)piperidin-4-yl)oxy)benzonitrile TFA salt (98.6 mg, 0.094 mmol) and triethylamine (0.039 mL, 0.283 mmol) in DCM (1.0 mL) was added acetyl chloride (0.013 mL, 0.188 mmol) at 0° C. The reaction mixture was stirred at 0° C. for 30 min and then concentrated via rotary evaporation. The crude material was diluted with DMSO, filtered, rinsed with DMSO, and purified by HPLC Method B, with the exception that a Waters XSelect® CSH C18, 5 μm, ID 4.6×50 mm was used, using an ACN gradient of 30% to 70% to give the title compound as a TFA salt (8.7 mg, 16%) as a yellow solid. $^1$H NMR (400 MHz, DMSO-$d_6$, mixture of rotamers) δ ppm 1.18 (d, J=6.6 Hz, 6H), 1.86-1.96 (m, 2H), 2.08 (s, 1.3H), 2.09 (s, 1.7H), 2.10-2.21 (m, 2H), 2.61 (t, J=5.6 Hz, 0.9H), 2.73 (t, J=5.2 Hz, 1.1H), 2.88-2.98 (m, 2H), 3.23-3.31 (m, 2H), 3.66-3.76 (m, 2H), 4.09-4.17 (m, 1H), 4.40 (s, 1.1H), 4.43 (s, 0.9H) 4.80-4.87 (m, 1H), 5.59-5.67 (m, 1H), 7.50 (t, J=8.6 Hz, 1H), 7.68 (dq, J=8.6, 1.7 Hz, 1H), 7.86 (dt, J=11.2, 1.7 Hz, 1H); ESI-MS m/z [M+H]$^+$ 453.5.

Example 20 4-((1-(6-(cyclopropanecarbonyl)-2-(isopropylamino)-5,6,7,8-tetrahydropyrido[3,4-b]pyrazin-3-yl)piperidin-4-yl)oxy)-3-fluorobenzonitrile

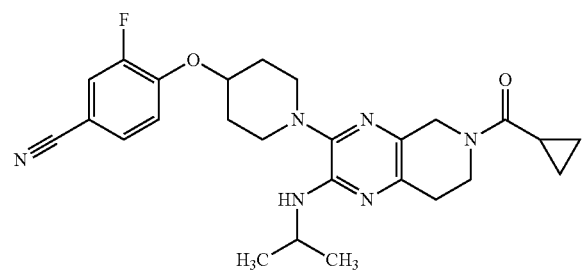 [SMILES: CC(C)Nc1nc2c(nc1N1CCC(Oc3ccc(C#N)cc3F)CC1)CN(C(=O)C1CC1)CC2]

To a solution of 3-fluoro-4-((1-(2-(isopropylamino)-5,6,7,8-tetrahydropyrido[3,4-b]pyrazin-3-yl)piperidin-4-yl)oxy)benzonitrile TFA salt (98.6 mg, 0.094 mmol) and triethylamine (0.039 mL, 0.283 mmol) in DCM (0.5 mL) was added cyclopropanecarboxylic acid chloride (0.017 mL, 0.188 mmol) at 0° C. The mixture was stirred at 0° C. for 30 min and then concentrated via rotary evaporation. The crude material was diluted with DMSO, filtered, rinsed with DMSO, and purified by HPLC Method B, with the exception that a Waters XSelect® CSH C18, 5 μm, ID 4.6×50 mm was used, using an ACN gradient of 30% to 70% to give the title compound as a TFA salt (8.1 mg, 15%) as a yellow solid. $^1$H NMR (400 MHz, DMSO-$d_6$, mixture of rotamers) δ ppm 0.69-0.79 (m, 4H), 1.18 (d, J=6.6 Hz, 6H), 1.91 (dd, J=19.5, 5.6 Hz, 2H), 2.13 (dd, J=14.3, 6.2 Hz, 2H), 2.52-2.53 (m, 1H), 2.57-2.64 (m, 0.9H), 2.75 (t, J=6.2 Hz, 1.1H), 2.88-2.99 (m, 2H), 3.22-3.31 (m, 2H), 3.72-3.77 (m, 0.9H), 3.95 (t, J=5.8 Hz, 1H), 4.10-4.16 (m, 1H), 4.42 (br s, 1.1H), 4.67 (br s, 0.9H), 4.80-4.87 (m, 1H), 5.61-5.67 (m, 1H), 7.50 (t, J=8.5 Hz, 1H), 7.65-7.70 (m, 1H), 7.86 (dd, J=11.2, 1.9 Hz, 1H); ESI-MS m/z [M+H]$^+$ 479.5.

Example 21 2-(4-(2,4-difluorophenoxy)piperidin-1-yl)-N-isopropyl-6-(isopropylsulfonyl)-5,6,7,8-tetrahydropyrido[3,4-b]pyrazin-3-amine

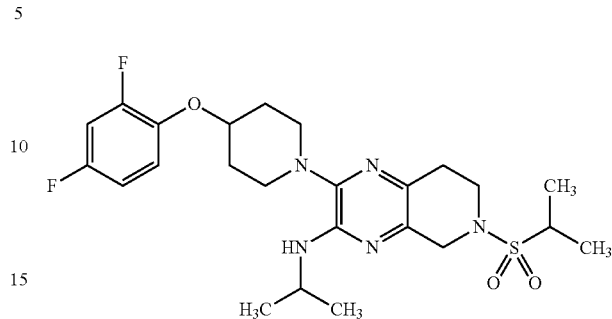

A solution of 2-(4-(2,4-difluorophenoxy)piperidin-1-yl)-N-isopropyl-5,6,7,8-tetrahydropyrido[3,4-b]pyrazin-3-amine TFA salt (47 mg, 0.091 mmol) in DCM (908 μL) at 0° C. was treated with triethylamine (38.0 μL, 0.272 mmol), followed by propane-2-sulfonyl chloride (15.3 μL, 0.136 mmol). The reaction mixture was allowed to stir for 45 min, gradually warming to room temperature. The reaction mixture was concentrated under reduced pressure and was purified by HPLC Method B, with the exception that a Waters SunFire™ C18, 5 μm, ID 30×75 mm column was used, using a 60% to 95% ACN gradient to give the title compound, as a TFA salt, as a yellow oil (16.4 mg, 29.0%). $^1$H NMR (400 MHz, methanol-d4) δ ppm 1.29 (d, J=6.6 Hz, 6H), 1.35 (d, J=6.8 Hz, 6H), 1.95 (m, 2H), 2.13 (m, 2H), 2.82 (t, J=5.9 Hz, 2H), 3.07 (m, 2H), 3.42 (m, 3H), 3.67 (t, J=5.8 Hz, 2H), 4.12 (septet, J=6.5 Hz, 1H), 4.41 (s, 2H), 4.48 (dt, J=7.5, 3.6 Hz, 1H) 6.87 (m, 1H), 6.98 (ddd, J=11.3, 8.5, 2.9 Hz, 1H), 7.17 (td, J=9.2, 5.6 Hz, 1H); ESI-MS m/z [M+H]$^+$ 510.5.

Example 22 2-(4-(2,4-difluorophenoxy)piperidin-1-yl)-3-(isopropylamino)-6-(methyl-L-prolyl)-5,6,7,8-tetrahydropyrido[3,4-b]pyrazine

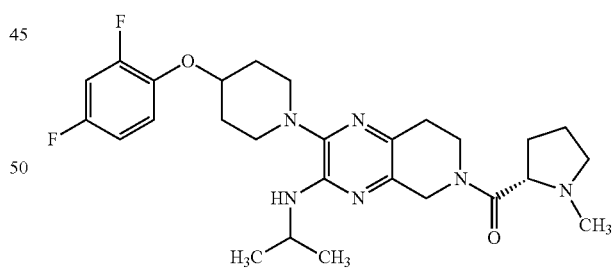

A solution of (S)-1-methylpyrrolidine-2-carboxylic acid (16.8 mg, 0.130 mmol) in DMA (0.4 mL) was treated with HATU (49.6 mg, 0.130 mmol) and DIPEA (45.6 μL, 0.261 mmol) at room temperature. To this was added a solution of 2-(4-(2,4-difluorophenoxy)piperidin-1-yl)-N-isopropyl-5,6,7,8-tetrahydropyrido[3,4-b]pyrazin-3-amine TFA salt (45 mg, 0.087 mmol) in DMA (0.47 mL). The reaction mixture was stirred at 60° C. for 45 min. The reaction mixture was allowed to cool to room temperature and was purified directly directly by HPLC Method B, with the exception that a Phenomenex Gemini® C18, 5 μm, ID 30×75 mm column was used, using a 25% to 60% ACN gradient to give the title compound, as a TFA salt, as a white solid (2.8 mg, 5.1%). ¹H NMR (400 MHz, methanol-d4) δ ppm 1.26 (dd, J=6.6, 4.5 Hz, 6H), 1.97 (m, 4H), 2.09 (m, 3H), 2.24 (m, 1H), 2.76 (m, 3H), 2.93 (app d, J=7.6 Hz, 3H), 3.03 (m, 2H), 3.20 (m, 1H), 3.40 (m, 2H), 3.69-4.19 (m, 4H), 4.48 (m, 2H), 4.66 (m, 2H), 6.87 (m, 1H), 6.98 (ddd, J=11.2, 8.5, 3.0 Hz, 1H), 7.17 (td, J=9.2, 5.6 Hz, 1H); ESI-MS m/z [M+H]⁺ 515.6.

Example 23 (2-(4-(2,4-difluorophenoxy)piperidin-1-yl)-3-(isopropylamino)-7,8-dihydropyrido[3,4-b]pyrazin-6(5H)-yl)(pyrrolidin-1-yl)methanone

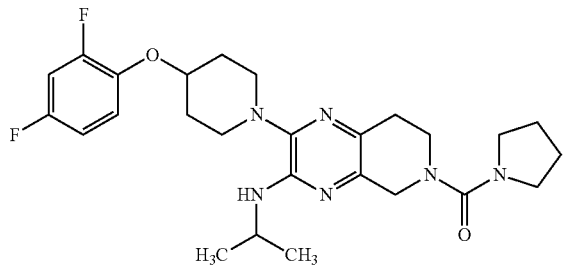

A solution of 2-(4-(2,4-difluorophenoxy)piperidin-1-yl)-N-isopropyl-5,6,7,8-tetrahydropyrido[3,4-b]pyrazin-3-amine TFA salt (45 mg, 0.087 mmol) in DCM (870 µL) at 0° C. was treated with triethylamine (36.4 µL, 0.261 mmol), followed by pyrrolidine-1-carbonyl chloride (19.2 µL, 0.174 mmol). The reaction mixture was allowed to stir for 30 min, gradually warming to room temperature. The reaction mixture was concentrated under reduced pressure and purified directly by HPLC Method B, with the exception that a Phenomenex Gemini® C18, 5 µm, ID 30×75 mm column was used, using a 50% to 80% ACN gradient to give the title compound, as a TFA salt, as a pale yellow solid (10.6 mg, 19.8%). ¹H NMR (400 MHz, methanol-d4) δ ppm 1.33 (d, J=6.3 Hz, 6H), 1.89 (m, 4H), 1.97 (m, 2H), 2.14 (m, 2H), 2.81 (t, J=5.8 Hz, 2H), 3.13 (m, 2H), 3.46 (m, 6H), 3.61 (t, J=5.8 Hz, 2H), 4.12 (septet, J=6.4 Hz, 1H), 4.38 (s, 2H), 4.51 (tt, J=7.2, 3.6 Hz, 1H), 6.88 (m, 1H), 6.99 (ddd, J=11.4, 8.5, 3.0 Hz, 1H), 7.18 (td, J=9.2, 5.6 Hz, 1H); ESI-MS m/z [M+H]⁺ 501.6.

Example 24 1-(2-(4-(2,4-difluorophenoxy)piperidin-1-yl)-3-(isopropylamino)-7,8-dihydropyrido[3,4-b]pyrazin-6(5H)-yl)-2,2-difluoroethan-1-one

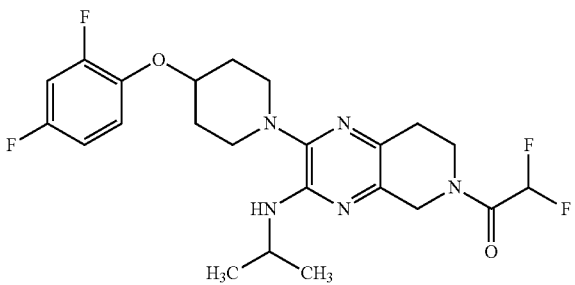 [SMILES: CC(C)Nc1nc2c(nc1N1CCC(Oc3ccc(F)cc3F)CC1)CCN(C(=O)C(F)F)C2]

A solution of 2,2-difluoroacetic acid (8.2 µL, 0.13 mmol) in DMA (0.4 mL) was treated with HATU (49.6 mg, 0.130 mmol) and DIPEA (45.6 µL, 0.261 mmol). To this was added a solution of 2-(4-(2,4-difluorophenoxy)piperidin-1-yl)-N-isopropyl-5,6,7,8-tetrahydropyrido[3,4-b]pyrazin-3-amine TFA salt (45 mg, 0.087 mmol) in DMA (0.47 mL). The reaction mixture was heated at 60° C. for 50 min. The reaction mixture was allowed to cool to room temperature and was purified directly by HPLC Method B, with the exception that a Phenomenex Gemini® C18, 5 µm, ID 30×75 mm column was used, using a 55% to 90% ACN gradient to give the title compound, as a TFA salt, as a yellow solid (10.0 mg, 19.3%). ¹H NMR (400 MHz, methanol-d4, mixture of rotamers) δ ppm 1.28 (m, 6H), 1.96 (m, 2H), 2.12 (m, 2H), 2.79 (t, J=5.9 Hz, 0.7H), 2.85 (t, J=5.8 Hz, 1.3H), 3.05 (m, 2H), 3.42 (m, 2H), 3.92 (dt, J=11.3, 5.8 Hz, 2H), 4.15 (m, 1H), 4.48 (m, 1H), 4.65 (s, 2H), 6.56 (m, 1H), 6.88 (m, 1H), 6.98 (ddd, J=11.3, 8.5, 2.9 Hz, 1H), 7.17 (td, J=9.2, 5.3 Hz, 1H); ESI-MS m/z [M+H]⁺ 482.5.

Example 25 3-fluoro-4-((1-(2-(isopropylamino)-6-(methylsulfonyl)-5,6,7,8-tetrahydropyrido[3,4-b]pyrazin-3-yl)piperidin-4-yl)oxy)benzonitrile

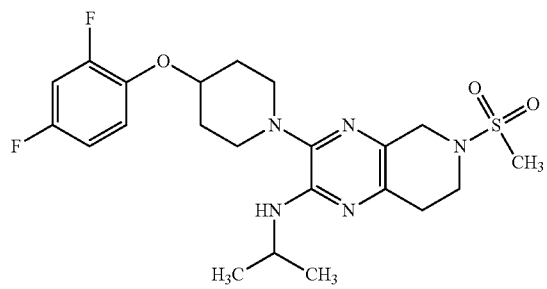 [SMILES: CC(C)Nc1nc2c(nc1N1CCC(Oc3ccc(F)cc3F)CC1)CN(S(C)(=O)=O)CC2]

To a solution of 3-fluoro-4-((1-(2-(isopropylamino)-5,6,7,8-tetrahydropyrido[3,4-b]pyrazin-3-yl)piperidin-4-yl)oxy)benzonitrile TFA salt (98.6 mg, 0.094 mmol) and triethylamine (0.039 mL, 0.283 mmol) in DCM (1.0 mL) was added methanesulfonyl chloride (10.9 µL, 0.141 mmol) at 0° C. The mixture was stirred at 0° C. for 30 min and then concentrated via rotary evaporation. The crude material was diluted with DMSO, filtered, rinsed with DMSO, and purified by HPLC Method B, with the exception that a Waters XSelect® CSH C18, 5 µm, ID 4.6×50 mm was used, using an ACN gradient of 30% to 70% to give the title compound as a TFA salt (3.5 mg, 6.2%) as a yellow solid. ¹H NMR (400 MHz, DMSO-d₆) δ ppm 1.18 (d, J=6.3 Hz, 6H), 1.88-1.96 (m, 2H), 2.09-2.16 (m, 2H), 2.76 (t, J=5.9 Hz, 2H), 2.89-2.96 (m, 2H), 2.97 (s, 3H), 3.24-3.30 (m, 2H), 3.45 (t, J=5.9 Hz, 2H), 4.10-4.16 (m, 3H), 4.81-4.85 (m, 1H), 5.66 (d, J=8.3 Hz, 1H), 7.50 (t, J=8.7 Hz, 1H), 7.68 (ddd, J=8.6, 2.0, 1.3 Hz, 1H), 7.86 (dd, J=11.4, 2.0 Hz, 1H); ESI-MS m/z [M+H]⁺ 489.5.

Example 26 3-fluoro-4-((1-(2-(isopropylamino)-6-(2-methoxyacetyl)-5,6,7,8-tetrahydropyrido[3,4-b]pyrazin-3-yl)piperidin-4-yl)oxy)benzonitrile

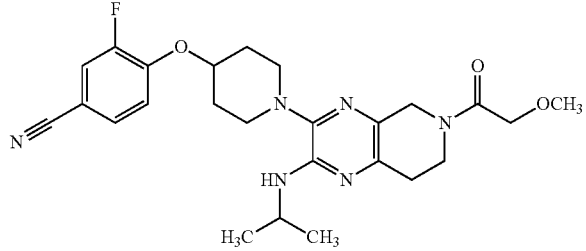 [SMILES: COCC(=O)N1CCc2nc(NC(C)C)c(N3CCC(Oc4ccc(C#N)cc4F)CC3)nc2C1]

To a solution of 3-fluoro-4-((1-(2-(isopropylamino)-5,6,7,8-tetrahydropyrido[3,4-b]pyrazin-3-yl)piperidin-4-yl)oxy)benzonitrile 2,2,2-trifluoroacetate (98.6 mg, 0.094 mmol) and triethylamine (0.039 mL, 0.283 mmol) in DCM (1.0 mL) was added methoxyacetyl chloride (0.017 mL, 0.188 mmol) at 0° C. The mixture was stirred at 0° C. for 30 min and then concentrated via rotary evaporation. The crude material was diluted with DMSO, filtered, rinsed with DMSO, and purified by HPLC Method B, with the exception that a Waters XSelect® CSH C18, 5 μm, ID 4.6×50 mm was used, using an ACN gradient of 30% to 70% to give the title compound as a TFA salt (2.9 mg, 5.2%) as a yellow solid. $^1$H NMR (400 MHz, DMSO-$d_6$, mixture of rotamers) δ ppm 1.18 (d, J=6.6 Hz, 6H), 1.87-1.97 (m, 2H), 2.08-2.16 (m, 2H), 2.62 (t, J=5.8 Hz, 0.9H), 2.72 (t, J=6.1 Hz, 1.1H), 2.89-2.97 (m, 2H), 3.22-3.28 (m, 1H), 3.29 (br s, 1.3H), 3.30 (s, 1.7H), 3.64-3.67 (m, 1.1H), 3.72-3.75 (m, 0.9H), 4.10-4.16 (m, 1H), 4.17 (br s, 0.9H), 4.19 (s, 1.1H), 4.36 (br s, 0.9H), 4.41 (s, 1.1H), 4.80-4.86 (m, 1H), 5.58-5.63 (m, 1H), 7.50 (t, J=8.7 Hz, 1H), 7.66-7.70 (m, 1H), 7.87 (dd, J=11.2, 1.9 Hz, 1H); ESI-MS m/z [M+H]$^+$ 483.5.

Example 27 3-fluoro-4-((1-(2-(isopropylamino)-6-methyl-5,6,7,8-tetrahydropyrido[3,4-b]pyrazin-3-yl)piperidin-4-yl)oxy)benzonitrile

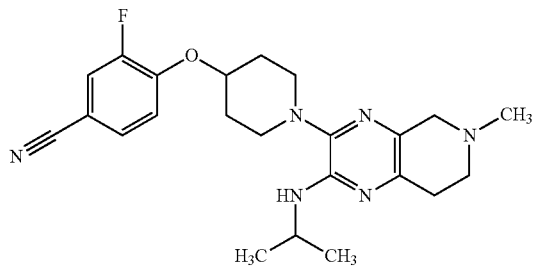 [SMILES: CC(C)Nc1nc2c(nc1N1CCC(Oc3ccc(C#N)cc3F)CC1)CN(C)CC2]

To a solution of 3-fluoro-4-((1-(2-(isopropylamino)-5,6,7,8-tetrahydropyrido[3,4-b]pyrazin-3-yl)piperidin-4-yl)oxy)benzonitrile TFA salt (20.7 mg, 0.039 mmol) and formaldehyde (3.2 μL, 0.043 mmol) in MeOH (0.5 mL) was added DIPEA (0.014 mL, 0.079 mmol) and sodium triacetoxyborohydride (16.7 mg, 0.079 mmol) at 23° C. The mixture was stirred at 23° C. for 2 hr and then concentrated via rotary evaporation. The crude material was diluted with DMSO, filtered, rinsed with DMSO, and purified by with the exception that a Waters XSelect® CSH C18, 5 μm, ID 4.6×50 mm was used, using a 30% to 40% ACN gradient to give the title compound as a TFA salt (5.3 mg, 25%) as a light yellow solid. $^1$H NMR (400 MHz, DMSO-$d_6$, mixture of rotamers) δ ppm 1.16-1.24 (m, 6H), 1.87-1.96 (m, 2H), 2.08-2.16 (m, 2H), 2.74-2.85 (m, 0.9H), 2.85-2.92 (m, 1.1H), 2.95 (br s, 1.3H), 2.96 br s, 1.7H), 2.97-3.00 (m, 1H), 3.25-3.42 (m, 3H), 3.65-3.71 (m, 1H), 4.12-4.19 (m, 2H), 4.25-4.31 (m, 1H), 4.82-4.88 (m, 1H), 5.89 (d, J=8.3 Hz, 1H), 7.50 (t, J=8.6 Hz, 1H), 7.66-7.71 (m, 1H), 7.87 (dd, J=11.4, 2.0 Hz, 1H), 9.96 (br s, 1H); ESI-MS m/z [M+H]$^+$ 425.5.

Example 28 3-(4-(4-cyano-2-fluorophenoxy)piperidin-1-yl)-2-(isopropylamino)-N,N-dimethyl-7,8-dihydropyrido[3,4-b]pyrazine-6(5H)-carboxamide

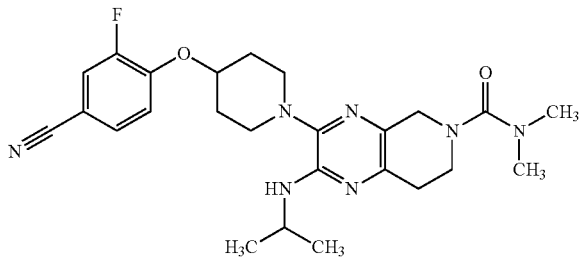 [SMILES: CC(C)Nc1nc2c(nc1N1CCC(Oc3ccc(C#N)cc3F)CC1)CN(C(=O)N(C)C)CC2]

To a solution of 3-fluoro-4-((1-(2-(isopropylamino)-5,6,7,8-tetrahydropyrido[3,4-b]pyrazin-3-yl)piperidin-4-yl)oxy)benzonitrile TFA salt (20.7 mg, 0.039 mmol) and triethylamine (0.017 mL, 0.118 mmol) in DCM (0.5 mL) was added dimethylcarbamoyl chloride (7.3 μL, 0.079 mmol) at 0° C. The mixture was stirred at 0° C. for 30 min and then concentrated via rotary evaporation. The crude material was diluted with DMSO, filtered, rinsed with DMSO, and purified by HPLC Method B, with the exception that a Waters XSelect® CSH C18, 5 μm, ID 4.6×50 mm was used, using a 30% to 70% ACN gradient to give the title compound as a TFA salt (11.6 mg, 49.4%) as a light yellow solid. $^1$H NMR (400 MHz, DMSO-$d_6$) δ ppm 1.13-1.26 (m, 6H), 1.87-1.96 (m, 2H), 2.08-2.16 (m, 2H), 2.81-2.99 (m, 6H), 3.25-3.42 (m, 3H), 3.65-3.71 (m, 1H), 4.12-4.19 (m, 2H), 4.25-4.31 (m, 1H), 4.82-4.88 (m, 1H), 5.89 (d, J=8.3 Hz, 1H), 7.50 (t, J=8.6 Hz, 1H), 7.66-7.71 (m, 1H), 7.87 (dd, J=11.4, 2.0 Hz, 1H), 9.96 (br s, 1H); ESI-MS m/z [M+H]$^+$ 482.5.

Example 29 1-(3-(2,2-difluoroethylamino)-2-(4-(2,4-difluorophenoxy)piperidin-1-yl)-5-methyl-7,8-dihydropyrido[3,4-b]pyrazin-6(5H)-yl)ethanone

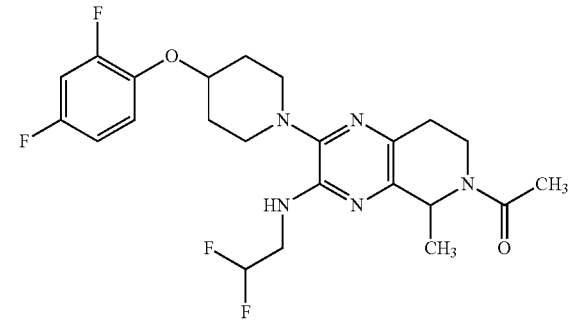 [SMILES: CC(=O)N1CCc2nc(N3CCC(Oc4ccc(F)cc4F)CC3)c(NCC(F)F)nc2C1C]

A solution of N-(2,2-difluoroethyl)-2-(4-(2,4-difluorophenoxy)piperidin-1-yl)-5-methyl-5,6,7,8-tetrahydropyrido[3,4-b]pyrazin-3-amine TFA salt (15 mg, 0.027 mmol), DIPEA (14.20 μL, 0.081 mmol), and acetic anhydride (3.8 μL, 0.041 mmol) in DCM (271 μL) was stirred at room temperature overnight. Purification by HPLC Method A gave the title compound as a TFA salt (8.9 mg) as an off-white film. $^1$H NMR (500 MHz, methanol-d4, mixture of rotamers) δ ppm 1.45 (d, J=6.8 Hz, 1.9H), 1.58 (d, J=6.8 Hz, 1.1H), 1.93-2.02 (m, 2H), 2.14 (dd, J=12.7, 3.4 Hz, 2H), 2.19-2.23 (m, 3H), 2.62-2.83 (m, 1.5H), 2.87-3.08 (m, 3.2H), 3.35-3.43 (m, 2H), 3.48-3.55 (m, 0.7H), 3.78 (sxtd, J=14.4, 4.2 Hz, 2H), 4.06 (dd, J=14.2, 5.4 Hz, 0.6H), 4.46 (dt, J=7.6, 3.5, Hz, 1H), 4.73 (dd, J=13.2, 5.4 Hz, 0.4H), 5.34 (q, J=6.8 Hz, 0.6H), 5.92-5.97 (m, 1H), 6.06 (dt, J=9.0, 4.3, Hz, 1H), 6.15-6.20 (m, 1H), 6.86-6.91 (m, 1H), 6.99 (ddd, J=11.2, 8.5, 3.2 Hz, 1H), 7.18 (td, J=9.3, 5.4 Hz, 1H); ESI-MS m/z [M+H]$^+$ 482.

Example 30 N-(2,2-difluoroethyl)-2-(4-(2,4-difluorophenoxy)piperidin-1-yl)-5-methyl-6-(methylsulfonyl)-5,6,7,8-tetrahydropyrido[3,4-b]pyrazin-3-amine

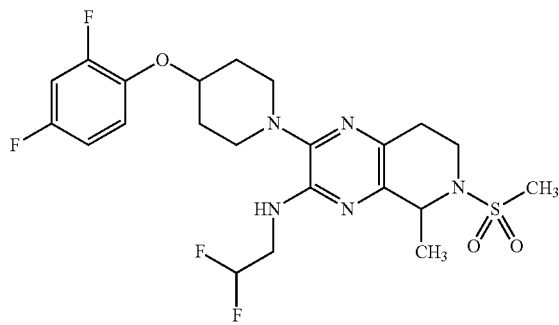 [SMILES: CC1c2nc(NCC(F)F)c(N3CCC(Oc4ccc(F)cc4F)CC3)nc2CCN1S(C)(=O)=O]

A solution of N-(2,2-difluoroethyl)-2-(4-(2,4-difluorophenoxy)piperidin-1-yl)-5-methyl-5,6,7,8-tetrahydropyrido[3,4-b]pyrazin-3-amine TFA salt (15 mg, 0.027 mmol), DIPEA (14.2 µL, 0.081 mmol), and methanesulfonyl chloride (3.2 µL, 0.041 mmol) in DCM (271 µL) was stirred overnight. Purification by HPLC Method A gave the title compound as a TFA salt (6.4 mg) as a white film. $^1$H NMR (500 MHz, methanol-d4) δ ppm 1.54 (d, J=6.8 Hz, 3H), 1.91-2.02 (m, 2H), 2.07-2.19 (m, 2H), 2.66 (dd, J=16.8, 3.2 Hz, 1H), 2.91 (s, 3H), 2.93-3.06 (m, 3H), 3.34-3.48 (m, 3H), 3.68-3.88 (m, 2H), 3.98 (dd, J=14.2, 6.4 Hz, 1H), 4.45 (dt, J=7.4, 3.8, Hz, 1H), 4.77 (q, J=6.8 Hz, 1H), 5.87-6.21 (m, 1H), 6.82-6.92 (m, 1H), 6.98 (ddd, J=11.4, 8.7, 2.9 Hz, 1H), 7.17 (td, J=9.2, 5.6 Hz, 1H); ESI-MS m/z [M+H]$^+$ 518.80.

Example 31 1-(3-(2,2-difluoroethylamino)-2-(4-(2,4-difluorophenoxy)piperidin-1-yl)-5-methyl-7,8-dihydropyrido[3,4-b]pyrazin-6(5H)-yl)-2-methoxyethanone

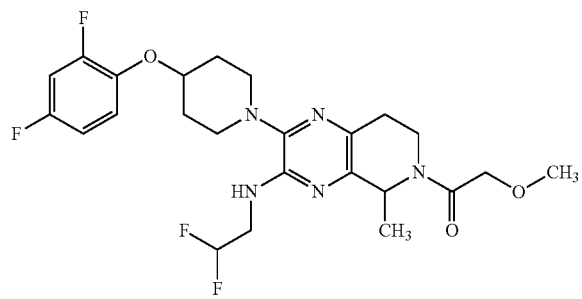 [SMILES: COCC(=O)N1CCc2nc(N3CCC(Oc4ccc(F)cc4F)CC3)c(NCC(F)F)nc2C1C]

A solution of 2-methoxyacetic acid (2.4 mg, 0.027 mmol), HATU (10.3 mg, 0.027 mmol), and DIPEA (14.2 µL, 0.081 mmol) in DMF (271 µl) was stirred at room temperature for 10 min. To this was then added N-(2,2-difluoroethyl)-2-(4-(2,4-difluorophenoxy)piperidin-1-yl)-5-methyl-5,6,7,8-tetrahydropyrido[3,4-b]pyrazin-3-amine TFA salt (15 mg, 0.027 mmol) in DCM (271 µL) and the reaction mixture was stirred overnight. Purification by HPLC Method A afforded the title compound as a TFA salt (7.4 mg) as an off-white film. $^1$H NMR (500 MHz, methanol-d4, mixture of rotamers) δ ppm 1.47 (d, J=6.8 Hz, 2H), 1.58 (d, J=6.8 Hz, 1H), 1.93-2.03 (m, 2H), 2.10-2.18 (m, 2H), 2.63-3.06 (m, 4.1H), 3.12 (td, J=12.9, 3.9 Hz, 0.3H), 3.36-3.51 (m, 5.6H), 3.70-3.88 (m, 2H), 4.02 (dd, J=13.9, 5.6 Hz, 0.7H), 4.18-4.33 (m, 2H), 4.46 (dt, J=7.3, 3.7 Hz, 1H), 4.71 (dd, J=13.4, 5.6 Hz, 0.3H), 4.79-4.84 (m, 0.3H), 5.30 (q, J=6.8 Hz, 0.7H), 5.91-6.21 (m, 1H), 6.85-6.92 (m, 1H), 6.99 (ddd, J=11.3, 8.7, 2.9 Hz, 1H), 7.18 (td, J=9.2, 5.6 Hz, 1H); ESI-MS m/z [M+H]$^+$ 512.85.

Example 32 1-(2-(2,2-difluoroethylamino)-3-(4-(2,4-difluorophenoxy)piperidin-1-yl)-5-methyl-7,8-dihydropyrido[3,4-b]pyrazin-6(5H)-yl)ethanone

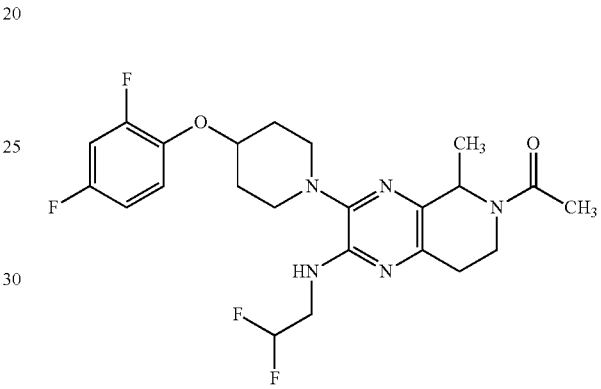

The title compound was prepared as an off-white film in a manner similar to Example 29 using N-(2,2-difluoroethyl)-3-(4-(2,4-difluorophenoxy)piperidin-1-yl)-5-methyl-5,6,7,8-tetrahydropyrido[3,4-b]pyrazin-2-amine $^1$H NMR (500 MHz, methanol-d4, mixture of rotamers) δ ppm 1.43 (d, J=6.8 Hz, 1.8H), 1.56 (d, J=6.8 Hz, 1.2H), 1.95-2.03 (m, 2H), 2.10-2.23 (m, 5H), 2.63-2.83 (m, 1.6H), 2.88-3.10 (m, 3.2H), 3.35-3.47 (m, 2H), 3.48-3.57 (m, 0.5H), 3.78 (td, J=14.4, 4.4 Hz, 2H), 4.05 (dd, J=13.9, 5.6 Hz, 0.6H), 4.42-4.51 (m, 1H), 4.73 (dd, J=13.7, 5.9 Hz, 0.6H), 5.35 (q, J=6.7 Hz, 0.5H), 5.92-6.20 (m, 1H), 6.84-6.93 (m, 1H), 6.96-7.04 (m, 1H), 7.14-7.23 (m, 1H); ESI-MS m/z [M+H]$^+$ 482.

Example 33 N-(2,2-difluoroethyl)-3-(4-(2,4-difluorophenoxy)piperidin-1-yl)-5-methyl-6-(methylsulfonyl)-5,6,7,8-tetrahydropyrido[3,4-b]pyrazin-2-amine

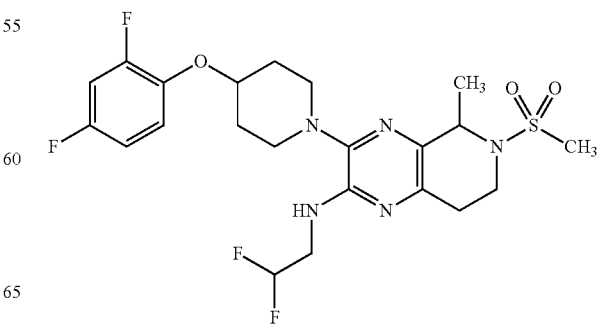

The title compound was prepared as a white film in a manner similar to Example 30 using N-(2,2-difluoroethyl)-3-(4-(2,4-difluorophenoxy)piperidin-1-yl)-5-methyl-5,6,7,8-tetrahydropyrido[3,4-b]pyrazin-2-amine $^1$H NMR (500 MHz, methanol-d4) δ ppm 1.52 (d, J=6.8 Hz, 3H), 1.91-2.01 (m, 2H), 2.08-2.19 (m, 2H), 2.66 (dd, J=17.1, 2.9 Hz, 1H), 2.91 (s, 3H), 2.93-3.08 (m, 3H), 3.34-3.48 (m, 3H), 3.77 (td, J=14.4, 4.4 Hz, 2H), 3.97 (dd, J=14.2, 6.4 Hz, 1H), 4.40-4.51 (m, 1H), 4.78 (q, J=6.7 Hz, 1H), 5.88-6.21 (m, 1H), 6.82-6.92 (m, 1H), 6.98 (ddd, J=11.2, 8.3, 2.9 Hz, 1H), 7.17 (td, J=9.2, 5.6 Hz, 1H); ESI-MS m/z [M+H]+ 518.80.

Example 34 1-(2-(2,2-difluoroethylamino)-3-(4-(2,4-difluorophenoxy)piperidin-1-yl)-5-methyl-7,8-dihydropyrido[3,4-b]pyrazin-6(5H)-yl)-2-methoxyethanone

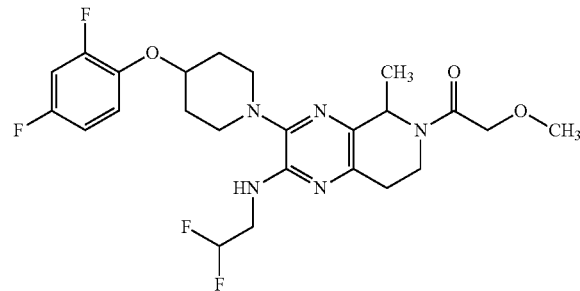 [SMILES: COCC(=O)N1CCc2nc(NCC(F)F)c(N3CCC(Oc4ccc(F)cc4F)CC3)nc2C1C]

The title compound was prepared as an off-white film in a manner similar to Example 31 using N-(2,2-difluoroethyl)-3-(4-(2,4-difluorophenoxy)piperidin-1-yl)-5-methyl-5,6,7,8-tetrahydropyrido[3,4-b]pyrazin-2-amine $^1$H NMR (500 MHz, methanol-d4, mixture of rotamers) δ ppm 1.45 (d, J=6.8 Hz, 2H), 1.56 (d, J=6.8 Hz, 1H), 1.93-2.02 (m, 2H), 2.11-2.18 (m, 2H), 2.63-3.18 (m, 4.5H), 3.35-3.51 (m, 5.5H), 3.78 (td, J=14.5, 4.1 Hz, 2H), 4.01 (dd, J=13.7, 5.4 Hz, 0.7H), 4.19-4.33 (m, 2H), 4.47 (dd, J=7.3, 3.9 Hz, 1H), 4.70 (dd, J=13.2, 5.9 Hz, 0.3H), 4.80-4.84 (m, 0.3H), 5.31 (q, J=6.7 Hz, 0.7H), 5.93-6.20 (m, 1H), 6.85-6.92 (m, 1H), 6.99 (ddd, J=11.3, 8.7, 2.9 Hz, 1H), 7.18 (td, J=9.2, 5.6 Hz, 1H); ESI-MS m/z [M+H]+ 512.80.

Example 35 1-(3-(4-(2,4-difluorophenoxy)piperidin-1-yl)-2-(isopropylamino)-5-methyl-7,8-dihydropyrido[3,4-b]pyrazin-6(5H)-yl)ethanone

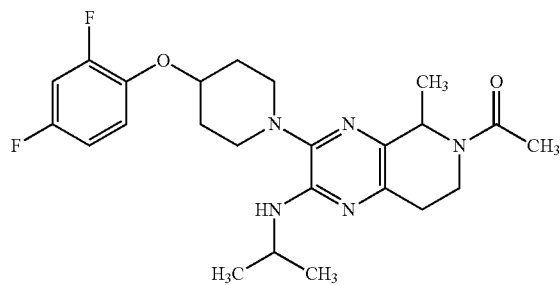 [SMILES: CC(=O)N1CCc2nc(NC(C)C)c(N3CCC(Oc4ccc(F)cc4F)CC3)nc2C1C]

The title compound was prepared as a light yellow film in a manner similar to Example 29 using 3-(4-(2,4-difluorophenoxy)piperidin-1-yl)-N-isopropyl-5-methyl-5,6,7,8-tetrahydropyrido[3,4-b]pyrazin-2-amine TFA salt. $^1$H NMR (500 MHz, methanol-d4, mixture of rotamers) δ ppm 1.30-1.36 (m, 6H), 1.45 (d, J=6.8 Hz, 1.8H), 1.58 (d, J=6.8 Hz, 1.2H), 1.98 (d, J=6.8 Hz, 2H), 2.15 (dd, J=8.5, 4.6 Hz, 2H), 2.19-2.23 (m, 3H), 2.70-2.85 (m, 1.4H), 2.91-3.17 (m, 3.3H), 3.44-3.57 (m, 2.7H), 4.06-4.19 (m, 1.6H), 4.48-4.55 (m, 1H), 4.76 (dd, J=13.7, 5.4 Hz, 0.4H), 5.35 (q, J=6.8 Hz, 0.6H), 6.86-6.92 (m, 1H), 7.00 (ddd, J=11.3, 8.7, 2.9 Hz, 1H), 7.19 (td, J=9.2, 5.6 Hz, 1H); ESI-MS m/z [M+H]+ 460.2.

Example 36 3-(4-(2,4-difluorophenoxy)piperidin-1-yl)-N-isopropyl-5-methyl-6-(methylsulfonyl)-5,6,7,8-tetrahydropyrido[3,4-b]pyrazin-2-amine

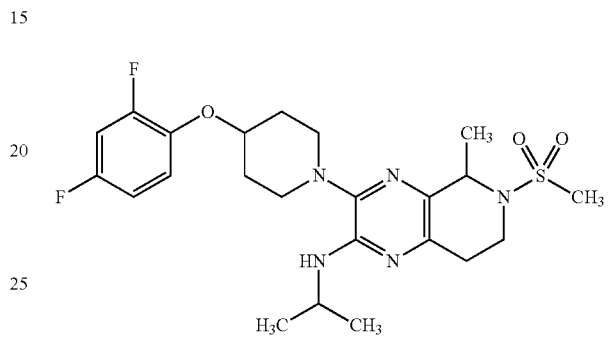

The title compound was prepared as an off-white film in a manner similar to Example 30 using 3-(4-(2,4-difluorophenoxy)piperidin-1-yl)-N-isopropyl-5-methyl-5,6,7,8-tetrahydropyrido[3,4-b]pyrazin-2-amine TFA salt. $^1$H NMR (500 MHz, methanol-d4) δ ppm 1.25-1.31 (m, 6H), 1.52 (d, J=6.4 Hz, 3H), 1.90-2.02 (m, 2H), 2.09-2.19 (m, 2H), 2.70 (dd, J=17.3, 3.2 Hz, 1H), 2.88-3.13 (m, 6H), 3.37-3.50 (m, 3H), 3.98 (dd, J=14.2, 6.4 Hz, 1H), 4.15 (dt, J=13.1, 6.4 Hz, 1H), 4.48 (dt, J=7.4, 3.8 Hz, 1H), 4.77 (q, J=7.0 Hz, 1H), 6.84-6.92 (m, 1H), 6.99 (ddd, J=11.4, 8.7, 2.9 Hz, 1H), 7.18 (td, J=9.2, 5.6 Hz, 1H); ESI-MS m/z [M+H]+ 496.90.

Example 37 1-(3-(4-(2,4-difluorophenoxy)piperidin-1-yl)-2-(isopropylamino)-5-methyl-7,8-dihydropyrido[3,4-b]pyrazin-6(5H)-yl)-2-methoxyethanone

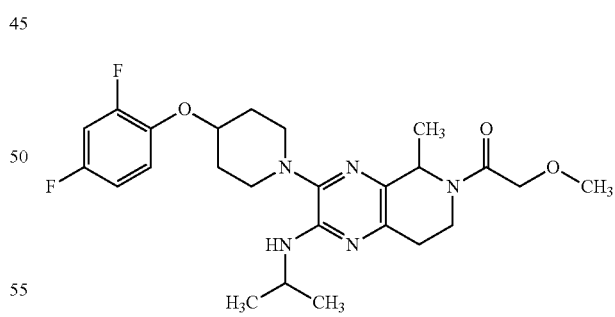

The title compound was prepared as an off-white film in a manner similar to Example 31 using N-(2,2-difluoroethyl)-3-(4-(2,4-difluorophenoxy)piperidin-1-yl)-5-methyl-5,6,7,8-tetrahydropyrido[3,4-b]pyrazin-2-amine $^1$H NMR (500 MHz, methanol-d4, mixture of rotamers) δ ppm 1.29-1.37 (m, 6H), 1.47 (d, J=6.8 Hz, 2H), 1.58 (d, J=6.8 Hz, 1H), 1.98 (d, J=9.8 Hz, 2H), 2.14 (br s, 2H), 2.72-2.88 (m, 1.5H), 2.92-3.00 (m, 0.8H), 3.09-3.17 (m, 2.5H), 3.41-3.53 (m, 5.7H), 4.06 (dd, J=14.2, 5.4 Hz, 0.8H), 4.10-4.33 (m, 3.2H), 4.52 (d, J=3.4 Hz, 1H), 4.72 (dd, J=13.4, 5.6 Hz, 0.4H), 4.80-4.84 (m, 0.4H), 5.31 (q, J=6.3 Hz, 0.7H), 6.89 (t, J=8.5 Hz, 1H), 7.00 (ddd, J=11.2, 8.5, 3.2 Hz, 1H), 7.19 (td, J=9.3, 5.4 Hz, 1H); ESI-MS m/z [M+H]⁺ 490.95.

Example 38 Cyclopropyl(3-(2,2-difluoroethylamino)-2-(4-(2,4-difluorophenoxy)piperidin-1-yl)-5-methyl-7,8-dihydropyrido[3,4-b]pyrazin-6(5H)-yl)methanone

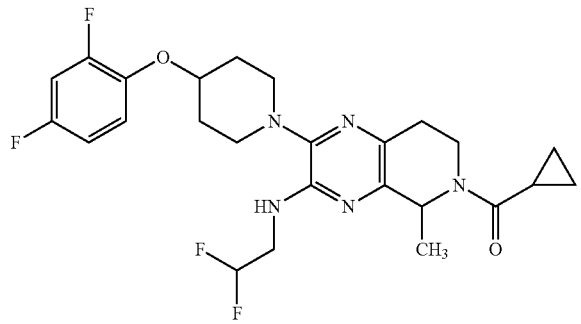 [SMILES: CC1c2nc(NCC(F)F)c(N3CCC(Oc4ccc(F)cc4F)CC3)nc2CCN1C(=O)C1CC1]

The title compound was prepared as an off-white film in a manner similar to Example 31 using N-(2,2-difluoroethyl)-2-(4-(2,4-difluorophenoxy)piperidin-1-yl)-5-methyl-5,6,7,8-tetrahydropyrido[3,4-b]pyrazin-3-amine TFA salt. ¹H NMR (500 MHz, methanol-d4, mixture of rotamers) δ ppm 0.81-1.05 (m, 4H), 1.45 (d, J=6.8 Hz, 1.6H), 1.64 (d, J=6.8 Hz, 1.4H), 1.94-2.18 (m, 5.4H), 2.61-2.83 (m, 1.6H), 2.89-3.12 (m, 3.2H), 3.35-3.44 (m, 2.1H), 3.51-3.60 (m, 0.6H), 3.71-3.86 (m, 2H), 4.42-4.51 (m, 1.6H), 4.70 (dd, J=13.2, 4.9 Hz, 0.5H), 5.21-5.37 (m, 1H), 5.91-6.20 (m, 1H), 6.85-6.91 (m, 1H), 6.99 (ddd, J=11.3, 8.7, 2.9 Hz, 1H), 7.18 (td, J=9.3, 5.4 Hz, 1H); ESI-MS m/z [M+H]⁺ 508.85.

Example 39 Cyclopropyl(2-(2,2-difluoroethylamino)-3-(4-(2,4-difluorophenoxy)piperidin-1-yl)-5-methyl-7,8-dihydropyrido[3,4-b]pyrazin-6(5H)-yl)methanone

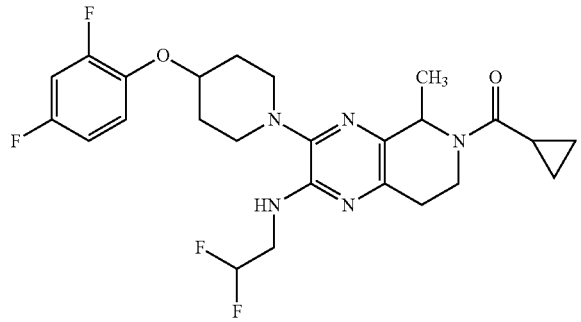 [SMILES: CC1c2nc(N3CCC(Oc4ccc(F)cc4F)CC3)c(NCC(F)F)nc2CCN1C(=O)C1CC1]

The title compound was prepared as a white film in a manner similar to Example 31 using N-(2,2-difluoroethyl)-3-(4-(2,4-difluorophenoxy)piperidin-1-yl)-5-methyl-5,6,7,8-tetrahydropyrido[3,4-b]pyrazin-2-amine TFA salt. ¹H NMR (500 MHz, methanol-d4, mixture of rotamers) δ ppm 0.80-1.06 (m, 4H), 1.43 (d, J=6.8 Hz, 1.5H), 1.62 (d, J=6.8 Hz, 1.5H), 1.91-2.20 (m, 5.5H), 2.62-2.83 (m, 1.6H), 2.90-3.13 (m, 3.2H), 3.35-3.48 (m, 2.1H), 3.52-3.61 (m, 0.5H), 3.78 (td, J=14.4, 3.9 Hz, 2H), 4.46 (dd, J=8.3, 4.4 Hz, 1.6H), 4.69 (dd, J=13.2, 4.9 Hz, 0.5H), 5.21-5.38 (m, 1H), 5.92-6.20 (m, 1H), 6.88 (t, J=8.5 Hz, 1H), 6.96-7.03 (m, 1H), 7.18 (td, J=9.2, 5.6 Hz, 1H); ESI-MS m/z [M+H]⁺ 508.85.

Example 40 Cyclopropyl(3-(4-(2,4-difluorophenoxy)piperidin-1-yl)-2-(isopropylamino)-5-methyl-7,8-dihydropyrido[3,4-b]pyrazin-6(5H)-yl)methanone

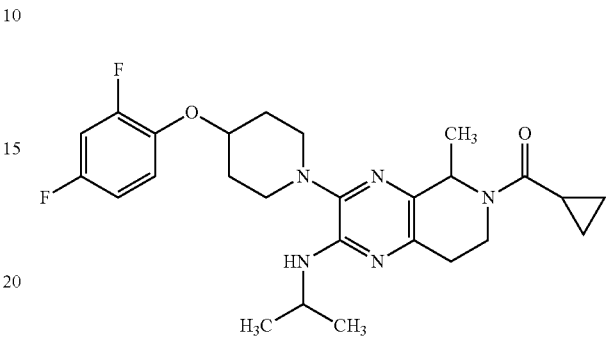

The title compound was prepared as a light yellow film in a manner similar to Example 31 using 3-(4-(2,4-difluorophenoxy)piperidin-1-yl)-N-isopropyl-5-methyl-5,6,7,8-tetrahydropyrido[3,4-b]pyrazin-2-amine TFA salt. ¹H NMR (500 MHz, methanol-d4, mixture of rotamers) δ ppm 0.79-1.05 (m, 4H), 1.30 (t, J=6.3 Hz, 6H), 1.44 (d, J=6.8 Hz, 1.5H), 1.63 (d, J=6.8 Hz, 1.5H), 1.92-2.18 (m, 5.1H), 2.67-2.84 (m, 1.5H), 2.91-3.13 (m, 3H), 3.44 (td, J=7.9, 3.7 Hz, 2H), 3.53-3.61 (m, 0.5H), 4.16 (dt, J=11.8, 6.0 Hz, 1H), 4.49 (d, J=7.3 Hz, 1.5H), 4.70 (dd, J=12.9, 5.1 Hz, 0.4H), 5.21-5.37 (m, 1H), 6.89 (t, J=8.3 Hz, 1H), 6.96-7.04 (m, 1H), 7.19 (td, J=9.3, 5.4 Hz, 1H); ESI-MS m/z [M+H]⁺ 486.90.

Example 41 1-(3-(2,2-difluoroethylamino)-2-(4-(2,4-difluorophenoxy)piperidin-1-yl)-5-methyl-7,8-dihydropyrido[3,4-b]pyrazin-6(5H)-yl)-2,2-difluoroethanone

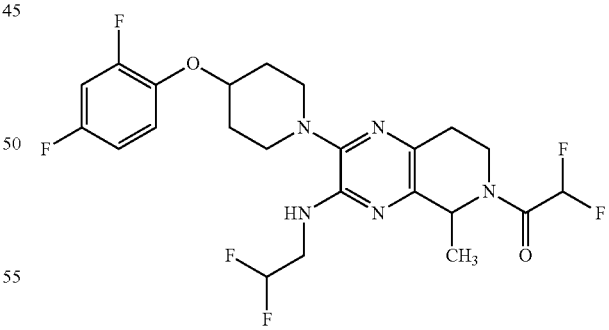

A solution of 2,2-difluoroacetic acid (2.86 mg, 0.030 mmol), HATU (11.3 mg, 0.030 mmol), and DIPEA (14.2 µL, 0.081 mmol) in DMF (136 µL) was stirred at room temperature for 10 min. Then, N-(2,2-difluoroethyl)-2-(4-(2,4-difluorophenoxy)piperidin-1-yl)-5-methyl-5,6,7,8-tetrahydropyrido[3,4-b]pyrazin-3-amine TFA salt (15 mg, 0.027 mmol) was added and stirring was continued overnight. No desired product was detected by LCMS. To this was added 2,2-difluoroacetic anhydride (7.08 mg, 0.041 mmol) and after 1 h, purification by HPLC Method A afforded the title compound as a TFA salt (4.4 mg) as an off-white film. $^1$H NMR (500 MHz, methanol-d4, mixture of rotamers) δ ppm 1.51 (d, J=6.8 Hz, 2.1H), 1.62 (d, J=6.8 Hz, 0.9H), 1.94-2.02 (m, 2H), 2.10-2.18 (m, 2H), 2.68-2.78 (m, 1H), 2.82-3.06 (m, 3.2H), 3.36-3.44 (m, 2H), 3.53-3.61 (m, 0.7H), 3.71-3.88 (m, 2.1H), 4.16 (dd, J=14.2, 5.4 Hz, 0.7H), 4.46 (dt, J=7.4, 3.8 Hz, 1H), 4.67 (dd, J=13.2, 5.9 Hz, 0.3H), 4.97 (q, J=6.7 Hz, 0.3H), 5.27 (q, J=6.8 Hz, 0.7H), 5.93-6.20 (m, 1H), 6.43-6.70 (m, 1H), 6.85-6.92 (m, 1H), 6.99 (ddd, J=11.3, 8.4, 3.2 Hz, 1H), 7.18 (td, J=9.3, 5.4 Hz, 1H); ESI-MS m/z [M+H]$^+$ 518.80.

Example 42 1-(2-(2,2-difluoroethylamino)-3-(4-(2,4-difluorophenoxy)piperidin-1-yl)-5-methyl-7,8-dihydropyrido[3,4-b]pyrazin-6(5H)-yl)-2,2-difluoroethanone

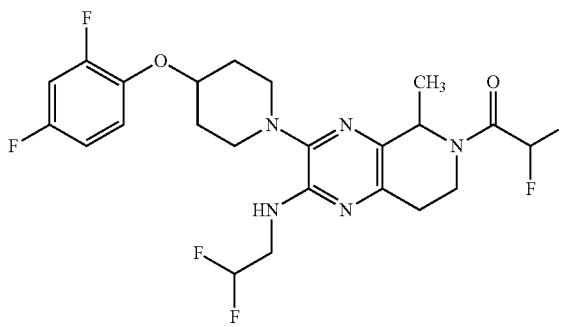

The title compound was prepared as an off-white film in a manner similar to Example 41 using N-(2,2-difluoroethyl)-3-(4-(2,4-difluorophenoxy)piperidin-1-yl)-5-methyl-5,6,7,8-tetrahydropyrido[3,4-b]pyrazin-2-amine TFA salt. $^1$H NMR (500 MHz, methanol-d4, mixture of rotamers) δ ppm 1.50 (d, J=6.8 Hz, 2.1H), 1.60 (d, J=6.8 Hz, 0.9H), 1.92-2.03 (m, 2H), 2.11-2.18 (m, 2H), 2.68-2.77 (m, 1H), 2.82-3.08 (m, 3H), 3.26 (td, J=12.9, 12.9, 3.9 Hz, 0.4H), 3.36-3.47 (m, 2H), 3.53-3.62 (m, 0.6H), 3.78 (td, J=14.4, 4.4 Hz, 2H), 4.15 (dd, J=13.9, 5.6 Hz, 0.7H), 4.43-4.49 (m, 1H), 4.66 (dd, J=13.2, 5.9 Hz, 0.3H), 4.98 (q, J=6.8 Hz, 0.3H), 5.28 (q, J=6.8 Hz, 0.7H), 5.93-6.19 (m, 1H), 6.43-6.69 (m, 1H), 6.86-6.91 (m, 1H), 6.99 (ddd, J=11.2, 8.3, 2.9 Hz, 1H), 7.18 (td, J=9.2, 5.6 Hz, 1H); ESI-MS m/z [M+H]$^+$ 518.85.

Example 43 1-(2-(2,2-difluoroethylamino)-3-(4-(2,4-difluorophenoxy)piperidin-1-yl)-5-methyl-7,8-dihydropyrido[3,4-b]pyrazin-6(5H)-yl)-2,2-difluoroethanone

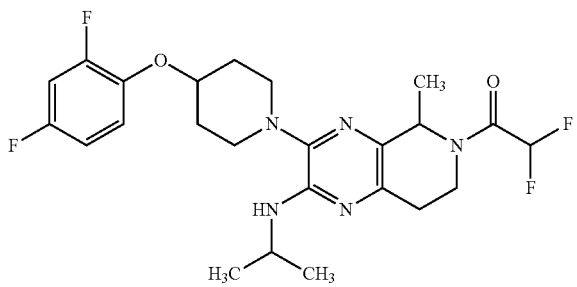 [SMILES: CC(C)Nc1nc2c(nc1N1CCC(Oc3ccc(F)cc3F)CC1)C(C)N(C(=O)C(F)F)CC2]

The title compound was prepared as an off-white film in a manner similar to Example 41 using 3-(4-(2,4-difluorophenoxy)piperidin-1-yl)-N-isopropyl-5-methyl-5,6,7,8-tetrahydropyrido[3,4-b]pyrazin-2-amine TFA salt. $^1$H NMR (500 MHz, methanol-d4, mixture of rotamers) δ ppm 1.25-1.30 (m, 6H), 1.49 (d, J=6.8 Hz, 2H), 1.60 (d, J=6.3 Hz, 1H), 1.91-2.01 (m, 2H), 2.10-2.18 (m, 2H), 2.70-2.80 (m, 1H), 2.81-3.09 (m, 3H), 3.22-3.30 (m, 0.5H), 3.37-3.47 (m, 2H), 3.54-3.62 (m, 0.6H), 4.12-4.21 (m, 1.6H), 4.45-4.52 (m, 1H), 4.66 (dd, J=13.4, 6.1 Hz, 0.3H), 4.93-4.99 (m, 0.3H), 5.26 (q, J=6.5 Hz, 0.7H), 6.43-6.69 (m, 1H), 6.86-6.92 (m, 1H), 7.00 (ddd, J=11.3, 8.7, 2.9 Hz, 1H), 7.19 (td, J=9.3, 5.4 Hz, 1H); ESI-MS m/z [M+H]$^+$ 496.90.

Example 44 1-(3-(4-(2-fluoro-4-methoxyphenoxy)piperidin-1-yl)-2-(isopropylamino)-7,8-dihydropyrido[3,4-b]pyrazin-6(5H)-yl)ethanone

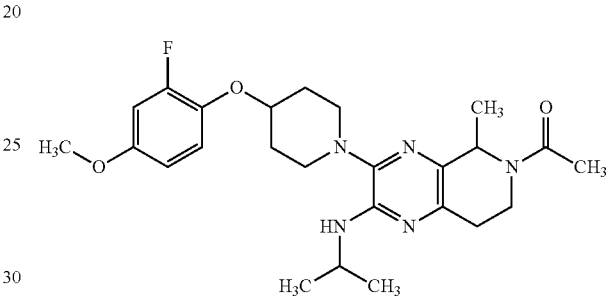

Acetic anhydride (9 μL, 0.095 mmol) was added to a solution of 3-(4-(2-fluoro-4-methoxyphenoxy)piperidin-1-yl)-N-isopropyl-5,6,7,8-tetrahydropyrido[3,4-b]pyrazin-2-amine TFA salt (25.2 mg, 0.048 mmol) and pyridine (11.5 μL, 0.143 mmol) in DCM (500 μL) at rt. After 1 h, the mixture was purified by HPLC Method A to give the title compound as a TFA salt (25.2 mg, 93%) as a yellow film. $^1$H NMR (400 MHz, methanol-d$_4$, mixture of rotamers) δ ppm 1.32 (d, J=6.6 Hz, 6H), 1.89-2.00 (m, 2H), 2.06-2.15 (m, 2H), 2.19 (s, 1.4H), 2.21 (s, 1.6H), 2.77-2.83 (m, 0.9H), 2.87-2.93 (m, 1.1H), 3.04-3.14 (m, 2H), 3.42-3.50 (m, 2H), 3.75 (s, 3H), 3.80-3.85 (m, 1.1H), 3.85-3.90 (m, 0.9H), 4.09-4.19 (m, 1H), 4.35-4.42 (m, 1H), 4.55 (br s, 2H), 6.67 (dt, J=9.0, 1.4 Hz, 1H), 6.74 (dd, J=12.8, 2.9 Hz, 1H), 7.08 (t, J=9.2 Hz, 1H); ESI-MS m/z [M+H]$^+$ 458.4.

Example 45 1-(2-(4-(2-fluoro-4-methoxyphenoxy)piperidin-1-yl)-3-(isopropylamino)-7,8-dihydropyrido[3,4-b]pyrazin-6(5H)-yl)ethanone

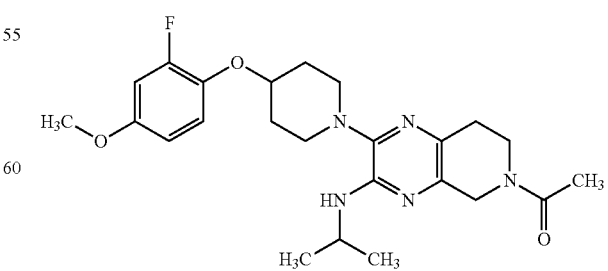

The title compound was prepared in a manner similar to Example 29 using 2-(4-(2-fluoro-4-methoxyphenoxy)piperidin-1-yl)-N-isopropyl-5,6,7,8-tetrahydropyrido[3,4-b]pyrazin-3-amine TFA salt. ESI-MS m/z [M+H]+ 458.40.

Example 46 2-(4-(2-fluoro-4-methoxyphenoxy)piperidin-1-yl)-3-(isopropylamino)-N,N-dimethyl-7,8-dihydropyrido[3,4-b]pyrazine-6(5H)-carboxamide

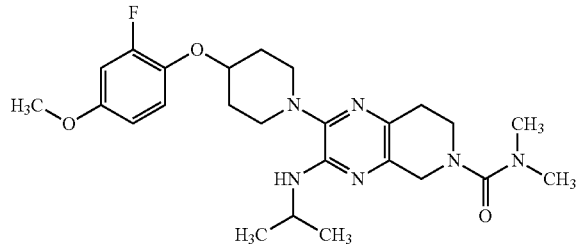

Dimethylcarbamic chloride (4.9 mg, 0.046 mmol) was added to a solution of 2-(4-(2-fluoro-4-methoxyphenoxy)piperidin-1-yl)-N-isopropyl-5,6,7,8-tetrahydropyrido[3,4-b]pyrazin-3-amine TFA salt (12.1 mg, 0.023 mmol) and triethylamine (10 µL, 0.069 mmol) in DCM (230 µL) at rt. After 1 h, the mixture was purified by HPLC Method A to give the title compound as a TFA salt (12.1 mg, 88%) as a yellow film. $^1$H NMR (400 MHz, methanol-$d_4$) δ ppm 1.27-1.32 (m, 6H), 1.89-1.99 (m, 2H), 2.06-2.15 (m, 2H), 2.81 (s, 2H), 2.91 (s, 6H), 3.00-3.09 (m, 2H), 3.39-3.46 (m, 2H), 3.55 (t, J=5.8 Hz, 2H), 3.75 (s, 3H), 4.13 (quin, J=6.4 Hz, 1H), 4.30 (s, 2H), 4.34-4.40 (m, 1H), 6.67 (ddd, J=8.9, 3.0, 1.5 Hz, 1H), 6.74 (dd, J=12.8, 2.9 Hz, 1H), 7.08 (t, J=9.2 Hz, 1H); ESI-MS m/z [M+H]+ 487.4.

Example 47 1-(2-(4-(2,4-difluorophenoxy)piperidin-1-yl)-3-(isopropylamino)-7,8-dihydropyrido[3,4-b]pyrazin-6(5H)-yl)ethanone

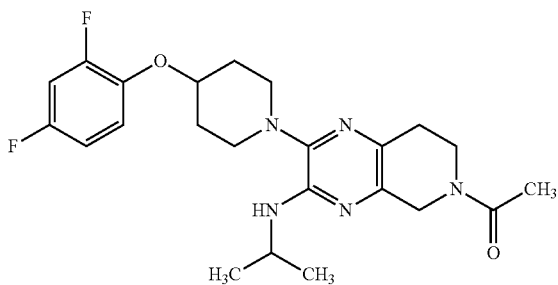

A mixture of 2-(4-(2,4-difluorophenoxy)piperidin-1-yl)-N-isopropylpyrido[3,4-b]pyrazin-3-amine (100 mg, 0.250 mmol), acetic anhydride (0.09 mL, 1.00 mmol) and 10% Pd/C (9.0 mg) in a mixture of dioxane (2.5 mL) and acetone (1.5 mL) was stirred at room temperature for 24 h. Then, 4.0 equivalents of acetic anhydride was added and stirring was continued for 2 days. After filtration, the reaction solution was quenched with saturated NaHCO$_3$ and the aqueous layer was extracted with ethyl acetate (3×5 mL). The combined organic phase was dried with anhydrous Na$_2$SO$_4$ and concentrated under vacuum. Purification by silica gel column chromatography using a 30% to 100% gradient of EtOAc in heptane gave the title compound (57 mg, 51%) as a white solid. $^1$H NMR (400 MHz, methanol-$d_4$, mixture of rotamers) δ ppm 1.23 (d, J=6.6 Hz, 3.3H), 1.24 (d, J=6.6 Hz, 2.7H), 1.93 (m, 2H), 2.11 (m, 2H), 2.18 (s, 1.3H), 2.20 (s, 1.7H), 2.71 (t, J=6.1 Hz, 0.9H), 2.80 (t, J=6.1 Hz, 1.1H), 2.95 (m, 2H), 3.34 (m, 2H), 3.79 (t, J=5.9 Hz, 1.1H), 3.84 (t, J=6.1 Hz, 0.9H), 4.15 (m, 1H), 4.44 (tt, J=7.5, 3.7 Hz, 1H), 4.53 (s, 0.9H), 4.54 (s, 1.1H), 6.86 (m, 1H), 6.97 (ddd, J=11.2, 8.5, 3.2 Hz, 1H), 7.16 (td, J=9.2, 5.6 Hz, 1H); ESI-MS m/z [M+H]+ 446.00.

Example 49 2-(2,2-difluoroethylamino)-3-(4-(2,4-difluorophenoxy)piperidin-1-yl)-N,N-dimethyl-7,8-dihydropyrido[3,4-b]pyrazine-6(5H)-carboxamide

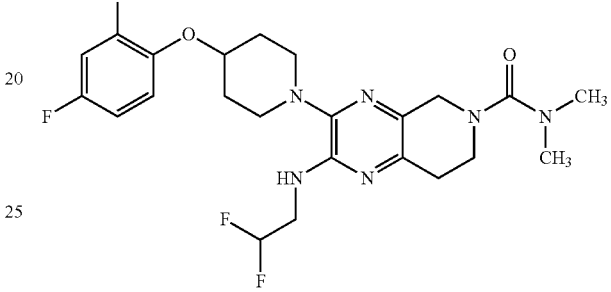

A solution of N-(2,2-difluoroethyl)-3-(4-(2,4-difluorophenoxy)piperidin-1-yl)-5,6,7,8-tetrahydropyrido[3,4-b]pyrazin-2-amine TFA salt (15 mg, 0.028 mmol) in DCM (278 µL) at room temperature was treated with dimethylcarbamic chloride (3.0 mg, 0.028 mmol) and DIPEA (4.9 µL, 0.028 mmol), and the resulting reaction mixture was stirred overnight. The crude reaction mixture was diluted in DMF, filtered through a hydrophilic PTFE 0.45 µm filter (Millipore® Millex-LCR), and purified via HPLC Method A to give the title compound as a TFA salt (7 mg) as a white solid. $^1$H NMR (400 MHz, methanol-$d_4$) δ ppm 1.92-2.02 (m, 2H), 2.09-2.18 (m, 2H), 2.81-2.86 (m, 2H), 2.90 (s, 6H), 2.96-3.04 (m, 2H), 3.34-3.42 (m, 2H), 3.54 (t, J=5.9 Hz, 2H), 3.74-3.84 (m, 2H), 4.28 (s, 2H), 4.46 (tt, J=7.7, 3.9 Hz, 1H), 5.90-6.22 (m, 1H), 6.88 (dddd, J=9.1, 8.1, 3.2, 1.9 Hz, 1H), 6.99 (ddd, J=11.4, 8.6, 3.0 Hz, 1H), 7.18 (td, J=9.2, 5.6 Hz, 1H); ESI-MS m/z [M+H]+ 497.4.

Example 50 1-(2-((2,2-difluoroethyl)amino)-3-(4-(2,4-difluorophenoxy)piperidin-1-yl)-7,8-dihydropyrido[3,4-b]pyrazin-6(5H)-yl)-2-methoxyethanone

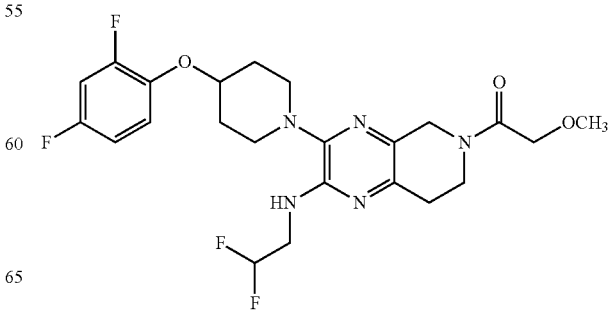

A solution of N-(2,2-difluoroethyl)-3-(4-(2,4-difluorophenoxy)piperidin-1-yl)-5,6,7,8-tetrahydropyrido[3,4-b]pyrazin-2-amine TFA salt (17 mg, 0.032 mmol), DIPEA (12.2 mg, 0.095 mmol), and 2-methoxyacetyl chloride (5.1 mg, 0.047 mmol) in DCM (315 µL) was stirred at room temperature overnight. The crude reaction mixture was diluted in DMF, filtered through a hydrophilic PTFE 0.45 µm filter (Millipore® Millex-LCR), and purified via HPLC Method A to give the title compound as a TFA salt (7 mg) as a clear oil. $^1$H NMR (400 MHz, methanol-d$_4$, mixture of rotamers) δ ppm 1.92-2.03 (m, 2H), 2.09-2.18 (m, 2H), 2.77 (t, J=5.8 Hz, 0.9H), 2.84 (t, J=5.8 Hz, 1.1H), 2.96-3.04 (m, 2H), 3.37 (d, J=10.4 Hz, 2H), 3.41 (s, 1.5H), 3.42 (s, 1.5H), 3.73-3.83 (m, 3H), 3.88 (t, J=5.9 Hz, 1H), 4.24 (s, 0.9H), 4.27 (s, 1.1H), 4.41-4.49 (m, 1H), 4.50 (s, 0.9H), 4.53 (s, 1.1H), 5.89-6.21 (m, 1H), 6.84-6.91 (m, 1H), 6.98 (ddd, J=11.2, 8.5, 3.0 Hz, 1H), 7.17 (td, J=9.2, 5.6 Hz, 1H); ESI-MS m/z [M+H]$^+$ 498.3.

Example 51 (R)-1-(2-(2,2-difluoroethylamino)-3-(4-(2,4-difluorophenoxy)piperidin-1-yl)-7,8-dihydropyrido[3,4-b]pyrazin-6(5H)-yl)-2-methoxypropan-1-one

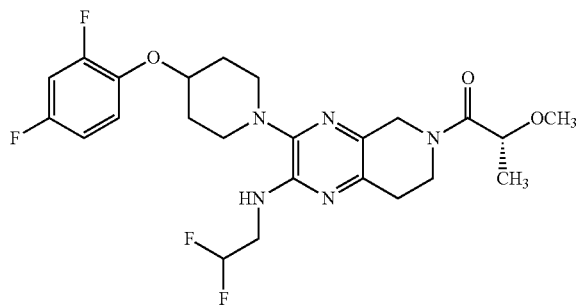 [SMILES: CO[C@H](C)C(=O)N1CCc2nc(NCC(F)F)c(N3CCC(Oc4ccc(F)cc4F)CC3)nc2C1]

A solution of N-(2,2-difluoroethyl)-3-(4-(2,4-difluorophenoxy)piperidin-1-yl)-5,6,7,8-tetrahydropyrido[3,4-b]pyrazin-2-amine TFA salt (17 mg, 0.032 mmol), DIPEA (12.2 mg, 0.095 mmol), and HATU (13.2 mg, 0.035 mmol) in DMF (158 µL) was stirred for 10 min at rt. To this was added (R)-2-methoxypropanoic acid (3.6 mg, 0.035 mmol), and the resulting reaction mixture stirred overnight. The crude reaction mixture was diluted in DMF, filtered through a hydrophilic PTFE 0.45 µm filter (Millipore® Millex-LCR), and purified via HPLC Method A to give the title compound as a TFA salt (6 mg) as a clear oil. $^1$H NMR (400 MHz, methanol-d$_4$, mixture of rotamers) δ ppm 1.32 (d, J=6.8 Hz, 1.3H), 1.38 (d, J=6.6 Hz, 1.7H), 1.92-2.03 (m, 2H), 2.09-2.18 (m, 2H), 2.78 (t, J=6.2 Hz, 0.9H), 2.86 (m, 1.1H), 2.97-3.06 (m, 2H), 3.33 (s, 3H), 3.35-3.43 (m, 2H), 3.79 (td, J=14.5, 4.3 Hz, 2H), 3.85-3.97 (m, 2H), 4.36 (dq, J=12.7, 6.5 Hz, 1H), 4.42-4.49 (m, 1H), 4.58 (m, 0.9H), 4.68 (m, 1.1H), 5.90-6.22 (m, 1H), 6.84-6.91 (m, 1H), 6.98 (ddd, J=11.4, 8.5, 3.0 Hz, 1H), 7.18 (td, J=9.2, 5.3 Hz, 1H); ESI-MS m/z [M+H]$^+$ 512.4.

Example 52 1-(2-(4-(2,4-difluorophenoxy)piperidin-1-yl)-3-(isopropylamino)-5-methyl-7,8-dihydropyrido[3,4-b]pyrazin-6(5H)-yl)ethanone

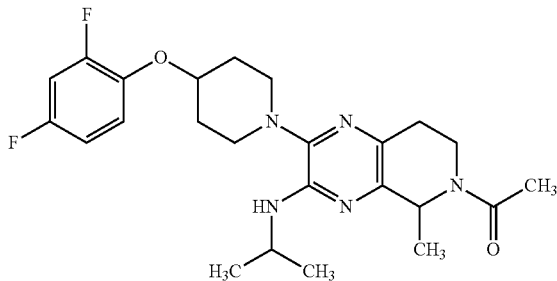 [SMILES: CC(=O)N1CCc2nc(N3CCC(Oc4ccc(F)cc4F)CC3)c(NC(C)C)nc2C1C]

The title compound was prepared as a yellow film in a manner similar to Example 29 using 2-(4-(2,4-difluorophenoxy)piperidin-1-yl)-N-isopropyl-5-methyl-5,6,7,8-tetrahydropyrido[3,4-b]pyrazin-3-amine TFA salt. $^1$H NMR (500 MHz, methanol-d4, mixture of rotamers) δ ppm 1.24-1.31 (m, 6H), 1.46 (d, J=6.8 Hz, 2H), 1.59 (d, J=6.8 Hz, 1H), 1.92-2.00 (m, 2H), 2.09-2.17 (m, 2H), 2.19-2.23 (m, 3H), 2.61-2.82 (m, 1.5H), 2.87-2.96 (m, 0.7H), 2.99-3.09 (m, 2.4H), 3.40 (td, J=7.7, 3.7 Hz, 2H), 3.49-3.57 (m, 0.6H), 4.06 (dd, J=13.9, 5.6 Hz, 0.6H), 4.13-4.20 (m, 1H), 4.48 (td, J=7.2, 3.7 Hz, 1H), 4.73 (dd, J=13.4, 5.6 Hz, 0.4H), 4.84 (br s, 0.2H), 5.39 (q, J=6.5 Hz, 0.6H), 6.85-6.91 (m, 1H), 6.99 (ddd, J=11.2, 8.3, 2.9 Hz, 1H), 7.18 (td, J=9.3, 5.4 Hz, 1H); ESI-MS m/z [M+H]$^+$ 460.90.

Example 53 1-(2-(4-(2,4-difluorophenoxy)piperidin-1-yl)-3-(isopropylamino)-5-methyl-7,8-dihydropyrido[3,4-b]pyrazin-6(5H)-yl)-2,2-difluoroethanone

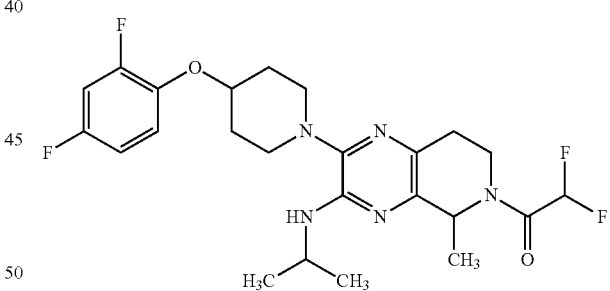

A solution of 2-(4-(2,4-difluorophenoxy)piperidin-1-yl)-N-isopropyl-5-methyl-5,6,7,8-tetrahydropyrido[3,4-b]pyrazin-3-amine TFA salt (15 mg, 0.028 mmol), 2,2-difluoroacetic anhydride (7.4 mg, 0.042 mmol), and DIPEA (10.94 mg, 0.085 mmol) in DCM (141 µL) was stirred at room temperature for 1 h. Purification by HPLC Method A gave the title compound as a TFA salt (8.2 mg) as an off-white film. $^1$H NMR (500 MHz, methanol-d4, mixture of rotamers) δ ppm 1.27 (dd, J=7.6, 6.6 Hz, 6H), 1.51 (d, J=6.8 Hz, 2.1H), 1.62 (d, J=6.8 Hz, 0.9H), 1.90-2.00 (m, 2H), 2.09-2.17 (m, 2H), 2.65-2.75 (m, 1H), 2.80-3.03 (m, 3H), 3.25 (td, J=12.9, 3.9 Hz, 0.3H), 3.34-3.42 (m, 2H), 3.52-3.61 (m, 0.7H), 4.11-4.21 (m, 1.7H), 4.46 (dt, J=7.3, 3.7 Hz, 1H), 4.66 (dd, J=13.4, 5.6 Hz, 0.3H), 4.91-4.98 (m, 0.3H), 5.25 (q, J=6.7 Hz, 0.7H), 6.44-6.69 (m, 1H), 6.84-6.92 (m, 1H), 6.99 (ddd, J=11.3, 8.4, 3.2 Hz, 1H), 7.18 (td, J=9.3, 5.4 Hz, 1H); ESI-MS m/z [M+H]⁺ 496.90.

Example 54 2-(4-(2,4-difluorophenoxy)piperidin-1-yl)-N-isopropyl-5-methyl-6-(methylsulfonyl)-5,6,7,8-tetrahydropyrido[3,4-b]pyrazin-3-amine

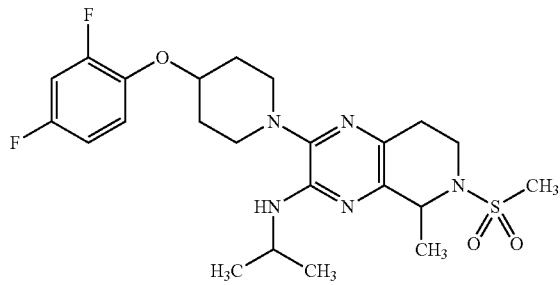 [SMILES: CC(C)Nc1nc2c(nc1N1CCC(Oc3ccc(F)cc3F)CC1)CCN(S(C)(=O)=O)C2C]

The title compound was prepared as an off-white film in a manner similar to Example 30 using 2-(4-(2,4-difluorophenoxy)piperidin-1-yl)-N-isopropyl-5-methyl-5,6,7,8-tetrahydropyrido[3,4-b]pyrazin-3-amine TFA salt. ¹H NMR (500 MHz, methanol-d4) δ ppm 1.26 (dd, J=10.7, 6.4 Hz, 6H), 1.54 (d, J=6.8 Hz, 3H), 1.88-2.00 (m, 2H), 2.07-2.18 (m, 2H), 2.64 (dd, J=16.6, 2.9 Hz, 1H), 2.89-2.92 (m, 4H), 2.94-3.03 (m, 3H), 3.34-3.48 (m, 3H), 3.97 (dd, J=14.2, 6.4 Hz, 1H), 4.15 (quin, J=6.5 Hz, 1H), 4.46 (dt, J=7.4, 3.8 Hz, 1H), 4.76 (q, J=6.7 Hz, 1H), 6.81-6.92 (m, 1H), 6.98 (ddd, J=11.4, 8.4, 3.2 Hz, 1H), 7.17 (td, J=9.2, 5.6 Hz, 1H); ESI-MS m/z [M+H]⁺ 496.95.

Example 55 2-(4-(2,4-difluorophenoxy)piperidin-1-yl)-3-(isopropylamino)-N,N,5-trimethyl-7,8-dihydropyrido[3,4-b]pyrazine-6(5H)-carboxamide

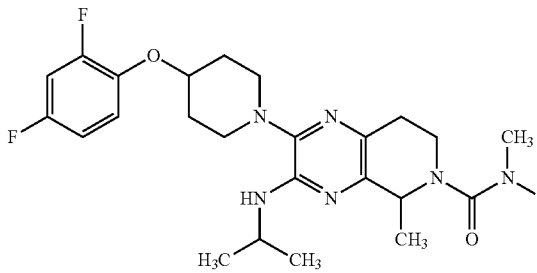

A solution of 2-(4-(2,4-difluorophenoxy)piperidin-1-yl)-N-isopropyl-5-methyl-5,6,7,8-tetrahydropyrido[3,4-b]pyrazin-3-amine TFA salt (15 mg, 0.028 mmol), dimethylcarbamic chloride (6.1 mg, 0.056 mmol), and DIPEA (10.9 mg, 0.085 mmol) in DCM (282 µL) was stirred at room temperature overnight. Purification by HPLC Method A afforded the title compound as a TFA salt (6.1 mg) as an off-white film. ¹H NMR (500 MHz, methanol-d4) δ ppm 1.26 (dd, J=9.3, 6.4 Hz, 6H), 1.50 (d, J=6.8 Hz, 3H), 1.89-1.98 (m, 2H), 2.12 (dq, J=13.2, 3.6 Hz, 2H), 2.55-2.64 (m, 1H), 2.88 (s, 6H), 2.94-3.03 (m, 3H), 3.34-3.41 (m, 3H), 3.72-3.82 (m, 1H), 4.14 (quin, J=6.5 Hz, 1H), 4.45 (dt, J=7.4, 3.8 Hz, 1H), 4.67 (q, J=6.8 Hz, 1H), 6.83-6.91 (m, 1H), 6.98 (ddd, J=11.4, 8.4, 3.2 Hz, 1H), 7.17 (td, J=9.3, 5.4 Hz, 1H); ESI-MS m/z [M+H]⁺ 489.90.

Example 56 3-(4-(2,4-difluorophenoxy)piperidin-1-yl)-2-(isopropylamino)-N,N,5-trimethyl-7,8-dihydropyrido[3,4-b]pyrazine-6(5H)-carboxamide

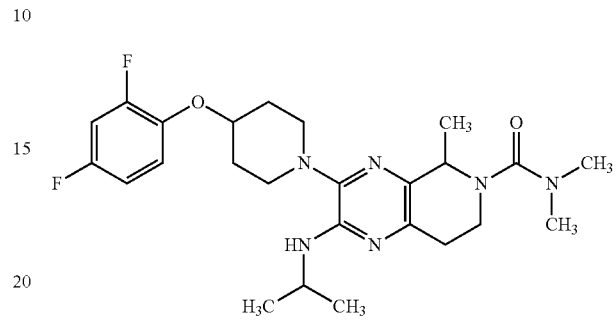

The title compound was prepared as an light yellow film in a manner similar to Example 55 using 3-(4-(2,4-difluorophenoxy)piperidin-1-yl)-N-isopropyl-5-methyl-5,6,7,8-tetrahydropyrido[3,4-b]pyrazin-2-amine TFA salt. ¹H NMR (500 MHz, methanol-d4) δ ppm 1.34 (dd, J=6.4, 5.4 Hz, 6H), 1.51 (d, J=6.8 Hz, 3H), 1.91-2.03 (m, 2H), 2.10-2.18 (m, 2H), 2.70 (dd, J=17.1, 2.9 Hz, 1H), 2.89 (s, 6H), 3.03 (s, 1H), 3.09-3.19 (m, 2H), 3.33-3.39 (m, 1H), 3.43-3.53 (m, 2H), 3.79 (dd, J=14.2, 5.8 Hz, 1H), 4.08-4.18 (m, 1H), 4.46-4.57 (m, 1H), 4.62 (d, J=6.8 Hz, 1H), 6.84-6.93 (m, 1H), 6.99 (ddd, J=11.2, 8.3, 2.9 Hz, 1H), 7.18 (td, J=9.3, 5.4 Hz, 1H); ESI-MS m/z [M+H]⁺ 489.95.

Example 57 2-(2,2-difluoroethylamino)-3-(4-(2,4-difluorophenoxy)piperidin-1-yl)-N,N,5-trimethyl-7,8-dihydropyrido[3,4-b]pyrazine-6(5H)-carboxamide

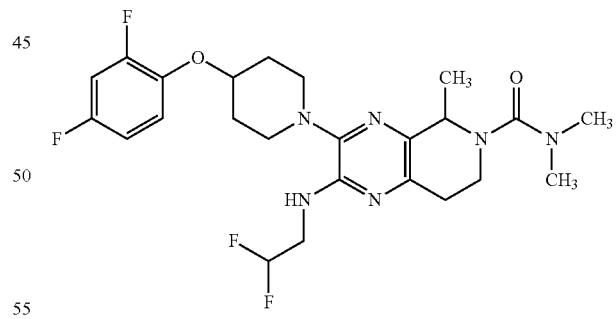

The title compound was prepared as an off-white film in a manner similar to Example 55 using N-(2,2-difluoroethyl)-3-(4-(2,4-difluorophenoxy)piperidin-1-yl)-5-methyl-5,6,7,8-tetrahydropyrido[3,4-b]pyrazin-2-amine TFA salt. ¹H NMR (500 MHz, methanol-d4) δ ppm 1.47 (d, J=6.8 Hz, 3H), 1.96 (d, J=8.3 Hz, 2H), 2.12 (d, J=3.4 Hz, 2H), 2.64 (s, 1H), 2.88 (s, 6H), 2.97 (d, J=11.7 Hz, 3H), 3.34-3.45 (m, 3H), 3.71-3.83 (m, 3H), 4.41-4.49 (m, 1H), 4.67 (d, J=6.8 Hz, 1H), 6.05 (s, 1H), 6.87 (s, 1H), 6.95-7.02 (m, 1H), 7.13-7.21 (m, 1H); ESI-MS m/z [M+H]⁺ 511.90.

Example 58 3-(4-(2-fluoro-4-methoxyphenoxy)piperidin-1-yl)-N-isopropyl-6-methyl-5,6,7,8-tetrahydropyrido[3,4-b]pyrazin-2-amine

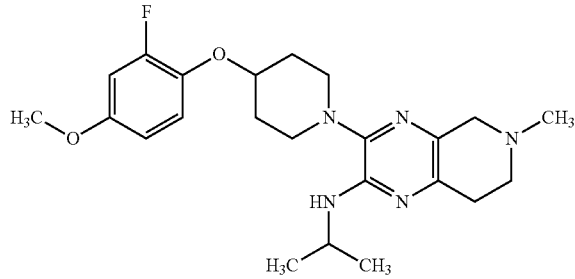

Sodium triacetoxyborohydride (22.3 mg, 0.105 mmol) was added to a mixture of DIPEA (18 µL, 0.105 mmol), 3-(4-(2-fluoro-4-methoxyphenoxy)piperidin-1-yl)-N-isopropyl-5,6,7,8-tetrahydropyrido[3,4-b]pyrazin-2-amine TFA salt (27.9 mg, 0.053 mmol) and formaldehyde (4 µL, 0.053 mmol) in MeOH (550 µL) at rt. After 30 min, the mixture was purified by HPLC Method A to give the title compound as a TFA salt (27.9 mg, 97%) as a yellow film. $^1$H NMR (400 MHz, methanol-$d_4$) δ ppm 1.25 (d, J=6.3 Hz, 6H), 1.88-1.98 (m, 2H), 2.04-2.14 (m, 2H), 2.93-3.05 (m, 3H), 3.07 (br s, 4H), 3.33-3.40 (m, 2H), 3.41-3.69 (m, 2H), 3.75 (s, 3H), 4.15-4.32 (m, 3H), 4.32-4.39 (m, 1H), 6.66 (ddd, J=8.9, 3.0, 1.5 Hz, 1H), 6.73 (dd, J=12.8, 2.9 Hz, 1H), 7.07 (t, J=9.2 Hz, 1H); ESI-MS m/z [M+H]$^+$ 430.4.

Example 59 1-(3-((2,2-difluoroethyl)amino)-2-(4-(2,4-difluorophenoxy)piperidin-1-yl)-7,8-dihydropyrido[3,4-b]pyrazin-6(5H)-yl)ethan-1-one

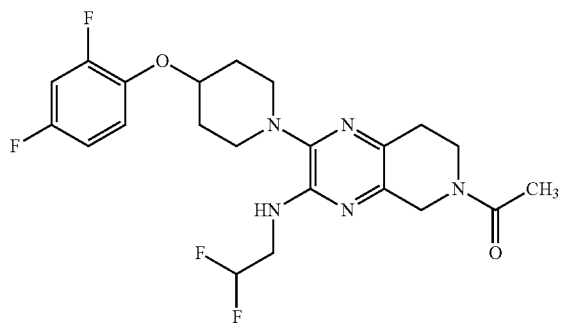 [SMILES: CC(=O)N1CCc2nc(N3CCC(Oc4ccc(F)cc4F)CC3)c(NCC(F)F)nc2C1]

A solution of N-(2,2-difluoroethyl)-2-(4-(2,4-difluorophenoxy)piperidin-1-yl)-5,6,7,8-tetrahydropyrido[3,4-b]pyrazin-3-amine TFA salt (114 mg, 0.211 mmol) in DCM (2.11 mL) at 0° C. was treated with pyridine (0.051 mL, 0.63 mmol) and acetic anhydride (0.040 mL, 0.42 mmol). The reaction mixture was stirred for 30 min at 0° C. The reaction mixture was concentrated under reduced pressure. The residue was taken up in MeOH, filtered, and purified by HPLC Method B, using a 40% to 70% ACN gradient to give the title compound, as a TFA salt, as a yellow solid (39.7 mg, 32.3%). $^1$H NMR (500 MHz, methanol-d4, mixture of rotamers) δ ppm 1.96 (m, 2H), 2.12 (m, 2H), 2.18 (s, 1.3H), 2.20 (s, 1.7H), 2.73 (t, J=5.9 Hz, 0.8H), 2.83 (t, J=5.9 Hz, 1.2H), 3.01 (m, 2H), 3.39 (m, 2H), 3.80 (m, 4H), 4.45 (dt, J=7.0, 3.6 Hz, 1H), 4.57 (app d, 2H), 6.05 (m, 1H), 6.86 (m, 1H), 6.96 (ddd, J=11.2, 8.5, 3.2 Hz, 1H), 7.15 (td, J=9.2, 5.6 Hz, 1H); ESI-MS m/z [M+H]$^+$ 468.4.

Example 60 N-(2,2-difluoroethyl)-2-(4-(2,4-difluorophenoxy)piperidin-1-yl)-6-methyl-5,6,7,8-tetrahydropyrido[3,4-b]pyrazin-3-amine

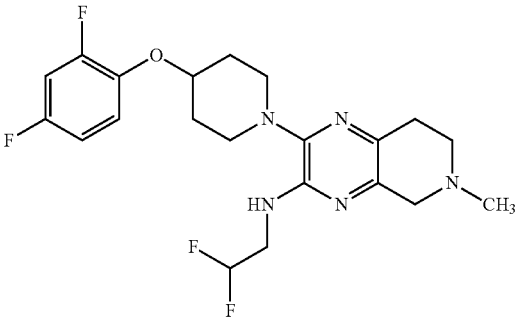 [SMILES: CN1CCc2nc(N3CCC(Oc4ccc(F)cc4F)CC3)c(NCC(F)F)nc2C1]

A solution of N-(2,2-difluoroethyl)-2-(4-(2,4-difluorophenoxy)piperidin-1-yl)-5,6,7,8-tetrahydropyrido[3,4-b]pyrazin-3-amine TFA salt (155 mg, 0.287 mmol) in MeOH (2.87 mL) was treated with DIPEA (0.100 mL, 0.575 mmol), formaldehyde (0.021 mL, 0.29 mmol), and after stirring for 5 min, sodium triacetoxyborohydride (122 mg, 0.575 mmol). The reaction mixture was stirred for 30 min at room temperature. The reaction mixture was filtered and purified by HPLC (Pump: Waters 2525 or 2545; MS: ZQ; Software: MassLynx. A Xbridge™ C18, 5 µm, ID 30×75 mm column was used and eluted with 40% to 95% of 20/80 (v/v) water/ACN (10 mmol NH$_4$HCO$_3$, pH 9.5-10) and water (10 mmol NH$_4$HCO$_3$, pH 9.5-10)) to give the title compound as an off-white semisolid (35.4 mg, 28.0%). $^1$H NMR (500 MHz, methanol-d4) δ ppm 1.95 (m, 2H), 2.12 (m, 2H), 2.47 (s, 3H), 2.79 (m, 4H), 2.96 (ddd, J=12.4, 8.8, 3.2 Hz, 2H), 3.35 (m, 2H), 3.49 (s, 2H), 3.75 (td, J=14.6, 4.4 Hz, 2H), 4.43 (tt, J=7.7, 3.5 Hz, 1H), 6.03 (m, 1H), 6.86 (m, 1H), 6.97 (ddd, J=11.2, 8.5, 3.2 Hz, 1H), 7.16 (td, J=9.3, 5.4 Hz, 1H); ESI-MS m/z [M+H]$^+$ 440.4.

Example 61 Methyl 3-(4-(2,4-difluorophenoxy)piperidin-1-yl)-2-(isopropylamino)-7,8-dihydropyrido[3,4-b]pyrazine-6(5H)-carboxylate

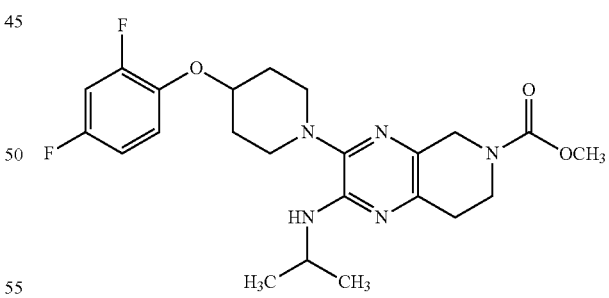

To a solution of 3-(4-(2,4-difluorophenoxy)piperidin-1-yl)-N-isopropyl-5,6,7,8-tetrahydropyrido[3,4-b]pyrazin-2-amine TFA salt (50 mg, 0.080 mmol) and triethylamine (0.026 mL, 0.185 mmol) in DCM (0.75 mL) was added methyl carbonochloridate (9.3 µL, 0.121 mmol) at 0° C. The reaction mixture was stirred at 0° C. for 1 hr, warmed to 23° C., and concentrated via rotary evaporation. The resulting crude material was reconstituted in DMSO, rinsed with DMSO, and purified by HPLC Method B using a 30% to 70% ACN gradient to give the title compound as a TFA salt (11.0 mg, 23.8%) as a yellow solid. $^1$H NMR (500 MHz, DMSO-$d_6$) δ ppm 1.18 (d, J=6.8 Hz, 6H), 1.82-1.94 (m, 2H), 2.02-2.12 (m, 2H), 2.65 (t, J=5.9 Hz, 2H), 2.83-2.93 (m, 2H), 3.21-3.33 (m, 2H), 3.63 (s, 3H), 3.64-3.68 (m, 2H), 4.06-4.17 (m, 1H), 4.34 (br s, 2H), 4.51 (tt, J=8.1, 3.9 Hz, 1H), 5.51-5.65 (m, 1H), 6.99-7.05 (m, 1H), 7.25-7.35 (m, 2H); ESI-MS m/z [M+H]$^+$ 462.4.

Example 62 3-(4-(2,4-difluorophenoxy)piperidin-1-yl)-6-(2-fluoroethyl)-N-isopropyl-5,6,7,8-tetrahydropyrido[3,4-b]pyrazin-2-amine

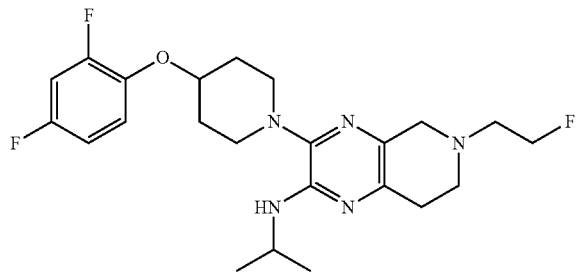 [SMILES: CC(C)Nc1nc2c(nc1N1CCC(Oc3ccc(F)cc3F)CC1)CN(CCF)CC2]

To a suspension of 3-(4-(2,4-difluorophenoxy)piperidin-1-yl)-N-isopropyl-5,6,7,8-tetrahydropyrido[3,4-b]pyrazin-2-amine TFA salt (50 mg, 0.080 mmol) and K$_2$CO$_3$ (44.4 mg, 0.322 mmol) in acetone (2.0 mL) was added 1-bromo-2-fluoroethane (5.4 μL, 0.072 mmol) at 23° C. The reaction mixture was stirred at 23° C. for 1 h and then at 50° C. for 3 days. The reaction mixture was cooled to 23° C., an additional portion of 1-bromo-2-fluoroethane (2.7 μL, 0.036 mmol) was added, and the reaction mixture was heated for an additional 1.5 hr at 50° C., cooled to 23° C., and concentrated via rotary evaporation. The resulting crude material was reconstituted in DMSO, filtered, rinsed with DMSO, and purified by HPLC Method B using a 30% to 70% ACN gradient to give the title compound as a TFA salt (10.7 mg, 23.6%) as a yellow film. $^1$H NMR (500 MHz, DMSO-d$_6$, mixture of rotamers) δ ppm 1.19 (d, J=6.8 Hz, 6H), 1.83-1.92 (m, 2H), 2.02-2.13 (m, 2H), 2.79-2.96 (m, 3H), 2.96-3.11 (m, 0.9H), 3.24-3.36 (m, 2H), 3.38-3.55 (m, 1.1H) 3.65 (br s, 1.1H), 3.71 (m, 0.9H), 3.73-3.84 (m, 1H), 4.12-4.19 (m, 1H), 4.28 (br s, 0.9H), 4.30 (br s, 1.1H), 4.54 (ddd, J=11.7, 7.8, 3.9 Hz, 1H), 4.87 (t, J=4.4 Hz, 0.9H), 4.88-4.95 (m, 1H), 4.97 (t, J=4.4 Hz, 1.1H), 5.86 (d, J=8.3 Hz, 1H), 6.97-7.08 (m, 1H), 7.25-7.37 (m, 2H); ESI-MS m/z [M+H]$^+$ 450.5.

Example 63 (R)-1-(2-(4-((2,4-difluorophenyl)fluoromethyl)piperidin-1-yl)-3-(isopropylamino)-7,8-dihydropyrido[3,4-b]pyrazin-6(5H)-yl)ethan-1-one

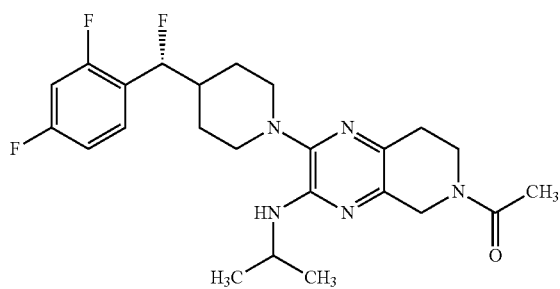 [SMILES: CC(=O)N1CCc2nc(N3CCC([C@@H](F)c4ccc(F)cc4F)CC3)c(NC(C)C)nc2C1]

Acetic anhydride (14.1 μL, 0.149 mmol) and formic acid (38.1 μL, 0.994 mmol) were combined in THF (99 μL) and stirred at room temperature for 10 min. This solution was cooled to 0° C. and was added to a stirring solution of (R)-2-(4-((2,4-difluorophenyl)fluoromethyl)piperidin-1-yl)-N-isopropyl-5,6,7,8-tetrahydropyrido[3,4-b]pyrazin-3-amine (41.7 mg, 0.099 mmol) in THF (895 μL) at 0° C. After 10 min, UPLC-MS showed conversion not to the formylated product, but to the acetylated product. The reaction mixture was treated with MeOH, concentrated under reduced pressure, taken up in MeOH, filtered, and purified by HPLC Method B to give the title compound, as a TFA salt, as a pale yellow solid (17.5 mg, 30.6%). $^1$H NMR (500 MHz, methanol-d4, mixture of rotamers) δ ppm 1.28 (m, 6H), 1.45 (d, J=12.7 Hz, 1H), 1.65 (m, 2H), 2.01 (m, 1H), 2.09 (m, 1H), 2.18 (s, 1.1H), 2.20 (s, 1.9H), 2.76 (m, 4H), 3.49 (m, 2H), 3.81 (t, J=6.1 Hz, 1.3H), 3.85 (t, J=5.9 Hz, 0.7H), 4.13 (m, 1H), 4.57 (s, 0.7H), 4.61 (s, 1.3H), 5.52 (m, 1H), 7.02 (m, 2H), 7.50 (m, 1H); ESI-MS m/z [M+H]$^+$ 462.4.

Example 65 N-cyclopropyl-2-(4-(2-fluoro-4-methoxyphenoxy)piperidin-1-yl)-6-methyl-5,6,7,8-tetrahydropyrido[3,4-b]pyrazin-3-amine

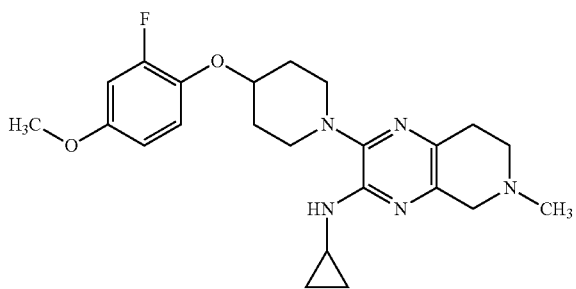

A mixture of cyclopropanamine (13.6 mg, 0.237 mmol), 3-chloro-2-(4-(2-fluoro-4-methoxyphenoxy)piperidin-1-yl)-6-methyl-5,6,7,8-tetrahydropyrido[3,4-b]pyrazine TFA salt (30.9 mg, 0.059 mmol), sodium tert-butoxide (11.4 mg, 0.119 mmol), BINAP (5.5 mg, 8.90 nmol) and Pd$_2$(dba)$_3$ (2.7 mg, 2.97 nmol) in toluene (200 μL) was heated at 90° C. for 14 h. The mixture was directly purified by HPLC Method A to give the title compound as a TFA salt (12.9 mg, 40.2%) as a yellow film. $^1$H NMR (400 MHz, methanol-d$_4$) δ ppm 0.53-0.58 (m, 2H), 0.75-0.81 (m, 2H), 1.86-1.96 (m, 2H), 2.02-2.12 (m, 2H), 2.64-2.70 (m, 1H), 2.94-3.02 (m, 1H), 3.08-3.12 (m, 3H), 3.17-3.27 (m, 3H), 3.34-3.42 (m, 2H), 3.59-3.68 (m, 2H), 3.75 (s, 3H), 4.25-4.41 (m, 3H), 6.64-6.69 (m, 1H), 6.70-6.76 (m, 1H), 7.03-7.10 (m, 1H); ESI-MS m/z [M+H]$^+$ 428.4.

Example 66 N-cyclopropyl-3-(4-(2-fluoro-4-methoxyphenoxy)piperidin-1-yl)-6-methyl-5,6,7,8-tetrahydropyrido[3,4-b]pyrazin-2-amine

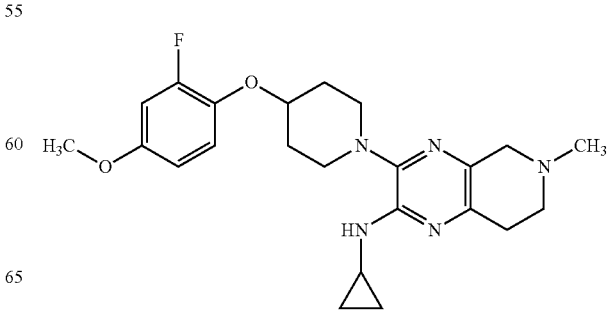

A mixture of 4-(2-fluoro-4-methoxyphenoxy)piperidine hydrochloride (15.8 mg, 0.060 mmol), 3-chloro-N-cyclopropyl-6-methyl-5,6,7,8-tetrahydropyrido[3,4-b]pyrazin-2-amine (12 mg, 0.050 mmol), sodium tert-butoxide (14.5 mg, 0.151 mmol), BINAP (4.7 mg, 7.54 nmol) and Pd$_2$(dba)$_3$ (2.3 mg, 2.51 nmol) in toluene (250 μL) was heated at 90° C. for 14 h. The mixture was purified by HPLC Method A to give the title compound as a TFA salt (14.4 mg, 52.9%) as a yellow film. $^1$H NMR (400 MHz, methanol-d$_4$) δ ppm 0.56-0.62 (m, 2H), 0.79-0.87 (m, 2H), 1.85-1.96 (m, 2H), 2.02-2.11 (m, 2H), 2.66-2.75 (m, 1H), 2.94-3.02 (m, 2H), 3.08-3.12 (m, 3H), 3.13-3.27 (m, 2H), 3.33-3.43 (m, 2H), 3.53-3.69 (m, 2H), 3.75 (s, 3H), 4.19-4.42 (m, 3H), 6.63-6.69 (m, 1H) 6.73 (dd, J=12.9, 3.0 Hz, 1H), 7.02-7.09 (m, 1H); ESI-MS m/z [M+H]$^+$ 428.4.

Example 67 N-cyclopropyl-3-(4-((2,4-difluorophenyl)fluoromethyl)piperidin-1-yl)-6-methyl-5,6,7,8-tetrahydropyrido[3,4-b]pyrazin-2-amine

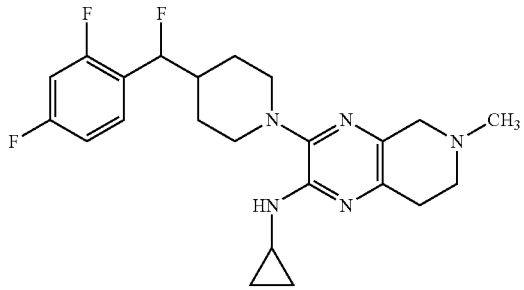 [SMILES: CN1CCc2nc(NC3CC3)c(N3CCC(C(F)c4ccc(F)cc4F)CC3)nc2C1]

A mixture of 4-((2,4-difluorophenyl)fluoromethyl)piperidine hydrochloride (16.0 mg, 0.060 mmol), 3-chloro-N-cyclopropyl-6-methyl-5,6,7,8-tetrahydropyrido[3,4-b]pyrazin-2-amine (12 mg, 0.050 mmol), sodium tert-butoxide (14.5 mg, 0.151 mmol), BINAP (4.7 mg, 7.54 μmol) and Pd$_2$(dba)$_3$ (2.3 mg, 2.51 nmol) in toluene (250 μL) was heated at 90° C. for 14 h. The mixture was purified by HPLC Method A to give the title compound as a TFA salt (11.1 mg, 40.5%) as a yellow film. $^1$H NMR (400 MHz, methanol-d$_4$) δ ppm 0.57 (dt, J=3.5, 1.4 Hz, 2H), 0.78-0.85 (m, 2H), 1.36-1.45 (m, 1H), 1.52-1.73 (m, 2H), 1.93-2.15 (m, 2H), 2.60-2.87 (m, 3H), 3.08 (s, 3H), 3.09-3.15 (m, 2H), 3.38-3.74 (m, 4H), 4.26 (br s, 2H), 5.51 (dd, J=46.2, 7.3 Hz, 1H), 6.96-7.08 (m, 2H), 7.45-7.53 (m, 1H); ESI-MS m/z [M+H]$^+$ 432.4.

Example 68 (S)—N-cyclopropyl-3-(4-((2,4-difluorophenyl)fluoromethyl)piperidin-1-yl)-6-methyl-5,6,7,8-tetrahydropyrido[3,4-b]pyrazin-2-amine

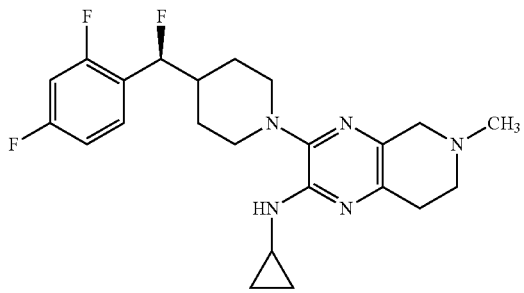 [SMILES: CN1CCc2nc(NC3CC3)c(N3CCC([C@H](F)c4ccc(F)cc4F)CC3)nc2C1]

A mixture of (S)-4-((2,4-difluorophenyl)fluoromethyl)piperidine hydrochloride (14.7 mg, 0.055 mmol), 3-chloro-N-cyclopropyl-6-methyl-5,6,7,8-tetrahydropyrido[3,4-b]pyrazin-2-amine (11 mg, 0.046 mmol), sodium tert-butoxide (13.3 mg, 0.138 mmol), BINAP (4.3 mg, 6.91 μmol), and Pd$_2$(dba)$_3$ (2.1 mg, 2.30 μmol) in toluene (230 μL) was heated at 90° C. for 14 h. The mixture was purified by HPLC Method A to give the title compound as a TFA salt (11.1 mg, 44.2%) as a yellow film. $^1$H NMR (400 MHz, methanol-d$_4$) δ ppm 0.56-0.63 (m, 2H), 0.84 (m, J=6.8 Hz, 2H), 1.40 (d, J=12.9 Hz, 1H), 1.52-1.74 (m, 2H), 1.92-2.14 (m, 2H), 2.61-2.75 (m, 3H), 3.08 (s, 3H), 3.09-3.16 (m, 2H), 3.40-3.55 (m, 2H), 3.55-3.80 (m, 2H), 4.31 (br s, 2H), 5.50 (dd, J=46.0, 7.6 Hz, 1H), 6.96-7.08 (m, 2H), 7.45-7.54 (m, 1H); ESI-MS m/z [M+H]$^+$ 432.4.

Example 69 (R)—N-cyclopropyl-3-(4-((2,4-difluorophenyl)fluoromethyl)piperidin-1-yl)-6-methyl-5,6,7,8-tetrahydropyrido[3,4-b]pyrazin-2-amine

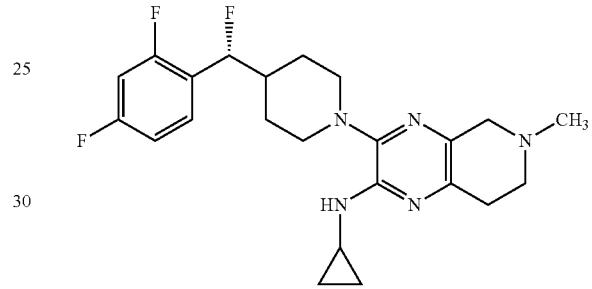

A mixture of (R)-4-((2,4-difluorophenyl)fluoromethyl)piperidine hydrochloride (14.7 mg, 0.055 mmol), 3-chloro-N-cyclopropyl-6-methyl-5,6,7,8-tetrahydropyrido[3,4-b]pyrazin-2-amine (11 mg, 0.046 mmol), sodium tert-butoxide (13.3 mg, 0.138 mmol), BINAP (4.3 mg, 6.91 μmol) and Pd$_2$(dba)$_3$ (2.1 mg, 2.30 μmol) in toluene (230 μL) was heated at 90° C. for 14 h. The mixture was purified by HPLC Method A to give the title compound as a TFA salt (10.5 mg, 41.8%) as a yellow film. $^1$H NMR (400 MHz, methanol-d$_4$) δ ppm 0.55-0.62 (m, 2H), 0.79-0.87 (m, 2H), 1.40 (br d, J=12.4 Hz, 1H), 1.52-1.73 (m, 2H), 1.93-2.14 (m, 2H), 2.61-2.74 (m, 3H), 3.08 (s, 3H), 3.10-3.15 (m, 2H), 3.40-3.54 (m, 2H), 3.55-3.81 (m, 2H), 4.26 (br s, 2H), 5.50 (dd, J=46.2, 7.8 Hz, 1H), 6.97-7.08 (m, 2H), 7.45-7.53 (m, 1H); ESI-MS m/z [M+H]$^+$ 432.3.

Example 70 3-(4-((2,4-difluorophenyl)fluoromethyl)piperidin-1-yl)-N-isopropyl-6-methyl-5,6,7,8-tetrahydropyrido[3,4-b]pyrazin-2-amine

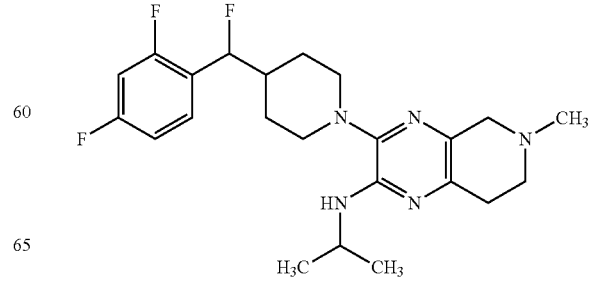

Sodium triacetoxyborohydride (15.3 mg, 0.072 mmol) was added to a mixture of DIPEA (9.4 mg, 0.072 mmol), 3-(4-((2,4-difluorophenyl)fluoromethyl)piperidin-1-yl)-N-isopropyl-5,6,7,8-tetrahydropyrido[3,4-b]pyrazin-2-amine TFA salt (19.3 mg, 0.036 mmol) and formaldehyde (3 μL, 0.036 mmol) in MeOH (360 μL) at rt. After 30 min, the mixture was purified by HPLC Method A to give the title compound as a TFA salt (19.3 mg, 97%) as a yellow film. $^1$H NMR (400 MHz, methanol-$d_4$) δ ppm 1.24 (dd, J=6.4, 2.2 Hz, 6H), 1.40-1.48 (m, 1H), 1.53-1.74 (m, 2H), 1.96-2.14 (m, 2H), 2.60-2.73 (m, 2H), 2.93-3.06 (br m, 2H), 3.06 (s, 3H), 3.39-3.54 (m, 3H), 3.69-3.81 (m, 1H), 4.18 (dt, J=13.1, 6.4 Hz, 2H), 4.16-4.36 (br m, 1H), 5.52 (dd, J=46.2, 7.6 Hz, 1H), 6.97-7.08 (m, 2H), 7.47-7.54 (m, 1H); ESI-MS m/z [M+H]$^+$ 434.4.

Example 71 1-(3-(4-((2,4-difluorophenyl)fluoromethyl)piperidin-1-yl)-2-(isopropylamino)-7,8-dihydropyrido[3,4-b]pyrazin-6(5H)-yl)ethanone

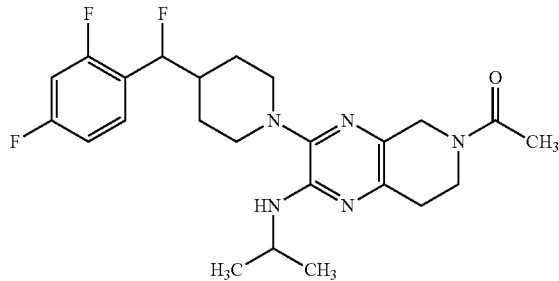 [SMILES: CC(=O)N1CCc2nc(NC(C)C)c(N3CCC(C(F)c4ccc(F)cc4F)CC3)nc2C1]

Acetic anhydride (7 μL, 0.075 mmol) was added to a solution of 3-(4-((2,4-difluorophenyl)fluoromethyl)piperidin-1-yl)-N-isopropyl-5,6,7,8-tetrahydropyrido[3,4-b]pyrazin-2-amine TFA salt (20.1 mg, 0.038 mmol) and pyridine (9 μL, 0.113 mmol) in DCM (380 μL) at rt. After 1 h, the mixture was purified by HPLC Method A to give the title compound as a TFA salt (20.1 mg, 93%) as a yellow film. $^1$H NMR (400 MHz, methanol-$d_4$) δ ppm 1.29 (dd, J=6.4, 1.9 Hz, 6H), 1.46 (br s, 1H), 1.56-1.77 (m, 2H), 2.00 (d, J=12.9 Hz, 1H), 2.04-2.15 (m, 1H), 2.18 (s, 1.3H), 2.20 (s, 1.7H), 2.76 (qd, J=12.8, 2.4 Hz, 3H), 2.87 (t, J=5.9 Hz, 1H), 3.40-3.56 (m, 2H), 3.78-3.83 (m, 1.1H), 3.83-3.89 (m, 0.9H), 4.09-4.17 (m, 1H), 4.52 (s, 2H), 5.53 (dd, J=46.7, 7.6 Hz, 1H), 6.97-7.08 (m, 2H), 7.47-7.55 (m, 1H); ESI-MS m/z [M+H]$^+$ 462.4.

Example 72 3-(4-((2,4-difluorophenyl)fluoromethyl)piperidin-1-yl)-2-(isopropylamino)-N,N-dimethyl-7,8-dihydropyrido[3,4-b]pyrazine-6(5H)-carboxamide

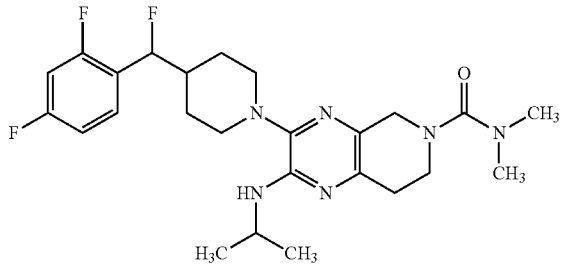

Dimethylcarbamic chloride (8.4 mg, 0.078 mmol) was added to a solution of 3-(4-((2,4-difluorophenyl)fluoromethyl)piperidin-1-yl)-N-isopropyl-5,6,7,8-tetrahydropyrido[3,4-b]pyrazin-2-amine TFA salt (20.8 mg, 0.039 mmol) and triethylamine (16 μL, 0.117 mmol) in DCM (390 μL) at rt. After 1 h, the mixture was purified by HPLC Method A to give the title compound as a TFA salt (20.8 mg, 88%) as a yellow film. $^1$H NMR (400 MHz, methanol-$d_4$) δ ppm 1.31 (dd, J=6.6, 1.8 Hz, 6H), 1.40-1.48 (m, 1H), 1.58-1.78 (m, 2H), 1.95-2.03 (m, 1H), 2.03-2.18 (m, 1H), 2.71-2.88 (m, 4H), 2.90 (s, 6H), 3.42-3.52 (m, 2H), 3.54 (t, J=5.7 Hz, 2H), 4.07-4.16 (m, 1H), 4.22-4.27 (m, 2H), 5.53 (dd, J=46.5, 7.3 Hz, 1H), 6.97-7.08 (m, 2H), 7.47-7.55 (m, 1H); ESI-MS m/z [M+H]$^+$ 491.4.

Example 73 3-(4-(2-fluoro-4-methoxyphenoxy)piperidin-1-yl)-2-(isopropylamino)-N,N-dimethyl-7,8-dihydropyrido[3,4-b]pyrazine-6(5H)-carboxamide

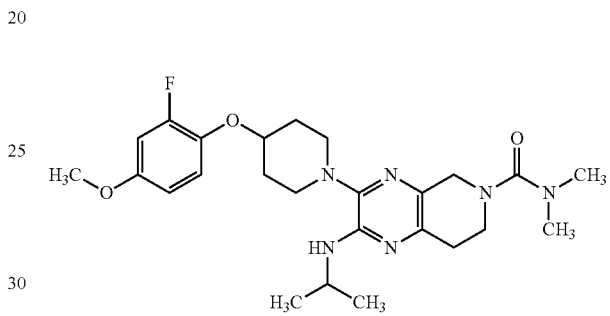

Dimethylcarbamic chloride (10.5 mg, 0.097 mmol) was added to a solution of 3-(4-(2-fluoro-4-methoxyphenoxy)piperidin-1-yl)-N-isopropyl-5,6,7,8-tetrahydropyrido[3,4-b]pyrazin-2-amine TFA salt (25.8 mg, 0.049 mmol) and triethylamine (20.5 μL, 0.146 mmol) in DCM (500 μL) at rt. After 1 h, the mixture was purified by HPLC Method A to give the title compound as a TFA salt (25.8 mg, 88%) as a yellow film. $^1$H NMR (400 MHz, methanol-$d_4$) δ ppm 1.33 (d, J=6.3 Hz, 6H), 1.89-2.00 (m, 2H), 2.06-2.16 (m, 2H), 2.85-2.89 (m, 2H), 2.90 (s, 6H), 3.04-3.13 (m, 2H), 3.41-3.50 (m, 2H), 3.55 (t, J=5.8 Hz, 2H), 3.76 (s, 3H), 4.08-4.18 (m, 1H), 4.27 (s, 2H), 4.35-4.42 (m, 1H), 6.67 (ddd, J=9.0, 2.9, 1.5 Hz, 1H), 6.74 (dd, J=12.9, 3.0 Hz, 1H), 7.08 (t, J=9.2 Hz, 1H); ESI-MS m/z [M+H]$^+$ 487.4.

Example 74 2-(4-(2-fluoro-4-methoxyphenoxy)piperidin-1-yl)-N-isopropyl-6-methyl-5,6,7,8-tetrahydropyrido[3,4-b]pyrazin-3-amine

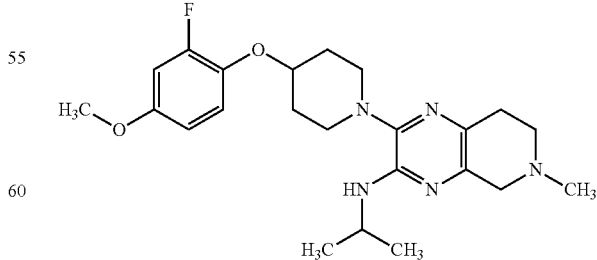

Sodium triacetoxyhydroborate (9.7 mg, 0.046 mmol) was added to a solution of DIPEA (8 μL, 0.046 mmol), 2-(4-(2-fluoro-4-methoxyphenoxy)piperidin-1-yl)-N-isopropyl-5,6,7,8-tetrahydropyrido[3,4-b]pyrazin-3-amine TFA salt (12.1 mg, 0.023 mmol) and formaldehyde (1.9 μL, 0.023 mmol) in MeOH (229 μL) at rt. After 30 min, the mixture was purified by HPLC Method A to give the title compound as a TFA salt (12.1 mg, 97%) as a yellow film. $^1$H NMR (400 MHz, methanol-$d_4$) δ ppm 1.24 (d, J=6.3 Hz, 6H), 1.88-1.99 (m, 2H), 2.04-2.14 (m, 2H), 2.93-3.04 (m, 3H), 3.08 (br s, 4H), 3.35-3.53 (m, 3H), 3.76 (br s, 4H), 4.10-4.19 (m, 1H), 4.20-4.40 (m, 3H), 6.64-6.69 (m, 1H), 6.74 (dd, J=12.8, 2.1 Hz, 1H), 7.07 (t, J=9.2 Hz, 1H); ESI-MS m/z [M+H]$^+$ 430.4.

Example 75 2-(4-((2,4-difluorophenyl)fluoromethyl)piperidin-1-yl)-N-isopropyl-6-methyl-5,6,7,8-tetrahydropyrido[3,4-b]pyrazin-3-amine

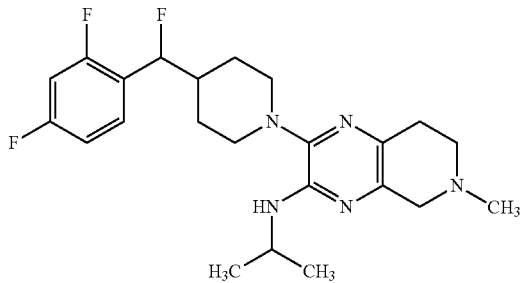 [SMILES: CC(C)Nc1nc2c(nc1N1CCC(C(F)c3ccc(F)cc3F)CC1)CCN(C)C2]

Sodium triacetoxyhydroborate (11.0 mg, 0.052 mmol) was added to a solution of DIPEA (9 μL, 0.052 mmol), 2-(4-((2,4-difluorophenyl)fluoromethyl)piperidin-1-yl)-N-isopropyl-5,6,7,8-tetrahydropyrido[3,4-b]pyrazin-3-amine TFA salt (13.9 mg, 0.026 mmol) and formaldehyde (2 μL, 0.026 mmol) in MeOH (260 μL) at rt. After 30 min, the mixture was purified by HPLC Method A to give the title compound as a TFA salt (13.9 mg, 97%) as a yellow film. $^1$H NMR (400 MHz, methanol-$d_4$) δ ppm 1.23 (dd, J=6.4, 2.4 Hz, 6H), 1.41-1.49 (m, 1H), 1.52-1.74 (m, 2H), 1.97-2.15 (m, 2H), 2.61-2.75 (m, 2H), 2.89-3.04 (m, 2H), 3.07 (s, 3H), 3.40-3.56 (m, 3H), 3.75 (br s, 1H), 4.13 (quin, J=6.5 Hz, 1H), 4.18-4.38 (m, 2H), 5.53 (dd, J=46.2, 7.6 Hz, 1H), 6.97-7.08 (m, 2H), 7.47-7.54 (m, 1H); ESI-MS m/z [M+H]$^+$ 434.4.

Example 76 1-(2-(4-((2,4-difluorophenyl)fluoromethyl)piperidin-1-yl)-3-(isopropylamino)-7,8-dihydropyrido[3,4-b]pyrazin-6(5H)-yl)ethanone

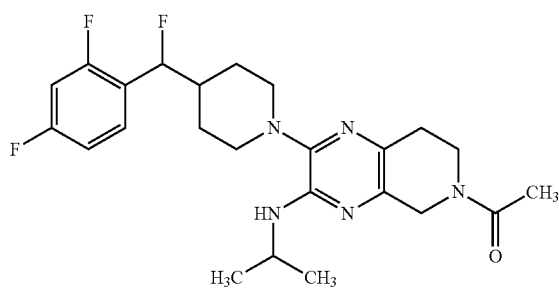 [SMILES: CC(=O)N1CCc2nc(N3CCC(C(F)c4ccc(F)cc4F)CC3)c(NC(C)C)nc2C1]

Acetic anhydride (5 μL, 0.054 mmol) was added to a solution of 2-(4-((2,4-difluorophenyl)fluoromethyl)piperidin-1-yl)-N-isopropyl-5,6,7,8-tetrahydropyrido[3,4-b]pyrazin-3-amine TFA salt (14.3 mg, 0.027 mmol) and pyridine (6.5 μL, 0.080 mmol) in DCM (270 μL) at rt. After 1 h, the mixture was purified by HPLC Method A to give the title compound as a TFA salt (14.3 mg, 93%) as a yellow film. $^1$H NMR (400 MHz, methanol-$d_4$, mixture of rotamers) δ ppm 1.23-1.31 (m, 6H), 1.45 (d, J=12.9 Hz, 1H), 1.53-1.76 (m, 2H), 1.96-2.15 (m, 2H), 2.18 (s, 1.2H), 2.21 (s, 1.8H), 2.67-2.84 (m, 4H), 3.38-3.55 (m, 2H), 3.78-3.83 (m, 1.2H), 3.83-3.87 (m, 0.8H), 4.13 (dq, J=12.6, 6.3 Hz, 1H), 4.56 (s, 0.8H), 4.59 (s, 1.2H), 5.53 (dd, J=46.2, 7.6 Hz, 1H), 6.97-7.09 (m, 2H), 7.47-7.55 (m, 1H); ESI-MS m/z [M+H]$^+$ 462.4.

Example 77 2-(4-((2,4-difluorophenyl)fluoromethyl)piperidin-1-yl)-3-(isopropylamino)-N,N-dimethyl-7,8-dihydropyrido[3,4-b]pyrazine-6(5H)-carboxamide

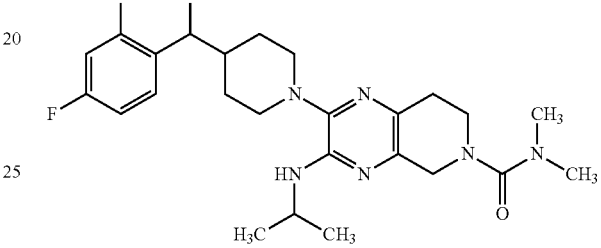

Dimethylcarbamic chloride (5.8 mg, 0.054 mmol) was added to a solution of 2-(4-((2,4-difluorophenyl)fluoromethyl)piperidin-1-yl)-N-isopropyl-5,6,7,8-tetrahydropyrido[3,4-b]pyrazin-3-amine TFA salt (14.3 mg, 0.027 mmol) and triethylamine (11 μL, 0.080 mmol) in DCM (270 μL) at rt. After 1 h, the mixture was purified by HPLC Method A to give the title compound as a TFA salt (14.3 mg, 88%) as a yellow film. $^1$H NMR (400 MHz, methanol-$d_4$) δ ppm 1.29 (dd, J=6.4, 1.9 Hz, 6H), 1.40-1.49 (m, 1H), 1.55-1.77 (m, 2H), 2.01 (d, J=13.1 Hz, 2H), 2.70-2.84 (m, 4H), 2.87-2.94 (m, 6H), 3.40-3.52 (m, 2H), 3.53-3.57 (m, 2H), 4.11 (quin, J=6.4 Hz, 1H) 4.29 (s, 2H) 5.53 (dd, J=46.2, 7.3 Hz, 1H), 6.97-7.09 (m, 2H), 7.47-7.55 (m, 1H); ESI-MS m/z [M+H]$^+$ 491.4.

Example 78 (5-chloro-2-fluorophenyl)(1-(2-(isopropylamino)-6-methyl-5,6,7,8-tetrahydropyrido[3,4-b]pyrazin-3-yl)piperidin-4-yl)methanone

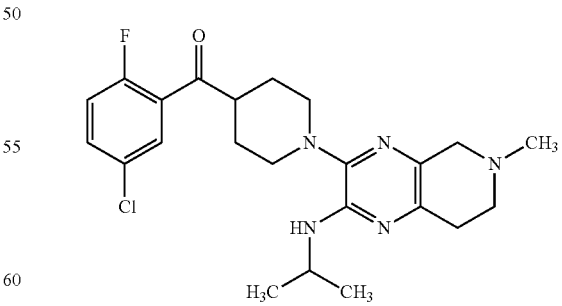

Sodium triacetoxyhydroborate (6.9 mg, 0.033 mmol) was added to a solution of DIPEA (6 μL, 0.033 mmol), (5-chloro-2-fluorophenyl)(1-(2-(isopropylamino)-5,6,7,8-tetrahydropyrido[3,4-b]pyrazin-3-yl)piperidin-4-yl)methanone TFA salt (8.9 mg, 0.016 mmol) and formaldehyde (1.5 μL, 0.016 mmol) in MeOH (160 μL) at rt. After 30 min, the mixture was purified by HPLC Method A to give the title compound as a TFA salt (2.2 mg, 24.1%) as a yellow film. $^1$H NMR (400 MHz, methanol-$d_4$) δ ppm 1.24 (d, J=6.6 Hz, 6H), 1.81-1.94 (m, 2H), 1.96-2.05 (m, 2H), 2.85 (t, J=11.5 Hz, 2H), 3.00 (d, J=6.3 Hz, 2H), 3.07 (s, 3H), 3.44-3.53 (m, 4H), 3.71-3.82 (m, 1H), 4.14-4.23 (m, 2H), 4.28-4.37 (m, 1H), 7.28 (dd, J=10.6, 8.8 Hz, 1H), 7.61 (ddd, J=8.8, 4.1, 2.8 Hz, 1H), 7.75 (dd, J=6.1, 2.8 Hz, 1H); ESI-MS m/z [M+H]$^+$ 446.3.

Example 79 1-(3-(4-(5-chloro-2-fluorobenzoyl)piperidin-1-yl)-2-(isopropylamino)-7,8-dihydropyrido[3,4-b]pyrazin-6(5H)-yl)ethanone

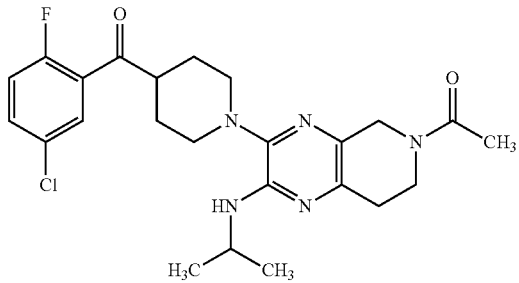 [SMILES: CC(=O)N1CCc2nc(NC(C)C)c(N3CCC(C(=O)c4cc(Cl)ccc4F)CC3)nc2C1]

Acetic anhydride (3 μL, 0.034 mmol) was added to a solution of (5-chloro-2-fluorophenyl)(1-(2-(isopropylamino)-5,6,7,8-tetrahydropyrido[3,4-b]pyrazin-3-yl)piperidin-4-yl)methanone TFA salt (9.2 mg, 0.017 mmol) and pyridine (4 μL, 0.051 mmol) in DCM (170 μL) at rt. After 1 h, the mixture was purified by HPLC Method A to give the title compound as a TFA salt (4.0 mg, 40.4%) as a yellow film. $^1$H NMR (400 MHz, methanol-$d_4$, mixture of rotamers) δ ppm 1.30-1.34 (m, 6H), 1.88-2.04 (m, 4H), 2.19 (s, 1.4H), 2.21 (s, 1.6H), 2.77-2.83 (m, 0.9H), 2.87-2.92 (m, 1.1H), 2.93-3.02 (m, 2H), 3.34-3.43 (m, 1H), 3.50-3.59 (m, 2H), 3.80-3.85 (m, 1.1H), 3.85-3.90 (m, 0.9H), 4.08-4.17 (m, 1H), 4.54 (br s, 2H), 7.25-7.32 (m, 1H), 7.59-7.63 (m, 1H), 7.76 (dd, J=6.1, 2.8 Hz, 1H); ESI-MS m/z [M+H]$^+$ 474.3.

Example 80 3-(4-(5-chloro-2-fluorobenzoyl)piperidin-1-yl)-2-(isopropylamino)-N,N-dimethyl-7,8-dihydropyrido[3,4-b]pyrazine-6(5H)-carboxamide

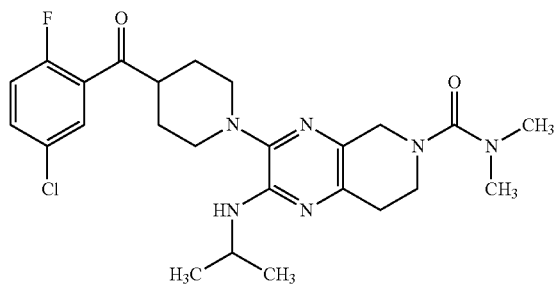 [SMILES: CC(C)Nc1nc2c(nc1N1CCC(C(=O)c3cc(Cl)ccc3F)CC1)CN(C(=O)N(C)C)CC2]

Dimethylcarbamic chloride (3.8 mg, 0.036 mmol) was added to a solution of (5-chloro-2-fluorophenyl)(1-(2-(isopropylamino)-5,6,7,8-tetrahydropyrido[3,4-b]pyrazin-3-yl)piperidin-4-yl)methanone TFA salt (9.7 mg, 0.018 mmol) and triethylamine (7 μL, 0.053 mmol) in DCM (180 μL) at rt. After 1 h, the mixture was purified by HPLC Method A to give the title compound as a TFA salt (3.6 mg, 32.8%) as a yellow film. $^1$H NMR (400 MHz, methanol-$d_4$) δ ppm 1.31-1.34 (m, 6H), 1.89-2.06 (m, 4H), 2.85-2.89 (m, 2H), 2.90-2.92 (m, 6H), 2.93-3.02 (m, 2H), 3.35-3.41 (m, 1H), 3.50-3.58 (m, 4H), 4.08-4.16 (m, 1H), 4.27 (s, 2H), 7.29 (dd, J=10.6, 8.8 Hz, 1H), 7.61 (ddd, J=8.8, 4.0, 2.8 Hz, 1H), 7.76 (dd, J=6.1, 2.8 Hz, 1H); ESI-MS m/z [M+H]$^+$ 504.4.

Example 81 3-(4-(2,4-difluorophenoxy)piperidin-1-yl)-N-isopropyl-6-methyl-5,6,7,8-tetrahydropyrido[3,4-b]pyrazin-2-amine

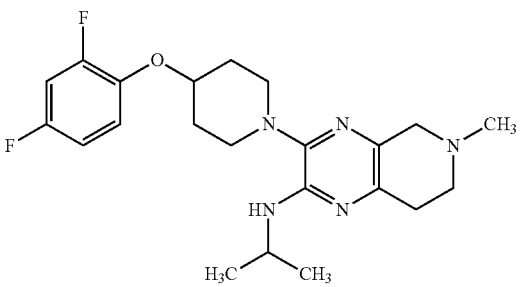 [SMILES: CC(C)Nc1nc2c(nc1N1CCC(Oc3ccc(F)cc3F)CC1)CN(C)CC2]

Sodium triacetoxyhydroborate (12.3 mg, 0.058 mmol) was added to a solution of DIPEA (10 μL, 0.058 mmol), 3-(4-(2,4-difluorophenoxy)piperidin-1-yl)-N-isopropyl-5,6,7,8-tetrahydropyrido[3,4-b]pyrazin-2-amine TFA salt (15.0 mg, 0.029 mmol) and formaldehyde (2 μL, 0.029 mmol) in MeOH (290 μL) at rt. After 30 min, the mixture was purified by HPLC Method A to give the title compound as a TFA salt (12.3 mg, 80%) as a yellow film. $^1$H NMR (400 MHz, methanol-$d_4$) δ ppm 1.25 (d, J=6.6 Hz, 6H), 1.90-2.00 (m, 2H), 2.07-2.16 (m, 2H), 2.96-3.05 (m, 3H), 3.08 (br s, 4H), 3.33-3.42 (m, 2H), 3.43-3.85 (m, 2H), 4.14-4.38 (m, 3H), 4.44-4.51 (m, 1H), 6.84-6.91 (m, 1H), 6.95-7.02 (m, 1H), 7.17 (td, J=9.2, 5.6 Hz, 1H); ESI-MS m/z [M+H]$^+$ 418.3.

Example 82 1-(3-(4-(2,4-difluorophenoxy)piperidin-1-yl)-2-(isopropylamino)-7,8-dihydropyrido[3,4-b]pyrazin-6(5H)-yl)ethanone

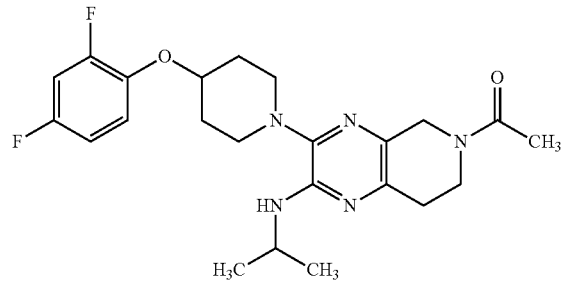 [SMILES: CC(=O)N1CCc2nc(NC(C)C)c(N3CCC(Oc4ccc(F)cc4F)CC3)nc2C1]

Acetic anhydride (5 μL, 0.058 mmol) was added to a solution of 3-(4-(2,4-difluorophenoxy)piperidin-1-yl)-N-isopropyl-5,6,7,8-tetrahydropyrido[3,4-b]pyrazin-2-amine TFA salt (15.1 mg, 0.029 mmol) and pyridine (7 μL, 0.088 mmol) in DCM (290 μL) at rt. After 1 h, the mixture was purified by HPLC Method A to give the title compound as a TFA salt (12.7 mg, 78%) as a yellow film. $^1$H NMR (400 MHz, methanol-$d_4$, mixture of rotamers) δ ppm 1.33 (d, J=6.6 Hz, 6H), 1.91-2.02 (m, 2H), 2.09-2.18 (m, 2H), 2.19 (s, 1.4H), 2.21 (s, 1.6H), 2.77-2.83 (m, 0.9H), 2.88-2.94 (m, 1.1H), 3.12 (td, J=8.5, 4.0 Hz, 2H), 3.43-3.51 (m, 2H), 3.80-3.85 (m, 1.1H), 3.86-3.91 (m, 0.9H), 4.10-4.18 (m, 1H), 4.47-4.54 (m, 1H), 4.55 (br s, 2H), 6.85-6.92 (m, 1H), 6.99 (ddd, J=11.4, 8.6, 3.0 Hz, 1H), 7.18 (td, J=9.2, 5.6 Hz, 1H); ESI-MS m/z [M+H]+ 446.4.

Example 83 3-(4-(2,4-difluorophenoxy)piperidin-1-yl)-2-(isopropylamino)-N,N-dimethyl-7,8-dihydropyrido[3,4-b]pyrazine-6(5H)-carboxamide

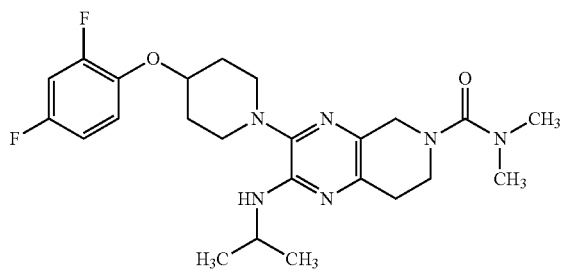 [SMILES: CC(C)Nc1nc2c(nc1N1CCC(Oc3ccc(F)cc3F)CC1)CN(C(=O)N(C)C)CC2]

Dimethylcarbamic chloride (6.4 mg, 0.059 mmol) was added to a solution of 3-(4-(2,4-difluorophenoxy)piperidin-1-yl)-N-isopropyl-5,6,7,8-tetrahydropyrido[3,4-b]pyrazin-2-amine TFA salt (15.3 mg, 0.030 mmol) and triethylamine (12 µL, 0.089 mmol) in DCM (300 µL) at rt. After 1 h, the mixture was purified by HPLC Method A to give the title compound as a TFA salt (11.1 mg, 63.8%) as a yellow film. 1H NMR (400 MHz, methanol-d4) δ ppm 1.31 (d, J=6.3 Hz, 6H), 1.91-2.01 (m, 2H), 2.09-2.18 (m, 2H), 2.86 (t, J=5.7 Hz, 2H), 2.90 (s, 6H), 3.03-3.11 (m, 2H), 3.39-3.47 (m, 2H), 3.55 (t, J=5.7 Hz, 2H), 4.14 (quin, J=6.4 Hz, 1H), 4.27 (s, 2H), 4.49 (tt, J=7.3, 3.6 Hz, 1H), 6.84-6.91 (m, 1H), 6.99 (ddd, J=11.2, 8.5, 3.0 Hz, 1H), 7.18 (td, J=9.2, 5.6 Hz, 1H); ESI-MS m/z [M+H]+ 475.4.

Example 84 2-(4-(2,4-difluorophenoxy)piperidin-1-yl)-N-isopropyl-6-methyl-5,6,7,8-tetrahydropyrido[3,4-b]pyrazin-3-amine

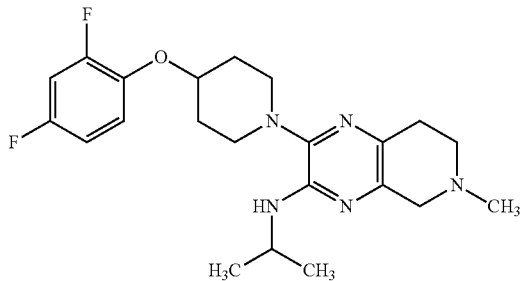 [SMILES: CC(C)Nc1nc2c(nc1N1CCC(Oc3ccc(F)cc3F)CC1)CCN(C)C2]

Sodium triacetoxyhydroborate (9.9 mg, 0.047 mmol) was added to a solution of DIPEA (8 µL, 0.047 mmol), 2-(4-(2,4-difluorophenoxy)piperidin-1-yl)-N-isopropyl-5,6,7,8-tetrahydropyrido[3,4-b]pyrazin-3-amine TFA salt (12.1 mg, 0.023 mmol) and formaldehyde (2 µL, 0.023 mmol) in MeOH (230 µL) at rt. After 30 min, the mixture was purified by HPLC Method A to give the title compound as a TFA salt (8.9 mg, 71.6%) as a yellow film. 1H NMR (400 MHz, methanol-d4) δ ppm 1.24 (d, J=6.3 Hz, 6H), 1.90-2.00 (m, 2H), 2.08-2.17 (m, 2H), 2.95-3.06 (m, 3H), 3.12 (br s, 4H), 3.35-3.53 (m, 3H), 3.76 (br s, 1H), 4.15 (dt, J=13.1, 6.5, 6.5 Hz, 1H), 4.19-4.38 (m, 2H), 4.48 (tt, J=7.3, 3.7 Hz, 1H), 6.85-6.92 (m, 1H), 6.99 (ddd, J=11.4, 8.5, 3.0 Hz, 1H), 7.17 (td, J=9.2, 5.6 Hz, 1H); ESI-MS m/z [M+H]+ 418.3.

Example 85 2-(4-(2,4-difluorophenoxy)piperidin-1-yl)-3-(isopropylamino)-N,N-dimethyl-7,8-dihydropyrido[3,4-b]pyrazine-6(5H)-carboxamide

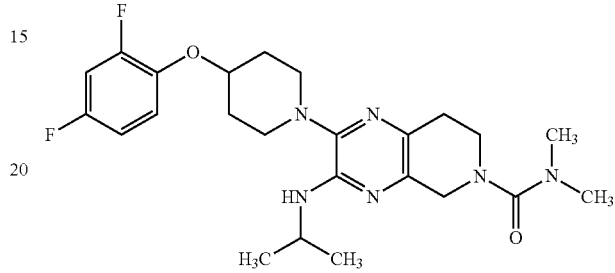

Dimethylcarbamic chloride (5.2 mg, 0.049 mmol) was added to a solution of 2-(4-(2,4-difluorophenoxy)piperidin-1-yl)-N-isopropyl-5,6,7,8-tetrahydropyrido[3,4-b]pyrazin-3-amine TFA salt (12.6 mg, 0.024 mmol) and triethylamine (10 µL, 0.073 mmol) in DCM (240 µL) at rt. After 1 h, the mixture was purified by HPLC Method A to give the title compound as a TFA salt (8.0 mg, 55.8%) as a yellow film. 1H NMR (400 MHz, methanol-d4) δ ppm 1.28 (d, J=6.6 Hz, 6H), 1.90-2.00 (m, 2H), 2.08-2.17 (m, 2H), 2.77-2.84 (m, 2H), 2.91 (s, 6H), 2.99-3.08 (m, 2H), 3.35-3.44 (m, 2H), 3.55 (t, J=5.8 Hz, 2H), 4.09-4.17 (m, 1H), 4.29 (s, 2H), 4.44-4.51 (m, 1H), 6.84-6.91 (m, 1H), 6.99 (s, 1H), 7.18 (td, J=9.2, 5.3 Hz, 1H); ESI-MS m/z [M+H]+ 475.4.

Example 86 (5-chloro-2-fluorophenyl)(1-(3-(isopropylamino)-6-methyl-5,6,7,8-tetrahydropyrido[3,4-b]pyrazin-2-yl)piperidin-4-yl)methanone

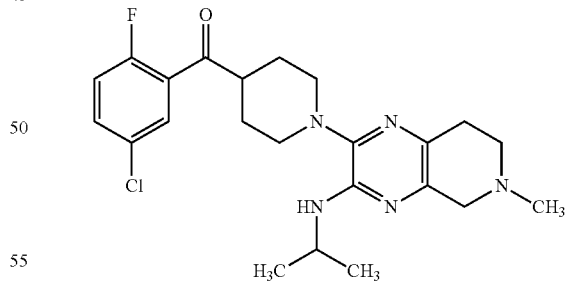

Sodium triacetoxyhydroborate (6.5 mg, 0.031 mmol) was added to a solution of DIPEA (5 µL, 0.031 mmol), (5-chloro-2-fluorophenyl)(1-(3-(isopropylamino)-5,6,7,8-tetrahydropyrido[3,4-b]pyrazin-2-yl)piperidin-4-yl)methanone TFA salt (8.4 mg, 0.015 mmol) and formaldehyde (1.5 µL, 0.015 mmol) in MeOH (150 µL) at rt. After 30 min, the mixture was purified by HPLC Method A to give the title compound as a TFA salt (4.7 mg, 54.6%) as a yellow solid. 1H NMR (400 MHz, methanol-d4) δ ppm 1.24 (d, J=6.6 Hz, 6H), 1.82-1.93 (m, 2H), 1.97-2.05 (m, 2H), 2.81-3.05 (m, 4H), 3.08 (s, 3H), 3.35-3.54 (m, 4H), 3.72-3.83 (m, 1H), 4.10-4.18 (m, 1H), 4.19-4.40 (m, 2H), 7.25-7.32 (m, 1H), 7.61 (ddd, J=8.8, 4.3, 2.8 Hz, 1H), 7.75 (dd, J=6.1, 2.8 Hz, 1H); ESI-MS m/z [M+H]+ 446.3.

Example 87 1-(2-(4-(5-chloro-2-fluorobenzoyl)piperidin-1-yl)-3-(isopropylamino)-7,8-dihydropyrido[3,4-b]pyrazin-6(5H)-yl)ethanone

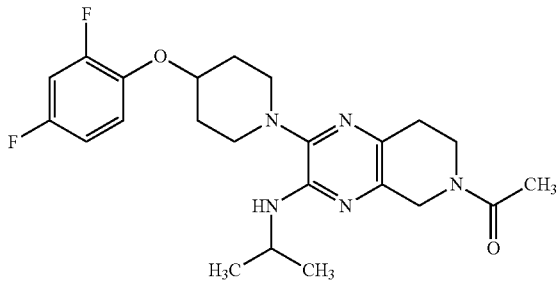

Acetic anhydride (3 µL, 0.029 mmol) was added to a solution of (5-chloro-2-fluorophenyl)(1-(3-(isopropylamino)-5,6,7,8-tetrahydropyrido[3,4-b]pyrazin-2-yl)piperidin-4-yl)methanone TFA salt (8.0 mg, 0.015 mmol) and pyridine (4 µL, 0.044 mmol) in DCM (150 µL) at rt. After 1 h, the mixture was purified by HPLC Method A to give the title compound as a TFA salt (3.6 mg, 42%) as a yellow solid. $^1$H NMR (400 MHz, methanol-$d_4$, mixture of rotamers) δ ppm 1.26-1.32 (m, 6H), 1.84-1.96 (m, 2H), 1.97-2.06 (m, 2H), 2.19 (s, 1.1H), 2.21 (s, 1.9H), 2.70-2.76 (m, 0.7H), 2.80-2.86 (m, 1.3H), 2.87-3.00 (m, 2H), 3.34-3.41 (m, 1H), 3.46-3.56 (m, 2H), 3.79-3.84 (m, 1.3H), 3.84-3.89 (m, 0.7H), 4.07-4.18 (m, 1H), 4.57 (s, 1.1H), 4.62 (s, 0.9H), 7.28 (dd, J=10.4, 8.8 Hz, 1H), 7.61 (ddd, J=8.9, 4.2, 2.9 Hz, 1H), 7.76 (dd, J=6.1, 2.8 Hz, 1H); ESI-MS m/z [M+H]+ 474.3.

Example 88 2-(4-(5-chloro-2-fluorobenzoyl)piperidin-1-yl)-3-(isopropylamino)-N,N-dimethyl-7,8-dihydropyrido[3,4-b]pyrazine-6(5H)-carboxamide

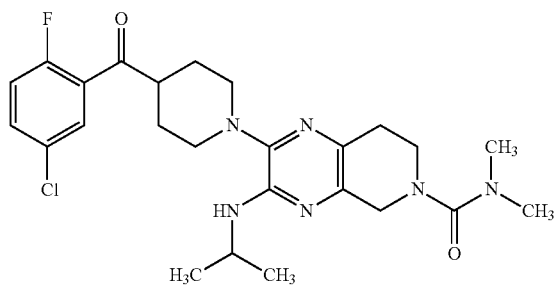 [SMILES: CC(C)Nc1nc2c(nc1N1CCC(C(=O)c3cc(Cl)ccc3F)CC1)CCN(C(=O)N(C)C)C2]

Dimethylcarbamic chloride (3.2 mg, 0.029 mmol) was added to a solution of (5-chloro-2-fluorophenyl)(1-(3-(isopropylamino)-5,6,7,8-tetrahydropyrido[3,4-b]pyrazin-2-yl)piperidin-4-yl)methanone TFA salt (8.0 mg, 0.015 mmol) and triethylamine (6 µL, 0.044 mmol) in DCM (150 µL) at rt. After 1 h, the mixture was purified by HPLC Method A to give the title compound as a TFA salt (3.9 mg, 43.1%) as a yellow solid. $^1$H NMR (400 MHz, methanol-$d_4$) δ ppm 1.31 (d, J=6.6 Hz, 6H), 1.85-2.05 (m, 4H), 2.77-2.84 (m, 2H), 2.91 (s, 6H), 2.93-3.01 (m, 2H), 3.36-3.41 (m, 1H), 3.51-3.59 (m, 4H), 4.07-4.15 (m, 1H), 4.31 (s, 2H), 7.28 (dd, J=10.4, 8.8 Hz, 1H), 7.61 (ddd, J=8.8, 4.3, 2.8 Hz, 1H), 7.76 (dd, J=6.1, 2.8 Hz, 1H); ESI-MS m/z [M+H]+ 504.4.

Example 89 1-(2-(tert-butylamino)-3-(4-(2,4-difluorophenoxy)piperidin-1-yl)-7,8-dihydropyrido[3,4-b]pyrazin-6(5H)-yl)ethanone

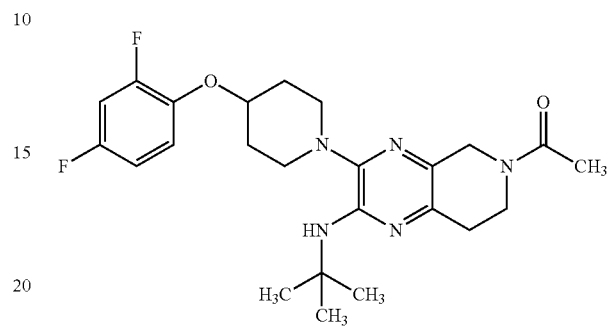

A solution of N-(tert-butyl)-3-(4-(2,4-difluorophenoxy)piperidin-1-yl)-5,6,7,8-tetrahydropyrido[3,4-b]pyrazin-2-amine TFA salt (16 mg, 0.030 mmol), acetic anhydride (5.7 µL, 0.060 mmol), and DIPEA (15.8 µL, 0.090 mmol) in DCM (151 µL) was stirred at room temperature overnight. The crude reaction mixture was diluted in DMF, filtered through a hydrophilic PTFE 0.45 µm filter (Millipore® Millex-LCR), and purified via HPLC Method A to give the title compound as a TFA salt (15 mg) as a clear oil. $^1$H NMR (400 MHz, methanol-$d_4$, mixture of rotamers) δ ppm 1.48 (s, 9H), 1.87-1.98 (m, 2H), 2.07-2.17 (m, 2H), 2.19 (s, 1.3H), 2.21 (s, 1.7H), 2.74 (t, J=5.9 Hz, 0.9H), 2.84 (t, J=5.9 Hz, 1.1H), 2.97 (ddd, J=12.4, 8.6, 3.3 Hz, 2H), 3.33-3.37 (m, 2H), 3.80 (t, J=5.9 Hz, 1.1H), 3.85 (t, J=5.9 Hz, 0.9H), 4.43-4.51 (m, 1H), 4.53 (d, J=1.3 Hz, 2H), 6.88 (ddddd, J=9.1, 8.1, 2.9, 1.9, 0.8 Hz, 1H), 6.95-7.02 (m, 1H), 7.18 (td, J=9.2, 5.3 Hz, 1H); ESI-MS m/z [M+H]+ 460.4.

Example 90 2-(tert-butylamino)-3-(4-(2,4-difluorophenoxy)piperidin-1-yl)-N,N-dimethyl-7,8-dihydropyrido[3,4-b]pyrazine-6(5H)-carboxamide

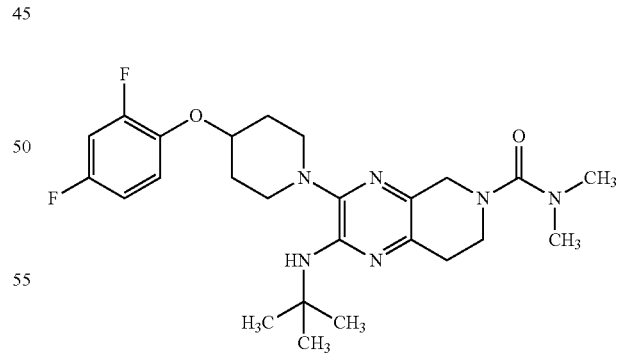

A solution of N-(tert-butyl)-3-(4-(2,4-difluorophenoxy)piperidin-1-yl)-5,6,7,8-tetrahydropyrido[3,4-b]pyrazin-2-amine TFA salt (16 mg, 0.030 mmol), dimethylcarbamic chloride (3.2 mg, 0.030 mmol), and DIPEA (5.3 µL, 0.030 mmol) in DCM (151 µL) was stirred at room temperature overnight. The crude reaction mixture was diluted in DMF, filtered through a hydrophilic PTFE 0.45 µm filter (Millipore® Millex-LCR), and purified via HPLC Method A to give the title compound as a TFA salt (10 mg) as a clear oil. ¹H NMR (400 MHz, methanol-d₄) δ ppm 1.48 (s, 9H), 1.87-1.97 (m, 2H), 2.07-2.17 (m, 2H), 2.82 (t, J=5.9 Hz, 2H), 2.90 (s, 6H), 2.95 (ddd, J=12.2, 8.5, 3.3 Hz, 2H), 3.29-3.35 (m, 2H), 3.53 (t, J=5.8 Hz, 2H), 4.25 (s, 2H), 4.46 (tt, J=7.5, 3.8 Hz, 1H), 6.84-6.91 (m, 1H), 6.99 (ddd, J=11.4, 8.6, 3.0 Hz, 1H), 7.18 (td, J=9.3, 5.4 Hz, 1H); ESI-MS m/z [M+H]⁺ 489.4.

Example 91 1-(2-((2,2-difluoroethyl)amino)-3-(4-(2,4-difluorophenoxy)piperidin-1-yl)-7,8-dihydropyrido[3,4-b]pyrazin-6(5H)-yl)ethanone

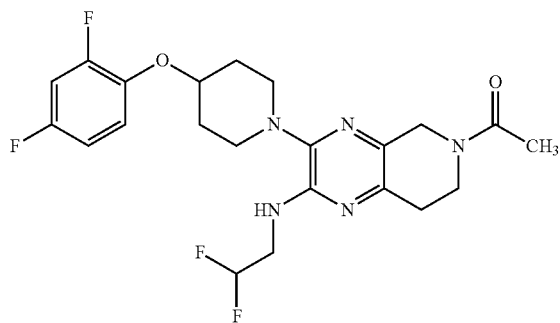 [SMILES: CC(=O)N1CCc2nc(NCC(F)F)c(N3CCC(Oc4ccc(F)cc4F)CC3)nc2C1]

A solution of N-(2,2-difluoroethyl)-3-(4-(2,4-difluorophenoxy)piperidin-1-yl)-5,6,7,8-tetrahydropyrido[3,4-b]pyrazin-2-amine TFA salt (15 mg, 0.028 mmol), acetic anhydride (5.2 μL, 0.056 mmol), and DIPEA (14.6 μL, 0.083 mmol) in DCM (139 μL) was stirred at room temperature overnight. The crude reaction mixture was diluted in DMF, filtered through a hydrophilic PTFE 0.45 μm filter (Millipore® Millex-LCR), and purified via HPLC Method A to give the title compound as a TFA salt (13 mg) as a clear oil. ¹H NMR (400 MHz, methanol-d₄, mixture of rotamers) δ ppm 1.91-2.03 (m, 2H), 2.09-2.17 (m, 2H), 2.19 (s, 1.3H), 2.21 (s, 1.7H), 2.75 (t, J=5.9 Hz, 0.9H), 2.85 (t, J=5.9 Hz, 1.1H), 2.95-3.05 (m, 2H), 3.34-3.42 (m, 2H), 3.73-3.79 (m, 2H), 3.81 (t, J=5.9 Hz, 1.2H), 3.86 (t, J=6.1 Hz, 0.8H), 4.46 (tq, J=7.9, 3.9 Hz, 1H), 4.56 (d, J=0.8 Hz, 2H), 5.89-6.22 (m, 1H), 6.84-6.91 (m, 1H), 6.98 (dddd, J=11.4, 8.5, 3.0, 1.0 Hz, 1H), 7.17 (td, J=9.2, 5.3 Hz, 1H); ESI-MS m/z [M+H]⁺ 468.3.

Example 92 1-(2-(cyclobutylamino)-3-(4-(2-fluoro-4-methoxyphenoxy)piperidin-1-yl)-7,8-dihydropyrido[3,4-b]pyrazin-6(5H)-yl)ethanone

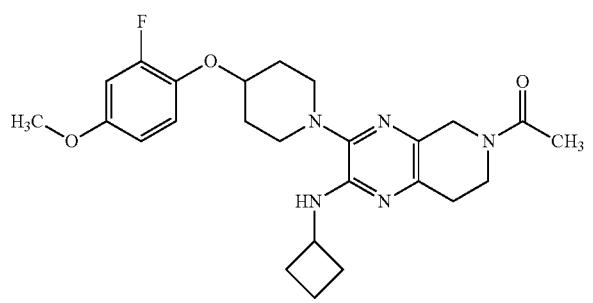 [SMILES: COc1ccc(OC2CCN(c3nc4c(nc3NC3CCC3)CCN(C(C)=O)C4)CC2)c(F)c1]

A mixture of N-cyclobutyl-3-(4-(2-fluoro-4-methoxyphenoxy)piperidin-1-yl)-5,6,7,8-tetrahydropyrido[3,4-b]pyrazin-2-amine TFA salt (10 mg, 0.018 mmol), acetic anhydride (3.8 mg, 0.037 mmol) and pyridine (4.4 mg, 0.055 mmol) in DCM (190 μL) was stirred at room temperature for 30 min. The mixture was purified by HPLC Method A to give the title compound as a TFA salt (6.4 mg, 59%) as a yellow film. ¹H NMR (400 MHz, methanol-d₄, mixture of rotamers) δ ppm 1.76-1.86 (m, 2H), 1.89-2.00 (m, 2H), 2.01-2.15 (m, 4H), 2.19 (s, 1.4H), 2.20 (s, 1.6H), 2.38-2.48 (m, 2H), 2.73-2.79 (m, 0.9H), 2.81-2.88 (m, 1.1H), 2.99-3.08 (m, 2H), 3.38-3.47 (m, 2H), 3.76 (s, 3H), 3.78-3.83 (m, 1.1H), 3.83-3.88 (m, 0.9H), 4.32-4.48 (m, 2H), 4.54 (s, 2H), 6.64-6.70 (m, 1H), 6.74 (dd, J=12.8, 2.9 Hz, 1H), 7.08 (t, J=9.2 Hz, 1H); ESI-MS m/z [M+H]⁺ 470.4.

Example 93 2-(cyclobutylamino)-3-(4-(2-fluoro-4-methoxyphenoxy)piperidin-1-yl)-N,N-dimethyl-7,8-dihydropyrido[3,4-b]pyrazine-6(5H)-carboxamide

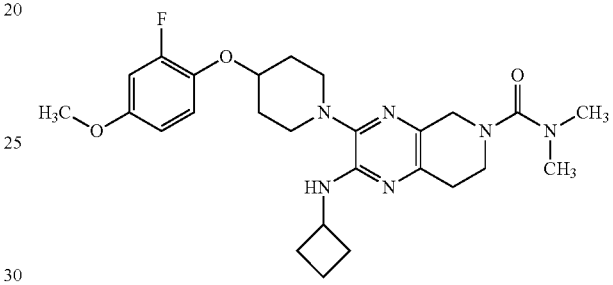

A mixture of N-cyclobutyl-3-(4-(2-fluoro-4-methoxyphenoxy)piperidin-1-yl)-5,6,7,8-tetrahydropyrido[3,4-b]pyrazin-2-amine TFA salt (10.6 mg, 0.020 mmol), dimethylcarbamic chloride (4.2 mg, 0.039 mmol) and triethylamine (5.9 mg, 0.059 mmol) in DCM (200 μL) was stirred at room temperature for 30 min. The mixture was purified by HPLC Method A to give the title compound as a TFA salt (7.1 mg, 59.2%) as a yellow film. ¹H NMR (400 MHz, methanol-d₄) δ ppm 1.77-1.87 (m, 2H), 1.90-2.00 (m, 2H), 2.03-2.15 (m, 4H), 2.39-2.49 (m, 2H), 2.81-2.87 (m, 2H), 2.90 (s, 6H), 2.98-3.08 (m, 2H), 3.38-3.47 (m, 2H), 3.54 (t, J=5.8 Hz, 2H), 3.76 (s, 3H), 4.26 (s, 2H), 4.33-4.47 (m, 2H), 6.67 (dd, J=9.1, 1.5 Hz, 1H), 6.74 (dd, J=12.8, 2.9 Hz, 1H), 7.08 (t, J=9.2 Hz, 1H); ESI-MS m/z [M+H]⁺ 499.4.

Example 94 1-(3-(cyclobutylamino)-2-(4-(2-fluoro-4-methoxyphenoxy)piperidin-1-yl)-7,8-dihydropyrido[3,4-b]pyrazin-6(5H)-yl)ethanone

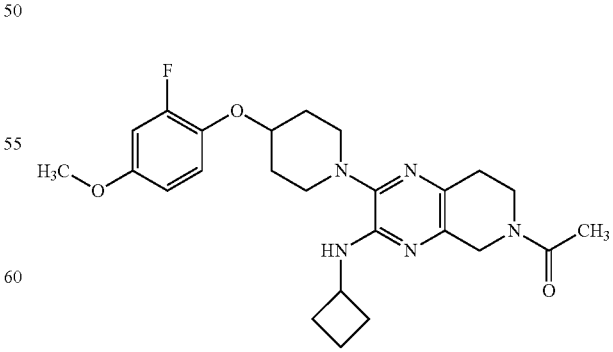

A mixture of N-cyclobutyl-2-(4-(2-fluoro-4-methoxyphenoxy)piperidin-1-yl)-5,6,7,8-tetrahydropyrido[3,4-b]pyrazin-3-amine TFA salt (10.1 mg, 0.019 mmol), acetic anhydride (3.8 mg, 0.037 mmol) and pyridine (4 mg, 0.056 mmol) in DCM (190 μL) was stirred at room temperature for 30 min. The mixture was purified by HPLC Method A to give the title compound as a TFA salt (9.7 mg, 89%) as a yellow film. $^1$H NMR (400 MHz, methanol-$d_4$, mixture of rotamers) δ ppm 1.78-1.87 (m, 2H), 1.91-2.01 (m, 2H), 2.03-2.16 (m, 4H), 2.19 (s, 1.2H), 2.21 (s, 1.8H), 2.38-2.50 (m, 2H), 2.70-2.76 (m, 0.8H), 2.80-2.87 (m, 1.2H), 3.00-3.11 (m, 2H), 3.40-3.50 (m, 2H), 3.76 (s, 3H), 3.79-3.83 (m, 1.2H), 3.84-3.88 (m, 0.8H), 4.34-4.48 (m, 2H), 4.57 (s, 0.8H), 4.61 (s, 1.2H), 6.64-6.69 (m, 1H), 6.74 (dd, J=12.8, 2.9 Hz, 1H), 7.08 (t, J=9.2 Hz, 1H); ESI-MS m/z [M+H]$^+$ 470.4.

Example 95 3-(cyclobutylamino)-2-(4-(2-fluoro-4-methoxyphenoxy)piperidin-1-yl)-N,N-dimethyl-7,8-dihydropyrido[3,4-b]pyrazine-6(5H)-carboxamide

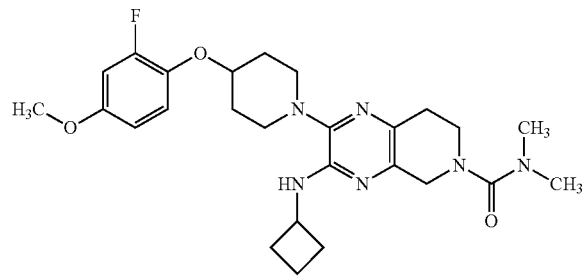

A mixture of N-cyclobutyl-2-(4-(2-fluoro-4-methoxyphenoxy)piperidin-1-yl)-5,6,7,8-tetrahydropyrido[3,4-b]pyrazin-3-amine TFA salt (9.1 mg, 0.017 mmol), dimethylcarbamic chloride (3.6 mg, 0.034 mmol) and triethylamine (5.1 mg, 0.050 mmol) in DCM (170 μL) was stirred at room temperature for 30 min. The mixture was purified by HPLC Method A to give the title compound as a TFA salt (6.0 mg, 58.3%) as a yellow film. $^1$H NMR (400 MHz, methanol-$d_4$) δ ppm 1.74-1.84 (m, 2H), 1.89-2.04 (m, 4H), 2.06-2.15 (m, 2H), 2.36-2.46 (m, 2H), 2.79 (t, J=5.7 Hz, 2H), 2.90 (s, 6H), 2.94-3.02 (m, 2H), 3.34-3.43 (m, 2H), 3.51-3.56 (m, 2H), 3.76 (s, 3H), 4.26 (s, 2H), 4.43 (s, 2H), 6.64-6.69 (m, 1H), 6.74 (dd, J=12.9, 3.0 Hz, 1H), 7.08 (t, J=9.2 Hz, 1H); ESI-MS m/z [M+H]$^+$ 499.4.

Example 96 3-(2,2-difluoroethylamino)-2-(4-(2,4-difluorophenoxy)piperidin-1-yl)-N,N-dimethyl-7,8-dihydropyrido[3,4-b]pyrazine-6(5H)-carboxamide

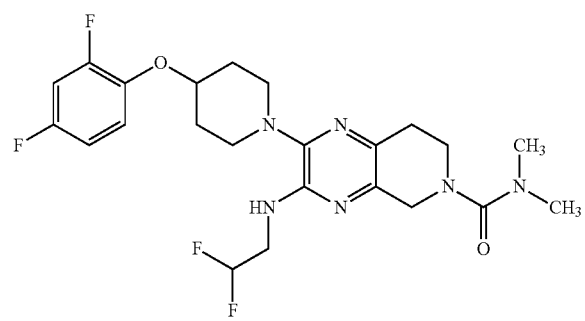 [SMILES: CN(C)C(=O)N1CCc2nc(N3CCC(Oc4ccc(F)cc4F)CC3)c(NCC(F)F)nc2C1]

A solution of N-(2,2-difluoroethyl)-2-(4-(2,4-difluorophenoxy)piperidin-1-yl)-5,6,7,8-tetrahydropyrido[3,4-b]pyrazin-3-amine TFA salt (15 mg, 0.028 mmol), dimethylcarbamic chloride (3.0 mg, 0.028 mmol), and DIPEA (4.9 μL, 0.028 mmol) in DCM (278 μL) was stirred at room temperature overnight. The crude reaction mixture was diluted in DMF, filtered through a hydrophilic PTFE 0.45 μm filter (Millipore® Millex-LCR), and purified via HPLC Method to give the title compound as a TFA salt (5 mg) as a clear oil. $^1$H NMR (400 MHz, methanol-$d_4$) δ ppm 1.92-2.02 (m, 2H), 2.09-2.18 (m, 2H), 2.82 (t, J=5.8 Hz, 2H), 2.90 (s, 6H), 2.99 (ddd, J=12.4, 8.6, 3.4 Hz, 2H), 3.34-3.41 (m, 2H), 3.55 (t, J=5.8 Hz, 2H), 3.77 (td, J=14.5, 4.3 Hz, 2H), 4.28 (s, 2H), 4.42-4.49 (m, 1H), 5.89-6.21 (m, 1H), 6.84-6.91 (m, 1H), 6.98 (ddd, J=11.4, 8.6, 3.0 Hz, 1H), 7.17 (td, J=9.2, 5.3 Hz, 1H); ESI-MS m/z [M+H]$^+$ 497.4.

Example 97 N-(2,2-difluoroethyl)-3-(4-(2,4-difluorophenoxy)piperidin-1-yl)-6-(methylsulfonyl)-5,6,7,8-tetrahydropyrido[3,4-b]pyrazin-2-amine

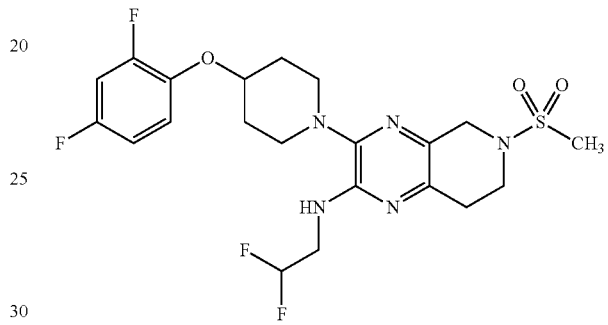

A solution of N-(2,2-difluoroethyl)-3-(4-(2,4-difluorophenoxy)piperidin-1-yl)-5,6,7,8-tetrahydropyrido[3,4-b]pyrazin-2-amine TFA salt (17 mg, 0.032 mmol), DIPEA (12.2 mg, 0.095 mmol) and methanesulfonyl chloride (4.9 μL, 0.063 mmol) in DCM (315 μL) was stirred at room temperature overnight. The crude reaction mixture was diluted in DMF, filtered through a hydrophilic PTFE 0.45 μm filter (Millipore® Millex-LCR), and purified via HPLC Method A to give the title compound as a TFA salt (6 mg) as a clear oil. $^1$H NMR (400 MHz, methanol-$d_4$) δ ppm 1.92-2.02 (m, 2H), 2.09-2.18 (m, 2H), 2.88 (t, J=5.9 Hz, 2H), 2.93 (s, 3H), 3.00 (ddd, J=12.4, 8.8, 3.3 Hz, 2H), 3.34-3.42 (m, 2H), 3.57 (t, J=5.9 Hz, 2H), 3.78 (td, J=14.5, 4.3 Hz, 2H), 4.28 (s, 2H), 4.46 (tt, J=7.5, 3.6 Hz, 1H), 5.89-6.22 (m, 1H), 6.84-6.91 (m, 1H), 6.98 (ddd, J=11.4, 8.6, 3.0 Hz, 1H), 7.17 (td, J=9.2, 5.6 Hz, 1H); ESI-MS m/z [M+H]$^+$ 504.3.

Example 98 1-(2-(2,2-difluoroethylamino)-3-(4-(2,4-difluorophenoxy)piperidin-1-yl)-7,8-dihydropyrido[3,4-b]pyrazin-6(5H)-yl)-2,2-difluoroethanone

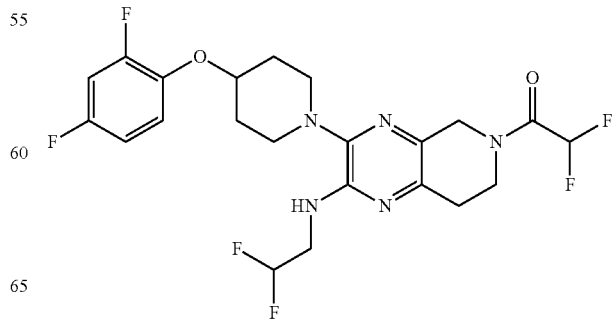

A solution of N-(2,2-difluoroethyl)-3-(4-(2,4-difluorophenoxy)piperidin-1-yl)-5,6,7,8-tetrahydropyrido[3,4-b]pyrazin-2-amine TFA salt (17 mg, 0.032 mmol), DIPEA (12.2 mg, 0.095 mmol), and 2,2-difluoroacetic anhydride (8.2 mg, 0.047 mmol) in DCM (315 µL) was stirred at room temperature overnight. The crude reaction mixture was diluted in DMF, filtered through a hydrophilic PTFE 0.45 µm filter (Millipore® Millex-LCR), and purified via HPLC Method A to give the title compound as a TFA salt (5 mg) as a clear oil. $^1$H NMR (400 MHz, methanol-$d_4$, mixture of rotamers) δ ppm 1.92-2.02 (m, 2H), 2.09-2.18 (m, 2H), 2.81 (t, J=5.9 Hz, 0.8H), 2.87 (t, J=5.9 Hz, 1.2H), 2.97-3.05 (m, 2H), 3.35-3.43 (m, 2H), 3.78 (td, J=14.5, 4.3 Hz, 2H), 3.87-3.96 (m, 2H), 4.42-4.50 (m, 1H), 4.60 (s, 1.2H), 4.62 (s, 0.8H), 5.89-6.22 (m, 1H), 6.41-6.71 (m, 1H), 6.84-6.91 (m, 1H), 6.98 (ddd, J=11.4, 8.6, 3.0 Hz, 1H), 7.17 (td, J=9.2, 5.3 Hz, 1H); ESI-MS m/z [M+H]$^+$ 504.3.

Example 99 (S)-1-(2-(2,2-difluoroethylamino)-3-(4-(2,4-difluorophenoxy)piperidin-1-yl)-7,8-dihydropyrido[3,4-b]pyrazin-6(5H)-yl)-2-methoxypropan-1-one

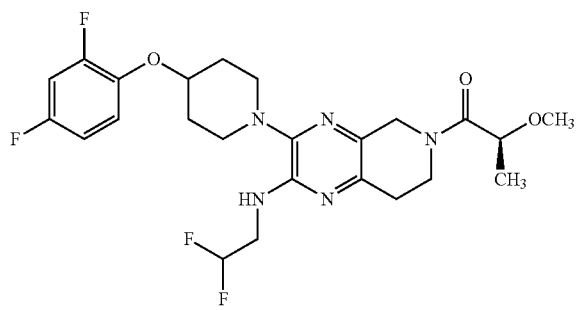 [SMILES: CO[C@@H](C)C(=O)N1CCc2nc(NCC(F)F)c(N3CCC(Oc4ccc(F)cc4F)CC3)nc2C1]

A solution of N-(2,2-difluoroethyl)-3-(4-(2,4-difluorophenoxy)piperidin-1-yl)-5,6,7,8-tetrahydropyrido[3,4-b]pyrazin-2-amine TFA salt (17 mg, 0.032 mmol), HATU (13.2 mg, 0.035 mmol), and DIPEA (12.2 mg, 0.095 mmol) in DMF (158 µL) was stirred for 10 min. Then, (S)-2-methoxypropanoic acid (3.6 mg, 0.035 mmol) was added at room temperature and the resulting reaction mixture stirred overnight. The crude reaction mixture was diluted in DMF, filtered through a hydrophilic PTFE 0.45 µm filter (Millipore® Millex-LCR), and purified via HPLC Method A to give the title compound as a TFA salt (6 mg) as a clear oil. $^1$H NMR (400 MHz, methanol-$d_4$, mixture of rotamers) δ ppm 1.32 (d, J=6.6 Hz, 1.3H), 1.38 (d, J=6.6 Hz, 1.7H), 1.91-2.02 (m, 2H), 2.09-2.18 (m, 2H), 2.77 (t, J=5.8 Hz, 0.9H), 2.85 (t, J=4.9 Hz, 1.1H), 2.96-3.05 (m, 2H), 3.33 (s, 3H), 3.35-3.43 (m, 2H), 3.78 (td, J=14.5, 4.3 Hz, 2H), 3.84-3.97 (m, 2H), 4.31-4.40 (m, 1H), 4.42-4.49 (m, 1H), 4.59 (m, 0.9H), 4.67 (m, 1.1H), 5.90-6.22 (m, 1H), 6.84-6.91 (m, 1H), 6.98 (ddd, J=11.4, 8.6, 3.0 Hz, 1H), 7.18 (td, J=9.2, 5.3 Hz, 1H); ESI-MS m/z [M+H]$^+$ 512.4.

Example 100 1-(3-(2,2-difluoroethylamino)-2-(4-(2,4-difluorophenoxy)piperidin-1-yl)-7,8-dihydropyrido[3,4-b]pyrazin-6(5H)-yl)-2,2-difluoroethanone

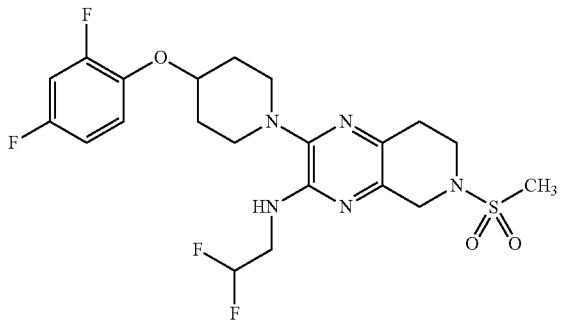 [SMILES: CS(=O)(=O)N1CCc2nc(N3CCC(Oc4ccc(F)cc4F)CC3)c(NCC(F)F)nc2C1]

A solution of N-(2,2-difluoroethyl)-2-(4-(2,4-difluorophenoxy)piperidin-1-yl)-5,6,7,8-tetrahydropyrido[3,4-b]pyrazin-3-amine TFA salt (15 mg, 0.028 mmol), DIPEA (10.8 mg, 0.083 mmol) and methanesulfonyl chloride (4.3 µL, 0.056 mmol) in DCM (280 µL) was stirred at room temperature for 2 h. The crude reaction mixture was diluted in DMF, filtered through a hydrophilic PTFE 0.45 µm filter (Millipore® Millex-LCR), and purified via HPLC Method A to give the title compound as a TFA salt (3 mg) as a clear oil. $^1$H NMR (400 MHz, methanol-$d_4$) δ ppm 1.92-2.02 (m, 2H), 2.09-2.18 (m, 2H), 2.87 (t, J=5.9 Hz, 2H), 2.93 (s, 3H), 2.96-3.04 (m, 2H), 3.34-3.42 (m, 2H), 3.57 (t, J=5.8 Hz, 2H), 3.76 (td, J=14.5, 4.3 Hz, 2H), 4.28 (s, 2H), 4.42-4.49 (m, 1H), 5.89-6.21 (m, 1H), 6.85-6.91 (m, 1H), 6.98 (ddd, J=11.2, 8.5, 3.0 Hz, 1H), 7.17 (td, J=9.2, 5.6 Hz, 1H); ESI-MS m/z [M+H]$^+$ 504.4.

Example 101 1-(3-(2,2-difluoroethylamino)-2-(4-(2,4-difluorophenoxy)piperidin-1-yl)-7,8-dihydropyrido[3,4-b]pyrazin-6(5H)-yl)-2,2-difluoroethanone

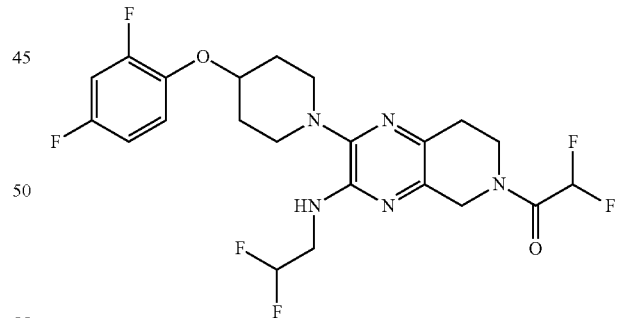

A solution of N-(2,2-difluoroethyl)-2-(4-(2,4-difluorophenoxy)piperidin-1-yl)-5,6,7,8-tetrahydropyrido[3,4-b]pyrazin-3-amine TFA salt (15 mg, 0.028 mmol), DIPEA (10.8 mg, 0.083 mmol), and 2,2-difluoroacetic anhydride (7.3 mg, 0.042 mmol) in DCM (278 µL) was stirred at room temperature for 2 h. The crude reaction mixture was diluted in DMF, filtered through a hydrophilic PTFE 0.45 µm filter (Millipore® Millex-LCR), and purified via HPLC Method A to give the title compound as a TFA salt (3 mg) as a clear oil. $^1$H NMR (400 MHz, methanol-$d_4$, mixture of rotamers) δ ppm 1.92-2.02 (m, 2H), 2.09-2.17 (m, 2H), 2.80 (t, J=5.9 Hz, 0.8H), 2.86 (t, J=5.4 Hz, 1.2H), 2.96-3.04 (m, 2H), 3.34-3.43 (m, 2H), 3.77 (td, J=14.3, 4.0 Hz, 2H), 3.90 (t, J=5.8 Hz, 1.2H), 3.93 (t, J=6.1 Hz, 0.8H), 4.46 (tt, J=7.6, 3.7 Hz, 1H), 4.61 (s, 0.8H), 4.63 (s, 1.2H), 5.89-6.21 (m, 1H), 6.42-6.71 (m, 1H), 6.84-6.91 (m, 1H), 6.98 (ddd, J=11.2, 8.5, 3.0 Hz, 1H), 7.17 (td, J=9.2, 5.6 Hz, 1H); ESI-MS m/z [M+H]$^+$ 504.4.

Example 102 (S)-1-(3-(2,2-difluoroethylamino)-2-(4-(2,4-difluorophenoxy)piperidin-1-yl)-7,8-dihydropyrido[3,4-b]pyrazin-6(5H)-yl)-2-methoxypropan-1-one

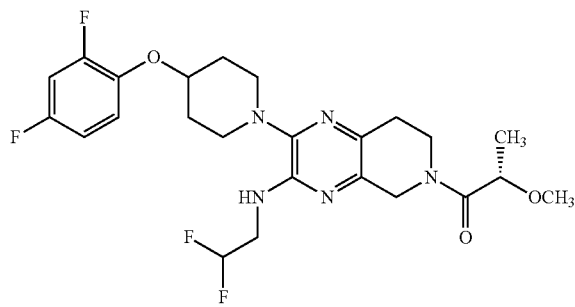 [SMILES: CO[C@@H](C)C(=O)N1CCc2nc(N3CCC(Oc4ccc(F)cc4F)CC3)c(NCC(F)F)nc2C1]

A solution of (S)-2-methoxypropanoic acid (2.9 mg, 0.028 mmol), DIPEA (3.9 mg, 0.028 mmol), and HATU (10.6 mg, 0.028 mmol) in DMF (278 µL) was stirred at room temperature for 10 min then treated with N-(2,2-difluoroethyl)-2-(4-(2,4-difluorophenoxy)piperidin-1-yl)-5,6,7,8-tetrahydropyrido[3,4-b]pyrazin-3-amine TFA salt (15 mg, 0.028 mmol). Stirring was continued overnight. The crude reaction mixture was diluted in DMF, filtered through a hydrophilic PTFE 0.45 µm filter (Millipore® Millex-LCR), and purified via HPLC Method A to give the title compound as a TFA salt (3 mg) as a clear oil. $^1$H NMR (400 MHz, methanol-d$_4$, mixture of rotamers) δ ppm 1.32 (d, J=6.6 Hz, 1.3H), 1.38 (d, J=6.6 Hz, 1.7H), 1.91-2.04 (m, 2H), 2.09-2.19 (m, 2H), 2.76 (t, J=6.2 Hz, 0.9H), 2.84 (t, J=5.4 Hz, 1.1H), 2.95-3.05 (m, 2H), 3.33 (s, 3H), 3.35-3.43 (m, 2H), 3.78 (td, J=14.6, 4.3 Hz, 2H), 3.83-3.98 (m, 2H), 4.32-4.41 (m, 1H), 4.42-4.49 (m, 1H), 4.56 (m, 1.1H), 4.68 (m, 0.9H), 5.89-6.22 (m, 1H), 6.85-6.91 (m, 1H), 6.98 (ddd, J=11.2, 8.5, 3.0 Hz, 1H), 7.17 (td, J=9.2, 5.6 Hz, 1H); ESI-MS m/z [M+H]$^+$ 512.4.

Example 103 (R)-1-(3-(2,2-difluoroethylamino)-2-(4-(2,4-difluorophenoxy)piperidin-1-yl)-7,8-dihydropyrido[3,4-b]pyrazin-6(5H)-yl)-2-methoxypropan-1-one

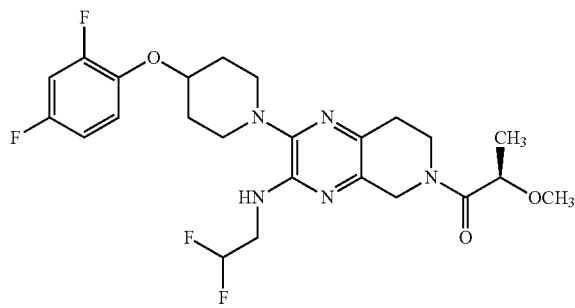 [SMILES: CO[C@H](C)C(=O)N1CCc2nc(N3CCC(Oc4ccc(F)cc4F)CC3)c(NCC(F)F)nc2C1]

A solution of (R)-2-methoxypropanoic acid (2.9 mg, 0.028 mmol), DIPEA (10.8 mg, 0.083 mmol), and HATU (10.6 mg, 0.028 mmol) in DMF (278 µL) was stirred at room temperature for 10 min followed by the addition of N-(2,2-difluoroethyl)-2-(4-(2,4-difluorophenoxy)piperidin-1-yl)-5,6,7,8-tetrahydropyrido[3,4-b]pyrazin-3-amine TFA salt (15 mg, 0.028 mmol) and stirring overnight. The crude reaction mixture was diluted in DMF, filtered through a hydrophilic PTFE 0.45 µm filter (Millipore® Millex-LCR), and purified via HPLC Method A to give the title compound as a TFA salt (3 mg) as a clear oil. $^1$H NMR (400 MHz, methanol-d$_4$, mixture of rotamers) δ ppm 1.32 (d, J=6.8 Hz, 1.3H), 1.38 (d, J=6.6 Hz, 1.6H), 1.90-2.04 (m, 2H), 2.09-2.18 (m, 2H), 2.76 (t, J=6.6 Hz, 0.9H), 2.84 (t, J=6.1 Hz, 1.1H), 3.00 (ddd, J=12.3, 8.6, 3.3 Hz, 2H), 3.33 (s, 3H), 3.34-3.43 (m, 2H), 3.72-3.84 (m, 2H), 3.84-3.98 (m, 2H), 4.32-4.41 (m, 1H), 4.42-4.50 (m, 1H), 4.51-4.55 (m, 0.6H), 4.62-4.69 (m, 1.4H), 5.89-6.22 (m, 1H), 6.84-6.91 (m, 1H), 6.98 (ddd, J=11.2, 8.5, 3.0 Hz, 1H), 7.17 (td, J=9.2, 5.6 Hz, 1H); ESI-MS m/z [M+H]$^+$ 512.4.

Example 104 1-(2-(cyclopropylamino)-3-(4-(2,4-difluorophenoxy)piperidin-1-yl)-5-methyl-7,8-dihydropyrido[3,4-b]pyrazin-6(5H)-yl)ethanone

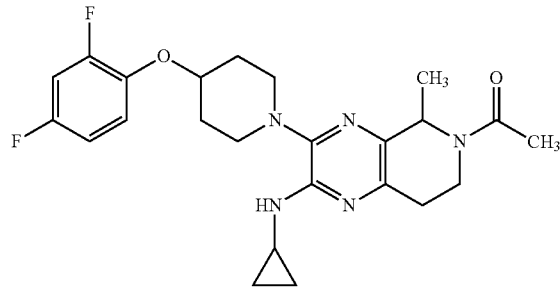 [SMILES: CC(=O)N1CCc2nc(NC3CC3)c(N3CCC(Oc4ccc(F)cc4F)CC3)nc2C1C]

The title compound was prepared in a manner similar to Example 29 using N-cyclopropyl-3-(4-(2,4-difluorophenoxy)piperidin-1-yl)-5-methyl-5,6,7,8-tetrahydropyrido[3,4-b]pyrazin-2-amine TFA salt. $^1$H NMR (400 MHz, methanol-d4, mixture of rotamers) δ ppm 0.78-0.84 (m, 2H), 1.01-1.07 (m, 2H), 1.47 (d, J=6.8 Hz, 2H), 1.60 (d, J=6.8 Hz, 1H), 1.90-2.03 (m, 2H), 2.09-2.19 (m, 2H), 2.23 (s, 3H), 2.76 (tt, J=6.9, 3.5 Hz, 1H), 2.85-2.96 (m, 2H), 2.99-3.20 (m, 3H), 3.46-3.60 (m, 3H), 4.14 (dd, J=13.6, 5.6 Hz, 0.5H), 4.52 (td, J=7.4, 3.4 Hz, 1H), 5.38 (q, J=6.6 Hz, 0.5H), 6.86-6.94 (m, 1H), 7.01 (ddd, J=11.2, 8.5, 3.0 Hz, 1H), 7.19 (td, J=9.2, 5.3 Hz, 1H); ESI-MS m/z [M+H]$^+$ 458.35.

Example 105 2-(cyclopropylamino)-3-(4-(2,4-difluorophenoxy)piperidin-1-yl)-N,N,5-trimethyl-7,8-dihydropyrido[3,4-b]pyrazine-6(5H)-carboxamide

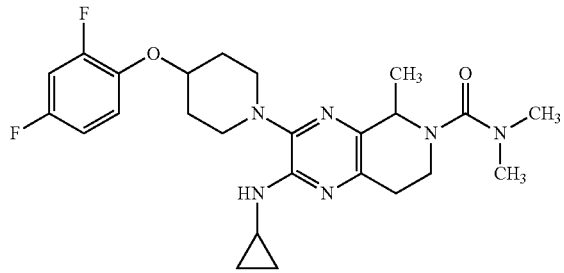 [SMILES: CC1c2nc(N3CCC(Oc4ccc(F)cc4F)CC3)c(NC3CC3)nc2CCN1C(=O)N(C)C]

The title compound was prepared in a manner similar to Example 55 using N-cyclopropyl-3-(4-(2,4-difluorophenoxy)piperidin-1-yl)-5-methyl-5,6,7,8-tetrahydropyrido[3,4-b]pyrazin-2-amine TFA salt. $^1$H NMR (400 MHz, methanol-d4) δ ppm 0.82-0.89 (m, 1H), 1.05-1.12 (m, 1H), 1.53-1.58 (m, 3H), 1.92-2.04 (m, 2H), 2.10-2.20 (m, 2H), 2.63-2.87 (m, 2H), 2.91-2.94 (m, 5H), 3.02-3.25 (m, 3H), 3.35-3.59 (m, 3H), 3.78-3.86 (m, 1H), 4.49-4.57 (m, 1H), 4.66 (q, J=6.8 Hz, 1H), 6.86-6.94 (m, 1H), 6.97-7.05 (m, 1H), 7.15-7.25 (m, 1H); ESI-MS m/z [M+H]$^+$ 487.40.

Example 106 N-cyclopropyl-3-(4-(2,4-difluorophenoxy)piperidin-1-yl)-5,6-dimethyl-5,6,7,8-tetrahydropyrido[3,4-b]pyrazin-2-amine

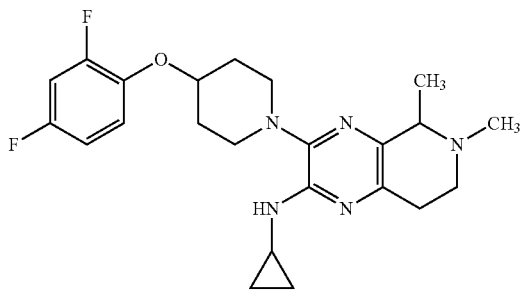 [SMILES: CC1c2nc(N3CCC(Oc4ccc(F)cc4F)CC3)c(NC3CC3)nc2CCN1C]

A solution of N-cyclopropyl-3-(4-(2,4-difluorophenoxy)piperidin-1-yl)-5-methyl-5,6,7,8-tetrahydropyrido[3,4-b]pyrazin-2-amine TFA salt (15 mg, 0.028 mmol), formaldehyde (1.5 μL, 0.057 mmol), and DIPEA (5.0 μL, 0.028 mmol) in DCM (283 μL) was stirred for 10 min. To this was then added sodium triacetoxyborohydride (18.0 mg, 0.085 mmol) and the reaction mixture was stirred overnight. Purification by HPLC Method A afforded the title compound as a TFA salt (4 mg). $^1$H NMR (400 MHz, methanol-d4) δ ppm 0.60-0.67 (m, 2H), 0.83-0.92 (m, 2H), 1.64-1.80 (m, 3H), 1.87-2.04 (m, 2H), 2.05-2.21 (m, 2H), 2.74 (tt, J=7.0, 3.6 Hz, 1H), 2.98-3.21 (m, 7H), 3.35-3.51 (m, 2H), 3.59 (d, J=6.6 Hz, 1H), 3.78 (br s, 1H), 4.42 (br s, 1H), 4.49 (td, J=7.4, 3.7 Hz, 1H), 6.86-6.93 (m, 1H), 6.96-7.05 (m, 1H), 7.18 (td, J=9.2, 5.3 Hz, 1H).

Example 107 1-(2-(2,2-difluoroethylamino)-3-(4-(2,4-difluorophenoxy)piperidin-1-yl)-7-methyl-7,8-dihydropyrido[3,4-b]pyrazin-6(5H)-yl)ethanone

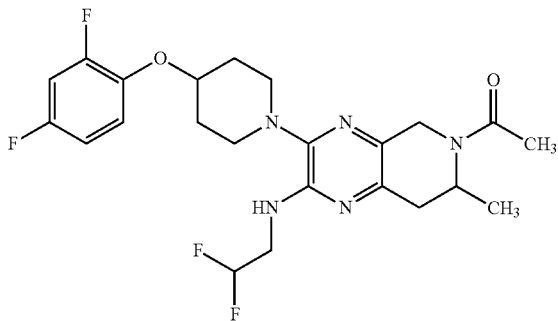 [SMILES: CC(=O)N1Cc2nc(N3CCC(Oc4ccc(F)cc4F)CC3)c(NCC(F)F)nc2CC1C]

A solution of N-(2,2-difluoroethyl)-3-(4-(2,4-difluorophenoxy)piperidin-1-yl)-7-methyl-5,6,7,8-tetrahydropyrido[3,4-b]pyrazin-2-amine TFA salt (15 mg, 0.027 mmol), acetic anhydride (5.1 μL, 0.054 mmol), and DIPEA (14.2 μL, 0.081 mmol) in DCM (136 μL) was stirred at room temperature overnight. The crude reaction mixture was diluted in DMF, filtered through a hydrophilic PTFE 0.45 nm filter (Millipore® Millex-LCR), and purified via HPLC Method A to give the title compound as a TFA salt (8 mg) as a clear oil. $^1$H NMR (400 MHz, methanol-d$_4$, mixture of rotamers) δ ppm 1.13 (d, J=6.8 Hz, 1.4H), 1.23 (d, J=6.8 Hz, 1.6H), 1.92-2.03 (m, 2H), 2.09-2.17 (m, 2H), 2.18 (s, 1.4H), 2.22 (s, 1.6H), 2.54-2.67 (m, 1H), 2.95-3.04 (m, 2.4H), 3.13 (dd, J=16.7, 6.3 Hz, 0.6H), 3.34-3.44 (m, 2H), 3.74-3.83 (m, 2.4H), 3.99 (d, J=18.2 Hz, 0.6H), 4.40-4.49 (m, 1H), 4.55 (quin, J=6.6 Hz, 0.5H), 4.66 (d, J=16.7 Hz, 0.5H), 5.07 (d, J=17.7 Hz, 0.5H), 5.18 (m, 0.5H), 5.90-6.22 (m, 1H), 6.84-6.91 (m, 1H), 6.98 (ddd, J=11.2, 8.5, 3.0 Hz, 1H), 7.18 (td, J=9.2, 5.3 Hz, 1H); ESI-MS m/z [M+H]$^+$ 481.9.

Example 108 2-(2,2-difluoroethylamino)-3-(4-(2,4-difluorophenoxy)piperidin-1-yl)-N,N,7-trimethyl-7,8-dihydropyrido[3,4-b]pyrazine-6(5H)-carboxamide

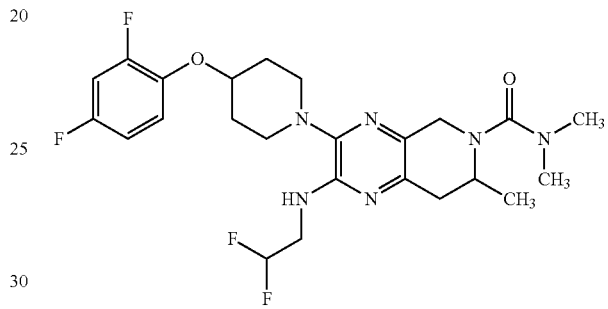

A solution of N-(2,2-difluoroethyl)-3-(4-(2,4-difluorophenoxy)piperidin-1-yl)-7-methyl-5,6,7,8-tetrahydropyrido[3,4-b]pyrazin-2-amine TFA salt (15 mg, 0.027 mmol), dimethylcarbamic chloride (5.8 mg, 0.054 mmol), and DIPEA (14.2 μL, 0.081 mmol) in DCM (136 μL) was stirred at room temperature overnight. The crude reaction mixture was diluted in DMF, filtered through a hydrophilic PTFE 0.45 nm filter (Millipore® Millex-LCR), and purified via HPLC Method A to give the title compound as a TFA salt (10 mg) as a clear oil. $^1$H NMR (400 MHz, methanol-d$_4$) δ ppm 1.19 (d, J=6.8 Hz, 3H), 1.92-2.02 (m, 2H), 2.09-2.19 (m, 2H), 2.53 (d, J=17.2 Hz, 1H), 2.88 (s, 6H), 3.00 (ddd, J=12.3, 8.6, 3.3 Hz, 2H), 3.15 (dd, J=16.8, 5.9 Hz, 1H), 3.34-3.42 (m, 2H), 3.73-3.84 (m, 2H), 4.2-4.34 (m, 3H), 4.46 (tt, J=7.6, 3.6 Hz, 1H), 5.89-6.22 (m, 1H), 6.85-6.91 (m, 1H), 6.98 (ddd, J=11.2, 8.5, 3.0 Hz, 1H), 7.18 (td, J=9.2, 5.6 Hz, 1H); ESI-MS m/z [M+H]$^+$ 511.1.

Example 109 N-(2,2-difluoroethyl)-3-(4-(2,4-difluorophenoxy)piperidin-1-yl)-6,7-dimethyl-5,6,7,8-tetrahydropyrido[3,4-b]pyrazin-2-amine

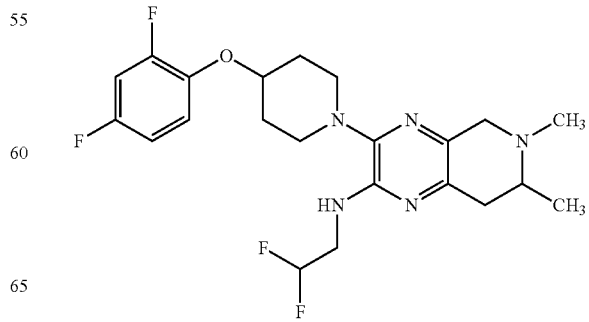

A solution of N-(2,2-difluoroethyl)-3-(4-(2,4-difluorophenoxy)piperidin-1-yl)-7-methyl-5,6,7,8-tetrahydropyrido[3,4-b]pyrazin-2-amine TFA salt (15 mg, 0.027 mmol), formaldehyde (4.0 µL, 0.054 mmol), and DIPEA (4.7 µL, 0.027 mmol) in DCM (136 µL) was stirred for 10 min at room temperature then treated with sodium triacetoxyborohydride (17.2 mg, 0.081 mmol). The resulting reaction mixture was stirred overnight. The crude reaction mixture was diluted in DMF, filtered through a hydrophilic PTFE 0.45 µm filter (Millipore® Millex-LCR), and purified via HPLC Method A to give the title compound as a TFA salt (8 mg) as a clear oil. $^1$H NMR (400 MHz, methanol-$d_4$) δ ppm 1.39-1.57 (m, 3H), 1.92-2.03 (m, 2H), 2.08-2.18 (m, 2H), 2.82-3.09 (m, 6H), 3.16 (d, J=14.9 Hz, 1H), 3.35-3.44 (m, 2H), 3.67-3.85 (m, 3H), 4.11-4.29 (m, 1H), 4.37-4.44 (m, 1H), 4.44-4.52 (m, 1H), 5.90-6.22 (m, 1H), 6.85-6.91 (m, 1H), 6.98 (ddd, J=11.2, 8.5, 3.0 Hz, 1H), 7.17 (td, J=9.2, 5.3 Hz, 1H); ESI-MS m/z [M+H]$^+$ 453.9.

Example 110 1-(2-(2,2-difluoroethylamino)-3-(4-(2,4-difluorophenoxy)piperidin-1-yl)-7-methyl-7,8-dihydropyrido[4,3-b]pyrazin-6(5H)-yl)-2,2-difluoroethanone

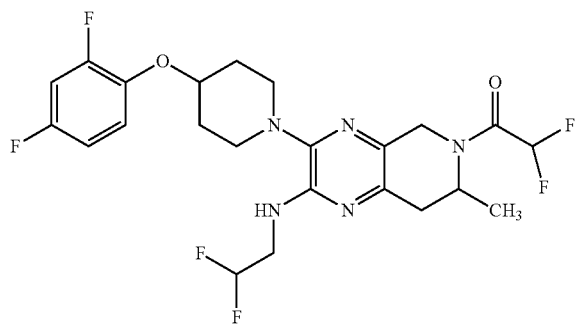 [SMILES: CC1Cc2nc(NCC(F)F)c(N3CCC(Oc4ccc(F)cc4F)CC3)nc2CN1C(=O)C(F)F]

A solution of N-(2,2-difluoroethyl)-3-(4-(2,4-difluorophenoxy)piperidin-1-yl)-7-methyl-5,6,7,8-tetrahydropyrido[3,4-b]pyrazin-2-amine TFA salt (10 mg, 0.018 mmol), 2,2-difluoroacetic anhydride (4.7 mg, 0.027 mmol), and DIPEA (7.0 mg, 0.054 mmol) in DCM (90 µL) was stirred at room temperature for 2 h. The crude reaction mixture was diluted in DMF, filtered through a hydrophilic PTFE 0.45 µm filter (Millipore® Millex-LCR), and purified via HPLC Method A to give the title compound as a TFA salt (5 mg) as a white solid. $^1$H NMR (400 MHz, methanol-$d_4$, mixture of rotamers) δ ppm 1.21 (d, J=7.1 Hz, 1.2H), 1.29 (d, J=6.6 Hz, 1.8H), 1.92-2.03 (m, 2H), 2.09-2.19 (m, 2H), 2.58-2.69 (m, 1H), 2.98-3.07 (m, 2.4H), 3.11-3.17 (m, 0.6H), 3.35-3.44 (m, 2H), 3.78 (td, J=14.5, 4.3 Hz, 2H), 4.11 (d, J=17.2 Hz, 1H), 4.42-4.51 (m, 1H), 4.60-4.67 (m, 0.6H), 4.73-4.77 (m, 0.4H), 5.05 (d, J=17.7 Hz, 0.6H), 5.11-5.18 (m, 0.4H), 5.89-6.22 (m, 1H), 6.39-6.73 (m, 1H), 6.85-6.91 (m, 1H), 6.99 (ddd, J=11.4, 8.6, 3.0 Hz, 1H), 7.18 (td, J=9.3, 5.4 Hz, 1H); ESI-MS m/z [M+H]$^+$ 517.9.

Example 111 1-(2-(2,2-difluoroethylamino)-3-(4-(2,4-difluorophenoxy)piperidin-1-yl)-7-methyl-7,8-dihydropyrido[3,4-b]pyrazin-6(5H)-yl)-2-methoxyethanone

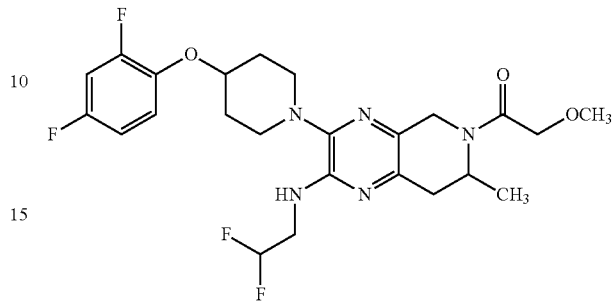

A solution of N-(2,2-difluoroethyl)-3-(4-(2,4-difluorophenoxy)piperidin-1-yl)-7-methyl-5,6,7,8-tetrahydropyrido[3,4-b]pyrazin-2-amine TFA salt (10 mg, 0.018 mmol), 2-methoxyacetyl chloride (2.9 mg, 0.027 mmol), and DIPEA (7.0 mg, 0.054 mmol) in DCM (90 µL) was stirred at room temperature for 2 h. The crude reaction mixture was diluted in DMF, filtered through a hydrophilic PTFE 0.45 µm filter (Millipore® Millex-LCR), and purified via HPLC Method A to give the title compound as a TFA salt (4 mg) as a white solid. $^1$H NMR (400 MHz, methanol-$d_4$, mixture of rotamers) δ ppm 1.16 (d, J=6.8 Hz, 1.4H), 1.24 (d, J=6.6 Hz, 1.6H), 1.91-2.04 (m, 2H), 2.09-2.19 (m, 2H), 2.59 (dd, J=16.9, 10.6 Hz, 1H), 2.97-3.00 (m, 2.4H), 3.09-3.15 (m, 0.6H), 3.35-3.41 (m, 2H), 3.43 (s, 3H), 3.78 (td, J=14.6, 4.3 Hz, 2H), 4.03 (d, J=17.9 Hz, 0.6H), 4.19-4.27 (m, 1.4H), 4.29-4.39 (m, 1H), 4.46-4.52 (m, 1.5H), 4.58-4.62 (m, 0.5H), 5.07 (d, J=18.8 Hz, 0.5H), 5.18 (t, J=5.3 Hz, 0.5H), 5.89-6.22 (m, 1H), 6.85-6.91 (m, 1H), 6.99 (ddd, J=11.2, 8.5, 3.0 Hz, 1H), 7.18 (td, J=9.2, 5.6 Hz, 1H); ESI-MS m/z [M+H]$^+$ 511.9.

Example 112 N-(2,2-difluoroethyl)-3-(4-(2,4-difluorophenoxy)piperidin-1-yl)-7-methyl-6-(methylsulfonyl)-5,6,7,8-tetrahydropyrido[3,4-b]pyrazin-2-amine

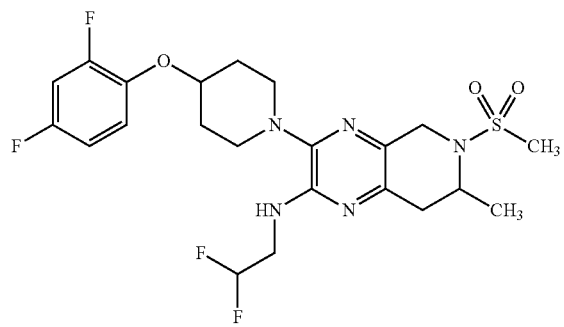 [SMILES: CC1Cc2nc(NCC(F)F)c(N3CCC(Oc4ccc(F)cc4F)CC3)nc2CN1S(C)(=O)=O]

A solution of N-(2,2-difluoroethyl)-3-(4-(2,4-difluorophenoxy)piperidin-1-yl)-7-methyl-5,6,7,8-tetrahydropyrido[3,4-b]pyrazin-2-amine TFA salt (10 mg, 0.018 mmol), methanesulfonyl chloride (3.1 mg, 0.027 mmol), and DIPEA (7.0 mg, 0.054 mmol) in DCM (181 µL) was stirred at room temperature for 2 h. The crude reaction mixture was diluted in DMF, filtered through a hydrophilic PTFE 0.45 µm filter (Millipore® Millex-LCR), and purified via HPLC Method A to give the title compound as a TFA salt (4 mg) as a white solid. ¹H NMR (400 MHz, methanol-d₄) δ ppm 1.25 (d, J=6.8 Hz, 3H), 1.92-2.03 (m, 2H), 2.09-2.19 (m, 2H), 2.57 (d, J=16.9 Hz, 1H), 2.94 (s, 3H), 3.01 (t, J=10.9 Hz, 2H), 3.14 (dd, J=16.7, 6.3 Hz, 1H), 3.34-3.43 (m, 2H), 3.78 (td, J=14.5, 4.3 Hz, 2H), 4.17-4.25 (m, 1H), 4.43-4.55 (m, 3H), 5.89-6.22 (m, 1H), 6.84-6.91 (m, 1H), 6.99 (ddd, J=11.2, 8.5, 3.0 Hz, 1H), 7.18 (td, J=9.2, 5.3 Hz, 1H); ESI-MS m/z [M+H]⁺ 517.9.

Example 113 (2S)-1-(2-(2,2-difluoroethylamino)-3-(4-(2,4-difluorophenoxy)piperidin-1-yl)-7-methyl-7,8-dihydropyrido[3,4-b]pyrazin-6(5H)-yl)-2-methoxypropan-1-one

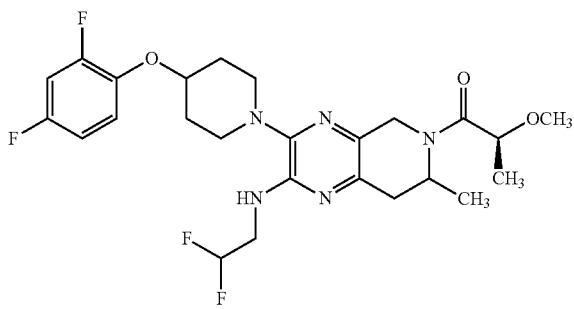 [SMILES: CO[C@@H](C)C(=O)N1Cc2nc(N3CCC(Oc4ccc(F)cc4F)CC3)c(NCC(F)F)nc2CC1C]

A solution of (S)-2-methoxypropanoic acid (1.9 mg, 0.018 mmol), DIPEA (7.0 mg, 0.054 mmol), and HATU (6.9 mg, 0.018 mmol) in DMF (90 µL) was stirred at room temperature for 10 min then treated with N-(2,2-difluoroethyl)-3-(4-(2,4-difluorophenoxy)piperidin-1-yl)-7-methyl-5,6,7,8-tetrahydropyrido[3,4-b]pyrazin-2-amine TFA salt (10 mg, 0.018 mmol). The resulting reaction mixture was stirred for 2 h. The crude reaction mixture was diluted in DMF, filtered through a hydrophilic PTFE 0.45 µm filter (Millipore® Millex-LCR), and purified via HPLC Method A to give the title compound as a TFA salt (5 mg) as a white solid. ¹H NMR (400 MHz, methanol-d₄, mixture of rotamers) δ ppm 1.17 (t, J=6.7 Hz, 1.4H), 1.27 (dd, J=6.7, 2.7 Hz, 1.6H), 1.33 (dd, J=11.5, 6.7 Hz, 1.4H), 1.38 (dd, J=6.7, 2.7 Hz, 1.6H), 1.92-2.03 (m, 2H), 2.09-2.19 (m, 2H), 2.58 (m, 0.6H), 2.64 (m, 0.4H), 2.95-3.05 (m, 2H), 3.08-3.10 (m, 0.5H), 3.12-3.14 (m, 0.5H), 3.35 (s, 3H), 3.37-3.44 (m, 2H), 3.71-3.86 (m, 2H), 4.03 (t, J=18.3 Hz, 1H), 4.30-4.41 (m, 1H), 4.43-4.50 (m, 1H), 4.70-4.83 (m, 1H), 5.08 (m, 0.5H), 5.21 (m, 0.5H), 5.89-6.21 (m, 1H), 6.84-6.91 (m, 1H), 6.99 (ddd, J=11.2, 8.5, 3.0 Hz, 1H), 7.18 (td, J=9.2, 5.3 Hz, 1H); ESI-MS m/z [M+H]⁺ 525.9.

Example 114 (2R)-1-(2-(2,2-difluoroethylamino)-3-(4-(2,4-difluorophenoxy)piperidin-1-yl)-7-methyl-7,8-dihydropyrido[3,4-b]pyrazin-6(5H)-yl)-2-methoxypropan-1-one

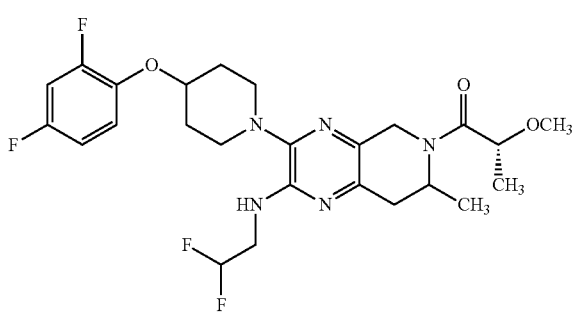 [SMILES: CO[C@H](C)C(=O)N1Cc2nc(N3CCC(Oc4ccc(F)cc4F)CC3)c(NCC(F)F)nc2CC1C]

A solution of (R)-2-methoxypropanoic acid (1.9 mg, 0.018 mmol), DIPEA (7.0 mg, 0.054 mmol), and HATU (6.9 mg, 0.018 mmol) in DMF (90 µL) was stirred for 10 min at room temperature then treated with N-(2,2-difluoroethyl)-3-(4-(2,4-difluorophenoxy)piperidin-1-yl)-7-methyl-5,6,7,8-tetrahydropyrido[3,4-b]pyrazin-2-amine TFA salt (10 mg, 0.018 mmol). The resulting reaction mixture was stirred for 2 h. The crude reaction mixture was diluted in DMF, filtered through a hydrophilic PTFE 0.45 µm filter (Millipore® Millex-LCR), and purified via HPLC Method A to give the title compound as a TFA salt (5 mg) as a white solid. ¹H NMR (400 MHz, methanol-d₄, mixture of rotamers) δ ppm 1.17 (t, J=6.6 Hz, 1.4H), 1.27 (dd, J=6.7, 2.7 Hz, 1.6H), 1.33 (dd, J=11.6, 6.8 Hz, 1.4H), 1.38 (dd, J=6.7, 2.7 Hz, 1.6H), 1.92-2.03 (m, 2H), 2.09-2.18 (m, 2H), 2.53-2.68 (m, 1H), 2.94-3.05 (m, 2H), 3.08-3.10 (m, 0.5H), 3.12-3.14 (m, 0.5H), 3.35 (s, 3H), 3.37-3.42 (m, 2H), 3.78 (td, J=14.5, 4.2 Hz, 2H), 4.03 (t, J=18.8 Hz, 1H), 4.30-4.41 (m, 1H), 4.43-4.51 (m, 1H), 4.70-4.82 (m, 1H), 5.03-5.14 (m, 0.5H), 5.18-5.23 (m, 0.5H), 5.90-6.22 (m, 1H), 6.85-6.91 (m, 1H), 6.99 (ddd, J=11.3, 8.5, 2.9 Hz, 1H), 7.18 (td, J=9.2, 5.4 Hz, 1H); ESI-MS m/z [M+H]⁺ 525.9.

Example 115 Cyclopropyl(2-(2,2-difluoroethylamino)-3-(4-(2,4-difluorophenoxy)piperidin-1-yl)-7-methyl-7,8-dihydropyrido[3,4-b]pyrazin-6(5H)-yl)methanone

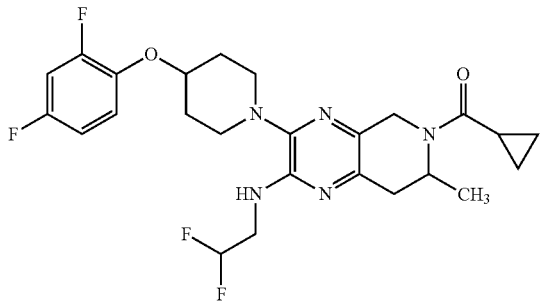 [SMILES: CC1Cc2nc(NCC(F)F)c(N3CCC(Oc4ccc(F)cc4F)CC3)nc2CN1C(=O)C1CC1]

A solution of cyclopropanecarboxylic acid (1.6 mg, 0.018 mmol), DIPEA (7.0 mg, 0.054 mmol), and HATU (6.9 mg, 0.018 mmol) in DMF (181 µL) was stirred at room temperature for 10 min followed by the addition of N-(2,2-difluoroethyl)-3-(4-(2,4-difluorophenoxy)piperidin-1-yl)-7-methyl-5,6,7,8-tetrahydropyrido[3,4-b]pyrazin-2-amine TFA salt (10 mg, 0.018 mmol). The resulting reaction mixture was stirred for 2 h. The crude reaction mixture was diluted in DMF, filtered through a hydrophilic PTFE 0.45 µm filter (Millipore® Millex-LCR), and purified via HPLC Method A to give the title compound as a TFA salt (5 mg) as a white solid. ¹H NMR (400 MHz, methanol-d₄, mixture of rotamers) δ ppm 0.80-1.01 (m, 4H), 1.13 (d, J=6.6 Hz, 1.4H), 1.27 (d, J=6.3 Hz, 1.6H), 1.91-2.04 (m, 2H), 2.06-2.20 (m, 2H), 2.56-2.60 (m, 0.5H), 2.66-2.70 (m, 0.5H), 3.02 (br s, 2H), 3.13-3.15 (m, 0.5H), 3.16-3.20 (m, 0.5H), 3.34-3.46 (m, 2H), 3.72-3.87 (m, 2H), 4.04 (d, J=18.2 Hz, 1H), 4.41-4.58 (m, 2H), 5.02 (d, J=17.4 Hz, 1.4H), 5.15-5.19 (m, 0.6H), 5.90-6.23 (m, 1H), 6.84-6.91 (m, 1H), 6.99 (ddd, J=11.4, 8.6, 3.0 Hz, 1H), 7.18 (td, J=9.2, 5.3 Hz, 1H); ESI-MS m/z [M+H]+ 507.9.

Example 116 6-(2,2-difluoroethyl)-3-(4-(2,4-difluorophenoxy)piperidin-1-yl)-N-isopropyl-5,6,7,8-tetrahydropyrido[3,4-b]pyrazin-2-amine

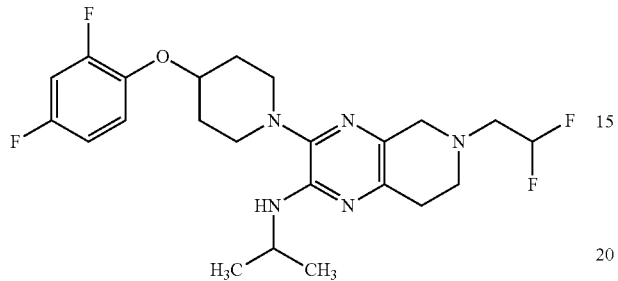

To a suspension of 3-(4-(2,4-difluorophenoxy)piperidin-1-yl)-N-isopropyl-5,6,7,8-tetrahydropyrido[3,4-b]pyrazin-2-amine TFA salt (50 mg, 0.080 mmol) and Cs$_2$CO$_3$ (92 mg, 0.281 mmol) in DMF (0.5 mL) was added 1,1-difluoro-2-iodoethane (0.071 mL, 0.804 mmol) at 23° C. The reaction mixture was stirred at 80° C. for 18 h. The resulting crude material was filtered, rinsed with DMSO (2×0.5 mL), and purified by HPLC Method B using a 30% to 70% ACN gradient to give the title compound as a TFA salt (6.1 mg, 13%) as a yellow film. $^1$H NMR (500 MHz, DMSO-d$_6$) δ ppm 1.19 (d, J=6.4 Hz, 6H), 1.82-1.93 (m, 2H), 2.03-2.10 (m, 2H), 2.79-2.98 (m, 4H), 3.24-3.32 (m, 2H), 3.33-3.75 (m, 4H), 4.05-4.18 (m, 3H), 4.52-4.55 (m, 1H), 5.76-5.82 (m, 1H), 6.39-6.72 (m, 1H), 7.00-7.04 (m, 1H), 7.25-7.34 (m, 2H); ESI-MS m/z [M+H]+ 468.3.

Example 117 (S)-1-(2-(4-((2,4-difluorophenyl)fluoromethyl)piperidin-1-yl)-3-(isopropylamino)-7,8-dihydropyrido[3,4-b]pyrazin-6(5H)-yl)ethan-1-one

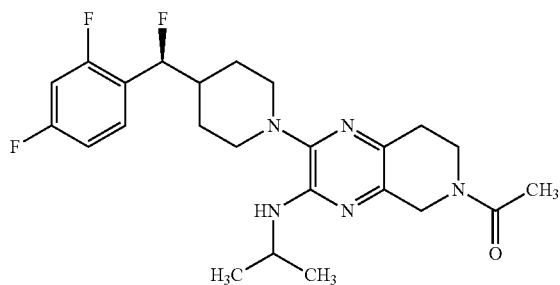 [SMILES: CC(=O)N1CCc2nc(N3CCC([C@H](F)c4ccc(F)cc4F)CC3)c(NC(C)C)nc2C1]

A solution of (S)-2-(4-((2,4-difluorophenyl)fluoromethyl)piperidin-1-yl)-N-isopropyl-5,6,7,8-tetrahydropyrido[3,4-b]pyrazin-3-amine TFA salt (56.0 mg, 0.105 mmol) in DCM (1.05 mL) at 0° C. was treated with acetic anhydride (19.8 μL, 0.210 mmol) and pyridine (25.5 μL, 0.315 mmol). The reaction mixture was concentrated under reduced pressure, taken up in MeOH, filtered, and purified by HPLC Method B. Fractions containing product were concentrated under reduced pressure. The material was repurified by HPLC Method A to give the title compound, as a TFA salt, as a pale yellow solid (5.4 mg, 8.9%). $^1$H NMR (500 MHz, methanol-d4, mixture of rotamers) δ ppm 1.31 (m, 6H), 1.45 (d, J=11.7 Hz, 1H), 1.67 (m, 2H), 2.00 (m, 1H), 2.11 (m, 1H), 2.19 (s, 1.1H), 2.21 (s, 1.9H), 2.80 (m, 4H), 3.53 (m, 2H), 3.82 (t, J=5.9 Hz, 1.3H), 3.86 (t, J=5.9 Hz, 0.7H), 4.11 (m, 1H), 4.60 (s, 0.7H), 4.64 (s, 1.3H), 5.53 (m, 1H), 7.02 (m, 2H), 7.50 (m, 1H); ESI-MS m/z [M+H]+ 462.5.

Example 118 (S)-2-(4-((2,4-difluorophenyl)fluoromethyl)piperidin-1-yl)-3-(isopropylamino)-7,8-dihydropyrido[3,4-b]pyrazine-6(5H)-carbaldehyde

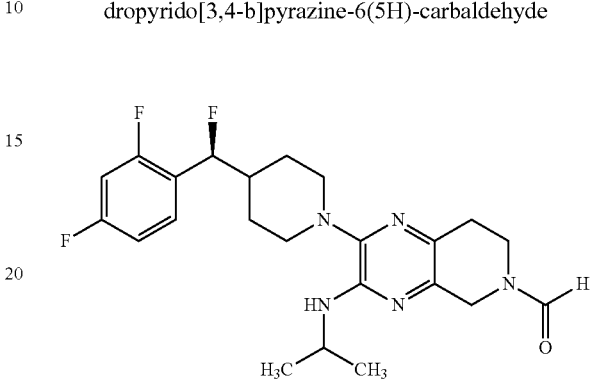

A solution of (S)-2-(4-((2,4-difluorophenyl)fluoromethyl)piperidin-1-yl)-N-isopropyl-5,6,7,8-tetrahydropyrido[3,4-b]pyrazin-3-amine (30.5 mg, 0.073 mmol) in THF (364 μL) at room temperature was treated with phenyl formate (140 μL, 1.09 mmol). The reaction mixture was stirred at 60° C. for 1 h. The reaction was purified by HPLC Method B using a 50% to 80% ACN gradient to give the title compound, as a TFA salt, as a pale yellow solid (9.4 mg, 23%). $^1$H NMR (500 MHz, methanol-d4, mixture of rotamers) δ ppm 1.29 (m, 6H), 1.45 (d, J=12.7 Hz, 1H), 1.66 (m, 2H), 2.00 (m, 1H), 2.10 (m, 1H), 2.77 (m, 4H), 3.49 (m, 2H), 3.76 (t, J=5.9 Hz, 1.4H), 3.82 (t, J=6.1 Hz, 0.6H), 4.12 (m, 1H), 4.48 (s, 0.6H), 4.52 (s, 1.4H), 5.53 (m, 1H), 7.02 (m, 2H), 7.50 (td, J=8.3, 6.3 Hz, 1H), 8.18 (s, 0.7H), 8.24 (s, 0.3H); ESI-MS m/z [M+H]+ 447.90.

Example 119 (R)-2-(4-((2,4-difluorophenyl)fluoromethyl)piperidin-1-yl)-3-(isopropylamino)-7,8-dihydropyrido[3,4-b]pyrazine-6(5H)-carbaldehyde

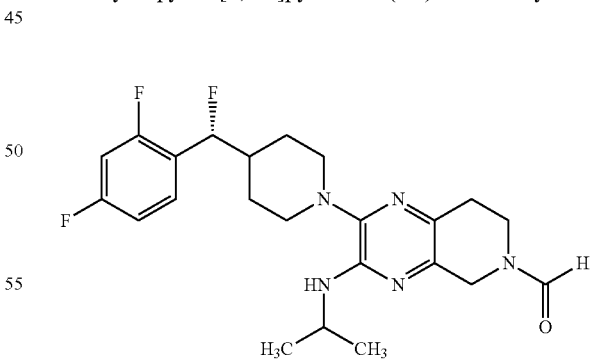

A solution of (R)-2-(4-((2,4-difluorophenyl)fluoromethyl)piperidin-1-yl)-N-isopropyl-5,6,7,8-tetrahydropyrido[3,4-b]pyrazin-3-amine (50.5 mg, 0.120 mmol) in THF (602 μL) at room temperature was treated with phenyl formate (232 μL, 1.806 mmol). The reaction mixture was stirred at 60° C. for 15 min. The reaction mixture was removed from heat and allowed to continue stirring at room temperature for 2 h. The reaction was purified by HPLC Method B using a 50% to 80% ACN gradient to give the title compound, as a TFA salt, as a pale yellow solid (6.0 mg, 8.9% yield). $^1$H NMR (500 MHz, methanol-d4, mixture of rotamers) δ ppm 1.30 (m, 7H), 1.45 (d, J=13.2 Hz, 1H), 1.67 (m, 2H), 2.01 (m, 1H), 2.11 (m, 1H), 2.79 (m, 4H), 3.51 (m, 2H), 3.77 (t, J=5.9 Hz, 1.4H), 3.83 (t, J=6.1 Hz, 0.6H), 4.13 (m, 1H), 4.51 (s, 0.6H), 4.56 (s, 1.4H), 5.53 (m, 1H), 7.02 (m, 2H), 7.50 (m, 1H), 8.19 (s, 0.7H), 8.24 (s, 0.3H); ESI-MS m/z [M+H]$^+$ 447.95.

Example 120 1-(3-(4-(3-fluorophenylsulfonyl)piperidin-1-yl)-2-(isopropylamino)-7,8-dihydropyrido[3,4-b]pyrazin-6(5H)-yl)ethanone

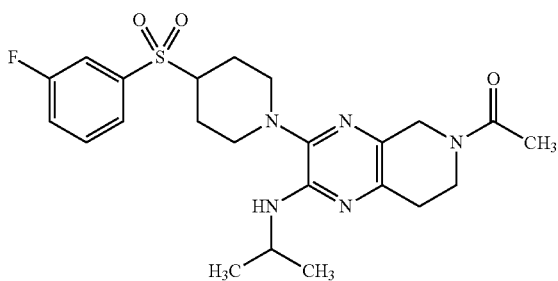

Combined 6-benzyl-3-chloro-N-isopropyl-5,6,7,8-tetrahydropyrido[3,4-b]pyrazin-2-amine (55 mg, 0.174 mmol), 4-((3-fluorophenyl)sulfonyl)piperidine, HCl (58.3 mg, 0.208 mmol)), Pd$_2$(dba)$_3$ (8.0 mg, 8.68 μmol), BINAP (16.2 mg, 0.026 mmol) and sodium tert-butoxide (66.7 mg, 0.694 mmol) and toluene (868 μL). The suspension was heated at 100° C. for 3.5 h then diluted in DMF, filtered through a hydrophilic PTFE 0.45 μm filter (Millipore® Millex-LCR), and purified via HPLC Method A to give 6-benzyl-3-(4-((3-fluorophenyl)sulfonyl)piperidin-1-yl)-N-isopropyl-5,6,7,8-tetrahydropyrido[3,4-b]pyrazin-2-amine as a TFA salt (68 mg) as a yellow film.

To a solution of 6-benzyl-3-(4-((3-fluorophenyl)sulfonyl)piperidin-1-yl)-N-isopropyl-5,6,7,8-tetrahydropyrido[3,4-b]pyrazin-2-amine TFA salt (68 mg, 0.107 mmol) in THF (1333 μL) was added Pd(OH)$_2$ (20 wt %, 22.5 mg, 0.032 mmol). The flask was purged with nitrogen then allowed to stir under an atmosphere of hydrogen (balloon) for 2 h. The reaction mixture was filtered through a hydrophilic PTFE 0.45 μm filter (Millipore® Millex-LCR) and washed with EtOAc. The crude material was concentrated in vacuo to give 3-(4-((3-fluorophenyl)sulfonyl)piperidin-1-yl)-N-isopropyl-5,6,7,8-tetrahydropyrido[3,4-b]pyrazin-2-amine as a TFA salt (58 mg) as a yellow film.

To a solution of 3-(4-((3-fluorophenyl)sulfonyl)piperidin-1-yl)-N-isopropyl-5,6,7,8-tetrahydropyrido[3,4-b]pyrazin-2-amine TFA salt (58 mg, 0.106 mmol) in DCM (1059 μL) at 0° C. was added acetic anhydride (20.0 μL, 0.212 mmol) and pyridine (25.7 μL, 0.318 mmol). After stirring at 0° C. for 30 min, the reaction mixture was concentrated in vacuo. The resulting crude material was dissolved in DCM and purified via automated flash silica gel chromatography using a gradient of 0% to 100% EtOAc in heptanes to give the title compound (19.2 mg) as a colorless oil. $^1$H NMR (500 MHz, methanol-d4) δ ppm 0.85-0.94 (m, 3H), 1.21-1.24 (m, 6H), 1.90-1.99 (m, 2H), 2.19 (d, J=13.7 Hz, 3H), 2.67-2.76 (m, 3H), 2.81 (t, J=5.9 Hz, 1H), 3.34-3.42 (m, 1H), 3.46-3.55 (m, 2H), 3.78 (t, J=6.1 Hz, 1H), 3.84 (t, J=5.9 Hz, 1H), 4.16 (td, J=6.5, 3.7 Hz, 1H), 4.49 (d, J=2.4 Hz, 2H), 7.51-7.57 (m, 1H), 7.68-7.75 (m, 2H), 7.76-7.80 (m, 1H); ESI-MS m/z [M+H]$^+$ 476.90.

Example 121 1-(2-(isopropylamino)-3-(4-(3-methoxyphenylsulfonyl)piperidin-1-yl)-7,8-dihydropyrido[3,4-b]pyrazin-6(5H)-yl)ethanone

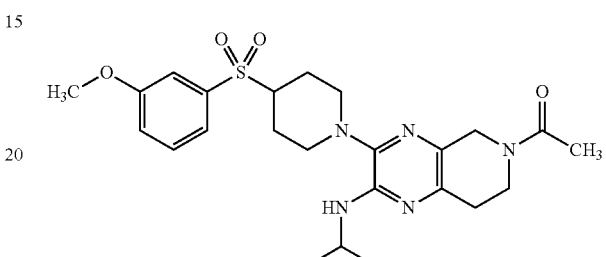

The title compound was prepared in a manner similar to Example 120 using 4-((3-methoxyphenyl)sulfonyl)piperidine, HCl to give the title compound as a white solid. $^1$H NMR (500 MHz, methanol-d4) δ ppm 0.82-0.94 (m, 2H), 1.21-1.24 (m, 6H), 1.87-1.98 (m, 4H), 2.19 (d, J=13.2 Hz, 3H), 2.66-2.75 (m, 3H), 2.81 (t, J=6.1 Hz, 1H), 3.46-3.54 (m, 2H), 3.78 (t, J=5.9 Hz, 1H), 3.84 (t, J=5.9 Hz, 1H), 3.91 (s, 3H), 4.15 (dd, J=10.7, 4.4 Hz, 1H), 4.46-4.50 (m, 2H), 7.29-7.34 (m, 1H), 7.42-7.44 (m, 1H), 7.48-7.52 (m, 1H), 7.56-7.61 (m, 1H); ESI-MS m/z [M+H]$^+$ 488.90.

Example 122 1-(3-(4-((2-fluorophenyl)sulfonyl)piperidin-1-yl)-2-(isopropylamino)-7,8-dihydropyrido[3,4-b]pyrazin-6(5H)-yl)ethan-1-one

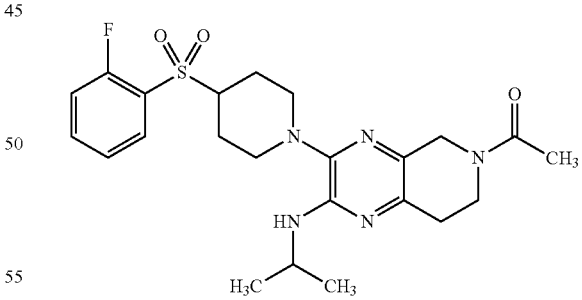

The title compound was prepared in a manner similar to Example 120 using 4-((2-fluorophenyl)sulfonyl)piperidine to give the title compound, as a TFA salt, as a pale yellow solid (26.6 mg, 28.9% over two steps, mixture of rotamers). $^1$H NMR (500 MHz, DMSO-d6) δ ppm 1.16 (d, J=6.8 Hz, 6H), 1.95 (m, 4H), 2.07 (app d, 3H), 2.65 (m, 4H), 3.49 (m, 3H), 3.69 (m, 2H), 4.13 (m, 1H), 4.37 (app d, 2H), 5.69 (br s, 1H), 7.52 (m, 2H), 7.87 (m, 2H); ESI-MS m/z [M+H]$^+$ 476.00.

Example 123 1-(3-(4-(4-fluorophenylsulfonyl)piperidin-1-yl)-2-(isopropylamino)-7,8-dihydropyrido[3,4-b]pyrazin-6(5H)-yl)ethanone

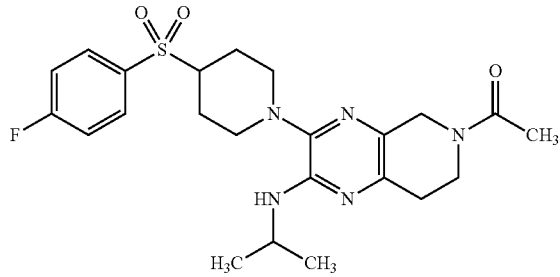 [SMILES: CC(=O)N1CCc2nc(NC(C)C)c(N3CCC(S(=O)(=O)c4ccc(F)cc4)CC3)nc2C1]

The title compound was prepared in a manner similar to Example 120 using 4-((4-fluorophenyl)sulfonyl)piperidine, HCl to give the title compound as a colorless oil. $^1$H NMR (500 MHz, methanol-d4) δ ppm 0.90 (d, J=6.8 Hz, 1H), 1.20-1.24 (m, 6H), 1.90-1.99 (m, 2H), 1.99-2.06 (m, 2H), 2.19 (d, J=13.7 Hz, 3H), 2.67-2.76 (m, 3H), 2.82 (t, J=5.9 Hz, 1H), 3.45-3.55 (m, 2H), 3.79 (t, J=5.9 Hz, 1H), 3.84 (t, J=5.9 Hz, 1H), 4.12-4.20 (m, 1H), 4.49 (s, 2H), 4.58 (s, 1H), 7.42 (td, J=8.7, 1.7 Hz, 2H), 7.97-8.02 (m, 2H); ESI-MS m/z [M+H]$^+$ 476.90.

Example 124 3-(4-(2,4-difluorophenoxy)piperidin-1-yl)-2-(isopropylamino)-7,8-dihydropyrido[3,4-b]pyrazine-6(5H)-carbaldehyde

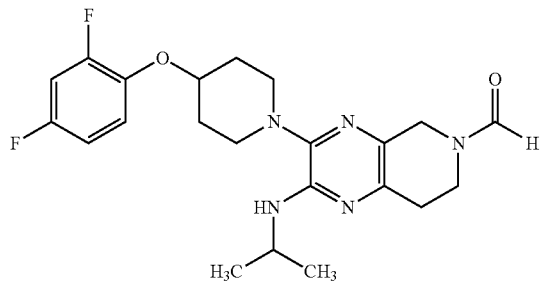 [SMILES: CC(C)Nc1nc2c(nc1N1CCC(Oc3ccc(F)cc3F)CC1)CN(C=O)CC2]

A mixture of 3-(4-(2,4-difluorophenoxy)piperidin-1-yl)-N-isopropyl-5,6,7,8-tetrahydropyrido[3,4-b]pyrazin-2-amine TFA salt (36 mg, 0.058 mmol), Cs$_2$CO$_3$ (66.0 mg, 0.203 mmol), and difluoroiodomethane (0.051 mL, 0.579 mmol) in DMA (0.5 mL) was heated in a microwave on high absorbance for 15 min at 50° C. The resulting crude material was filtered, rinsed with DMSO (2×0.5 mL), and purified by HPLC Method B using a 30% to 70% ACN gradient to give the title compound as a TFA salt (11.2 mg, 35.5%) as a yellow solid. $^1$H NMR (500 MHz, methanol-d$_4$) δ ppm 1.29 (d, J=6.4 Hz, 6H), 1.90-2.01 (m, 2H), 2.07-2.18 (m, 2H), 2.78-2.89 (m, 2H), 3.02-3.10 (m, 2H), 3.39-3.45 (m, 2H), 3.76-3.86 (m, 2H), 4.14 (quin, J=6.4 Hz, 1H), 4.46-4.49 (m, 3H), 6.85-6.91 (m, 1H), 6.95-7.01 (m, 1H), 7.14-7.21 (m, 1H), 8.16-8.27 (m, 1H); ESI-MS m/z [M+H]$^+$ 432.4.

Example 125 1-(3-(4-(2-fluoro-4-methoxyphenylsulfonyl)piperidin-1-yl)-2-(isopropylamino)-7,8-dihydropyrido[4,3-b]pyrazin-6(5H)-yl)ethanone

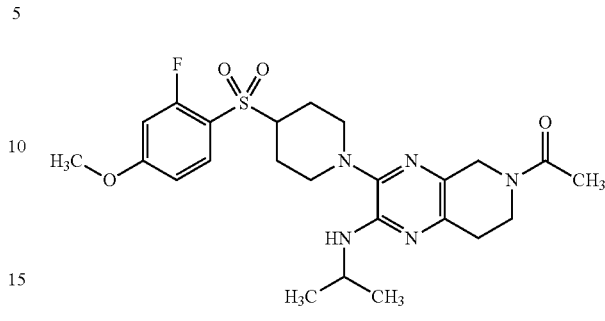

The title compound was prepared in a manner similar to Example 120 using 4-((2-fluoro-4-methoxyphenyl)sulfonyl)piperidine, HCl to give the title compound as a colorless oil. $^1$H NMR (500 MHz, methanol-d4) δ ppm 0.87-0.90 (m, 2H), 1.23 (dd, J=6.8, 1.0 Hz, 6H), 1.95-2.02 (m, 3H), 2.19 (d, J=12.2 Hz, 3H), 2.69-2.79 (m, 3H), 2.82 (t, J=5.9 Hz, 1H), 3.35-3.42 (m, 1H), 3.52 (td, J=8.3, 4.4 Hz, 2H), 3.79 (t, J=5.9 Hz, 1H), 3.85 (t, J=6.1 Hz, 1H), 3.93 (s, 3H), 4.17 (dtt, J=9.8, 6.4, 3.3 Hz, 1H), 4.50 (s, 2H), 6.95-7.02 (m, 2H), 7.78-7.84 (m, 1H); ESI-MS m/z [M+H]$^+$ 506.90.

Example 126 (S)-1-(2-(4-(2,4-difluorophenoxy)piperidin-1-yl)-3-((1-methoxypropan-2-yl)amino)-7,8-dihydropyrido[3,4-b]pyrazin-6(5H)-yl)ethan-1-one

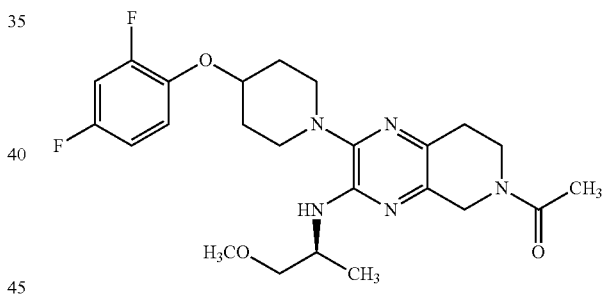

A solution of (S)-6-benzyl-2-(4-(2,4-difluorophenoxy)piperidin-1-yl)-N-(1-methoxypropan-2-yl)-5,6,7,8-tetrahydropyrido[3,4-b]pyrazin-3-amine TFA salt (127.7 mg, 0.200 mmol) in THF (2.00 mL) at room temperature was treated with Pd(OH)$_2$ (20 wt %, 42.2 mg, 0.060 mmol). Hydrogen gas (balloon) was bubbled through the reaction mixture for 5 min. The vent needle was removed and the reaction mixture was stirred under hydrogen atmosphere for 1 h. The reaction mixture was opened to air and was filtered through a pad of Celite™, eluting with EtOAc and MeOH. The filtrate was concentrated under reduced pressure to give (S)-2-(4-(2,4-difluorophenoxy)piperidin-1-yl)-N-(1-methoxypropan-2-yl)-5,6,7,8-tetrahydropyrido[3,4-b]pyrazin-3-amine, as a TFA salt, as a yellow oil, which was carried forward without additional purification. ESI-MS m/z [M+H]$^+$ 434.5.

A solution of (S)-2-(4-(2,4-difluorophenoxy)piperidin-1-yl)-N-(1-methoxypropan-2-yl)-5,6,7,8-tetrahydropyrido[3,4-b]pyrazin-3-amine TFA salt in DCM (2.009 mL) at 0° C. was treated with pyridine (0.049 mL, 0.603 mmol), followed by acetic anhydride (0.038 mL, 0.402 mmol). The reaction mixture was stirred for 1 h 30 min at 0° C. The reaction mixture was concentrated under reduced pressure and taken up in MeOH, filtered through a Millipore® 0.45 μm syringe filter, and purified by HPLC Method A to give the title compound, as a TFA salt, as a yellow-orange semisolid (46.7 mg, 39.4% over two steps). ¹H NMR (500 MHz, methanol-d4, mixture of rotamers) δ ppm 1.27 (m, 3H), 1.95 (m, 2H), 2.13 (m, 2H), 2.19 (s, 1.1H), 2.21 (s, 1.9H), 2.79 (app t, 0.7H), 2.84 (app t, 1.3H), 3.05 (m, 2H), 3.39 (m, 3H), 3.43 (m, 2H), 3.51 (dt, J=5.5, 3.5 Hz, 2H), 3.82 (app t, 1.3H), 3.86 (app t, 0.7H), 4.25 (m, 1H), 4.49 (m, 1H), 4.57 (s, 0.7H), 4.60 (s, 1.3H), 6.88 (m, 1H), 6.99 (ddd, J=11.2, 8.3, 2.9 Hz, 1H), 7.18 (td, J=9.3, 5.4 Hz, 1H); ESI-MS m/z [M+H]⁺ 476.00.

Example 127 (R)-1-(2-(4-(2,4-difluorophenoxy)piperidin-1-yl)-3-((1-methoxypropan-2-yl)amino)-7,8-dihydropyrido[3,4-b]pyrazin-6(5H)-yl)ethan-1-one

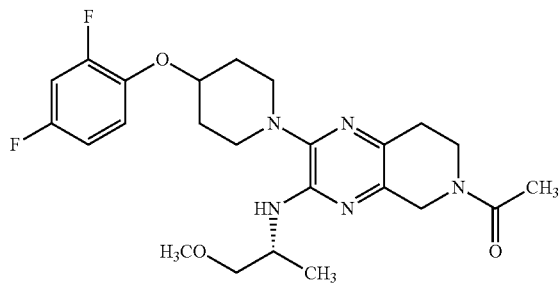 [SMILES: COC[C@@H](C)Nc1nc2c(nc1N1CCC(Oc3ccc(F)cc3F)CC1)CCN(C(C)=O)C2]

A solution of (R)-6-benzyl-2-(4-(2,4-difluorophenoxy)piperidin-1-yl)-N-(1-methoxypropan-2-yl)-5,6,7,8-tetrahydropyrido[3,4-b]pyrazin-3-amine TFA salt (161.4 mg, 0.253 mmol) in THF (2.53 mL) was treated with Pd(OH)₂ (20 wt %, 53.3 mg, 0.076 mmol). Hydrogen gas (balloon) was bubbled through the reaction mixture for 5 min. The vent needle was removed and the reaction mixture was allowed to stir under hydrogen atmosphere at room temperature for 2 h. The reaction mixture was opened to air and filtered through a pad of Celite™, eluting with MeOH and EtOAc. The filtrate was collected and concentrated under reduced pressure to give (R)-2-(4-(2,4-difluorophenoxy)piperidin-1-yl)-N-(1-methoxypropan-2-yl)-5,6,7,8-tetrahydropyrido[3,4-b]pyrazin-3-amine, as a TFA salt, as a yellow oil, which was carried forward without additional purification. ESI-MS m/z [M+H]⁺ 434.5.

A solution of (R)-2-(4-(2,4-difluorophenoxy)piperidin-1-yl)-N-(1-methoxypropan-2-yl)-5,6,7,8-tetrahydropyrido[3,4-b]pyrazin-3-amine TFA salt in DCM (2.539 mL) at 0° C. was treated with pyridine (0.062 mL, 0.762 mmol), followed by acetic anhydride (0.048 mL, 0.508 mmol). The reaction mixture was stirred at 0° C. for 1 h 30 min. The reaction mixture was concentrated under reduced pressure and taken up in MeOH, filtered through a 0.45 μm Millipore® syringe filter, and purified by HPLC Method A to give the title compound, as a TFA salt, as a yellow semisolid (41.4 mg, 27.7% over two steps). ¹H NMR (500 MHz, methanol-d4, mixture of rotamers) δ ppm 1.29 (m, 3H), 1.95 (m, 2H), 2.13 (m, 2H), 2.19 (s, 1.1H), 2.21 (s, 1.9H), 2.74 (t, J=5.9 Hz, 0.7H), 2.84 (app t, 1.3H), 3.09 (m, 2H), 3.38 (m, 3H), 3.47 (m, 4H), 3.82 (t, J=6.1 Hz, 1.3H), 3.86 (t, J=5.9 Hz, 0.7H), 4.26 (m, 1H), 4.49 (m, 1H), 4.59 (br s, 0.7H), 4.62 (s, 1.3H), 6.87 (m, 1H), 6.98 (ddd, J=11.3, 8.7, 2.9 Hz, 1H), 7.27 (td, J=9.3, 5.4 Hz, 1H); ESI-MS m/z [M+H]⁺ 476.00.

Example 128 1-(3-(cyclobutylamino)-2-(4-(2,4-difluorophenoxy)piperidin-1-yl)-7,8-dihydropyrido[3,4-b]pyrazin-6(5H)-yl)ethan-1-one

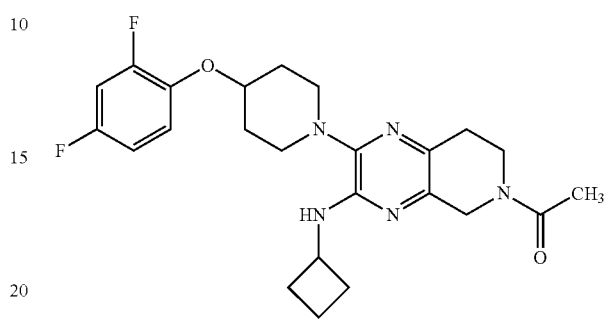

A solution of N-cyclobutyl-2-(4-(2,4-difluorophenoxy)piperidin-1-yl)-5,6,7,8-tetrahydropyrido[3,4-b]pyrazin-3-amine TFA salt (144 mg, 0.272 mmol) in DCM (2.72 mL) at 0° C. was treated with pyridine (66.0 μL, 0.816 mmol), followed by acetic anhydride (51.3 μL, 0.544 mmol). The reaction mixture was stirred at 0° C. for 2 h. The reaction mixture was concentrated under reduced pressure and taken up in MeOH, filtered through a 0.45 μm Millipore® syringe filter, and purified via HPLC Method A to give the title compound, as a TFA salt, as a yellow solid (74.9 mg, 48.2%). ¹H NMR (500 MHz, methanol-d4, mixture of rotamers) δ ppm 1.82 (m, 2H), 1.97 (m, 2H), 2.11 (m, 4H), 2.19 (s, 1.1H), 2.21 (s, 1.9H), 2.45 (m, 2H), 2.73 (t, J=5.9 Hz, 0.7H), 2.84 (t, J=5.9 Hz, 1.3H), 3.11 (m, 2H), 3.47 (m, 2H), 3.81 (t, J=5.9 Hz, 1.3H), 3.85 (t, J=5.9 Hz, 0.7H), 4.40 (m, 1H), 4.49 (m, 1H), 4.59 (s, 0.7H), 4.63 (s, 1.3H), 6.87 (m, 1H), 6.97 (ddd, J=11.2, 8.5, 3.2 Hz, 1H), 7.17 (td, J=9.2, 5.6 Hz, 1H); ESI-MS m/z [M+H]⁺ 458.00.

Example 128A 1-(3-(cyclobutylamino)-2-(4-(2,4-difluorophenoxy)piperidin-1-yl)-7,8-dihydropyrido[3,4-b]pyrazin-6(5H)-yl)ethan-1-one

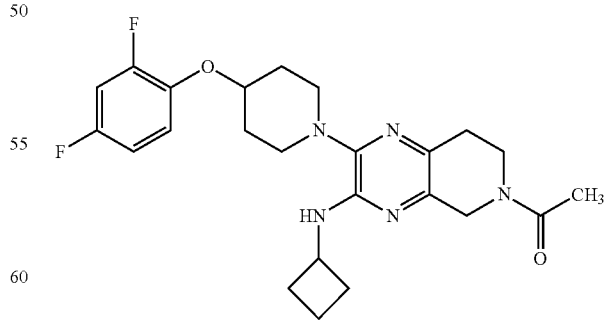

To a solution of N-cyclobutyl-2-(4-(2,4-difluorophenoxy)piperidin-1-yl)pyrido[3,4-b]pyrazin-3-amine (12.0 g, 29.2 mmol) in acetone (200 mL) and dioxane (300 mL) was added Ac₂O (30 mL, 318 mmol) and Pd/C (1.80 g, 16.91 mmol). The reaction was then stirred at 60° C. under H₂ atmosphere (345 kPa) for 72 h. Then the mixture was filtered through a pad of Celite™, washing with EtOAc. The reaction solution was diluted with EtOAc (50 mL) and poured into saturated aqueous NaHCO₃ (50 mL), then washed with brine (2×30 mL). The organic layer was dried over Na₂SO₄ and concentrated in vacuo. The crude product was recrystallized with PE/EtOAc, lyophilized and washed with PE/EtOAc (5:1) to give pure title compound (6.1 g). ¹H NMR (500 MHz, DMSO-d₆, mixture of rotamers) δ ppm 1.57-1.74 (m, 2H), 1.85-1.95 (m, 2H), 1.97-2.08 (m, 4H), 2.08 (s, 1.3H), 2.09 (s, 1.7H), 2.19-2.30 (m, 2H), 2.58 (t, J=5.9 Hz, 0.9H), 2.71 (t, J=5.9 Hz, 1.1H), 2.88 (t, J=10.5 Hz, 2H), 3.23-3.33 (m, 2H), 3.70 (dt, J=11.7, 5.9 Hz, 2H), 4.32-4.47 (m, 3H), 4.52 (tt, J=8.1, 3.8 Hz, 1H), 6.05 (d, J=7.8 Hz, 0.4H), 6.08 (d, J=8.3 Hz, 0.6H 6.96-7.07 (m, 1H), 7.24-7.36 (m, 2H); ESI-MS m/z [M+H]⁺ 458.00.

Example 129 (S)-1-(3-(sec-butylamino)-2-(4-(2,4-difluorophenoxy)piperidin-1-yl)-7,8-dihydropyrido[3,4-b]pyrazin-6(5H)-yl)ethan-1-one

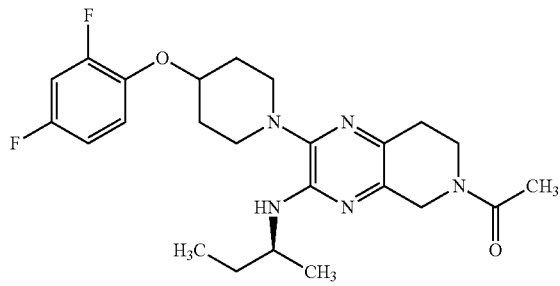 [SMILES: CC[C@H](C)Nc1nc2c(nc1N1CCC(Oc3ccc(F)cc3F)CC1)CCN(C(C)=O)C2]

A solution of (S)-6-benzyl-N-(sec-butyl)-2-(4-(2,4-difluorophenoxy)piperidin-1-yl)-5,6,7,8-tetrahydropyrido[3,4-b]pyrazin-3-amine TFA salt (212.2 mg, 0.341 mmol) in THF (3.4 mL) was treated with Pd(OH)₂ (20 wt %, 71.9 mg, 0.102 mmol). Hydrogen gas (balloon) was bubbled through the reaction mixture for 5 min. The vent needle was removed and the reaction mixture was stirred at room temperature under hydrogen atmosphere for 3 h. The reaction mixture was opened to air and filtered through a pad of Celite™, eluting with EtOAc and MeOH. The filtrate was collected and concentrated under reduced pressure to give (S)—N-(sec-butyl)-2-(4-(2,4-difluorophenoxy)piperidin-1-yl)-5,6,7,8-tetrahydropyrido[3,4-b]pyrazin-3-amine as a TFA salt (169.0 mg) as a yellow oil, which was carried forward without additional purification. ESI-MS m/z [M+H]⁺ 418.5.

A solution of (S)—N-(sec-butyl)-2-(4-(2,4-difluorophenoxy)piperidin-1-yl)-5,6,7,8-tetrahydropyrido[3,4-b]pyrazin-3-amine TFA salt (169.0 mg) in DCM (3.18 mL) at 0° C. was treated with pyridine (0.077 mL, 0.954 mmol), followed by acetic anhydride (0.060 mL, 0.636 mmol). The reaction mixture was stirred for 1 h. The reaction mixture was concentrated under reduced pressure. The residue was taken up in MeOH, filtered through a Millipore® 0.45 μm syringe filter, and purified by HPLC Method A to give the title compound, as a TFA salt, as a yellow semisolid (84.9 mg, 43.4% over two steps). ¹H NMR (500 MHz, methanol-d4, mixture of rotamers) δ ppm 0.98 (m, 3H), 1.27 (m, 3H), 1.68 (m, 2H), 1.97 (m, 2H), 2.13 (m, 2H), 2.19 (s, 1.1H), 2.21 (s, 1.9H), 2.74 (td, J=5.9, 1.5 Hz, 0.7H), 2.84 (td, J=5.9, 1.5 Hz, 1.3H), 3.11 (m, 2H), 3.45 (m, 2H), 3.82 (t, J=5.9 Hz, 1.3H), 3.86 (m, 0.7H), 3.97 (m, 1H), 4.50 (m, 1H), 4.61 (d, J=3.9 Hz, 0.7H), 4.64 (s, 1.3H), 6.87 (m, 1H), 6.97 (ddd, J=11.3, 8.7, 2.9 Hz, 1H), 7.17 (td, J=9.2, 5.6 Hz, 1H); ESI-MS m/z [M+H]⁺ 460.00.

Example 130 (R)-1-(3-(sec-butylamino)-2-(4-(2,4-difluorophenoxy)piperidin-1-yl)-7,8-dihydropyrido[3,4-b]pyrazin-6(5H)-yl)ethan-1-one

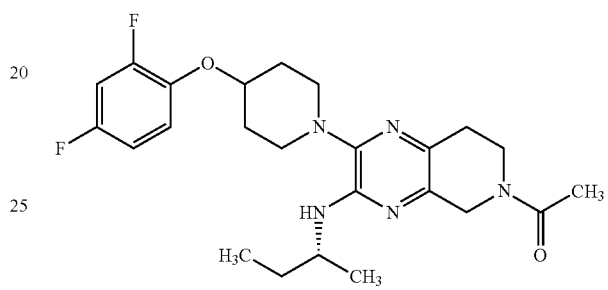

A solution of (R)-6-benzyl-N-(sec-butyl)-2-(4-(2,4-difluorophenoxy)piperidin-1-yl)-5,6,7,8-tetrahydropyrido[3,4-b]pyrazin-3-amine TFA salt (174.6 mg, 0.281 mmol) in THF (2.81 mL) was treated with Pd(OH)₂ (20 wt %, 59.2 mg, 0.084 mmol). Hydrogen gas (balloon) was bubbled through the reaction mixture for 5 min. The vent needle was removed and the reaction was allowed to stir at room temperature under hydrogen atmosphere for 1 h. The reaction mixture was opened to air and filtered through a pad of Celite™, eluting with EtOAc/MeOH. The filtrate was collected and concentrated under reduced pressure to give (R)—N-(sec-butyl)-2-(4-(2,4-difluorophenoxy)piperidin-1-yl)-5,6,7,8-tetrahydropyrido[3,4-b]pyrazin-3-amine as a TFA salt (136.4 mg) as a yellow oil, which was carried forward without additional purification. ESI-MS m/z [M+H]⁺ 418.5.

A solution of (R)—N-(sec-butyl)-2-(4-(2,4-difluorophenoxy)piperidin-1-yl)-5,6,7,8-tetrahydropyrido[3,4-b]pyrazin-3-amine TFA salt (136.4 mg) in DCM (2.57 mL) at 0° C. was treated with pyridine (0.062 mL, 0.770 mmol), followed by acetic anhydride (0.048 mL, 0.513 mmol). The reaction mixture was stirred for 1 h. The reaction mixture was concentrated under reduced pressure. The residue was taken up in MeOH, filtered through a Millipore® 0.45 μm syringe filter, and purified by HPLC Method A to give title compound, as a TFA salt, as a yellow solid (52.0 mg, 32.2% over two steps). ¹H NMR (500 MHz, methanol-d4) δ ppm 0.98 (m, 3H), 1.26 (m, 3H), 1.67 (m, 2H), 1.96 (m, 2H), 2.13 (m, 2H), 2.19 (s, 1.1H), 2.21 (s, 1.9H), 2.73 (td, J=5.9, 1.5 Hz, 0.7H), 2.84 (td, J=5.9, 1.5 Hz, 1.3H), 3.08 (m, 2H), 3.43 (m, 2H), 3.82 (t, J=5.9 Hz, 1.3H), 3.86 (m, 0.7H), 3.97 (m, 1H), 4.49 (m, 1H), 4.59 (m, 0.7H), 4.63 (s, 1.3H), 6.87 (m, 1H), 6.98 (ddd, J=11.3, 8.4, 3.2 Hz, 1H), 7.17 (td, J=9.3, 5.4 Hz, 1H); ESI-MS m/z [M+H]⁺ 460.0.

Example 131 1-(2-(4-(2,4-difluorophenoxy)piperidin-1-yl)-3-(isopropylamino)-7,8-dihydropyrido[3,4-b]pyrazin-6(5H)-yl)propan-1-one

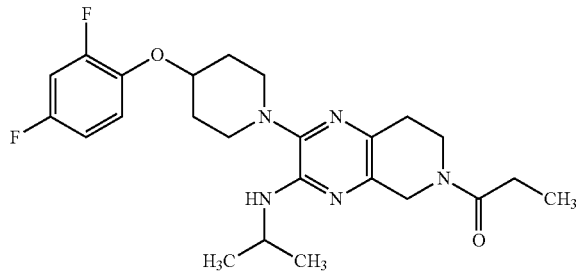 [SMILES: CCC(=O)N1CCc2nc(N3CCC(Oc4ccc(F)cc4F)CC3)c(NC(C)C)nc2C1]

To a solution of 2-(4-(2,4-difluorophenoxy)piperidin-1-yl)-N-isopropyl-5,6,7,8-tetrahydropyrido[3,4-b]pyrazin-3-amine (50 mg, 0.124 mmol) in DCM (1.24 mL) at 0° C. was added DIPEA (32.5 µL, 0.186 mmol) and propionic anhydride (19.2 µL, 0.149 mmol). The resulting solution was stirred at this temperature for 2 h. Purification by silica gel column chromatography using 0% to 100% EtOAc in heptanes gave the title compound as a white solid (53 mg, 93%). $^1$H NMR (400 MHz, methanol-$d_4$, mixture of rotamers) δ ppm $^1$H NMR (400 MHz, methanol-$d_4$, mixture of rotamers) δ ppm 1.10-1.20 (m, 3H), 1.25 (d, J=6.8 Hz, 3H), 1.26 (d, J=6.8 Hz, 3H), 1.90-2.00 (m, 2H), 2.09-2.18 (m, 2H), 2.47-2.58 (m, 2H), 2.72 (t, J=5.9 Hz, 0.8H), 2.81 (t, J=5.9 Hz, 1.2H), 2.92-3.01 (m, 2H), 3.81 (t, J=5.9 Hz, 1.2H), 3.87 (t, J=6.1 Hz, 0.8H), 4.13-4.21 (m, 1H), 4.46 (tt, J=7.5, 3.7 Hz, 1H), 4.55 (s, 0.8H), 4.56 (s, 1.2H), 6.85-6.92 (m, 1H), 6.99 (m, 1H), 7.18 (m, 1H); ESI-MS m/z [M+Na]$^+$ 482.9.

Example 132 Methyl 2-(4-(2,4-difluorophenoxy)piperidin-1-yl)-3-(isopropylamino)-7,8-dihydropyrido[3,4-b]pyrazine-6(5H)-carboxylate

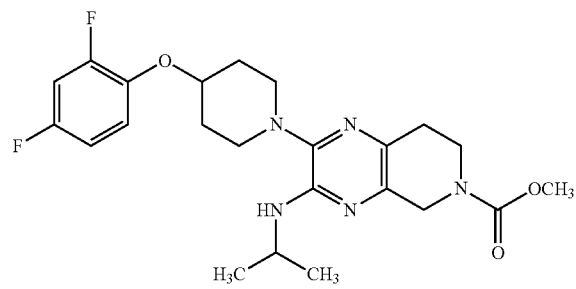 [SMILES: COC(=O)N1CCc2nc(N3CCC(Oc4ccc(F)cc4F)CC3)c(NC(C)C)nc2C1]

To a solution of 2-(4-(2,4-difluorophenoxy)piperidin-1-yl)-N-isopropyl-5,6,7,8-tetrahydropyrido[3,4-b]pyrazin-3-amine (45.6 mg, 0.113 mmol) and triethylamine (0.039 mL, 0.283 mmol) in DCM (0.75 mL) was added methyl carbonochloridate (0.013 mL, 0.170 mmol) at 0° C. The reaction mixture was stirred at 0° C. for 1 hr, warmed to 23° C., and concentrated via rotary evaporation. The resulting crude material was partitioned between EtOAc and H$_2$O. The organic phase was washed with brine, dried over Na$_2$SO$_4$, filtered, rinsed with EtOAc, and concentrated via rotary evaporation. The crude material was dissolved in toluene (0.5 mL) and purified via medium pressure chromatography using a 2% to 80% gradient eluant of EtOAc in heptane on a 12 g silica gel column (Single Step™) to give the title compound (48.7 mg, 93%) as a white foam. $^1$H NMR (500 MHz, DMSO-$d_6$) δ ppm 1.17-1.19 (m, 6H), 1.80-1.94 (m, 2H), 2.06 (ddd, J=9.5, 5.9, 3.2 Hz, 2H), 2.64 (t, J=5.9 Hz, 2H), 2.82-2.94 (m, 2H), 3.19-3.31 (m, 2H), 3.64 (s, 3H), 3.64-3.69 (m, 2H), 4.07-4.17 (m, 1H), 4.35 (br s, 2H), 4.51 (tt, J=8.1, 3.9 Hz, 1H), 5.53 (d, J=8.3 Hz, 1H), 7.01 (dddd, J=9.3, 8.1, 3.2, 1.5 Hz, 1H), 7.26-7.35 (m, 2H); ESI-MS m/z [M+H]$^+$ 461.9.

Example 133 2-(4-(2,4-difluorophenoxy)piperidin-1-yl)-6-(2-fluoroethyl)-N-isopropyl-5,6,7,8-tetrahydropyrido[3,4-b]pyrazin-3-amine

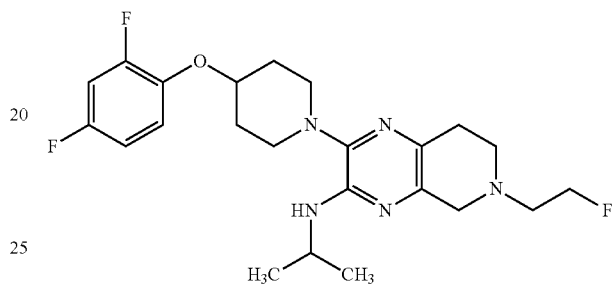

To a suspension of 2-(4-(2,4-difluorophenoxy)piperidin-1-yl)-N-isopropyl-5,6,7,8-tetrahydropyrido[3,4-b]pyrazin-3-amine (98.4 mg, 0.244 mmol) and K$_2$CO$_3$ (135 mg, 0.976 mmol) in acetone (4.0 mL) was added 1-bromo-2-fluoroethane (0.020 mL, 0.268 mmol) at 23° C. The reaction mixture was stirred at 50° C. for 1 hr. The reaction mixture was cooled to 23° C., an additional portion of 1-bromo-2-fluoroethane (8.2 µL, 0.110 mmol) was added, and the reaction mixture was heated for an additional 1.5 hr at 50° C., cooled to 23° C., and concentrated via rotary evaporation. The resulting crude material was reconstituted in DMSO, filtered, rinsed with DMSO, and purified by HPLC Method B using a 30% to 70% ACN gradient to give the title compound (42 mg, 38.3%) as a light yellow oil. $^1$H NMR (500 MHz, DMSO-$d_6$, mixture of rotamers) δ ppm 1.17 (d, J=6.8 Hz, 6H), 1.82-1.93 (m, 2H), 2.02-2.11 (m, 2H), 2.62-2.69 (m, 2H), 2.73-2.80 (m, 3H), 2.81-2.91 (m, 3H), 3.20-3.29 (m, 2H), 3.48 (s, 2H), 4.04-4.12 (m, 1H), 4.47-4.54 (m, 1H), 4.56 (t, J=4.9 Hz, 1H), 4.66 (t, J=4.9 Hz, 1H), 5.38 (d, J=7.8 Hz, 1H), 6.98-7.05 (m, 1H), 7.26-7.34 (m, 2H); ESI-MS m/z [M+H]$^+$ 450.0.

Example 134 1-(2-(4-(2,4-difluorobenzyl)piperazin-1-yl)-3-(isopropylamino)-7,8-dihydropyrido[3,4-b]pyrazin-6(5H)-yl)ethan-1-one

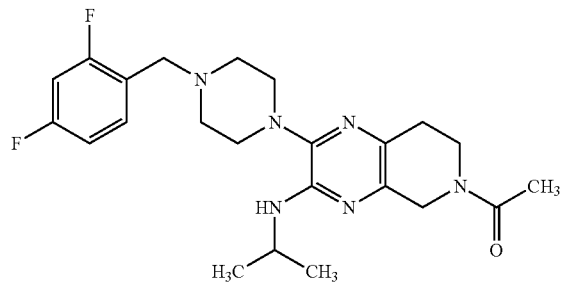 [SMILES: CC(=O)N1CCc2nc(N3CCN(Cc4ccc(F)cc4F)CC3)c(NC(C)C)nc2C1]

To a pressure reactor charged with a red-orange solution of 2-(4-(2,4-difluorobenzyl)piperazin-1-yl)-N-isopropylpyrido[3,4-b]pyrazin-3-amine (0.5 g, 1.255 mmol) in acetone (25 mL) and dioxane (25 mL) was added palladium, 10 wt % on activated carbon (0.053 g, 0.502 mmol) as a slurry in dioxane (3 mL) under nitrogen. Next, acetic anhydride (1.179 mL, 12.55 mmol) was added at 23° C. The mixture was stirred under hydrogen at 45° C. and 310 kPa for 9.5 hr. The reaction mixture was filtered through Celite™, rinsed with EtOAc, and concentrated via rotary evaporation. The crude material was dissolved in toluene (5 mL) and purified via medium pressure chromatography using a 10% to 100% gradient eluant of EtOAc in heptane on an NH 60 µM size 400 column (Shoko Scientific Purif-Pack™) to give the title compound (341 mg, 61.1%) as an off-white foam. $^1$H NMR (500 MHz, DMSO-d$_6$, mixture of rotamers) δ ppm 1.14-1.19 (m, 6H), 2.08 (s, 1.2H), 2.09 (s, 1.8H), 2.52-2.65 (m, 5H), 2.70 (t, J=5.9 Hz, 1H), 2.98 (br s, 4H), 3.58 (s, 2H), 3.70 (dt, J=12.0, 5.7 Hz, 2H), 4.00-4.15 (m, 1H), 4.40 (s, 0.8H), 4.43 (s, 1.2H), 5.35 (d, J=7.8 Hz, 0.4H), 5.38 (d, J=8.3 Hz, 0.6H) 7.08 (td, J=8.3, 2.4 Hz, 1H), 7.21 (td, J=10.0, 2.4 Hz, 1H), 7.44-7.51 (m, 1H); ESI-MS m/z [M+H]$^+$ 445.0.

Example 135 1-(3-(cyclobutylamino)-2-(4-(2,4-difluorobenzyl)piperazin-1-yl)-7,8-dihydropyrido[3,4-b]pyrazin-6(5H)-yl)ethan-1-one

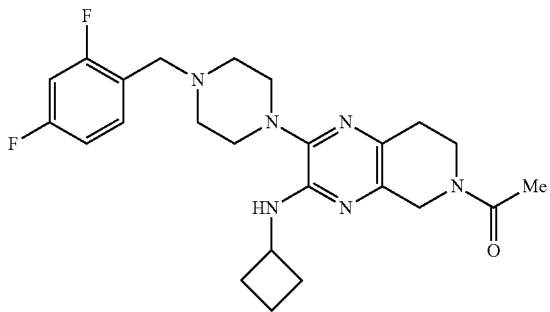 [SMILES: CC(=O)N1CCc2nc(N3CCN(Cc4ccc(F)cc4F)CC3)c(NC3CCC3)nc2C1]

To N-cyclobutyl-2-(4-(2,4-difluorobenzyl)piperazin-1-yl)pyrido[3,4-b]pyrazin-3-amine (0.500 g, 1.218 mmol) in acetone (25 mL) and dioxane (25 mL) was added palladium, 10 wt % on activated carbon (0.052 g, 0.487 mmol) as a slurry in dioxane (3 mL) under nitrogen. Next, acetic anhydride (1.144 mL, 12.18 mmol) was added at 23° C. The mixture was stirred under hydrogen at 310 kPa for 50 hr at 45° C. The crude mixture was filtered through Celite™, rinsed with dioxane, and concentrated via rotary evaporation. The crude material was purified via medium pressure chromatography using a 10% to 100% gradient eluant of EtOAc in heptanes on an NH 60 µM size 60 column (Shoko Scientific Purif-Pack™) to give the title compound 1-(3-(cyclobutylamino)-2-(4-(2,4-difluorobenzyl)piperazin-1-yl)-7,8-dihydropyrido[3,4-b]pyrazin-6(5H)-yl)ethanone (284 mg, 51.1%) as a yellow foam. $^1$H NMR (500 MHz, DMSO-d$_6$, mixture of rotamers) δ ppm 1.56-1.72 (m, 2H), 1.97-2.06 (m, 2H), 2.07 (s, 1.3H), 2.08 (s, 1.7H), 2.18-2.27 (m, 2H), 2.52-2.66 (m, 4.9H), 2.69 (t, J=5.9 Hz, 1.1H), 2.99 (br s, 4H), 3.59 (s, 2H), 3.69 (dt, J=11.5, 6.0 Hz, 2H), 4.27-4.46 (m, 3H), 5.89 (d, J=7.3 Hz, 0.4H), 5.93 (d, J=7.8 Hz, 0.6H), 7.02-7.13 (m, 1H), 7.17-7.27 (m, 1H), 7.41-7.55 (m, 1H); ESI-MS m/z [M+H]$^+$ 457.0.

Example 136 2-(4-(2,4-difluorobenzyl)piperazin-1-yl)-N-isopropyl-6-(methylsulfonyl)-5,6,7,8-tetrahydropyrido[3,4-b]pyrazin-3-amine

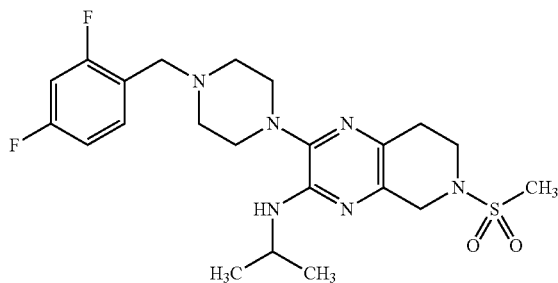 [SMILES: CC(C)Nc1nc2c(nc1N1CCN(Cc3ccc(F)cc3F)CC1)CCN(S(C)(=O)=O)C2]

To a solution of 2-(4-(2,4-difluorobenzyl)piperazin-1-yl)-N-isopropyl-5,6,7,8-tetrahydropyrido[3,4-b]pyrazin-3-amine (50 mg, 0.124 mmol) and DIPEA (0.032 mL, 0.186 mmol) in DCM (1 mL) was added methanesulfonyl chloride (10.6 µL, 0.137 mmol) at 0° C. The reaction mixture was stirred at 0° C. for 1 hr and concentrated via rotary evaporation. The resulting crude material was partitioned between EtOAc (2 mL) and water (1 mL). The organic phase was washed with brine, dried over Na$_2$SO$_4$, filtered, rinsed with EtOAc, and concentrated via rotary evaporation. The crude material was dissolved in EtOAc and MeOH, adsorbed on silica gel (0.75 g), and purified via medium pressure chromatography using a gradient eluant of 50% to 100% EtOAc in heptane on a 4 g silica gel column (Single Step™) to give the title compound (50.6 mg, 85%) as an off-white solid. $^1$H NMR (500 MHz, DMSO-d$_6$) δ ppm 1.12-1.19 (m, 6H), 2.53-2.61 (m, 4H), 2.74 (t, J=5.9 Hz, 2H), 2.97 (s, 3H), 3.00 (d, J=7.3 Hz, 4H), 3.44-3.48 (m, 1H), 3.59 (s, 2H), 4.02-4.10 (m, 1H), 4.16 (s, 2H), 5.41 (d, J=7.8 Hz, 1H), 7.08 (td, J=8.4, 2.2 Hz, 1H), 7.22 (td, J=9.9, 2.7 Hz, 1H), 7.44-7.54 (m, 1H); ESI-MS m/z [M+H]$^+$ 480.9.

Example 137 1-(2-(4-(2,4-difluorobenzyl)piperazin-1-yl)-3-(isopropylamino)-7,8-dihydropyrido[3,4-b]pyrazin-6(5H)-yl)propan-1-one

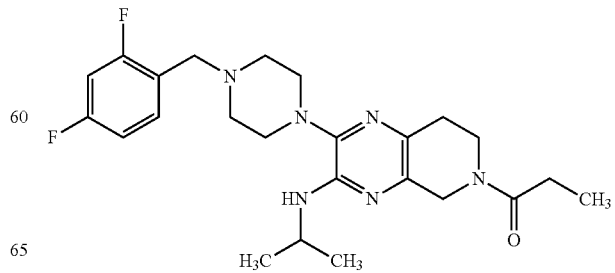

To a solution of 2-(4-(2,4-difluorobenzyl)piperazin-1-yl)-N-isopropyl-5,6,7,8-tetrahydropyrido[3,4-b]pyrazin-3-amine (50 mg, 0.124 mmol) and DIPEA (0.032 mL, 0.186 mmol) in DCM (1 mL) was added propionic anhydride (0.019 mL, 0.149 mmol) at 0° C. The reaction mixture was stirred at 0° C. for 1 hr, warmed to 23° C., and concentrated via rotary evaporation. The resulting crude material was partitioned between EtOAc and water. The organic phase was washed with brine, dried over $Na_2SO_4$, filtered, rinsed with EtOAc, and concentrated via rotary evaporation. The crude material was dissolved in EtOAc and MeOH, adsorbed on silica gel (0.75 g), and purified via medium pressure chromatography using a 20% to 100% gradient of EtOAc in heptane on a 4 g silica gel column (Single Step™) to give the title compound (48 mg, 84% yield) as an off-white foam. $^1$H NMR (500 MHz, DMSO-$d_6$, mixture of rotamers) δ ppm 0.94-1.05 (m, 3H), 1.16-1.18 (m, 6H), 2.41 (quin, J=7.8 Hz, 2H), 2.52-2.65 (m, 5H), 2.69 (t, J=5.6 Hz, 1H), 2.98 (br s, 3H), 3.58 (s, 2H), 3.70 (t, J=5.9 Hz, 1.1H), 3.73 (t, J=5.9 Hz, 0.9H), 4.03 (q, J=7.2 Hz, 2H), 4.06-4.15 (m, 1H), 4.42 (br s, 2H), 5.34 (d, J=7.8 Hz, 0.6H), 5.37 (d, J=8.3 Hz, 0.4H), 7.08 (td, J=8.5, 2.4 Hz, 1H), 7.21 (td, J=9.9, 2.7 Hz, 1H), 7.44-7.52 (m, 1H); ESI-MS m/z [M+F]$^+$ 459.0.

Example 138 Tert-butyl 4-(6-acetyl-3-(isopropylamino)-5,6,7,8-tetrahydropyrido[3,4-b]pyrazin-2-yl)piperazine-1-carboxylate

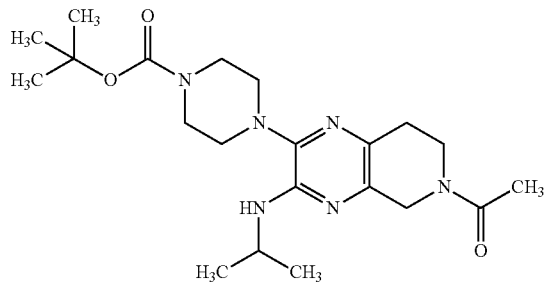 [SMILES: CC(=O)N1CCc2nc(N3CCN(C(=O)OC(C)(C)C)CC3)c(NC(C)C)nc2C1]

To a pressure reactor charged with a red-orange solution of tert-butyl 4-(3-(isopropylamino)pyrido[3,4-b]pyrazin-2-yl)piperazine-1-carboxylate (2.0 g, 5.37 mmol) in acetone (100 mL) and dioxane (100 mL) was added palladium, 10 wt % on activated carbon (0.229 g, 2.148 mmol) as a slurry in dioxane (3 mL) under nitrogen. Next, acetic anhydride (5.04 mL, 53.7 mmol) was added at 23° C. The mixture was stirred under hydrogen at 310 kPa for 17 hr at 45° C. The reaction mixture was filtered through Celite™, rinsed with dioxane, and concentrated via rotary evaporation. The crude material was purified via medium pressure chromatography using 10% to 100% gradient of EtOAc in heptane on an NH 60 μM size 400 column (Shoko Scientific Purif-Pack™) to give the title compound (1.068 g, 47.5%) as a yellow foam. $^1$H NMR (500 MHz, DMSO-$d_6$, mixture of rotamers) δ ppm 1.16-1.21 (m, 6H), 1.42 (s, 9H), 2.08 (s, 1.3H), 2.09 (s, 1.7H), 2.58 (t, J=5.9 Hz, 0.9H), 2.70 (t, J=5.6 Hz, 1.1H), 2.87-2.98 (m, 4H), 3.51 (br s, 4H), 3.67-3.75 (m, 2H), 4.06-4.15 (m, 1H), 4.41 (s, 1.1H), 4.44 (s, 0.9H), 5.50 (d, J=7.8 Hz, 1H), 5.53 (d, J=7.8 Hz, 1H); ESI-MS m/z [M+H]$^+$ 419.0.

Example 139 (1s,3s)-3-((6-acetyl-2-(4-(2,4-difluorobenzyl)piperazin-1-yl)-5,6,7,8-tetrahydropyrido[3,4-b]pyrazin-3-yl)amino)cyclobutyl acetate

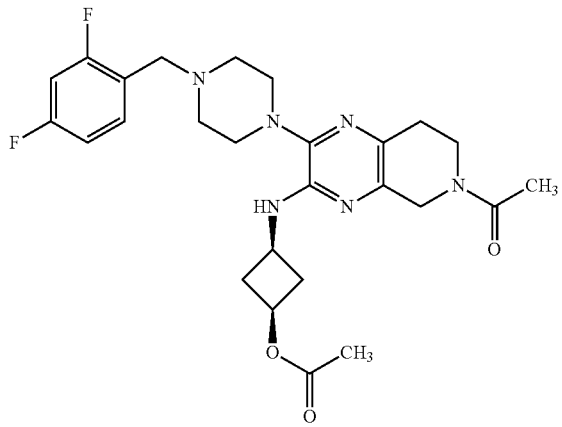 [SMILES: CC(=O)O[C@H]1C[C@@H](Nc2nc3c(nc2N2CCN(Cc4ccc(F)cc4F)CC2)CCN(C(C)=O)C3)C1]

To a pressure reactor charged with a red-orange solution of (1s,3s)-3-((2-(4-(2,4-difluorobenzyl)piperazin-1-yl)pyrido[3,4-b]pyrazin-3-yl)amino)cyclobutanol (0.3 g, 0.703 mmol) in acetone (15 mL) and dioxane (15 mL) was added palladium, 10 wt % on activated carbon (0.030 g, 0.281 mmol) as a slurry in dioxane (3 mL) under nitrogen. Next, acetic anhydride (0.661 mL, 7.03 mmol) was added at 23° C. The reaction mixture was stirred under hydrogen at 310 kPa for 4 days at 45° C. The reaction mixture was filtered through Celite™, rinsed with dioxane, and concentrated via rotary evaporation. The crude material was dissolved in toluene (3 mL) and purified via medium pressure chromatography using a gradient eluant of 30% to 100% EtOAc in heptane on a 90 g silica gel column (Single Step™) to give the title compound (119.7 mg, 33.1%) as a yellow foam. $^1$H NMR (500 MHz, DMSO-$d_6$, mixture of rotamers) δ ppm 1.97-2.00 (m, 3H), 2.07 (s, 1.3H), 2.08 (s, 1.7H), 2.10-2.17 (m, 2H), 2.55-2.63 (m, 5H), 2.67-2.74 (m, 3H), 2.90-3.10 (m, 4H), 3.59 (s, 2H), 3.66-3.74 (m, 2H), 4.02-4.12 (m, 1H), 4.39 (s, 1.1H), 4.42 (s, 0.9H), 4.68 (quind, J=7.3, 3.4 Hz, 1H), 6.11 (d, J=7.8 Hz, 0.6H), 6.15 (d, J=7.8 Hz, 0.4H), 7.08 (td, J=8.5, 2.4 Hz, 1H), 7.19-7.24 (m, 1H), 7.45-7.51 (m, 1H); ESI-MS m/z [M+H]$^+$ 515.0.

Example 140 1-(2-(4-(2,4-difluorobenzyl)piperazin-1-yl)-3-(((1s,3s)-3-hydroxycyclobutyl)amino)-7,8-dihydropyrido[3,4-b]pyrazin-6(5H)-yl)ethan-1-one

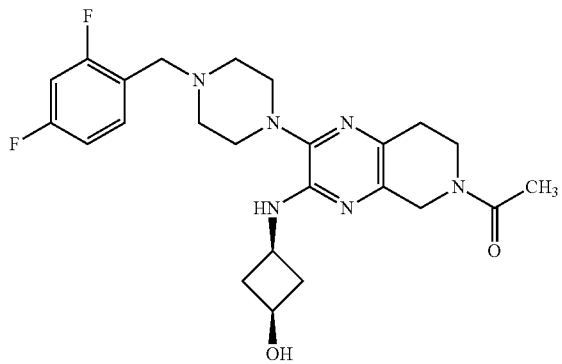 [SMILES: CC(=O)N1CCc2nc(N3CCN(Cc4ccc(F)cc4F)CC3)c(N[C@H]3C[C@@H](O)C3)nc2C1]

To a solution of (1s,3s)-3-((6-acetyl-2-(4-(2,4-difluorobenzyl)piperazin-1-yl)-5,6,7,8-tetrahydropyrido[3,4-b]pyrazin-3-yl)amino)cyclobutyl acetate (94.8 mg, 0.184 mmol) in MeOH (2 mL) was added sodium methoxide (5.1 µL, 0.028 mmol) at 0° C. The reaction was stirred at 0° C. for 1 h, concentrated via rotary evaporation at 30° C., re-constituted with MeOH (2 mL), cooled to 0° C., and quenched with HOAc (0.005 mL). The reaction mixture was concentrated via rotary evaporation, partitioned between EtOAc (4 mL) and saturated NH$_4$Cl (1 mL), and the layers were separated. The organic phase was washed with brine (1 mL), dried over Na$_2$SO$_4$, filtered, rinsed with EtOAc, and dried in vacuo to give the title compound (79.3 mg, 91%) as a yellowish-orange foam. $^1$H NMR (500 MHz, DMSO-d$_6$, mixture of rotamers) δ ppm 1.80-1.88 (m, 2H), 2.07 (s, 1.3H), 2.08 (s, 1.7H), 2.54-2.64 (m, 7H), 2.69 (t, J=5.9 Hz, 1H), 2.99 (br s, 4H), 3.59 (s, 2H), 3.69 (dt, J=11.5, 6.0 Hz, 2H), 3.77-3.91 (m, 2H), 4.38 (s, 1.1H), 4.41 (s, 0.9H), 4.95-5.00 (m, 1H), 5.82 (d, J=7.3 Hz, 1H), 5.85 (d, J=7.8 Hz, 1H) 7.08 (td, J=8.4, 2.2 Hz, 1H), 7.19-7.24 (m, 1H), 7.45-7.51 (m, 1H); ESI-MS m/z [M+H]$^+$ 473.0.

Example 141 1-(2-(4-(2,4-difluorophenoxy)piperidin-1-yl)-3-(isopropylamino)-7,8-dihydropyrido[3,4-b]pyrazin-6(5H)-yl)-2-d3-ethan-1-one

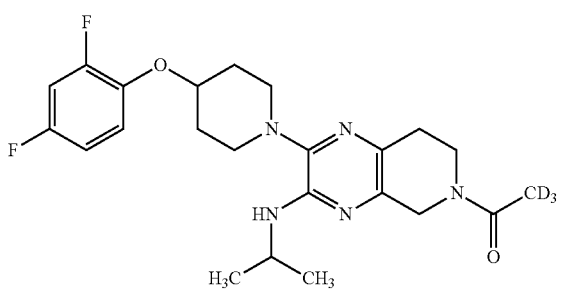

To a solution of 2-(4-(2,4-difluorophenoxy)piperidin-1-yl)-N-isopropyl-5,6,7,8-tetrahydropyrido[3,4-b]pyrazin-3-amine (2.4 g, 5.95 mmol) and DIPEA (1.56 mL, 8.92 mmol) in DCM (59.5 mL) at 0° C. was added acetyl chloride-d3 (0.42 mL, 5.95 mmol) dropwise. The resulting solution was stirred at this temperature for 1 h. After concentration, purification with silica gel column chromatography using 30% to 100% EtOAc in heptanes gave the title compound (1.89 g, 70.8%). $^1$H NMR (400 MHz, DMSO-d$_6$, mixture of rotamers) δ ppm 1.19 (d, J=6.4 Hz, 2.7H), 1.21 (d, J=6.4 Hz, 3.3H), 1.82-1.92 (m, 2H), 2.03-2.11 (m, 2H), 2.59 (t, J=5.9 Hz, 0.9H), 2.71 (t, J=5.9 Hz, 1.1H), 2.87 (m, 2H), 3.22-3.30 (m, 2H), 3.67-3.74 (m, 2H), 4.06-4.16 (m, 1H), 4.41 (s, 1.1H), 4.43 (s, 0.9H), 4.51 (m, 1H), 5.50 (d, J=8.3 Hz, 1.1H), 5.54 (d, J=7.8 Hz, 0.9H), 6.92-7.06 (m, 1H), 7.21-7.35 (m, 2H); ESI-MS m/z [M+H]$^+$ 449.0.

Example 142 (1s,3s)-3-((6-acetyl-2-(4-(2,4-difluorophenoxy)piperidin-1-yl)-5,6,7,8-tetrahydropyrido[3,4-b]pyrazin-3-yl)amino)cyclobutyl acetate

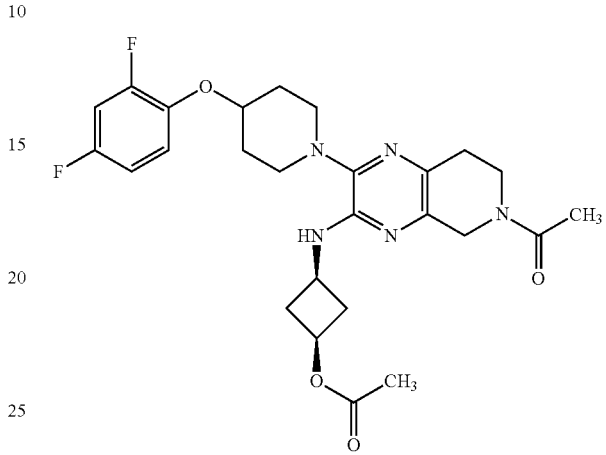

To a pressure reactor charged with a red-orange solution of (1s,3s)-3-((2-(4-(2,4-difluorophenoxy)piperidin-1-yl)pyrido[3,4-b]pyrazin-3-yl)amino)cyclobutanol (0.355 g, 0.831 mmol) in acetone (15 mL) and dioxane (15 mL) was added palladium, 10 wt % on activated carbon (0.035 g, 0.332 mmol) as a slurry in dioxane (3 mL) under nitrogen. Next, acetic anhydride (0.780 mL, 8.31 mmol) was added at 23° C. The reaction mixture was stirred under hydrogen at 310 kPa for 48 hr at 45° C. Additional portions of palladium, 10 wt % on activated carbon and acetic anhydride (0.156 mL, 1.661 mmol) were added to the pressure reactor and the reaction mixture was stirred under hydrogen at 310 kPa for an additional 4 days at 45° C. The reaction mixture was filtered through Celite™, rinsed with dioxane, and concentrated via rotary evaporation. The crude material was dissolved in toluene (3 mL) and purified via medium pressure chromatography using a gradient eluant of 30% to 100% EtOAc in heptane on a 90 g silica gel column (Single Step™) to give the title compound as a HOAc salt. The HOAc salt was dissolved in MeOH, passed through a 200 mg VariPure™ IPE cartridge (HCO$_3$MP) to remove HOAc, and the cartridge was rinsed with MeOH. The filtrate was concentrated via rotary evaporation and dried in vacuo to give the title compound (165 mg, 38.5%) as a yellow foam. $^1$H NMR (500 MHz, DMSO-d$_6$, mixture of rotamers) δ ppm 1.86-1.96 (m, 2H), 1.98-2.01 (m, 3H), 2.01-2.08 (m, 2H), 2.08 (s, 1.3H), 2.09 (s, 1.7H), 2.11-2.20 (m, 2H), 2.59 (t, J=5.9 Hz, 0.9H), 2.67-2.77 (m, 3.1H), 2.83-2.91 (m, 2H), 3.29 (d, J=10.3 Hz, 2H), 3.70 (dt, J=11.4, 5.8 Hz, 2H), 4.06-4.13 (m, 1H), 4.40 (s, 1H), 4.43 (s, 1H), 4.52 (dt, J=8.2, 4.0 Hz, 1H), 4.69 (td, J=7.3, 2.9 Hz, 1H), 6.24 (d, J=7.3 Hz, 0.6H), 6.28 (d, J=7.8 Hz, 0.4H), 6.98-7.05 (m, 1H), 7.26-7.34 (m, 2H); ESI-MS m/z [M+F]$^+$ 516.0.

Example 143 1-(2-(4-(2,4-difluorobenzyl)piperazin-1-yl)-3-(isopropylamino)-7,8-dihydropyrido[3,4-b]pyrazin-6(5H)-yl)-2-methylpropan-1-one

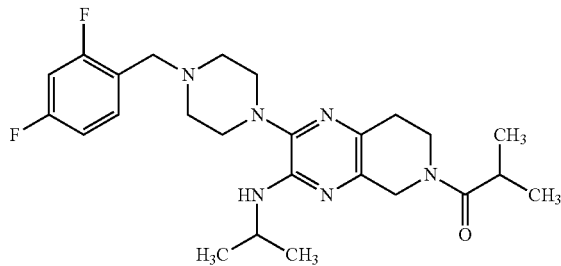

To a solution of 2-(4-(2,4-difluorobenzyl)piperazin-1-yl)-N-isopropyl-5,6,7,8-tetrahydropyrido[3,4-b]pyrazin-3-amine (50 mg, 0.124 mmol) and DIPEA (0.032 mL, 0.186 mmol) in DCM (1 mL) was added isobutyryl chloride (0.013 mL, 0.124 mmol) at 0° C. The reaction mixture was stirred at 0° C. for 1 h, warmed to 23° C. and stirred for an additional 15.5 h. The reaction mixture was concentrated via rotary evaporation and partitioned between EtOAc (4 mL) and NH$_4$Cl (2 mL). The layers were separated and the organic phase was washed with brine (2 mL), dried over Na$_2$SO$_4$, filtered, rinsed with EtOAc, and concentrated via rotary evaporation. The crude material was dissolved in EtOAc and MeOH, adsorbed on silica gel (0.25 g), and purified via medium pressure chromatography using a 50% to 100% gradient of EtOAc in heptane on a 4 g silica gel column (Single Step™) to give the title compound (39.3 mg, 66.9%) as a yellow foam. $^1$H NMR (500 MHz, DMSO-d$_6$, mixture of rotamers) δ ppm 0.99 (d, J=6.8 Hz, 2.7H), 1.03 (d, J=6.8 Hz, 3H), 1.11-1.22 (m, 6H), 2.58 (br s, 3.8H), 2.69 (t, J=5.4 Hz, 1.2H), 2.88-3.13 (m, 5H), 3.58 (s, 2H), 3.75 (dt, J=10.9, 5.6 Hz, 2H), 4.05-4.17 (m, 1H), 4.41 (s, 1.1H), 4.49 (s, 0.9H), 5.29-5.42 (m, 1H), 7.08 (td, J=8.5, 2.4 Hz, 1H), 7.21 (td, J=9.9, 2.7 Hz, 1H), 7.44-7.52 (m, 1H); ESI-MS m/z [M+F]$^+$ 473.0.

Example 144 1-(2-(4-(2,4-difluorophenoxy)piperidin-1-yl)-3-(((1s,3s)-3-hydroxycyclobutyl)amino)-7,8-dihydropyrido[3,4-b]pyrazin-6(5H)-yl)ethan-1-one

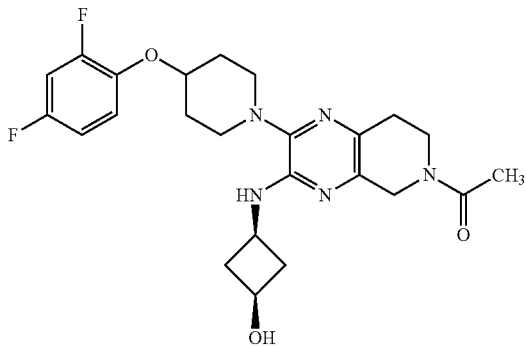 [SMILES: CC(=O)N1CCc2nc(N3CCC(Oc4ccc(F)cc4F)CC3)c(N[C@H]3C[C@@H](O)C3)nc2C1]

To a solution of (1s,3s)-3-((6-acetyl-2-(4-(2,4-difluorophenoxy)piperidin-1-yl)-5,6,7,8-tetrahydropyrido[3,4-b]pyrazin-3-yl)amino)cyclobutyl acetate (146.5 mg, 0.284 mmol) in MeOH (3 mL) was added sodium methoxide (7.89 μL, 0.043 mmol) at 0° C. The reaction was stirred at 0° C. for 1 h, concentrated via rotary evaporation at 30° C., re-constituted with MeOH (2 mL), cooled to 0° C., and quenched with HOAc (0.005 mL). The reaction mixture was concentrated via rotary evaporation, partitioned between EtOAc (6 mL) and saturated NH$_4$Cl (4 mL), and the layers were separated. The organic phase was washed with brine (2 mL), dried over Na$_2$SO$_4$, filtered, rinsed with EtOAc, and dried in vacuo to give the title compound (119.5 mg, 89%) as a yellow oil. $^1$H NMR (500 MHz, DMSO-d$_6$, mixture of rotamers) δ ppm 1.84-1.93 (m, 4H), 2.04-2.11 (m, 5H), 2.56-2.65 (m, 2.9H), 2.71 (t, J=5.9 Hz, 1.1H), 2.87 (t, J=10.3 Hz, 2H), 3.27 (dd, J=8.1, 4.2 Hz, 2H), 3.70 (dt, J=11.5, 6.0 Hz, 2H), 3.79-3.91 (m, 2H), 4.40 (s, 1.1H), 4.42 (s, 0.9H), 4.51 (tt, J=8.2, 4.0 Hz, 1H), 4.99-5.04 (m, 1H), 5.99 (d, J=7.3 Hz, 1.1H), 6.03 (d, J=7.8 Hz, 1H), 6.99-7.04 (m, 1H), 7.26-7.33 (m, 2H); ESI-MS m/z [M+H]$^+$ 473.9.

Example 145 1-(2-(4-(2,4-difluorobenzyl)piperazin-1-yl)-3-(((1r,3r)-3-fluorocyclobutyl)amino)-7,8-dihydropyrido[3,4-b]pyrazin-6(5H)-yl)ethan-1-one

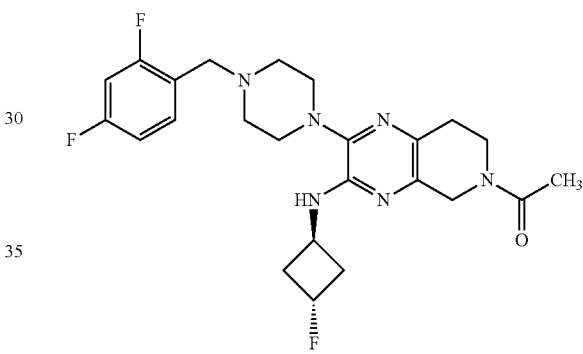

To a solution of 1-(2-(4-(2,4-difluorobenzyl)piperazin-1-yl)-34(1s,3s)-3-hydroxycyclobutyl)amino)-7,8-dihydropyrido[3,4-b]pyrazin-6(5H)-yl)ethanone (25 mg, 0.053 mmol) in DCM (1 mL) was added DAST (9.1 μL, 0.069 mmol) as a solution in DCM (0.5 mL) at −78° C. during 2 min. The reaction was stirred at −78° C. for 2 h, warmed slowly to 23° C., and stirred for an additional 14.5 h at 23° C. The reaction mixture was cooled to −78° C. and an additional portion of DAST (0.021 mL, 0.159 mmol) was added to the mixture. The reaction mixture was warmed slowly to 23° C. and stirred for an additional 24 hr, cooled to 0° C. and quenched with water (5 mL). The crude product was extracted with EtOAc (2×10 mL), the organic extracts were combined, dried over Na$_2$SO$_4$, filtered, rinsed with EtOAc, and dried in vacuo. The resulting crude material was re-constituted in DMSO (0.5 mL), rinsed with DMSO (2×0.25 mL), and purified by HPLC Method B using a 20% to 50% ACN gradient to give the title compound as a TFA salt (1.2 mg, 3.8%) as an off-white solid. $^1$H NMR (500 MHz, methanol-d$_4$, mixture of rotamers) δ ppm 2.18-2.23 (m, 3H), 2.36-2.50 (m, 2H), 2.55-2.69 (m, 2H), 2.73 (t, J=5.4 Hz, 0.9H), 2.80-2.86 (m, 1.1H), 3.26-3.30 (m, 4H), 3.47-3.72 (m, 4H), 3.81 (t, J=5.6 Hz, 1.1H), 3.87 (t, J=6.1 Hz, 0.9H), 4.49 (s, 2H), 4.55-4.59 (m, 2H), 4.83 (s, 2H), 5.15-5.21 (m, 0.6H), 5.26-5.33 (m, 0.4H), 7.65-7.71 (m, 1H); ESI-MS m/z [M+H]$^+$ 474.9.

Example 146 4-((4-(6-acetyl-3-(isopropylamino)-5,6,7,8-tetrahydropyrido[3,4-b]pyrazin-2-yl)piperazin-1-yl)methyl)-3-fluorobenzonitrile

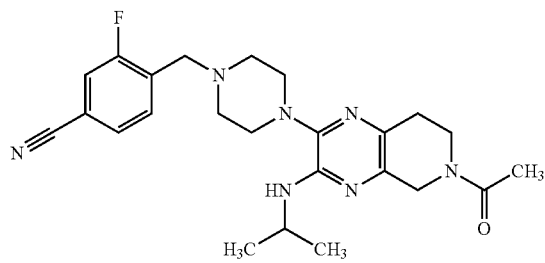 [SMILES: CC(=O)N1CCc2nc(N3CCN(Cc4ccc(C#N)cc4F)CC3)c(NC(C)C)nc2C1]

Combined 1-(3-(isopropylamino)-2-(piperazin-1-yl)-7,8-dihydropyrido[3,4-b]pyrazin-6(5H)-yl)ethanone hydrochloride (132.2 mg, 0.218 mmol) and 3-fluoro-4-formylbenzonitrile (32.6 mg, 0.218 mmol) in DCE (1 mL) and added sodium triacetoxyhydroborate (64.8 mg, 0.306 mmol) at 23° C. The reaction mixture was stirred at 23° C. for 43 h. An additional portion of sodium triacetoxyhydroborate (64.8 mg, 0.306 mmol) was added to the reaction mixture and the mixture was stirred for an additional 24 h at 23° C. The resulting residue was diluted with DCE (1 mL), filtered, rinsed with MeOH, and concentrated via rotary evaporation. The resulting crude material was reconstituted in DMSO (1 mL), filtered, rinsed with DMSO (2×0.5 mL), and purified by HPLC Method A to give the title compound as a TFA salt (28.0 mg, 22.68%) as a yellow solid. $^1$H NMR (500 MHz, DMSO-$d_6$, mixture of rotamers) δ ppm 1.13-1.28 (m, 6H), 2.08 (s, 1.3H), 2.09 (s, 1.7H), 2.59 (t, J=5.9 Hz, 0.9H), 2.67-2.75 (m, 1.1H), 2.90-3.21 (m, 2H), 3.28-3.63 (m, 6H), 3.67-3.77 (m, 2H), 4.06-4.19 (m, 1H), 4.42 (s, 1.1H), 4.45 (s, 0.9H), 4.50 (br s, 2H), 5.68-5.77 (m, 1H), 7.83-7.87 (m, 1H), 7.87-7.92 (m, 1H), 8.01-8.22 (m, 1H), 10.22 (br s, 1H); ESI-MS m/z [M+F]$^+$ 452.0.

Example 147 (1r,3r)-3-((6-acetyl-2-(4-(2,4-difluorophenoxy)piperidin-1-yl)-5,6,7,8-tetrahydropyrido[3,4-b]pyrazin-3-yl)amino)cyclobutyl acetate

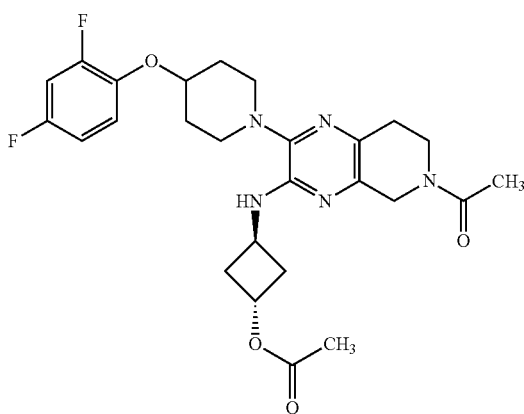 [SMILES: CC(=O)O[C@H]1C[C@H](Nc2nc3c(nc2N2CCC(Oc4ccc(F)cc4F)CC2)CCN(C(C)=O)C3)C1]

To a pressure reactor charged with an orange solution of (1r,3r)-3-((2-(4-(2,4-difluorophenoxy)piperidin-1-yl)pyrido[3,4-b]pyrazin-3-yl)amino)cyclobutanol (0.8 g, 1.872 mmol) in acetone (30 mL) and dioxane (30 mL) was added palladium, 10 wt % on activated carbon (0.100 g, 0.936 mmol) as a slurry in dioxane (3 mL) under nitrogen. Next, acetic anhydride (1.758 mL, 18.72 mmol) was added at 23° C. The mixture was stirred under hydrogen at 310 kPa for 3 days at 45° C. Additional portions of palladium, 10 wt % on activated carbon (0.100 g, 0.936 mmol) and acetic anhydride (0.352 mL, 3.74 mmol) were added to the reactor and the mixture was stirred under hydrogen at 45 kPa for 2 additional days at 45° C. The reaction mixture was filtered through Celite™, rinsed with dioxane, and concentrated via rotary evaporation. The crude material was dissolved in toluene (2 mL) and purified via medium pressure chromatography using a 30% to 100% gradient of EtOAc in heptane on a 160 g silica gel column (Single Step™) to give the title compound (270 mg, 28.0%) as an off-white solid. $^1$H NMR (500 MHz, DMSO-$d_6$, mixture of rotamers) δ ppm 1.83-1.97 (m, 2H), 2.03 (s, 3H), 2.04-2.12 (m, 5H), 2.33-2.41 (m, 2H), 2.41-2.49 (m, 2H), 2.59 (t, J=5.9 Hz, 0.9H), 2.71 (t, J=5.6 Hz, 1.1H), 2.89 (t, J=10.0 Hz, 2H), 3.20-3.34 (m, 4H), 3.56-3.79 (m, 2H), 4.40 (s, 1.1H), 4.43 (s, 0.9H), 4.47-4.59 (m, 2H), 5.05 (td, J=6.9, 3.2 Hz, 1H), 6.24 (d, J=6.8 Hz, 0.6H), 6.27 (d, J=6.8 Hz, 0.4H), 6.94-7.11 (m, 1H), 7.22-7.43 (m, 2H); ESI-MS m/z [M+F]$^+$ 515.9.

Example 148 1-(2-(4-(2,4-difluorophenoxy)piperidin-1-yl)-3-(((1r,3r)-3-hydroxycyclobutyl)amino)-7,8-dihydropyrido[3,4-b]pyrazin-6(5H)-yl)ethan-1-one

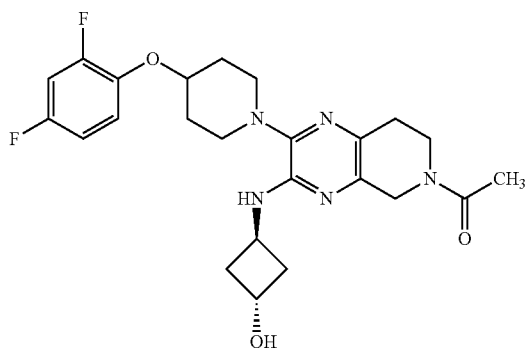 [SMILES: CC(=O)N1CCc2nc(N3CCC(Oc4ccc(F)cc4F)CC3)c(N[C@H]3C[C@H](O)C3)nc2C1]

To an off-white suspension of (1r,3r)-3-((6-acetyl-2-(4-(2,4-difluorophenoxy)piperidin-1-yl)-5,6,7,8-tetrahydropyrido[3,4-b]pyrazin-3-yl)amino)cyclobutyl acetate (108 mg, 0.209 mmol) in MeOH (2 mL) was added sodium methoxide (5.8 μL, 0.031 mmol) at 23° C. The reaction was stirred at 23° C. for 15 min, concentrated via rotary evaporation at 30° C., re-constituted with MeOH (2 mL), cooled to 23° C., and quenched with HOAc (0.010 mL). The reaction mixture was concentrated via rotary evaporation, partitioned between EtOAc (6 mL) and saturated NH$_4$Cl (4 mL), and the layers were separated. The organic phase was washed with brine (2 mL), dried over Na$_2$SO$_4$, filtered, rinsed with EtOAc, and dried in vacuo to give the title compound (99 mg, 100%) as a yellow foam. $^1$H NMR (500 MHz, DMSO-$d_6$, mixture of rotamers) δ ppm 1.87-1.93 (m, 2H), 2.00-2.12 (m, 5H), 2.12-2.20 (m, 2H), 2.21-2.32 (m, 2H), 2.55-2.62 (m, 0.9H), 2.71 (t, J=5.1 Hz, 1.1H), 2.88 (t, J=10.0 Hz, 2H), 3.28 (br s, 2H), 3.63-3.80 (m, 2H), 4.29 (d, J=3.9 Hz, 1H), 4.40 (s, 1.1H), 4.43 (s, 0.9H), 4.47-4.62 (m, 1H), 4.95 (d, J=4.9 Hz, 1H), 5.99 (d, J=6.3 Hz, 1H), 6.03 (d, J=6.8 Hz, 1H), 6.96-7.08 (m, 1H), 7.23-7.36 (m, 2H); ESI-MS m/z (M+H)$^+$ 474.0.

Example 149 (S)-1-(2-(4-(2,4-difluorophenoxy)piperidin-1-yl)-3-(tetrahydrofuran-3-ylamino)-7,8-dihydropyrido[3,4-b]pyrazin-6(5H)-yl)ethanone

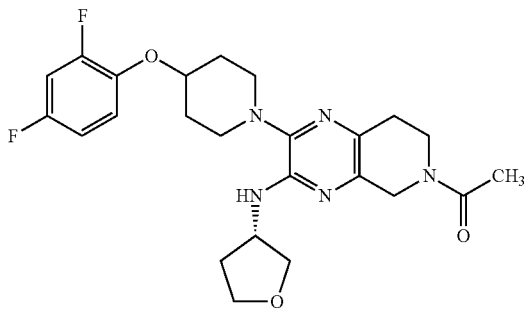 [SMILES: CC(=O)N1CCc2nc(N3CCC(Oc4ccc(F)cc4F)CC3)c(N[C@H]3CCOC3)nc2C1]

To a solution of (S)-2-(4-(2,4-difluorophenoxy)piperidin-1-yl)-N-(tetrahydrofuran-3-yl)pyrido[3,4-b]pyrazin-3-amine (2.0 g, 4.68 mmol) in dioxane:acetone (50 ml; 1.5:1) was added Ac$_2$O (4.8 mL, 50.9 mmol) and Pd/C (400 mg, 3.76 mmol); then, the reaction was stirred at 60° C. under H$_2$ atmosphere (345 kPa) for 72 h. The mixture was filtered through a pad of Celite™ and washed with EtOAc. The reaction solution was diluted with EtOAc (50 mL) and poured into sat. aqueous NaHCO$_3$ (50 ml), then washed with brine (2×30 mL). The organic layer was dried over Na$_2$SO$_4$ and concentrated to give the crude product, which was purified by flash column chromatography to yield the title compound (193.4 mg) as an off-white solid. $^1$H NMR (400 MHz, DMSO-d6) δ ppm 1.88-1.89 (m, 4H), 2.05-2.09 (m, 4H), 2.60-2.90 (m, 4H), 3.30-3.40 (m, 4H), 3.55-3.57 (m, 1H), 3.68-3.74 (m, 2H), 3.85-3.95 (m, 2H), 4.38-4.51 (m, 4H), 5.91 (dd, J=6.0, 4.4 Hz, 1H), 7.01 (m, 1H), 7.25-7.31 (m, 2H); ESI-MS m/z [M+H]$^+$ 474.3.

Example 150 (S)-1-(2-(4-(2,4-difluorophenoxy)piperidin-1-yl)-3-(tetrahydrofuran-3-ylamino)-7,8-dihydropyrido[3,4-b]pyrazin-6(5H)-yl)propan-1-one

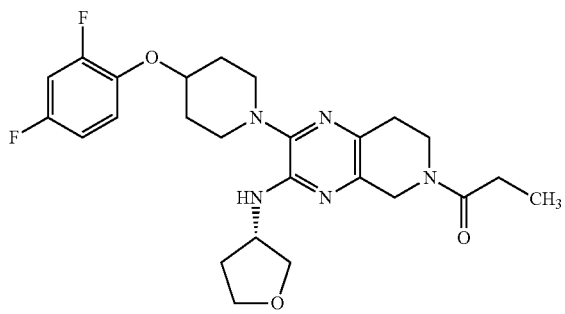 [SMILES: CCC(=O)N1CCc2nc(N3CCC(Oc4ccc(F)cc4F)CC3)c(N[C@H]3CCOC3)nc2C1]

To a solution of (S)-2-(4-(2,4-difluorophenoxy)piperidin-1-yl)-N-(tetrahydrofuran-3-yl)pyrido[3,4-b]pyrazin-3-amine (2.5 g, 5.85 mmol) in dioxane:acetone (105 ml, 1.5:1) was added propionic anhydride (7 mL, 3.76 mmol) and Pd/C (400 mg, 3.76 mmol); then, the reaction was stirred at 60° C. and under H$_2$ atmosphere (345 kPa) for 72 h. The mixture was filtered through a pad of Celite™ and washed with EtOAc. The reaction solution was diluted with EtOAc (50 mL) and poured into sat. aqueous NaHCO$_3$ (50 mL) then washed with brine (2×30 mL). The organic layer was dried over Na$_2$SO$_4$ and concentrated to give the crude product, which was purified by flash column chromatography to give the title compound (125 mg) as an off-white solid. $^1$H NMR (400 MHz, DMSO-d6) δ ppm 0.97-1.03 (m, 3H), 1.87-2.04 (m, 6H), 2.15-2.25 (m, 1H), 2.40-2.43 (m, 2H), 2.58-2.60 (m, 1H), 2.69-2.73 (m, 1H), 2.88 (q, J=9.6 Hz, 2H), 3.30-3.34 (m, 2H), 3.50-3.60 (m, 1H), 3.70-3.74 (m, 2H), 3.84-3.90 (m, 2H), 4.35-4.60 (m, 4H), 5.88-5.92 (m, 1H), 6.98-7.02 (m, 1H), 7.27-7.30 (m, 2H); ESI-MS m/z [M+H]$^+$ 488.3.

Example 151 1-(3-((3,3-difluorocyclobutyl)amino)-2-(4-(2,4-difluorophenoxy)piperidin-1-yl)-7,8-dihydropyrido[3,4-b]pyrazin-6(5H)-yl)ethan-1-one

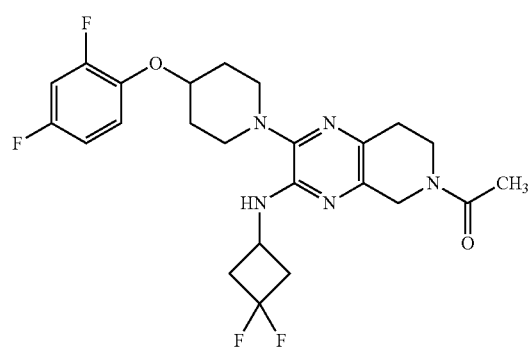 [SMILES: CC(=O)N1CCc2nc(N3CCC(Oc4ccc(F)cc4F)CC3)c(NC3CC(F)(F)C3)nc2C1]

To a pressure reactor charged with a yellow-orange solution of N-(3,3-difluorocyclobutyl)-2-(4-(2,4-difluorophenoxy)piperidin-1-yl)pyrido[3,4-b]pyrazin-3-amine (250 mg, 0.559 mmol) in acetone (10 mL) and dioxane (10 mL) was added palladium, 10 wt % on activated carbon (23.8 mg, 0.223 mmol) as a slurry in dioxane (2 mL) under nitrogen. Next, acetic anhydride (0.525 mL, 5.59 mmol) was added at 23° C. The mixture was stirred under hydrogen at 310 kPa for 45 h at 45° C. The reaction mixture was filtered through Celite™, rinsed with dioxane, and concentrated via rotary evaporation. The crude material was purified via medium pressure chromatography using a gradient eluant of 30% to 100% EtOAc in heptane on a 80 g silica gel column (Single Step™) to give the title compound (145 mg, 52.6%) as a yellow solid. $^1$H NMR (500 MHz, DMSO-d$_6$, mixture of rotamers) δ ppm 1.80-1.95 (m, 2H), 2.03-2.08 (m, 2H), 2.0 (s, 1.3H), 2.09 (s, 1.7H), 2.60 (t, J=5.6 Hz, 0.9H), 2.67-2.80 (m, 3.1H), 2.83-2.98 (m, 4H), 3.31-3.38 (m, 2H), 3.71 (dt, J=11.2, 5.6 Hz, 2H), 4.14-4.27 (m, 1H), 4.42 (s, 1.1H), 4.45 (s, 0.9H), 4.53 (tt, J=8.2, 3.8 Hz, 1H), 6.46 (dd, J=14.6, 6.8 Hz, 1H), 6.98-7.06 (m, 1H), 7.25-7.36 (m, 2H); ESI-MS m/z 493.9 (M+H)$^+$ 493.9.

Example 152 N-cyclobutyl-2-(4-(2,4-difluorophenoxy)piperidin-1-yl)-6-(methylsulfonyl)-5,6,7,8-tetrahydropyrido[3,4-b]pyrazin-3-amine

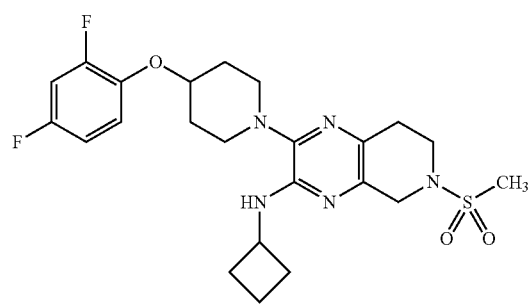 [SMILES: CS(=O)(=O)N1CCc2nc(N3CCC(Oc4ccc(F)cc4F)CC3)c(NC3CCC3)nc2C1]

The title compound was prepared in a manner similar to Example 11 using N-cyclobutyl-2-(4-(2,4-difluorophenoxy)piperidin-1-yl)-5,6,7,8-tetrahydropyrido[3,4-b]pyrazin-3-amine to give the title compound. ¹H NMR (500 MHz, DMSO-d₆) δ ppm 1.55-1.75 (m, 2H), 1.84-1.96 (m, 2H), 1.96-2.14 (m, 4H), 2.18-2.32 (m, 2H), 2.75 (t, J=5.9 Hz, 2H), 2.84-2.95 (m, 2H), 2.95-3.03 (m, 3H), 3.26-3.33 (m, 2H), 3.45 (t, J=5.9 Hz, 2H), 4.16 (s, 2H), 4.30-4.44 (m, 1H), 4.52 (tt, J=8.1, 3.8 Hz, 1H), 6.12 (d, J=7.8 Hz, 1H), 6.95-7.08 (m, 1H), 7.23-7.37 (m, 2H); ESI-MS m/z (M+H)⁺ 494.0.

Example 153 (R)-1-(2-(4-(2,4-difluorobenzyl)piperazin-1-yl)-3-(tetrahydrofuran-3-ylamino)-7,8-dihydropyrido[3,4-b]pyrazin-6(5H)-yl)ethanone

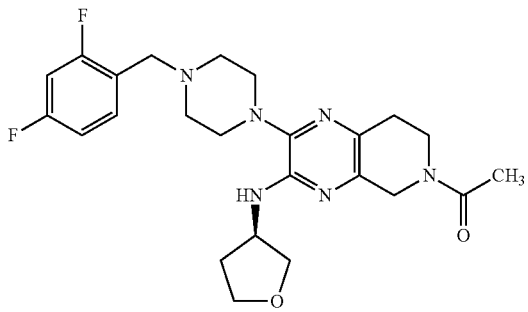 [SMILES: CC(=O)N1CCc2nc(N3CCN(Cc4ccc(F)cc4F)CC3)c(N[C@@H]3CCOC3)nc2C1]

The title compound was prepared in a manner similar to 149 using (R)-2-(4-(2,4-difluorobenzyl)piperazin-1-yl)-N-(tetrahydrofuran-3-yl)pyrido[3,4-b]pyrazin-3-amine to give the title compound as a yellow solid. ¹H NMR (400 MHz, CDCl₃) δ ppm 1.82-1.86 (m, 1H), 2.20 (s, 3H), 2.33-2.36 (m, 1H), 2.59-2.66 (m, 4H), 2.79 (m, 2H), 3.05-3.15 (m, 4H), 3.63 (s, 1H), 3.69-3.72 (m, 2H), 3.85-3.88 (m, 2H), 3.95-3.99 (m, 2H), 4.46-4.64 (m, 3H), 4.87-4.90 (m, 1H), 6.79-6.90 (m, 2H), 7.39-7.41 (m, 1H); ESI-MS m/z [M+H]⁺ 473.1.

Example 154 (S)-1-(2-(4-(2,4-difluorobenzyl)piperazin-1-yl)-3-(tetrahydrofuran-3-ylamino)-7,8-dihydropyrido[3,4-b]pyrazin-6(5H)-yl)ethanone

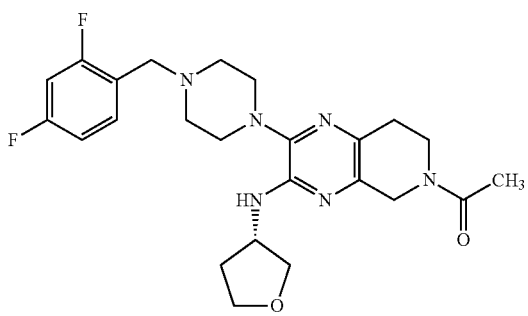

The title compound was prepared in a manner similar to 149 using (S)-2-(4-(2,4-difluorobenzyl)piperazin-1-yl)-N-(tetrahydrofuran-3-yl)pyrido[3,4-b]pyrazin-3-amine to give the title compound as an off-white solid. ¹H NMR (400 MHz, CDCl₃) δ ppm 1.82-1.86 (m, 1H), 2.20 (s, 3H), 2.33-2.36 (m, 1H), 2.59-2.66 (m, 4H), 2.79 (dt, J=21.6, 5.6 Hz, 2H), 3.05-3.15 (m, 4H), 3.63 (s, 1H), 3.69-3.72 (m, 2H), 3.85-3.88 (m, 2H), 3.98-4.00 (m, 2H), 4.48-4.64 (m, 3H), 4.88-4.92 (m, 1H), 6.82 (t, J=9.6 Hz, 1H), 6.84 (t, J=12.8 Hz, 1H), 7.39 (q, J=7.2 Hz, 1H); ESI-MS m/z [M+H]⁺ 473.1.

Example 155 (S)-1-(2-(4-(2,4-difluorobenzyl)piperazin-1-yl)-3-(tetrahydrofuran-3-ylamino)-7,8-dihydropyrido[3,4-b]pyrazin-6(5H)-yl)propan-1-one

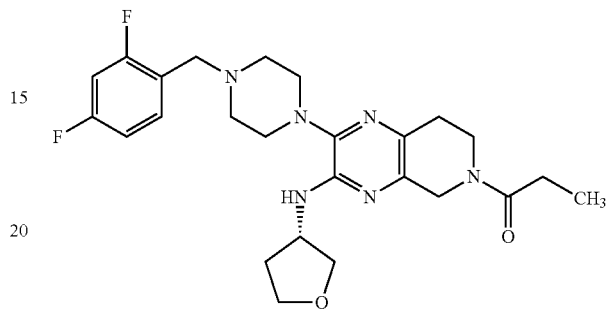

The title compound was prepared in a manner similar Example to 150 using (S)-2-(4-(2,4-difluorobenzyl)piperazin-1-yl)-N-(tetrahydrofuran-3-yl)pyrido[3,4-b]pyrazin-3-amine to give the title compound as a white solid. ¹H NMR (400 MHz, CDCl₃) δ ppm 1.18 (q, J=7.2 Hz, 3H), 1.75-1.85 (m, 1H), 2.25-2.46 (m, 3H), 2.55-2.65 (m, 4H), 2.75-2.80 (m, 2H), 3.00-3.10 (m, 4H), 3.59-3.70 (m, 4H), 3.87-3.90 (m, 2H), 3.96-3.98 (m, 2H), 4.46-4.62 (m, 3H), 4.85-4.95 (m, 1H), 6.75-6.90 (m, 2H), 7.35-7.45 (m, 1H); ESI-MS m/z [M+H]⁺ 487.3.

Example 156 1-(3-(4-(2,4-difluorophenoxy)piperidin-1-yl)-2-(isopropylamino)-7,8-dihydropyrido[3,4-b]pyrazin-6(5H)-yl)ethanone

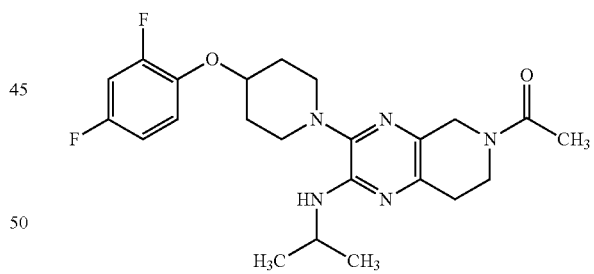

The title compound was prepared in a manner similar to Example 120 using 4-(2,4-difluorophenoxy)piperidine, HCl to give the title compound as a colorless film. ¹H NMR (500 MHz, methanol-d4) δ ppm 0.85-0.93 (m, 1H), 1.25 (d, J=6.4 Hz, 6H), 1.95 (ddd, J=12.1, 8.2, 3.7 Hz, 2H), 2.09-2.17 (m, 2H), 2.20 (d, J=8.8 Hz, 3H), 2.74 (t, J=5.9 Hz, 1H), 2.84 (t, J=5.6 Hz, 1H), 2.92-3.02 (m, 2H), 3.35 (dd, J=8.3, 3.9 Hz, 2H), 3.81 (t, J=5.6 Hz, 1H), 3.86 (t, J=5.9 Hz, 1H), 4.12-4.21 (m, 1H), 4.46 (dd, J=7.1, 3.7 Hz, 1H), 4.54 (s, 2H), 6.85-6.91 (m, 1H), 6.96-7.02 (m, 1H), 7.18 (td, J=8.8, 5.4 Hz, 1H); ESI-MS m/z [M+H]⁺ 446.90.

The compounds of the invention can be administered alone or in the form of a pharmaceutical composition. In practice, the compounds of the invention are usually administered in the form of pharmaceutical compositions, that is, in admixture with at least one pharmaceutically acceptable excipient. The proportion and nature of any pharmaceutically acceptable excipient(s) are determined by the properties of the selected compound of the invention, the chosen route of administration, and standard pharmaceutical practice.

In another embodiment, the present invention provides pharmaceutical compositions comprising: a compound of invention and at least one pharmaceutically acceptable excipient.

In effecting treatment of a patient in need of such treatment, a compound of the invention can be administered in any form and route which makes the compound bioavailable. The compounds of the invention can be administered by a variety of routes, including orally, in particularly by tablets and capsules. The compounds of the invention can be administered parenteral routes, more particularly by inhalation, subcutaneously, intramuscularly, intravenously, intraarterially, transdermally, intranasally, rectally, vaginally, occularly, topically, sublingually, and buccally, intraperitoneally, intraadiposally, intrathecally and via local delivery for example by catheter or stent.

One skilled in the art can readily select the proper form and route of administration depending upon the particular characteristics of the compound selected, the disorder or condition to be treated, the stage of the disorder or condition, and other relevant circumstances. The pharmaceutical compositions of the invention may be administered to the patient, for example, in the form of tablets, capsules, cachets, papers, lozenges, wafers, elixirs, ointments, transdermal patches, aerosols, inhalants, suppositories, solutions, and suspensions.

The pharmaceutical compositions of the present invention are prepared in a manner well known in the pharmaceutical art and include at least one of the compounds of the invention as the active ingredient. The amount of a compound of the present invention may be varied depending upon its particular form and may conveniently be between 1% to about 50% of the weight of the unit dose form. The term "pharmaceutically acceptable excipient" refers to those typically used in preparing pharmaceutical compositions and should be pharmaceutically pure and non-toxic in the amounts used. They generally are a solid, semisolid, or liquid material which in the aggregate can serve as a vehicle or medium for the active ingredient. Some examples of pharmaceutically acceptable excipients are found in Remington's Pharmaceutical Sciences and the Handbook of Pharmaceutical Excipients and include diluents, vehicles, carriers, ointment bases, binders, disintegrates, lubricants, glidants, sweetening agents, flavoring agents, gel bases, sustained release matrices, stabilizing agents, preservatives, solvents, suspending agents, buffers, emulsifiers, dyes, propellants, coating agents, and others.

The present pharmaceutical compositions are preferably formulated in a unit dose form, each dose typically containing from about 0.5 mg to about 100 mg of a compounds of the invention. The term "unit dose form" refers to a physically discrete unit containing a predetermined quantity of active ingredient, in association with a suitable pharmaceutical excipient, by which one or more is used throughout the dosing regimen to produce the desired therapeutic effect. One or more "unit dose form" may be taken to affect the treatment dosage on a daily schedule.

In one particular variation, the composition is a pharmaceutical composition adapted for oral administration, such as a tablet or a capsule or a liquid formulation, for example, a solution or suspension, adapted for oral administration. In still another particular variation, the pharmaceutical composition is a liquid formulation adapted for parenteral administration.

Compounds of the present invention are modulators of GPR6, specifically, antagonists or inverse agonists, and as such are useful in the treatment and prevention of conditions associated with GPR6. As mentioned above, the major striatal targets of dopaminergic innervation reside in the medium spiny neurons (MSNs) of the striatopallidal (indirect) and striatonigral (direct) output pathways. The MSNs of the direct output pathway express D1 dopamine receptors whereas those in the indirect pathway express D2 receptors. GPR6 is enriched in D2 receptor expressing MSNs in the striatum where GPR6 activity is functionally opposed to D2 receptor signaling. Antagonism or inverse agonism of Gs coupled GPR6 decreases cAMP in MSNs and provides a functional alternative to dopamine mediated activation of D2 receptors.

Antagonism or inverse agonism of Gs coupled GPR6 provides a functional alternative to dopamine mediated activation of D2 receptors. As such, compounds that modulate the activity of GPR6 are useful for treating in a variety of neurological and psychiatric disorders. For example movement disorders including Parkinson's disease and Huntington's disease either alone or in combination with other agents are approved for the treatment of Parkinson's disease including L-DOPA, dopaminergic agonists, MAO B inhibitors, DOPA decarboxylase inhibitors and C(O)MT inhibitors. Other disease indications that could be treated by modulation of GPR6 include drug addiction and eating disorders, cognitive disorders, schizophrenia, bipolar disorders, and depression.

In another embodiment, the invention provides methods of treating conditions associated with GPR6, comprising: administering to a patient in need thereof an effective amount of a compound of the invention. In another embodiment, a compound of the invention is provided for use as a medicament. The invention also provides the use of a compound of the invention, including the use for the manufacture of a medicament, to treat the conditions associated with GPR6 described herein. The compounds of the present invention are useful as GPR6 modulators for a variety of subjects (e.g., humans, non-human mammals and non-mammals).

As used herein terms "condition," "disorder," and "disease" relate to any unhealthy or abnormal state. The term "conditions associated with GPR6" includes conditions, disorders, and diseases in which the modulators of GPR6 provides a therapeutic benefit, such as Parkinson's disease, levodopa induced dyskinesias, and Huntington's disease, drug addiction, eating disorders, cognitive disorders, schizophrenia, bipolar disorders, and depression.

The terms "treat," "treatment," and "treating" include improvement of the conditions described herein. The terms "treat," "treatment," and "treating" include all processes providing slowing, interrupting, arresting, controlling, or stopping of the state or progression of the conditions described herein, but does not necessarily indicate a total elimination of all symptoms or a cure of the condition. The terms "treat," "treatment," and "treating" are intended to include therapeutic treatment of such disorders. The terms "treat," "treatment," and "treating" are intended to include prophylactic treatment of such disorders.

As used herein the terms "patient" and "subject" includes humans and non-human animals, for example, mammals, such as mice, rats, guinea pigs, dogs, cats, rabbits, cows, horses, sheep, goats, and pigs. The term also includes birds, fish, reptiles, amphibians, and the like. It is understood that a more particular patient is a human. Also, more particular patients and subjects are non-human mammals, such as mice, rats, and dogs.

As used herein, the term "effective amount" refers to the amount of compound of the invention which treats, upon single or multiple dose administration, a patient suffering from the mentioned condition. An effective amount can be readily determined by the attending diagnostician, as one skilled in the art, by the use of known techniques and by observing results obtained under analogous circumstances. In determining the effective amount, the dose, a number of factors are considered by the attending diagnostician, including, but not limited to, the species of patient, its size, age, and general health; the specific condition, disorder, or disease involved; the degree of or involvement or the severity of the condition, disorder, or disease, the response of the individual patient; the particular compound administered; the mode of administration; the bioavailability characteristics of the preparation administered; the dose regimen selected; the use of concomitant medication; and other relevant circumstances. An effective amount of the present invention, the treatment dosage, is expected to range from 1 mg to 200 mg. Specific amounts can be determined by the skilled person. Although these dosages are based on an average human subject having a mass of about 60 kg to about 70 kg, the physician will be able to determine the appropriate dose for other patients.

The pathological hallmark of Parkinson disease (PD) is neuronal cell loss within the substantia nigra. Degeneration of the nigrostriatal pathway causes reduction in the striatal concentration of dopamine which results in motor and nonmotor clinical manifestations. Many Parkinson's disease patients are treated with levodopa, a prodrug for dopamine Levodopa has common serious side effects including induced dyskinesia (LID), impulsive control disorders (ICD), psychotic symptoms and sleep disturbances. LID is progressive (90% of PD patients develop LID within 10 yrs). Irreversible adaptations occur in D1 receptor signaling in MSNs in rodent models of LID including reduced desensitization leading to hypersensitivity in the direct pathway. Genetic inactivation of D1 but not D2 receptors abolishes LID in mice. However blockade of D1 receptor signaling does not affect the antiparkinsonian efficacy of L-DOPA.

In a particular embodiment, the present invention provides a method of treating Parkinson's disease comprising: administering to a patient in need thereof an effective amount of a compound of the invention. That is, the invention also provides the use of a compound of the invention, including the use for the manufacture of a medicament, to treat Parkinson's disease.

The compounds of the invention may be combined with one or more other pharmacologically active compounds or therapies for the treatment of one or more disorders, diseases or conditions for which GPR6 is indicated may be administered simultaneously, sequentially or separately in combination with one or more compounds or therapies for treating Parkinson's disease, levodopa induced dyskinesias, and Huntington's disease, drug addiction, eating disorders, cognitive disorders, schizophrenia, bipolar disorders, and depression. Such combinations may offer significant therapeutic advantages, including fewer side effects, improved ability to treat underserved patient populations, or synergistic activity. In particular, the compounds of the invention may be administered with levodopa for treating Parkinson's disease. The present invention provides a method treating Parkinson's disease comprising: administering to a patient in need thereof an effective amount of a compound of the invention in combination with levadopa. The invention also provides the use of a compound of the invention in combination with levadopa, including the use for the manufacture of a medicament, to treat Parkinson's disease.

The activity of compounds as GPR6 modulators may be determined by a variety of methods, including in vitro and in vivo methods.

Example A.1

Inhibition of cAMP Activity of GPR6 In Vitro Assay

This cell based assay measures the ability of compounds to inhibit the constitutive cAMP activity of GPR6 receptor expressed in CHO-K1 cells. CHO cells were stably expressed with GPR6 receptor, whose expression is controlled by a tetracycline inducable element. The cells were cultured in medium containing F12K, 10% FBS, 1% Penn/Strep, 200 ug/mL Hygromycin. GPR6 receptor expression was induced for 20 hrs with 1 µg/ml doxycycline (sigma D9891) in growth media. After addition of doxycycline cells were plated at a density of 250-500 cells per well in half-volume black clear bottom plates (Costar) and place in an incubator (37°, 5% $C(O)_2$) for 20 hours prior to cAMP assays.

Culture media was removed from cells and they were washed with 50 µL of Ringer's Buffer ($MgCl_2$ 0.047 mg/mL, $NaH_2PO_4$ 0.18 mg/mL, $Na_2HPO_4$ 0.1 mg/mL, KCl 0.34 mg/mL, $NaHC(O)_3$ 1.26 mg/mL, D-glucose 1.8 mg/mL, NaCl 7 mg/mL; pH=7.4). Compounds suspended in DMSO were diluted in Ringer's Buffer containing 0.5% fatty acid free BSA and incubated on cells for 45 min at 37° and 5% $C(O)_2$. After incubation cells were incubated for 10 min at room temp with Eu-cAMP tracer solution from a Perkin Elmer Lance HTRF UltracAMP assay kit (TRF0264). Then ULight™-anti-cAMP solution from the Lance HTRF kit was added and incubated on a shaker at room temp for 1 hour prior to HTRF detection in a BMG PolarStar Omega.

$IC_{50}$ curves were generated with a four-parameter logistic equation using GraphPad Prism 5.03. Measured $IC_{50}$ value (µM) of example compounds in this assay is provided in the table below.

Example A.2

Inhibition of cAMP Activity of GPR6 In Vitro Assay

This cell based assay measures the ability of compounds to inhibit the constitutive cAMP activity of GPR6 receptor expressed in CHO-K1 cells. CHO cells were stably expressed with GPR6 receptor, whose expression is controlled by a tetracycline inducable element. The cells were cultured in medium containing F12K, 10% FBS, 1% Penn/Strep, 200 ug/mL Hygromycin. GPR6 receptor expression was induced for 20 hrs with 2 µg/ml doxycycline (sigma D9891) in growth media. After addition of doxycycline cells were plated at a density of 450-750 cells per well in 96-well half-volume black tissue culture plates (Costar) and placed in an incubator (37°, 5% $CO_2$) for 20 hours prior to cAMP assays.

Culture media was removed from cells and they were washed with 50 µL/well of Ringer's Buffer ($MgCl_2$ 0.047 mg/mL, $NaH_2PO_4$ 0.18 mg/mL, $Na_2HPO_4$ 0.1 mg/mL, KCl 0.34 mg/mL, $NaHCO_3$ 1.26 mg/mL, D-glucose 1.8 mg/mL, NaCl 7 mg/mL; pH=7.4). Compounds suspended in DMSO were diluted in Ringer's Buffer containing 0.5% fatty acid free BSA plus 300 µM IBMX and incubated on cells for 45 min at 37° and 5% $CO_2$. After incubation cells were incubated for 10 min at room temp with Eu-cAMP tracer solution from a Perkin Elmer Lance HTRF Ultra cAMP assay kit (TRF0263). Then ULight™-anti-cAMP solution from the Lance HTRF kit was added and incubated on a shaker at room temp for 1 hour prior to HTRF detection in a Perkin Elmer Envision plate reader.

$IC_{50}$ curves were generated with a four-parameter logistic equation using GraphPad Prism 5.03. Measured $IC_{50}$ value (μM) of example compounds in this assay is provided in the Table 1 below.

TABLE 1

| Ex. | A.1 $IC_{50}$ | A.2 $IC_{50}$ |
|---|---|---|
| 1 |  | 340.2 |
| 2 |  | 71.5 |
| 3 |  | 61.8 |
| 4 | 29.8 |  |
| 5 | 17.9 |  |
| 6 | 55.2 |  |
| 7 | 86.6 |  |
| 8 | 16.8 |  |
| 9 |  | 210.6 |
| 10 | 17.3 |  |
| 11 |  | 95.6 |
| 12 |  |  |
| 13 |  |  |
| 14 | 62.6 |  |
| 15 | 14.9 |  |
| 16 | 19.5 |  |
| 17 | 18 |  |
| 18 | 38.7 |  |
| 19 | 105 |  |
| 20 | 122 |  |
| 21 | 149 |  |
| 22 |  | 78.1 |
| 23 | 391 |  |
| 24 |  | 129.2 |
| 25 |  |  |
| 26 |  |  |
| 27 |  |  |
| 28 |  |  |
| 29 | 178 |  |
| 30 | 87 |  |
| 31 | 208 |  |
| 32 | 76 |  |
| 33 | 52 |  |
| 34 | 68 |  |
| 35 | 88 |  |
| 36 | 98 |  |
| 37 | 91 |  |
| 38 | 85 |  |
| 39 | 126 |  |
| 40 | 259 |  |
| 41 |  | 212.2 |
| 42 |  | 193.3 |
| 43 |  | 115.5 |
| 44 |  | 62.5 |
| 45 |  | 74.1 |
| 46 | 35 |  |
| 47 |  | 24.6 |
| 49 | 9.1 |  |
| 50 |  | 79.5 |
| 51 | 6.6 |  |
| 52 |  | 73.2 |
| 53 |  | 95 |
| 54 |  | 59.3 |
| 55 |  | 109.6 |
| 56 |  | 179.4 |
| 57 |  | 93.5 |
| 58 | 26.6 |  |
| 59 |  | 49.7 |
| 60 |  | >1000 |
| 61 |  | 131.7 |
| 62 |  | 69.2 |
| 63 |  | 37.8 |
| 65 |  |  |
| 66 | 145 |  |
| 67 | 9.4 |  |
| 68 | 15.2 |  |
| 69 | 26.5 |  |
| 70 |  | 17.1 |
| 71 | 8.5 |  |
| 72 | 23.7 |  |
| 73 | 16.6 |  |
| 74 |  | 140.2 |
| 75 |  | 30.3 |
| 76 | 13.4 |  |
| 77 | 19.7 |  |
| 78 | 8.8 |  |
| 79 | 9.8 |  |
| 80 | 24.9 |  |
| 81 |  | 59.5 |
| 82 |  | 73.7 |
| 83 | 13.8 |  |
| 84 |  | 90.1 |
| 85 | 10.4 |  |
| 86 | 13.7 |  |
| 87 | 13.8 |  |
| 88 | 32.7 |  |
| 89 |  |  |
| 90 |  |  |
| 91 | 11.5 |  |
| 92 | 12 |  |
| 93 | 13.8 |  |
| 94 | 19.9 |  |
| 95 | 32.5 |  |
| 96 | 26.9 |  |
| 97 |  | 163 |
| 98 |  | 110.6 |
| 99 | 8.3 |  |
| 100 | 57.2 |  |
| 101 | 78.8 |  |
| 102 | 111 |  |
| 103 | 64 |  |
| 104 |  |  |
| 105 |  |  |
| 106 |  |  |
| 107 | 24.9 |  |
| 108 | 31.4 |  |
| 109 | 23.2 |  |
| 110 | 22.1 |  |
| 111 | 23 |  |
| 112 | 10.4 |  |
| 113 | 20.9 |  |
| 114 | 18.5 |  |
| 115 | 23.9 |  |
| 116 |  | 199.7 |
| 117 |  | 27.4 |
| 118 |  | 11.4 |
| 119 |  | 23.6 |
| 120 |  | 249.8 |
| 121 |  | 341.5 |
| 122 |  | 247 |
| 123 |  | 187.7 |
| 124 |  | 43.2 |
| 125 |  | 200.2 |
| 126 |  | 107.1 |
| 127 |  | >1000 |
| 128 |  | 55 |
| 129 |  | 62 |
| 130 |  | 319.3 |
| 131 |  | 27.6 |
| 132 |  | 129.5 |
| 133 |  | 74.8 |
| 134 |  | 27 |
| 135 |  | 43.7 |
| 136 |  | 27.9 |
| 137 |  | 30.9 |
| 138 |  | >1000 |
| 139 |  | 219.8 |
| 140 |  | 122 |
| 141 |  | 33.7 |
| 142 |  | 113.5 |
| 143 |  | 29 |

TABLE 1-continued

| Ex. | A.1 IC$_{50}$ | A.2 IC$_{50}$ |
|---|---|---|
| 144 | | 61.5 |
| 145 | | 185.9 |
| 146 | | 362.9 |
| 147 | | 603.9 |
| 148 | | 78 |
| 149 | | 58.7 |
| 150 | | 39.2 |
| 151 | | 35.9 |
| 152 | | 49.3 |
| 153 | | 63.2 |
| 154 | | 97.8 |
| 155 | | 59.1 |
| 156 | 9.5 | |

Example B

Haloperidol-Induced Catalepsy—In Vivo Rodent Parkinson's Disease Model

The motor symptoms of Parkinson's disease include akinesia, bradykinesia, rigidity, tremor and postural abnormalities and are associated with the loss of nigral dopaminergic cells and a decline in striatal dopamine levels. Administration of haloperidol to rodents leads to a transient parkinsonian-like state that is reversed by the administration of L-Dopa (Duty, S.; Jenner, P. Br. J. Pharmacol. (2011), 164, 1357-1391) and other drugs that have been clinically validated for the treatment of Parkinson's disease. Haloperidol antagonizes dopamine D2 and, to a lesser extent, D1 receptors in medium spiny neurons that comprise the indirect and direct pathways of the motor circuit respectively. The resultant block of striatal dopamine transmission results in abnormal downstream firing within the basal ganglia circuits that is manifest as symptoms of muscle rigidity and catalepsy. Catalepsy has been postulated to reflect the clinical features of Parkinson's disease, whereby patients experience an inability of to initiate movements.

Male Sprague-Dawley rats (Charles River, Calco, Italy) weighing 175-200 g are used. Alternatively, male C57B16 mice weighing 25-35 g were used. The cataleptic state was induced by the subcutaneous administration of the dopamine receptor antagonist haloperidol (0.3 mg/kg, sc), 90 min before testing the animals on the vertical grid test. For this test, the rats or mice were placed on the wire mesh cover of a 25 cm×43 cm plexiglass cage placed at an angle of about 70 degrees with the bench table. The subject was placed on the grid with all four legs abducted and extended ("frog posture"). The use of such an unnatural posture is essential for the specificity of this test for catalepsy. The time span from placement of the paws until the first complete removal of one paw (descent latency) was measured maximally for 120 sec for rats. For mice, the front paws of a mouse was placed on a horizontal metal bar raised 2″ above a Plexiglas platform and time was recorded for up to 30 seconds per trial. The test ended when the animal's front paws returned to the platform or after 30 seconds. The test was repeated three times and the average of the three trials was reported as the intensity index of catalepsy.

Catalepsy was measured 30 min, 120 min, and/or 240 min after dosing the subjects a 0.3 mg/kg i.p. dose of haloperidol along with the GPR6 modulator test compound. Test compound plasma and brain levels were determined by collected tissue samples at the end of the experiment, which was either at the 120 or 240 min time point. A representative number of compounds of the invention were administered in a dose range from 0.1 to 100 mg/kg i.p, sc or po in conjunction with haloperidol. The A2a antagonist KW6002 (istradefylline) was dosed at 0.6 mg/kg i.p. as a positive control.

Measured % reversal of example compounds in this assay is provided in the Table 2 below.

TABLE 2

| Ex. | Species | Dose (mpk) | Route | % reversal 30 min | 120 min |
|---|---|---|---|---|---|
| 47 | Rat | 30 | i.p. | 75.7* | 82.1* |
| | | 10 | i.p. | 83.4* | 76.5* |
| | | 1 | i.p. | 39.1 | 57.9* |
| | | 0.1 | i.p. | −5.7 | 27.3 |

*significantly different than vehicle contol, one-way ANOVA with Bonferroni's multiple test correction.

Example C

6-Hydroxydopamine Lesion Model—In Vivo Rodent Parkinson's Disease Model

Adult female rats (10) were first assessed for pre-surgery motor activity using an automated activity tracking system that records beam breaks across the testing arena floor. Beam breaks were summed over the first 3 hours after the animals were placed into the arena and recorded as activity counts. To selectively damage dopaminergic nerve terminals in the striatum, 20 µg of the 6-hydroxydopamine was injected directly into the striatum bilaterally (i.e., on both sides of the brain). After 4 weeks of recovery, the rats were again tested for motor activity, and a significant reduction in activity counts was observed. Vehicle and the compound of Example 47 (0.5% methylcellulose) was orally dosed at 0.1, 1.0, or 10 mg/kg in a cross-over study design (5-10 day wash out period), and after dosing activity counts were measured for 3 hours. At the end of the study period, when each animal had received each treatment once, the data were analyzed. The activity counts (standard error of the mean) for the group pre-surgery and post-surgery and for treated and vehicle control were determined and are provide in Table 3 below:

TABLE 3

| Treatment Group | Mean | S.E.M |
|---|---|---|
| Pre-Surgery | 12171 | 1601 |
| Vehicle | 7253 | 768 |
| 0.1 mg/kg | 11422* | 1071 |
| 1.0 mg/kg | 15334* | 2013 |
| 10 mg/kg | 19368* | 1410 |

*significantly different than vehicle contol, one-way ANOVA with Bonferroni's multiple test correction.

What is claimed is:
1. The compound of formula II:

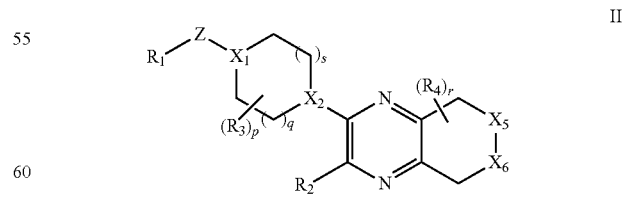

or a pharmaceutically acceptable salt thereof, wherein
R$_1$ is selected from the group consisting of C$_{3-8}$ cycloalkyl optionally substituted with 1 to 3 substituents independently selected from the group consisting of C$_{1-4}$ alkoxy, halo, hydroxy, and C$_{1-4}$ alkyl optionally substituted with $C_{1-4}$ alkoxy, halo, and hydroxy; $C_{3-6}$ heterocyclyl optionally substituted on ring carbons with 1 to 4 substituents independently selected from the group consisting of $C_{1-4}$ alkyl, $C_{1-4}$ alkoxy, $C_{1-9}$ amide, $C_{1-7}$ amido, amino, $C_{1-8}$ alkylamino, $C_{1-5}$ oxycarbonyl, cyano, $C_{3-8}$ cycloalkyl, $C_{3-8}$ cycloalkoxy, halo, hydroxy, nitro, oxo, and phenyl optionally substituted with 1 to 5 substituents independently selected from the group consisting of $C_{1-4}$ alkyl, $C_{1-4}$ alkoxy, $C_{1-9}$ amino, $C_{1-8}$ alkylamino, $C_{1-5}$ oxycarbonyl, cyano, halo, hydroxy, nitro, and trifluoromethyl and optionally substituted on any ring nitrogen with a substituent independently selected from the group consisting of $C_{1-4}$ alkyl, $C_{3-8}$ cycloalkyl, $C_{3-6}$ heterocyclyl, $C_{1-10}$ heteroaryl, and phenyl optionally substituted with 1 to 5 substituents independently selected from the group consisting of $C_{1-4}$ alkyl, $C_{1-4}$ alkoxy, $C_{1-9}$ amino, $C_{1-8}$ alkylamino, $C_{1-5}$ oxycarbonyl, cyano, halo, hydroxy, nitro, and trifluoromethyl; $C_{6-10}$ aryl optionally substituted with 1 to 5 substituents independently selected from the group consisting of $C_{1-4}$ alkyl, $C_{1-4}$ alkoxy, $C_{1-4}$ thioalkoxy, amino, $C_{1-8}$ alkylamino, $C_{1-9}$ amide, $C_{1-7}$ amido, $C_{1-5}$ oxycarbonyl, $C_{1-5}$ carbonyloxy, $C_{1-8}$ sulfonyl, $C_{1-5}$ carbamoyl, $C_{1-6}$ sulfonylamido, aminosulfonyl, $C_{1-10}$ aminosulfonyl, $C_{1-5}$ ureido, trifluoromethyl, trifluoromethoxy, cyano, halo, and hydroxy; and $C_{1-10}$ heteroaryl optionally substituted with 1 to 3 substituents on carbon independently selected from the group consisting of amino, $C_{1-8}$ alkylamino, $C_{1-9}$ amide, $C_{1-4}$ alkyl, $C_{1-4}$ alkoxy, cyano, halo, hydroxy, oxo, trifluoromethyl, and trifluoromethoxy and optionally substituted on a ring nitrogen with $C_{1-4}$ alkyl;

$X_1$ is N and $X_2$ is CH; or $X_1$ is CH and $X_2$ is N; or $X_1$ is N and $X_2$ is N;

when $X_1$ is N, Z is selected from the group consisting of $C_{1-6}$ alkylene, $C_{1-6}$ haloalkylene, —C(O)—, and —S(O)$_2$—;

when $X_1$ is CH, Z is selected from the group consisting of $C_{1-6}$ alkylene, $C_{1-6}$ haloalkylene, —O—, —C(O)—, —NH—, —S—, —S(O)—, and —S(O)$_2$—;

q is 0, 1, or 2;

s is 0, 1, or 2;

$R_2$ is OR$_5$ or NR$_6$R$_7$;

each $R_3$ is independently selected from the group consisting of $C_{1-6}$ alkyl, $C_{3-8}$ cycloalkyl, and trifluoromethyl;

p is 0, 1, or 2;

each $R_4$ is independently selected from the group consisting of $C_{1-6}$ alkyl, hydroxy, and halo;

r is 0 or 1;

$R_5$ is selected from the group consisting of $C_{1-6}$ alkyl and $C_{3-8}$ cycloalkyl;

$R_6$ is selected from the group consisting of hydrogen and $C_{1-6}$ alkyl;

$R_7$ is selected from the group consisting of $C_{1-6}$ alkyl optionally substituted with 1 to 7 substituents independently selected from the group consisting of $C_{1-4}$ alkoxy, $C_{1-9}$ amide, amino, $C_{1-8}$ alkylamino, $C_{1-5}$ oxycarbonyl, cyano, $C_{3-8}$ cycloalkyl, halo, hydroxy, $C_{3-6}$ heterocyclyl optionally substituted on any ring nitrogen by $C_{1-4}$ alkyl, $C_{1-10}$ heteroaryl, and phenyl optionally substituted with 1 to 5 substituents independently selected from the group consisting of $C_{1-4}$ alkyl, $C_{1-4}$ alkoxy, $C_{1-9}$ amino, $C_{1-8}$ alkylamino, $C_{1-5}$ oxycarbonyl, cyano, halo, hydroxy, nitro, and trifluoromethyl; $C_{3-8}$ cycloalkyl; $C_{6-10}$ aryl optionally substituted with 1 to 5 substituents independently selected from the group consisting of $C_{1-4}$ alkyl, $C_{1-4}$ alkoxy, cyano, halo, hydroxy, amino, trifluoromethyl, and trifluoromethoxy; $C_{1-10}$ heteroaryl optionally substituted with 1 to 3 substituents on carbon independently selected from the group consisting of amino, $C_{1-8}$ alkylamino, $C_{1-9}$ amide, $C_{1-4}$ alkyl, $C_{1-4}$ alkoxy, cyano, halo, hydroxy, oxo, trifluoromethyl, and trifluoromethoxy and optionally substituted on a ring nitrogen with $C_{1-4}$ alkyl; and $C_{3-6}$ heterocyclyl optionally substituted on ring carbons with 1 to 4 substituents independently selected from the group consisting of $C_{1-4}$ alkyl, $C_{1-4}$ alkoxy, halo, and hydroxy and optionally substituted on any ring nitrogen with $C_{1-4}$ alkyl; and $X_5$ is selected from the group consisting of CH and CR$_4$, and $X_6$ is selected from the group consisting of NH and N—CH$_2$-(phenyl optionally substituted with 1 to 5 substituents independently selected from the group consisting of $C_{1-4}$ alkyl, $C_{1-4}$ alkoxy, $C_{1-9}$ amino, $C_{1-8}$ alkylamino, $C_{1-5}$ oxycarbonyl, cyano, halo, hydroxy, nitro, and trifluoromethyl); or $X_5$ is selected from the group consisting of NH and N—CH$_2$-(phenyl optionally substituted with 1 to 5 substituents independently selected from the group consisting of $C_{1-4}$ alkyl, $C_{1-4}$ alkoxy, $C_{1-9}$ amino, $C_{1-8}$ alkylamino, $C_{1-5}$ oxycarbonyl, cyano, halo, hydroxy, nitro, and trifluoromethyl) and $X_6$ is selected from the group consisting of CH and CR$_4$.

2. The compound or pharmaceutically acceptable salt according to claim 1, wherein $R_2$ is —NR$_6$R$_7$.

3. The compound or pharmaceutically acceptable salt according to claim 2, wherein $X_5$ is selected from the group consisting of CH and CR$_4$ and $X_6$ is NH.

4. The compound or pharmaceutically acceptable salt according to claim 2, wherein $X_5$ is NH and $X_6$ is selected from the group consisting of CH and CR$_4$.

5. The compound or pharmaceutically acceptable salt according to claim 2, wherein $X_5$ is selected from the group consisting of CH and CR$_4$, and $X_6$ is N—CH$_2$-(phenyl optionally substituted with 1 to 5 substituents independently selected from the group consisting of $C_{1-4}$ alkyl, $C_{1-4}$ alkoxy, $C_{1-9}$ amino, $C_{1-8}$ alkylamino, $C_{1-5}$ oxycarbonyl, cyano, halo, hydroxy, nitro, and trifluoromethyl).

6. The compound or pharmaceutically acceptable salt according to claim 2, wherein $X_6$ is selected from the group consisting of CH and CR$_4$, and $X_5$ is N—CH$_2$-(phenyl optionally substituted with 1 to 5 substituents independently selected from the group consisting of $C_{1-4}$ alkyl, $C_{1-4}$ alkoxy, $C_{1-9}$ amino, $C_{1-8}$ alkylamino, $C_{1-5}$ oxycarbonyl, cyano, halo, hydroxy, nitro, and trifluoromethyl).

7. The compound or pharmaceutically acceptable salt according to claim 1, wherein $X_1$ is CH and $X_2$ is N.

8. The compound or pharmaceutically acceptable salt according to claim 1, wherein $X_1$ is N and $X_2$ is N.

9. The compound or pharmaceutically acceptable salt according to claim 1, wherein $R_1$ is $C_{6-10}$ aryl optionally substituted with 1 to 5 substituents independently selected from the group consisting of $C_{1-4}$ alkyl, $C_{1-4}$ alkoxy, $C_{1-4}$ thioalkoxy, amino, $C_{1-8}$ alkylamino, $C_{1-9}$ amide, $C_{1-7}$ amido, $C_{1-5}$ oxycarbonyl, $C_{1-5}$ carbonyloxy, $C_{1-8}$ sulfonyl, $C_{1-5}$ carbamoyl, $C_{1-6}$ sulfonylamido, aminosulfonyl, $C_{1-10}$ aminosulfonyl, $C_{1-5}$ ureido, trifluoromethyl, trifluoromethoxy, cyano, halo, and hydroxy.

10. The compound or pharmaceutically acceptable salt according to claim 1, wherein Z is $C_{1-6}$ alkylene.

11. The compound or pharmaceutically acceptable salt according to claim 1, wherein Z is $C_{1-6}$ haloalkylene.

12. The compound or pharmaceutically acceptable salt according to claim 1, wherein Z is —O—.

13. The compound or pharmaceutically acceptable salt according to claim 1, wherein Z is —C(O)—.

14. The compound according to claim 1, which is selected from the group consisting of:
- 6-benzyl-N-(2,2-difluoroethyl)-2-(4-(2,4-difluorophenoxy)piperidin-1-yl)-5,6,7,8-tetrahydropyrido[3,4-b]pyrazin-3-amine;
- 6-benzyl-2-(4-(2,4-difluorophenoxy)piperidin-1-yl)-N-isopropyl-5,6,7,8-tetrahydropyrido[3,4-b]pyrazin-3-amine;
- 6-benzyl-N-cyclobutyl-2-(4-(2,4-difluorophenoxy)piperidin-1-yl)-5,6,7,8-tetrahydropyrido[3,4-b]pyrazin-3-amine;
- (S)-6-benzyl-2-(4-(2,4-difluorophenoxy)piperidin-1-yl)-N-(1-methoxypropan-2-yl)-5,6,7,8-tetrahydropyrido[3,4-b]pyrazin-3-amine;
- (R)-6-benzyl-2-(4-(2,4-difluorophenoxy)piperidin-1-yl)-N-(1-methoxypropan-2-yl)-5,6,7,8-tetrahydropyrido[3,4-b]pyrazin-3-amine;
- (S)-6-benzyl-N-(sec-butyl)-2-(4-(2,4-difluorophenoxy)piperidin-1-yl)-5,6,7,8-tetrahydropyrido[3,4-b]pyrazin-3-amine;
- (R)-6-benzyl-N-(sec-butyl)-2-(4-(2,4-difluorophenoxy)piperidin-1-yl)-5,6,7,8-tetrahydropyrido[3,4-b]pyrazin-3-amine;
- 4-((1-(6-benzyl-3-(isopropylamino)-5,6,7,8-tetrahydropyrido[3,4-b]pyrazin-2-yl)piperidin-4-yl)oxy)-3-fluorobenzonitrile;
- (S)-6-benzyl-2-(4-((2,4-difluorophenyl)fluoromethyl)piperidin-1-yl)-N-isopropyl-5,6,7,8-tetrahydropyrido[3,4-b]pyrazin-3-amine;
- 6-benzyl-3-(4-((2-fluorophenyl)sulfonyl)piperidin-1-yl)-N-isopropyl-5,6,7,8-tetrahydropyrido[3,4-b]pyrazin-2-amine;
- 6-benzyl-N-cyclopropyl-3-(4-(2-fluoro-4-methoxyphenoxy)piperidin-1-yl)-5,6,7,8-tetrahydropyrido[3,4-b]pyrazin-2-amine;
- 6-benzyl-N-cyclopropyl-2-(4-(2-fluoro-4-methoxyphenoxy)piperidin-1-yl)-5,6,7,8-tetrahydropyrido[3,4-b]pyrazin-3-amine;
- 6-benzyl-N-cyclopropyl-3-(4-((2,4-difluorophenyl)fluoromethyl)piperidin-1-yl)-5,6,7,8-tetrahydropyrido[3,4-b]pyrazin-2-amine;
- 6-benzyl-N-cyclopropyl-2-(4-((2,4-difluorophenyl)fluoromethyl)piperidin-1-yl)-5,6,7,8-tetrahydropyrido[3,4-b]pyrazin-3-amine;
- 6-benzyl-3-(4-(2-fluoro-4-methoxyphenoxy)piperidin-1-yl)-N-isopropyl-5,6,7,8-tetrahydropyrido[3,4-b]pyrazin-2-amine;
- 6-benzyl-3-(4-((2,4-difluorophenyl)fluoromethyl)piperidin-1-yl)-N-isopropyl-5,6,7,8-tetrahydropyrido[3,4-b]pyrazin-2-amine;
- 6-benzyl-2-(4-(2-fluoro-4-methoxyphenoxy)piperidin-1-yl)-N-isopropyl-5,6,7,8-tetrahydropyrido[3,4-b]pyrazin-3-amine;
- 6-benzyl-2-(4-((2,4-difluorophenyl)fluoromethyl)piperidin-1-yl)-N-isopropyl-5,6,7,8-tetrahydropyrido[3,4-b]pyrazin-3-amine; and
- 4-((1-(6-benzyl-2-(isopropylamino)-5,6,7,8-tetrahydropyrido[3,4-b]pyrazin-3-yl)piperidin-4-yl)oxy)-3-fluorobenzonitrile;

or a pharmaceutically acceptable salt thereof.

15. The compound according to claim 1, which is selected from the group consisting of:
- 3-fluoro-4-((1-(3-(isopropylamino)-5,6,7,8-tetrahydropyrido[3,4-b]pyrazin-2-yl)piperidin-4-yl)oxy)benzonitrile;
- N-(2,2-difluoroethyl)-2-(4-(2,4-difluorophenoxy)piperidin-1-yl)-5,6,7,8-tetrahydropyrido[3,4-b]pyrazin-3-amine;
- N-cyclobutyl-2-(4-(2,4-difluorophenoxy)piperidin-1-yl)-5,6,7,8-tetrahydropyrido[3,4-b]pyrazin-3-amine;
- (S)-2-(4-((2,4-difluorophenyl)fluoromethyl)piperidin-1-yl)-N-isopropyl-5,6,7,8-tetrahydropyrido[3,4-b]pyrazin-3-amine;
- N-cyclobutyl-2-(4-(2-fluoro-4-methoxyphenoxy)piperidin-1-yl)-5,6,7,8-tetrahydropyrido[3,4-b]pyrazin-3-amine;
- 2-(4-(2,4-difluorophenoxy)piperidin-1-yl)-N-isopropyl-5-methyl-5,6,7,8-tetrahydropyrido[3,4-b]pyrazin-3-amine;
- N-(2,2-difluoroethyl)-2-(4-(2,4-difluorophenoxy)piperidin-1-yl)-5-methyl-5,6,7,8-tetrahydropyrido[3,4-b]pyrazin-3-amine;
- N-cyclopropyl-3-(4-(2-fluoro-4-methoxyphenoxy)piperidin-1-yl)-5,6,7,8-tetrahydropyrido[3,4-b]pyrazin-2-amine;
- N-cyclopropyl-2-(4-(2-fluoro-4-methoxyphenoxy)piperidin-1-yl)-5,6,7,8-tetrahydropyrido[3,4-b]pyrazin-3-amine;
- N-cyclopropyl-3-(4-((2,4-difluorophenyl)fluoromethyl)piperidin-1-yl)-5,6,7,8-tetrahydropyrido[3,4-b]pyrazin-2-amine;
- N-cyclopropyl-2-(4-((2,4-difluorophenyl)fluoromethyl)piperidin-1-yl)-5,6,7,8-tetrahydropyrido[3,4-b]pyrazin-3-amine;
- 3-(4-(2-fluoro-4-methoxyphenoxy)piperidin-1-yl)-N-isopropyl-5,6,7,8-tetrahydropyrido[3,4-b]pyrazin-2-amine;
- 3-(4-((2,4-difluorophenyl)fluoromethyl)piperidin-1-yl)-N-isopropyl-5,6,7,8-tetrahydropyrido[3,4-b]pyrazin-2-amine;
- 2-(4-(2-fluoro-4-methoxyphenoxy)piperidin-1-yl)-N-isopropyl-5,6,7,8-tetrahydropyrido[3,4-b]pyrazin-3-amine;
- 2-(4-((2,4-difluorophenyl)fluoromethyl)piperidin-1-yl)-N-isopropyl-5,6,7,8-tetrahydropyrido[3,4-b]pyrazin-3-amine;
- 2-(4-(2,4-difluorobenzyl)piperazin-1-yl)-N-isopropyl-5,6,7,8-tetrahydropyrido[3,4-b]pyrazin-3-amine;
- 3-fluoro-4-((1-(2-(isopropylamino)-5,6,7,8-tetrahydropyrido[3,4-b]pyrazin-3-yl)piperidin-4-yl)oxy)benzonitrile;
- 3-(4-(2,4-difluorophenoxy)piperidin-1-yl)-N-isopropyl-5,6,7,8-tetrahydropyrido[3,4-b]pyrazin-2-amine;
- N-(2,2-difluoroethyl)-3-(4-(2,4-difluorophenoxy)piperidin-1-yl)-5,6,7,8-tetrahydropyrido[3,4-b]pyrazin-2-amine;
- N-(tert-butyl)-3-(4-(2,4-difluorophenoxy)piperidin-1-yl)-5,6,7,8-tetrahydropyrido[3,4-b]pyrazin-2-amine;
- N-cyclobutyl-3-(4-(2-fluoro-4-methoxyphenoxy)piperidin-1-yl)-5,6,7,8-tetrahydropyrido[3,4-b]pyrazin-2-amine;
- N-cyclopropyl-3-(4-(2,4-difluorophenoxy)piperidin-1-yl)-5-methyl-5,6,7,8-tetrahydropyrido[3,4-b]pyrazin-2-amine; and
- 3-(4-(2,4-difluorophenoxy)piperidin-1-yl)-N-isopropyl-5-methyl-5,6,7,8-tetrahydropyrido[3,4-b]pyrazin-2-amine;

or a pharmaceutically acceptable salt thereof.

* * * * *

UNITED STATES PATENT AND TRADEMARK OFFICE
CERTIFICATE OF CORRECTION

PATENT NO. : 9,708,313 B2
APPLICATION NO. : 14/883174
DATED : July 18, 2017
INVENTOR(S) : Jason W. Brown et al.

It is certified that error appears in the above-identified patent and that said Letters Patent is hereby corrected as shown below:

- Column 24 Line 16 replace "Preparation 18" with "Preparation 15"

- Column 24 Line 26 replace "Preparation 20" with "Preparation 15"

- Column 26 Line 49 replace "Preparation 28" with "Preparation 29"

- Column 28 Line 59 replace "Preparation 38" with "Preparation 36"

- Column 30 Line 31 replace "Preparation 44" with "Preparation 42"

- Column 30 Line 43 replace "Preparation 46" with "Preparation 42"

- Column 31 Line 36 replace "Preparation 51" with "Preparation 47"

- Column 31 Line 46 replace "Preparation 53" with "Preparation 47"

- Column 31 Line 55 replace "Preparation 55" with "Preparation 47"

- Column 31 Line 65 replace "Preparation 57" with "Preparation 47"

- Column 32 Line 6 replace "Preparation 59" with "Preparation 47"

- Column 33 Lines 45-46 should read as follows:
The title compound as a TFA salt was prepared from a starting material made in Preparation 50 in a manner similar to Preparation 64, except that the reaction was stirred under hydrogen atmosphere for 2 h. ESI-MS m/z $[M+H]^+$ 416.5.

Signed and Sealed this
Sixteenth Day of October, 2018

Andrei Iancu
*Director of the United States Patent and Trademark Office*

CERTIFICATE OF CORRECTION (continued)
U.S. Pat. No. 9,708,313 B2

- Column 33 Lines 54-55 should read as follows:
The title compound as a TFA salt was prepared from a starting material made in Preparation 61 in a manner similar to Preparation 64, except that the reaction was stirred under hydrogen atmosphere for 2 h. The TFA salt was dissolved in DCM and washed with saturated aqueous $K_2CO_3$. The organics were dried over $Na_2SO_4$, filtered, and concentrated under reduced pressure to obtain the title compound as the free base. ESI-MS m/z $[M+H]^+$ 420.5.

- Column 33 Lines 66-67 should read as follows:
The title compound as a TFA salt was prepared from a starting material made in Preparation 62 in a manner similar to Preparation 64. The TFA salt was dissolved in DCM and washed with saturated aqueous $K_2CO_3$. The organics were dried over Na2SO4, filtered, and concentrated under reduced pressure to obtain the title compound as the free base. ESI-MS m/z $[M+H]^+$ 420.5.

- Column 35 Line 9 replace "Preparation 75" with "Preparation 73"

- Column 36 Line 58 replace "Preparation 82" with "Preparation 80"

- Column 36 Line 65 replace "Preparation 84" with "Preparation 80"

- Column 39 Line 21 delete "91"